(12) United States Patent
Mjalli et al.

(10) Patent No.: US 7,820,704 B2
(45) Date of Patent: Oct. 26, 2010

(54) SUBSTITUTED HETEROARYL DERIVATIVES, COMPOSITIONS, AND METHODS OF USE

(75) Inventors: Adnan M. M. Mjalli, Jamestown, NC (US); Bapu R. Gaddam, Greensboro, NC (US); Ghassan Qabaja, High Point, NC (US); Govindan Subramanian, High Point, NC (US); Jeff Zhu, Greensboro, NC (US); John Dankwardt, Westborough, MA (US); Murty N. Arimilli, Oak Ridge, NC (US); Robert C. Andrews, Jamestown, NC (US); Samuel Victory, Oak Ridge, NC (US); Ye E. Tian, Jamestown, NC (US)

(73) Assignee: TransTech Pharma, Inc., High Point, NC (US)

( * ) Notice: Subject to any disclaimer, the term of this patent is extended or adjusted under 35 U.S.C. 154(b) by 523 days.

(21) Appl. No.: 11/110,499

(22) Filed: Apr. 20, 2005

(65) Prior Publication Data

US 2005/0261294 A1    Nov. 24, 2005

Related U.S. Application Data

(60) Provisional application No. 60/563,882, filed on Apr. 20, 2004.

(51) Int. Cl.
*A61K 31/427* (2006.01)
*A61K 31/381* (2006.01)
*C07D 277/38* (2006.01)
*C07D 409/12* (2006.01)

(52) U.S. Cl. ............ 514/370; 514/444; 548/194; 549/59

(58) Field of Classification Search .......... 514/370, 514/444; 548/194; 549/59
See application file for complete search history.

(56) References Cited

U.S. PATENT DOCUMENTS

| | | | |
|---|---|---|---|
| 5,463,071 A | 10/1995 | Himmelsbach et al. | |
| 5,470,855 A | 11/1995 | Bernat et al. | |
| 5,502,025 A | 3/1996 | Bussler | |
| 5,627,131 A | 5/1997 | Shribbs et al. | |
| 5,643,932 A | 7/1997 | Chihiro et al. | |
| 6,011,048 A | 1/2000 | Mathvink et al. | |
| 6,303,749 B1 | 10/2001 | Jarosinski | |
| 6,344,470 B1 | 2/2002 | Fontaine et al. | |
| 6,596,746 B1 | 7/2003 | Das et al. | |
| 6,689,873 B1 | 2/2004 | Van der Ploeg et al. | |
| 6,699,896 B1 | 3/2004 | Malamas | |
| 6,734,175 B2 | 5/2004 | Hadcock et al. | |
| 6,787,542 B2 | 9/2004 | Wang et al. | |
| 7,056,942 B2 * | 6/2006 | Hildesheim et al. | 514/411 |
| 2002/0132807 A1 | 9/2002 | Wang et al. | |
| 2002/0151463 A1 | 10/2002 | Woychik et al. | |
| 2003/0082737 A1 | 5/2003 | Stark et al. | |
| 2003/0158199 A1 | 8/2003 | Stieber et al. | |
| 2004/0132788 A1 | 7/2004 | Chabrier De Lassauniere et al. | |
| 2005/0009891 A1 | 1/2005 | Lee | |
| 2005/0014746 A1 | 1/2005 | Wang et al. | |
| 2005/0014805 A1 | 1/2005 | Zhang et al. | |
| 2005/0038087 A1 | 2/2005 | Chabrier De Lassauniere et al. | |
| 2005/0065196 A1 | 3/2005 | Inaba et al. | |
| 2005/0261305 A1 | 11/2005 | Das et al. | |

FOREIGN PATENT DOCUMENTS

| | | |
|---|---|---|
| EP | 0 354 201 | 2/1990 |
| EP | 0 480 902 | 4/1992 |
| EP | 0 556 396 | 8/1993 |
| EP | 0 627 423 | 9/1995 |
| EP | 1 285 658 | 2/2003 |
| EP | 1 452 530 A1 | 9/2004 |
| EP | 1 553 091 A1 | 9/2004 |
| JP | 63203672 | 8/1988 |
| JP | 07149745 | 6/1995 |
| WO | WO 93-17681 | 9/1993 |
| WO | WO 97-47299 | 12/1997 |
| WO | WO 99-50295 | 10/1999 |
| WO | WO 99-58511 | 11/1999 |
| WO | WO 99-58514 | 11/1999 |
| WO | WO 00-11954 | 3/2000 |
| WO | WO 01-58871 | 8/2001 |
| WO | WO 02-02539 | 1/2002 |

(Continued)

OTHER PUBLICATIONS

Morissette et al. "High-throughput crystallization: polymorphs, salts, co-crystals and solvates of pharmaceutical solids" Advanced Drug Delivery Reviews, 2004, vol. 56, pp. 275-300.*
Database Chemcats, Chemical Abstracts Service, Columbus, Ohio, retrieved from STN Order Nos: Q-084349, Q-084359 abstract, "Ambinter Stock Screening Collection", Quai Louis Beriot, (2004).
Database Beilstein, Beilstein Institute for Organic Chemistry, Frankfurt-Maine, Database accession No. BRN: 14989 abstract, UKR. KHIM. ZH et al., vol. 25, pp. 767-771 (1959).
Database Beilstein, Beilstein Institute for Organic Chemistry, Frankfurt-Maine, Database accession No. BRN: 7541410 abstract & Farmaco, vol. 51, No. 2, pp. 137-140, (1996).

(Continued)

*Primary Examiner*—Joseph R Kosack
(74) *Attorney, Agent, or Firm*—Kilpatrick Stockton LLP

(57) ABSTRACT

The present invention provides substituted heteroaryl derivatives of Formula (I), methods of their preparation, pharmaceutical compositions comprising the compounds of Formula (I), and methods of use in treating human or animal disorders. The compounds of the invention can be useful as inhibitors of action of AgRP on a melanocortin receptor and thus can be useful for the management, treatment, control, or the adjunct treatment of diseases which may be responsive to the modulation of melanocortin receptors including obesity-related disorders.

42 Claims, No Drawings

FOREIGN PATENT DOCUMENTS

| WO | WO 03-040117 | 5/2003 |
|---|---|---|
| WO | WO 03-068738 | 8/2003 |
| WO | WO 2004-004447 | 1/2004 |
| WO | WO 2006-038594 | 4/2006 |

OTHER PUBLICATIONS

Database Beilstein, Beilstein Institute for Organic Chemistry, Frankfurt-Maine, Database accession No. BRN: 678128 abstract & Eur. J. Med. Chem. Chim. Ther. vol. 9, p. 11, (1974).

Database Beilstein, Beilstein Institute for Organic Chemistry, Frankfurt-Maine, Database accession No. BRN: 309225 abstract & J. Am. Chem. Soc. vol. 63, p. 3028 (1941).

Database Beilstein, Beilstein Institute for Organic Chemistry, Frankfurt-Maine, Database accession No. BRN: 644518 abstract & Chem. Pharm. Bull., vol. 35 No. 12 pp. 4705-4710, (1987).

Database Beilstein, Beilstein Institute for Organic Chemistry, Frankfurt-Maine, Database accession No. BRN: 687549 abstract & Chem. Heterocycl. Compd., vol. 2, p. 1181, (1976).

Database Beilstein, Beilstein Institute for Organic Chemistry, Frankfurt-Maine, Database accession No. BRN: 294410 abstract & Justus Liebigs Ann. Chem., vol. 467, p. 254, (1928).

Database Beilstein, Beilstein Institute for Organic Chemisgtry, Frankfurt-Maine, Database accession No. BRN: 326592 abstracts & J. Indian Chem. Soc., vol. 32, pp. 663-665, (1955).

Database Beilstein, Beilstein Institute for Organic Chemisgtry, Frankfurt-Maine, Database accession No. BRN: 2991 abstract & J. Am. Chem. Soc., vol. 72, 1950, p. 3138, (1950).

Database Beilstein, Beilstein Institute for Organic Chemisgtry, Frankfurt-Maine, Database accession No. BRN: 4957 abstract & Yakugaku Zasshi, Vo. 71, p. 1439, (1951).

Database Beilstein, Beilstein Institute for Organic Chemisgtry, Frankfurt-Maine, Database accession No. BRN: 13161 abstract & Helv. Chim. Acta., vol. 31, p. 1142, (1946).

International Search Report for PCT application PCT/US2005/013386 mailed Aug. 26, 2005.

Adan et al., "Inverse agonism gains weight" Trends in Pharmacological Sciences, vol. 24, pp. 315-321, (2003).

Argyropoulos et al., "A polymorphism in the human agouti-related protein is associated with late-onset obesity" The Journal of Clinical Endocrinology & Metabolism, vol. 87, pp. 4198-4202, (2002).

Bednarek et al., "Selective, high affinity peptide antagonists of α-melanotropin action at human melanocortin receptor 4: their synthesis and biological evaluation in vitro" Journal of Medicinal Chemistry, vol. 44, pp. 3665-3672, (2001).

Bolin et al., "NMR structure of a minimized human agouti related protein prepared by total chemical synthesis" FEBS Letters, vol. 451, pp. 125-131, (1999).

Brown et al., "The gene structure and minimal promoter of the human agouti related protein" Gene, vol. 277, pp. 231-238, (2001).

Bures et al., "Determination of disulfide structure in agouti-related protein (AgRP) by stepwise reduction and alkylation" Biochemistry, vol. 37, pp. 12172-12177, (1998).

Chai et al., "Inverse agonist activity of agouti and agouti-related protein" Peptides, vol. 24, pp. 603-609, (2003).

Claycombe et al., "Regulation of leptin by agouti" Physiological Genomics, vol. 2, pp. 101-105, (2000).

Cupples, "Peptides that regulate food intake" American Journal of Physiology, Regulatory, Integrative and Comparative Physiology, vol. 284, pp. R1370-R1374, (2003).

Dinulescu et al., "Agouti and agouti-related protein: analogies and contrasts" The Journal of Biological Chemistry, vol. 275, pp. 6695-6698, (2000).

Edwards et al., "Cocaine- and amphetamine-regulated transcript, glucagon-like peptide-1 and corticotrophin releasing factor inhibit feeding via agouti-related protein independnent pathways in the rat" Brain Research, vol. 866, pp. 128-134, (2000).

Fong et al., "ART (Protein product of agouti-related transcript) as an antagonist of MC-3 and MC-4 receptors" Biochemical and Biophysical Research Communications, vol. 237, pp. 629-631, (1997).

Hanada et al., "Differential Regulation of Melanin-concentrating hormone and orexin genes in the agouti-related protein/melanocortin-4 receptor system" Biochemical and Biophysical Research Communications, vol. 268, pp. 88-91, (2000).

Harrold et al., "Changes in hypothalamic agouti-related protein (AgRP), but not α-MSH or pro-apiomelanocortin concentrations in dietary-obese and food restricted rats" Biochemical and Biophysical Research Communications, vol. 258, pp. 574-577, (1999).

Haskell-Luevano et al., "Agouti-related protein functions as an inverse agonist at a constitutively active brain melanocortin-4 receptor" Regulatory Peptides, vol. 99, pp. 1-7, (2001).

Haskell-Luevano et al., "Structure activity studies of the melanocortin-4 receptor by in vitro Mutagenesis: identification of agouti-related protein (AgRP), Melanocortin agonist and synthetic peptide antagonist interaction determinants" Biochemistry, vol. 40, pp. 6164-6179, (2001).

Haskell-Luevano et al., "The agouti-related protein decapeptide (YC[CRFFNAFC]Y) possesses agonist activity at the murine melanocortin-1 receptor" Peptides, vol. 21, pp. 683-689, (2000).

Hoggard et al., "Plasma concentrations of α-MSH, AgRP and leptin in lean and obese men and their relationship to differing states of energy balance perturbation" Clinical Endocrinology, vol. 61, pp. 31-39, (2004).

Hruby et al., "Design in topographical space of peptide and peptidomimetic chemist's glimpse at the mind—body problem" Accounts of Chemical Research, vol. 34, pp. 389-397, (2001).

Jackson et al., "Design, Pharmacology, and NMR structure of a minimized cystine knot with agouti-related protein activity" Biochemistry, vol. 24, pp. 7565-7572, (2002).

Joseph et al., "Chimeric NDP-MSH and MTII melanocortin peptides with agouti-related protein (AgRP) Arg-Phe-Phe amino acids possess agonist melanocortin receptor activity" Peptides, vol. 24, pp. 1899-1908, (2003).

Kiefer et al., "Melanocortin receptor binding determinants in the agouti protein" Biochemistry, vol. 37, pp. 991-997, (1998).

Kiefer et al., "Mutations in the carboxyl terminus of the agouti protein decrease agouti inhibition of ligand binding to the melanocortin receptors" Biochemistry, vol. 36, pp. 2084-2090, (1997).

Kim et al., "Sustained orexigenic effect of agouti-related protein may be not mediated by the melanocortin 4 receptor" Peptides, vol. 23, 1069-1076, (2002).

Marsh et al., "Effects of Neuropeptide Y deficiency on hypothalamic agouti-related protein expression and responsiveness to melanocortin analogues" Brain Research, vol. 848, pp. 66-77, (1999).

Mayfield et al, "A role for the agouti-related protein promoter in obesity and type 2 diabetes" Biochemical and Biophysical Research Communications, vol. 287, pp. 568-573, (2001).

McNulty et al., "High-resolution NMR structure of the chemically-synthesized melanocortin receptor binding domain AgPR(87-132) of the agouti-related protein" Biochemistry, vol. 40, pp. 15520-15527, (2001).

Navarro et al., "MTII-induced reduction of voluntary ethanol drinking is blocked by pretreatment with AgRP-(83-132)" Neuropeptides, vol. 37, pp. 338-344, (2003).

Qu et al., "Agouti-related protein is a mediator of diabetic hyperphagia" Regulatory Peptides, vol. 98, pp. 69-75, (2001).

Quillan et al., "A synthetic human agouti-related protein-(83-132)-NH2 fragment is a potent inhibitor of melanocortin receptor function" FEBS Letters, vol. 428, pp. 59-62, (1998).

Reizes et al., "Transgenic expression of Syndecan-1 uncovers a physiological control of feeding behavior by syndecan-3" Cell, vol. 106, pp. 105-116, (2001).

Rosenfeld et al., "Biochemical, biophysical, and pharmacological characterization of bacterially expressed human agouti-related protein", Biochemistry, vol. 37, pp. 16041-16052, (1998).

Takeuchi et al., "Widespread expression of agouti-related protein (AgRP) in the chicken: a possible involvement of AgRP in regulating peripheral melanocortin systems in the chicken" Biochimica et Biophysica Acta, vol. 1496, pp. 261-269, (2000).

Thirumoorthy et al., "Novel agouti-related-protein based melanocortin-1 receptor antagonist" Journal of Medicinal Chemistry, vol. 44, pp. 4114-4124, (2001).

Thompson et al., "Peptoid Mimics of agouti related protein" Bioorganic & Medicinal Chemistry Letters, vol. 13, pp. 1409-1413, (2003).

Tota et al., "Molecular interaction of agouti protein and agouti-related protein with human melanocortin receptors" Biochemistry, vol. 38, pp. 897-904, (1999).

Wilczynski et al, "Identification of putative agouti-related protein(87-132)-melanocortin-4 receptor interactions by homology molecular modeling and validation using chimeric peptide ligands" Journal of Medicinal Chemistry, vol. 47, pp. 2194-2207, (2004).

Wilczynski et al., "Structural characterization and pharmacology of a potent (Cys101-Cys119, Cys110-Cys117) bicyclic agouti-related protein (AgRP) melanocortin receptor" Journal of Medicinal Chemistry, vol. 47, pp. 5662-5673, (2004).

Wirth et al., "Agouti-related protein in the hypothalamic paraventricular nucleus: effect on feeding" Peptides, vol. 21, pp. 1369-1375, (2000).

Wirth et al., "Effect of agouti-related protein delivered to the dorsomedial nucleus of the hypothalamus on intake of a preferred versus a non-preferred diet" Brain Research, vol. 897, pp. 169-174, (2001).

Yang et al., "Effects of recombinant agouti-signaling protein on melanocortin action" Molecular Endocrinology, vol. 11, pp. 274-280, (1997).

Yang et al, "Molecular determinants of ligand binding to the human melanocortin-4 receptor" Biochemistry, vol. 39, pp. 14900-14911, (2000).

Yang et al., "Molecular determination of agouti-related protein binding to human melanocortin-4 receptor" Molecular Pharmacology, vol. 64, pp. 94-103, (2003).

Ahluwalia et al., "Synthesis & Antimicrobial & Antifungal Activities of Some New 2-[N-(2'-Mercapto-1', 3', 4'-thiadiazol-5'-yl)amino]-4-arylthiazole Derivatives" Indian Journal Of Chemistry, Section B, Organic Chemistry Including Medicinal Chemistry, vol. 26, pp. 88-90, (1987).

Written Opinion of the International Searching Authority, Patent Cooperation Treaty, International Application No. PCT/US2005/013386; International Filing Date Apr. 20, 2005.

Byrn, et al., Hydrates and Solvates, Solid-State Chemistry of Drugs, Second Edition, Chapter 11, pp. 233-248, 1999.

Guillory, Generation of Polymorphs, Hydrates, Solvates, and Amorphous Solids, Polymorphism in Pharmaceutical Solids, Chapter 5, pp. 183-226 1999.

Vippagunta et al., Crystalline solids, Elsevier, Advanced Drug Delivery Reviews 48 (2001) 3-26.

Morissette et al.,High-throughput crystallization: polymorphs, salts,co-crystals and solvates of pharmaceutical solids,Elsevier,Advanced Drug Delivery Reviews 56(2004)275-300.

Caira, Crystalline Polymorphism of Organic Compounds, Topics in Current Chemistry, vol. 198, pp. 164-208, 1998.

Woods S.C., et al., "Signals that regulate food intake and energy homeostasis", *Science*, 280:1378-1383 (1998).

Flier J.S., et al., "Obesity and the hypothalamus: novel peptides for new pathways", *Cell*, 92:437-440 (1998).

Bultman SJ, et al., "Molecular characterization of the mouse agouti locus", *Cell*, 71:1195-1204 (1992).

Lu, D., et al., "Agouti protein is an antagonist of the melanocyte-stimulating-hormone receptor", *Nature*, 371:799-802 (1994).

Brash G., "From the agouti protein to POMC—100 years of fat blonde mice", *Nat. Med.*, 5:984-985 (1999).

Ollmann, M.M., et al., "Antagonism of central melanocortin receptors in vitro and in vivo by agouti-related protein", *Science*, 278:135-138 (1997).

Adan Rah, et al., "Differential effects of melanocortin peptides on neural melanocortin receptors", *Mol Pharmacol.*, 46:1182-1190 (1994).

Schioth HB, et al., "The melanocortin 1, 3, 4 or 5 receptors do not have a binding epitope for ACTH beyond the sequence of α-MSH", *Endocrinology*, 155:73-78 (1997).

Mountjoy K.G., et al., "Localization of the melanocortin-4 receptor (MC-4R) in neuroendocrine and autonomic control circuits in the brain", *Mol Endocrinol.*, 8:1298-1308 (1994).

Huszar, D., et al., "Targeted disruption of the melanocortin-4 receptor results in obesity in mice", *Cell*, 88:131-141 (1997).

Krude, H., et al., "Severe early-onset obesity, adrenal insufficiency and red hair pigmentation caused by POMC mutations in humans", *Nat Genet.*, 19:155-157 (1998).

Yaswen L, et al., "Obesity in the mouse model of pro-opiomelanocortin deficiency responds to peripheral melanocortin", *Nat. Med.*, 5:1066-1070 (1999).

Benoit S.C., et al., "A Novel selective melanocortin-4 receptor agonist reduces food intake in rats and mice without producing aversive consequences", *J Neurosci.*, 20:3442-3448 (2000).

Hinney, A., et al., "Several mutations in the melanocortin-4 receptor gene including a nonsense and a frameshift mutation associated with dominantly inherited obesity in humans", *J. Clin. Endocrinol. Metab.*, 84:1483-1486 (1999).

Gu, W., et al., "Identification and functional analysis of novel human melanocortin-4 receptor variants", *Diabetes*, 48:635-639 (1999).

Translation of Chinese Office Action issued Dec. 5, 2008 in corresponding Chinese application 200580012513.3.

European Patent Office Communication issued Apr. 29, 2008 in corresponding European Patent Application 05757033.5.

Canadian Office Action issued Mar. 11, 2010 in corresponding Canadian Patent Application 2,562,075.

\* cited by examiner

SUBSTITUTED HETEROARYL DERIVATIVES, COMPOSITIONS, AND METHODS OF USE

STATEMENT OF RELATED APPLICATION

The present application claims priority under 35 USC 119 from U.S. Provisional Patent Application Ser. No. 60/563,882, filed Apr. 20, 2004, entitled "Substituted Heteroaryl Derivatives As Therapeutic Agents", the entirety of which is herein incorporated by reference.

FIELD OF THE INVENTION

This invention relates to substituted heteroaryl derivatives, compositions, and methods of treatment using the compounds and compositions which may be useful for the management, treatment, control, or adjunct treatment of diseases which may be responsive to the modulation of a melanocortin receptor.

BACKGROUND OF THE INVENTION

The neuroendocrine regulation of homeostasis of body weight and energy expenditure is achieved by integrating peripheral hormonal signals such as leptin and insulin, and central signals generated from hypothalamic regions including the arcuate nucleus, mediobasal nucleus and paraventricular nucleus (Woods S. C., et al., 1998, "Signals that regulate food intake and energy homeostasis", *Science*, 280: 1378-1383; Flier J. S., et al., 1998, "Obesity and the hypothalamus: novel peptides for new pathways", *Cell*, 92:437-440).

Within the neuroendocrine regulatory pathway, the melanocortin system of the arcuate nucleus is of major importance. Melanocortin receptors (MC-R) have been identified in these hypothalamic regions. Pro-opiomelanocortin (POMC) containing neurons project to the arcuate nucleus to provide multiple neuropeptide neurotransmitters to stimulate these receptors. MC-Rs belong to the G-protein coupled receptor (GPCR) superfamily that contains a seven transmembrane structure. One unique characteristic that differentiates MC-Rs from other GPCRs is that endogenous antagonists/inverse agonists for these receptors have been discovered.

Striking evidence of endogenous antagonists/inverse agonists for MC-Rs has emerged from studies of the agouti protein, which exerts its effects through interacting with MC-R with competitive antagonism of the natural ligand alpha-MSH (Bultman S J, et al. 1992 "Molecular characterization of the mouse agouti locus", *Cell*, 71:1195-1204; Lu, D., et al., 1994, "Agouti protein is an antagonist of the melanocyte-stimulating-hormone receptor", *Nature*, 371:799-802; Brash G., 1999 "From the agouti protein to POMC-100 years of fat blonde mice", *Nat. Med.*, 5:984-985). The discovery of Agouti-related peptide (AgRP), an agouti protein homologue, that interacts specifically with subtypes of MC-Rs (MC-3R and MC-4R) and antagonizes MC-4R but not MC-1R further suggests that the central MC-R are involved in body weight regulation. (Ollmann, M. M., et al., 1997, "Antagonism of central melanocortin receptors in vitro and in vivo by agouti-related protein", *Science*, 278:135-138).

Five subtypes of MC-R (MC-1R-MC-5R) have been identified. Multiple POMC peptides are agonists on these receptors with overlapping activity (Adan Rah, et al., 1994, "Differential effects of melanocortin peptides on neural melanocortin receptors", *Mol Pharmacol.*, 46:1182-1190). MC-1R is primarily located in the peripheral nervous system. ACTH is the endogenous agonist for MC-2R, but is without much activity on other MC-R subtypes (Schioth H B, et al., 1997, "The melanocortin 1, 3, 4 or 5 receptors do not have a binding epitope for ACTH beyond the sequence of α-MSH", *Endocrinology*, 155:73-78). MC-3R and MC-4 and -5 are mainly located in the CNS, with high concentrations in the hypothalamic regions such as the arcuate nucleus and paraventricular nucleus (Mountjoy K. G., et al., 1994, "Localization of the melanocortin-4 receptor (MC-4R) in neuroendocrine and autonomic control circuits in the brain", *Mol Endocrinol.*, 8:1298-1308). Multiple lines of evidence indicate that hypothalamic MC-4R and MC-3R play a key role in regulating food intake and energy balance. Ectopically expressing Agouti peptide $A^{vy}$ mouse causes a lethal syndrome characterized by pronounced obesity and the development of diabetes and neoplasms (Lu, D., et al., 1994, "Agouti protein is an antagonist of the melanocyte stimulating-hormone receptor", *Nature*, 371:799-802). Transgenic mice over-expressing AgRP are obese, suggesting that blocking MC-3R or MC-4R is the cause of obesity. Further determination that MC-4R knock out mice (Brash, G., 1999 "From the agouti protein to POMC-100 years of fat blonde mice", *Nat Med.*, 5:984-985; Huszar, D., et al., 1997 "Targeted disruption of the melanocortin-4 receptor results in obesity in mice", *Cell*, 88:131-141) have a similar phenotype as that of AgRP over-expressing mice further confirms that MC-4R is a key component in the body weight regulation pathway whereas MC-3R seems to be more involved in energy regulation. Deficient synthesis of melanocortins causes obesity in human and mutant mice (Krude, H., et al., 1998, "Severe early-onset obesity, adrenal insufficiency and red hair pigmentation caused by POMC mutations in humans", *Nat Genet.*, 19:155-157; Yaswen L, et al., 1999, "Obesity in the mouse model of pro-opiomelanocortin deficiency responds to peripheral mela-nocortin", *Nat. Med.*, 5:1066-1070). Moreover, in animal models of obesity treatment with αMSH like agonist induced weight loss (Benoit S. C., et al., 2000, "A novel selective melanocortin-4 receptor agonist reduces food intake in rats and mice without producing aversive consequences", *J. Neurosci.*, 20:3442-3448).

In humans, mutations of the MC-4R have been identified in obese patients and linked to impaired ligand binding and signaling (Hinney, A., et al., 1999, "Several mutations in the melanocortin-4 receptor gene including a nonsense and a frameshift mutation associated with dominantly inherited obesity in humans", *J. Clin. Endocrinol. Metab.*, 84:1483-1486; Gu, W., et al., 1999, "Identification and functional analysis of novel human melanocortin-4 receptor variants", *Diabetes*, 48:635-639; Krude, H., et al., 1998, "Severe early-onset obesity, adrenal insufficiency and red hair pigmentation caused by POMC mutations in humans", *Nat Genet.*, 19:155-157).

Aberrant regulation of body weight, such as that in obese patients, is associated with physiological and psychological disorders. Therefore, it is desirable to find drugs that can regulate central melanocortin system and therefore treat related medical disorders. Here, we report the finding of compounds that can modulate MC-R/AgRP/αMSH system.

SUMMARY OF THE INVENTION

This invention provides substituted heteroaryl derivatives and compositions which modulate the functional interaction of AgRP (Agouti related protein) with a melanocortin receptor. In an embodiment, the present invention provides compounds of Formula (I) as depicted below. In another embodiment, the present invention provides methods of preparation of compounds of Formula (I). In another embodiment, the present invention provides pharmaceutical compositions comprising the compounds of Formula (I). In another embodiment, the present invention provides methods of treatment comprising: administering to a subject a compound of Formula (I).

The compounds of the invention are useful as modulators of AgRP interaction with a melanocortin receptor and thus may be useful for the management, treatment, control and adjunct treatment of diseases or conditions that may be responsive to the modulation of one or more melanocortin receptors. Such diseases or conditions may comprise bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type II diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The compounds of the present invention may also be useful for treating physiological disorders related to, for example, regulation of insulin sensitivity, inflammatory response, plasma triglycerides, HDL, LDL, and cholesterol levels and the like. The compounds of the present invention may also be useful for treating female sexual disfunction, male sexual disfunction, and erectile disfunction.

DETAILED DESCRIPTION

Embodiments of the present invention comprise substituted heteroaryl derivatives, compositions, and methods of use. The present invention may be embodied in a variety of ways.

In an first aspect, the present invention provides substituted heteroaryl derivatives as inhibitors of AgRP interaction with a melanocortion receptor which may be useful for the management and treatment of diseases and conditions associated obesity and obesity-related disorders.

In another aspect, the present invention provides compounds of Formula (I):

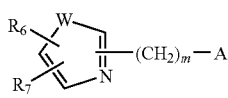

(I)

wherein m is 0, 1, or 2;

A is selected from the group consisting of:

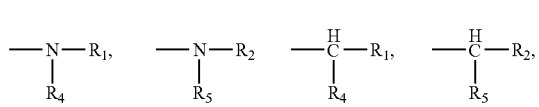

I)

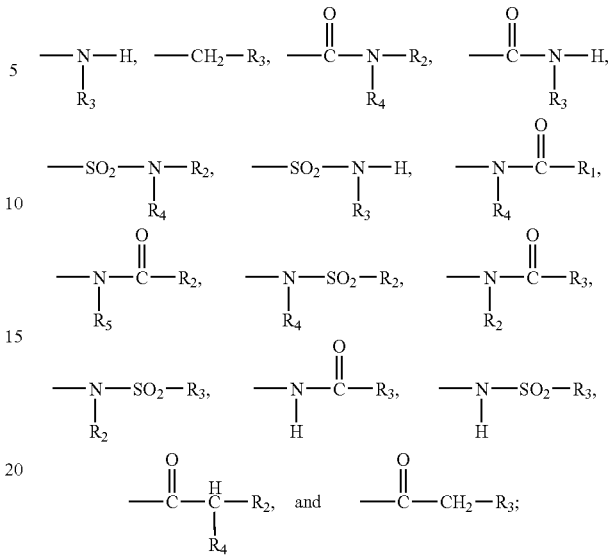

-continued

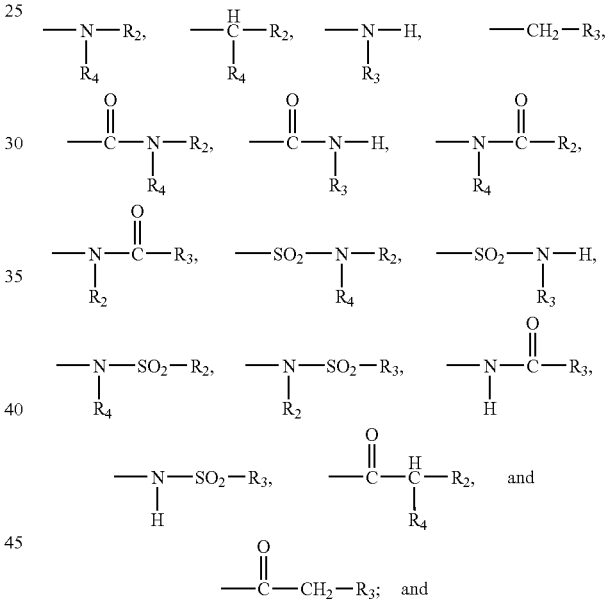

III) —K;

$R_1$ is selected from the group consisting of:
a) -L-$D_1$-$G_1$;
b) -L-$D_1$-alkyl;
c) -L-$D_1$-aryl;
d) -L-$D_1$-heteroaryl;
e) -L-$D_1$-cycloalkyl;
f) -L-$D_1$-heterocyclyl;
g) -L-$D_1$-arylene-alkyl;
h) -L-$D_1$-alkylene-arylene-alkyl;
i) -L-$D_1$-alkylene-aryl;
j) -L-$D_1$-alkylene-$G_1$;
k) -L-$D_1$-heteroarylene-$G_1$;
l) -L-$D_1$-cycloalkylene-$G_1$;
m) -L-$D_1$-heterocyclylene-$G_1$; and n)

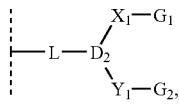

$R_2$ is selected from the group consisting of:
a) -L-$D_1$-$G_1$;
b) -L-$D_1$-alkyl;
c) -L-$D_1$-aryl;
d) -L-$D_1$-heteroaryl;
e) -L-$D_1$-cycloalkyl;
f) -L-$D_1$-heterocyclyl;
g) -L-$D_1$-arylene-alkyl;
h) -L-$D_1$-alkylene-arylene-alkyl;
i) -L-$D_1$-alkylene-aryl;
j) -L-$D_1$-alkylene-$G_1$;
k) -L-$D_1$-heteroarylene-$G_1$;
l) -L-$D_1$-cycloalkylene-$G_1$;
m) -L-$D_1$-heterocyclylene-$G_1$;
n)

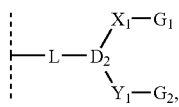

o) -L-$D_1$-arylene-$G_1$;
p) -L-$D_1$-arylene-alkylene-$G_1$;
q) -L-$D_1$-alkylene-arylene-alkylene-$G_1$; and
r) -L-$D_1$-alkylene-arylene-$G_1$;

$R_3$ is selected from the group consisting of:
a) -alkyl;
b) -L-$D_1$-H;
c) -L-$D_1$-alkyl;
d) -L-$D_1$-aryl;
e) -L-$D_1$-heteroaryl;
f) -L-$D_1$-alkylene-heteroaryl;
g) -L-$D_1$-cycloalkyl;
h) -L-$D_1$-heterocyclyl;
i) -L-$D_1$-arylene-alkyl;
j) -L-$D_1$-alkylene-arylene-alkyl;
k) -L-$D_1$-alkylene-aryl; and
l) -L-$D_1$-arylene-aryl;

$R_4$ is selected from the group consisting of:
a) -hydrogen;
b) -alkyl;
c) -L-$D_1$-H;
d) -L-$D_1$-alkyl;
e) -L-$D_1$-aryl;
f) -L-$D_1$-heteroaryl;
g) -L-$D_1$-cycloalkyl;
h) -L-$D_1$-heterocyclyl;
i) -L-$D_1$-arylene-alkyl;
j) -L-$D_1$-alkylene-arylene-alkyl;
k) -L-$D_1$-alkylene-aryl; and
l) -L-$D_1$-arylene-aryl;

$R_5$ is -cycloalkyl, -heteroaryl, or -alkylene-heteroaryl;

$R_6$ and $R_7$ are independently selected from the group consisting of:
a) -hydrogen;
b) -halo;
c) -alkyl;
d) -L-$D_1$-H;
e) -L-$D_1$-alkyl;
f) -L-$D_1$-aryl;
g) -L-$D_1$-heteroaryl;
h) -L-$D_1$-cycloalkyl;
i) -L-$D_1$-heterocyclyl;
j) -L-$D_1$-arylene-alkyl;
k) -L-$D_1$-alkylene-arylene-alkyl;
l) -L-$D_1$-alkylene-aryl;
m) -L-$D_1$-arylene-aryl;
n) -L-$D_2$-(aryl)$_2$; and
o) -L-$D_2$-(arylene-alkyl)$_2$;

wherein at least one of $R_6$ and $R_7$ is not hydrogen; or $R_6$ and $R_7$ may be taken together to form part of a fused carbocyclic, fused aromatic, fused heteroaromatic, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, or fused heteroarylheterocyclyl rings, wherein the ring is optionally substituted 1-8 times with the group
a) -halo;
b) -nitro;
c) -L-$D_1$-$G_1$;
d) -L-$D_1$-alkyl;
e) -L-$D_1$-aryl;
f) -L-$D_1$-heteroaryl;
g) -L-$D_1$-cycloalkyl;
h) -L-$D_1$-heterocyclyl;
i) -L-$D_1$-arylene-alkyl;
j) -L-$D_1$-alkylene-arylene-alkyl;
k) -L-$D_1$-alkylene-aryl;
l) -L-$D_1$-alkylene-$G_1$;
m) -L-$D_1$-heteroarylene-$G_1$;
n) -L-$D_1$-cycloalkylene-$G_1$;
o) -L-$D_1$-heterocyclylene-$G_1$; and
p)

W is S, 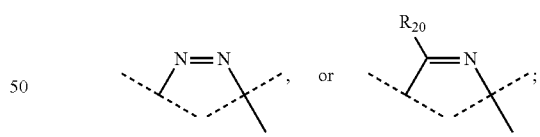

wherein
$R_{20}$ is
a) -hydrogen;
b) -halo;
c) -alkyl;
d) -L-$D_1$-H;
e) -L-$D_1$-alkyl;
f) -L-$D_1$-aryl;
g) -L-$D_1$-heteroaryl;
h) -L-$D_1$-cycloalkyl;
i) -L-$D_1$-heterocyclyl;
j) -L-$D_1$-arylene-alkyl;
k) -L-$D_1$-alkylene-arylene-alkyl;
l) -L-$D_1$-alkylene-aryl;

m) -L-$D_1$-arylene-aryl;
n) -L-$D_2$-(aryl)$_2$; or
o) -L-$D_2$-(arylene-alkyl)$_2$;

K is cycloalkyl, heterocyclyl, aryl, heteroaryl, fused cycloalkylaryl, arylcycloalkyl, fused heterocyclylaryl, fused arylheterocyclyl, fused cycloalkylheterocyclyl, fused heteroarylcycloalkyl, fused heterocyclylheteroaryl, or fused heteroarylheterocyclyl, wherein K may be optionally substituted 1-3 times with a group selected from the group consisting of: halo, nitro, and $R_2$;

$G_1$ is selected from the group consisting of: —CN, —$SO_3H$, —P(O)(OH)$_2$, —P(O)(O-alkyl)(OH), —$CO_2H$, —$CO_2$-alkyl, —C(O)NHS(O)$_2$-alkyl, —C(O)NHS(O)$_2$-aryl, —C(O)NHS(O)$_2$-heteroaryl, —C(O)NHS(O)$_2$-alkylene-aryl, —C(O)NHS(O)$_2$-alkylene-heteroaryl, —C(O)NHS(O)$_2$-arylene-alkyl, —S(O)$_2$NHC(O)-alkyl, —S(O)$_2$NHC(O)-aryl, —S(O)$_2$NHC(O)-heteroaryl, —S(O)$_2$NHC(O)-alkylene-aryl, S(O)$_2$NHC(O)-alkylene-heteroaryl, —NHC(O)NH—SO$_2$-alkyl, an acid isostere,

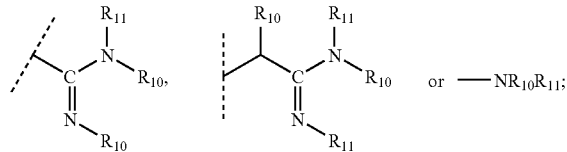

$G_2$ is selected from the group consisting of:
a) -hydrogen;
b) -alkylene;
c) -L-$D_1$-H;
d) -L-$D_1$-alkyl;
e) -L-$D_1$-aryl;
f) -L-$D_1$-heteroaryl;
g) -L-$D_1$-cycloalkyl;
h) -L-$D_1$-heterocyclyl;
i) -L-$D_1$-arylene-alkyl;
j) -L-$D_1$-alkylene-arylene-alkyl;
k) -L-$D_1$-alkylene-aryl; and
l) -L-$D_1$-arylene-aryl;

L is a direct bond, alkylene, alkenylene, alkynylene, or arylene;

$D_1$ is selected from the group consisting of: a direct bond, —$CH_2$—, —O—, —N($R_8$)—, —C(O)—, —CON($R_8$)—, —CON($R_9$)SO$_2$—, —N($R_9$)C(O)—, —N($R_9$)CON($R_8$)—, —N($R_8$)C(O)O—, —OC(O)N($R_8$)—, —N($R_8$)SO$_2$—, —SO$_2$N($R_8$)—, —C(O)—O—, —O—C(O)—, —S—, —S(O)—, —S(O$_2$)—, or —N($R_8$)SO$_2$N($R_9$)—, —N=N—, and —N($R_8$)—N($R_9$)—;

$D_2$ is N, alkylyne, or alkenylyne;

$X_1$ and $Y_1$ are independently selected from the group consisting of: a direct bond, alkylene, arylene, heteroarylene, cycloalkylene, heterocyclylene, arylene-alkylene, alkylene-arylene-alkylene, and alkylene-aryl;

$R_8$ and $R_9$ are independently selected from the group consisting of: -hydrogen, -alkyl, -aryl, -arylene-alkyl, -alkylene-aryl, and -alkylene-arylene-alkyl;

$R_{10}$ and $R_{11}$ are independently selected from the group consisting of: hydrogen, -alkyl, -L-$D_1$-alkyl, -L-$D_1$-aryl, —C(O)-alkyl, —C(O)-aryl, —SO$_2$-alkyl, and —SO$_2$-aryl, or $R_{10}$ and $R_{11}$ may be taken together to form a ring having the formula —(CH$_2$)$_m$-J-(CH$_2$)$_n$— bonded to the nitrogen atom to which $R_{10}$ and $R_{11}$ are attached, wherein m and n are 0, 1, 2, or 3, and J is selected from the group consisting of —$CH_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

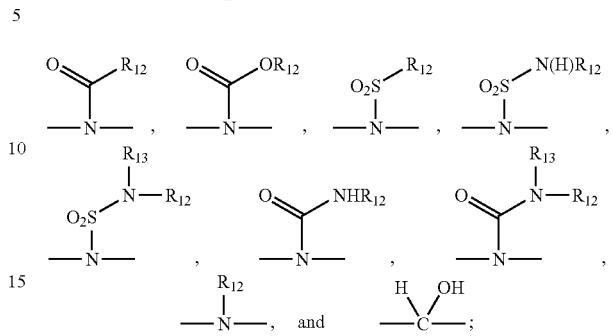

$R_{12}$ and $R_{13}$ are independently selected from the group consisting of hydrogen, aryl, alkyl, and alkylene-aryl;

and wherein the aryl, heteroaryl, heterocyclyl, cycloalkyl, and/or alkyl group(s) in $R_1$-$R_{13}$, and $R_{20}$, $G_1$, $G_2$, L, $X_1$, $Y_1$, may be optionally substituted 1-4 times with a substituent group selected from the group consisting of
a) -hydrogen;
b) halogen;
c) hydroxyl;
d) cyano;
e) carbamoyl;
f) —B-alkyl;
g) —B-perhaloalkyl;
h) —B-cycloalkyl;
i) —B-heterocyclyl;
j) —B-aryl;
k) —B-heteroaryl;
l) —B-alkylene-heteroaryl;
m) —B-alkylene-aryl;
n) —B-arylene-alkyl;
o) —B-perhaloalkyl;
p) —B-cycloalkylene-T-$R_{14}$;
q) —B-alkylene-N—$R_{14}R_{15}$;
r) —B-cycloalkylene-alkyl; and
s) —B-alkylene-cycloalkyl;
wherein
B and T are independently selected from the group consisting of: direct bond, alkylene, —$CH_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH, —O—S(O)$_2$—, and —O—C(O)—;
wherein
$R_{14}$ and $R_{15}$ are independently selected from the group consisting of: hydrogen, heteroaryl, cycloalkyl, heterocyclyl, aryl, alkyl, -alkylene-aryl, -alkylene-heteroaryl, and -alkylene-O-aryl; or $R_{14}$ and $R_{15}$ may be taken together to form a ring having the formula —(CH$_2$)$_q$-J-(CH$_2$)$_r$— bonded to the nitrogen atom to which $R_{14}$ and $R_{15}$ are attached wherein q and r are independently equal to 1, 2, 3, or 4; J comprises a direct bond, —$CH_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

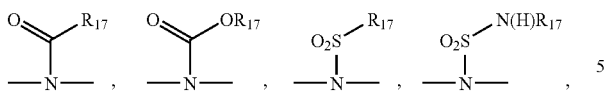

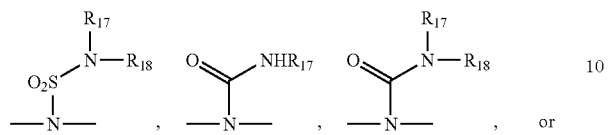

$R_{17}$ and $R_{18}$ are independently selected from the group consisting of: hydrogen, cycloalkyl, heterocyclyl, aryl, heteroaryl, alkyl, -alkylene-heteroaryl, or -alkylene-aryl;

or a pharmaceutically acceptable salt, prodrug, or solvate thereof.

In an embodiment of the compound of Formula (I), the compound of Formula (I) has the formula (Ia)

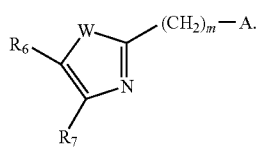
(Ia)

In another embodiment of the compound of Formula (I), the compound of Formula (I) has the formula (Ib)

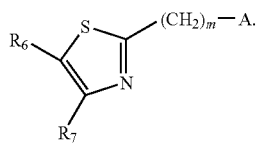
(Ib)

In another embodiment of the compound of Formula (I), the compound of Formula (I) has the formula (Ic)

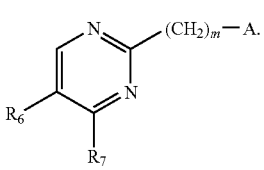
(Ic)

In another embodiment of the compound of Formula (I), the compound of Formula (I) has the formula (Id)

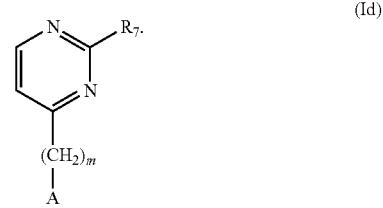
(Id)

In another embodiment of the compound of Formula (I), A is selected from the group consisting of

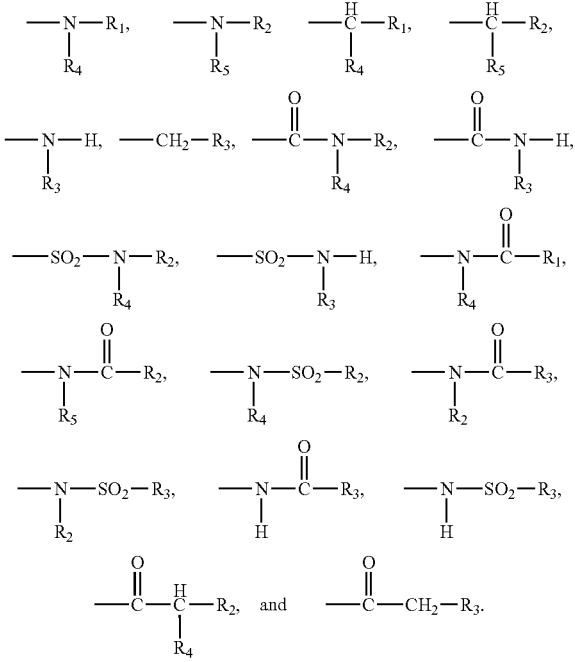
I)

In another embodiment of the compound of Formula (I), A is selected from the group consisting of:

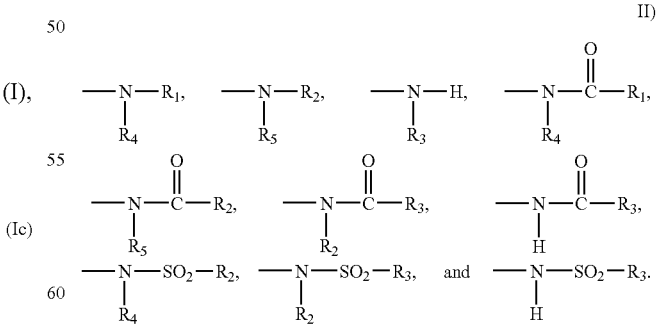
II)

In another embodiment of the compound of Formula (I), $R_6$ is selected from the group consisting of: hydrogen, halo, alkyl, and phenyl. In another embodiment, $R_6$ is selected from the group consisting of halo, alkyl, and phenyl.

In another embodiment of the compound of Formula (I), $R_7$ is selected from the group consisting of:
a) -L-$D_1$-alkyl;
b) -L-$D_1$-aryl;
c) -L-$D_1$-cycloalkyl;
d) -L-$D_1$-heterocyclyl;
e) -L-$D_1$-arylene-alkyl;
f) -L-$D_1$-alkylene-arylene-alkyl;
g) -L-$D_1$-alkylene-aryl;
h) -L-$D_1$-arylene-aryl;
i) -L-$D_2$-(aryl)$_2$; and
j) -L-$D_2$-(arylene-alkyl)$_2$;
wherein
L is a direct bond, $C_{1-6}$ alkylene, or phenylene;
$D_1$ is selected from the group consisting of: a direct bond, —$CH_2$—, —O—, —C(O)—, —C(O)—O—, and —O—C(O)—.

In another embodiment of the compound of Formula (I), $R_7$ is selected from the group consisting of:
a) -L-$D_1$-alkyl;
b) -L-$D_1$-aryl;
c) -L-$D_1$-cycloalkyl;
d) -L-$D_1$-heterocyclyl;
e) -L-$D_1$-arylene-alkyl;
f) -L-$D_1$-alkylene-arylene-alkyl;
g) -L-$D_1$-alkylene-aryl;
h) -L-$D_1$-arylene-aryl;
i) -L-$D_2$-(aryl)$_2$; and
j) -L-$D_2$-(arylene-alkyl)$_2$;
wherein
L is a direct bond, $C_{1-6}$ alkylene, or phenylene;
$D_1$ is selected from the group consisting of: a direct bond, —$CH_2$—, —O—, —C(O)—, —C(O)—O—, and —O—C(O)—.
wherein the aryl, heterocyclyl, cycloalkyl, and/or alkyl group(s) in $R_7$ and L may be optionally substituted 1-4 times with a substituent group selected from the group consisting of
a) —H;
b) halogen;
c) hydroxyl;
d) cyano;
e) —B-alkyl;
f) —B-perhaloalkyl;
g) —B-cycloalkyl;
h) —B-heterocyclyl;
i) —B-aryl;
j) —B-heteroaryl;
k) —B-alkylene-heteroaryl;
l) —B-alkylene-aryl;
m) —B-arylene-alkyl;
n) —B-perhaloalkyl;
o) —B-cycloalkylene-T-$R_{14}$;
p) —B-cycloalkylene-alkyl; and
q) —B-alkylene-cycloalkyl;
wherein
B and T are independently selected from the group consisting of: direct bond, alkylene, —$CH_2$—, and —O—;
wherein
$R_{14}$ is selected from the group consisting of: hydrogen, heteroaryl, cycloalkyl, heterocyclyl, aryl, alkyl, -alkylene-aryl, -alkylene-heteroaryl, and -alkylene-O-aryl.

In another embodiment of the compound of Formula (I), $R_7$ is selected from the group consisting of:
a) -L-$D_1$-alkyl;
b) -L-$D_1$-phenyl;
c) -L-$D_1$-$C_{5-8}$ cycloalkyl;
d) -L-$D_1$-tetrahydropyranyl;
e) -L-$D_1$-phenylene-alkyl;
f) -L-$D_1$-alkylene-phenylene-alkyl;
g) -L-$D_1$-alkylene-phenyl;
h) -L-$D_1$-phenylene-phenyl
i) -L-$D_2$-(phenyl)$_2$; and
j) -L-$D_2$-(phenylene-alkyl)$_2$;
wherein
L is a direct bond, $C_{1-6}$ alkylene, or phenylene;
$D_1$ is selected from the group consisting of: a direct bond, —$CH_2$—, —O—, —C(O)—, —C(O)—O—, and —O—C(O)—.
wherein the aryl, cycloalkyl, and/or alkyl group(s) in $R_7$ and L may be optionally substituted 1-4 times with a substituent group selected from the group consisting of
a) —H;
b) halogen;
c) hydroxyl;
d) cyano;
e) —B-alkyl;
f) —B-perhaloalkyl;
g) —B-cycloalkyl;
h) —B-aryl;
wherein
B is selected from the group consisting of: direct bond, alkylene, —$CH_2$—, and —O—.

In another embodiment of the compound of Formula (I), $R_6$ is selected from the group consisting of: hydrogen, halo, alkyl, and phenyl; and $R_7$ is selected from the group consisting of: phenyl, benzyloxy-phenyl, 4-biphenyl-3-yl, 4-biphenyl-4-yl, bromo-phenyl, chloro-methyl-phenyl, chloro-phenyl, cyano-phenyl, cyclohexylmethoxy-phenyl, cyclohexyloxy-phenyl, di-p-tolylmethyl, methoxy-phenyl, ethoxy-phenyl, isobutoxy-phenyl, trifluoromethoxy-phenyl, phenethyloxy-phenyl, phenoxy-phenyl, methylphenyl, isobutyl-phenyl, isopropyl-phenyl, tert-butyl-phenyl, trifluoromethyl-phenyl, dichloro-phenyl, difluoro-phenyl, dimethyl-phenyl, difluoro-phenyl, dihydroxy-phenyl, bis-trifluoromethyl-phenyl, di-tert-butyl-hydroxy-phenyl, benzoyl-phenyl, chloro-methyl-phenyl, (3-phenyl-propoxy)-phenyl, (methyl-cyclohexyloxy)-phenyl, (tert-butyl-cyclohexyloxy)-phenyl, and (tetrahydropyran-4-yloxy)-phenyl.

In another embodiment of the compound of Formula (I), $R_6$ is selected from the group consisting of: hydrogen, halo, alkyl, and phenyl; and $R_7$ is selected from the group consisting of: (tert-butyl-phenyl)-phenyl-methyl, bis-(chloro-fluoro-phenyl)-methyl, bis-(fluoro-phenyl)-methyl, bis-(trifluoromethyl-phenyl)-methyl, naphthalen-1-yl, naphthalen-2-yl, 5,5,8,8-tetramethyl-5,6,7,8-tetrahydro-naphthalen-2-yl, and 4-benzhydryl.

In another embodiment of the compound of Formula (I), A is selected from the group consisting of:

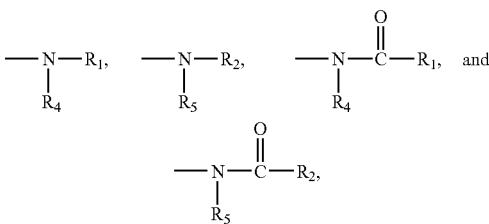

wherein
$R_1$ is selected from the group consisting of:
a) -L-$D_1$-$C_{1-5}$-alkylene-$G_1$; and
b) -L-$D_1$-$C_{3-8}$ cycloalkylene-$G_1$;

$R_2$ is selected from the group consisting of:
  a) -L-$D_1$-$C_{1-5}$-alkylene-$G_1$;
  b) -L-$D_1$-$C_{3-8}$ cycloalkylene-$G_1$;
  c) -L-$D_1$-$C_{1-3}$-alkylene-phenylene-$G_1$;
  d) -L-$D_1$-$C_{1-3}$-alkylene-phenylene-$C_{1-3}$-alkylene-$G_1$; and
  e) -L-$D_1$-phenylene-$G_1$;
$R_4$ is selected from the group consisting of:
  a) hydrogen;
  b) -L-$D_1$-phenyl;
  c) -L-$D_1$-$C_{1-4}$-alkylene-phenyl;
  d) -L-$D_1$-$C_{1-4}$-alkylene-$C_{3-8}$ cycloalkyl;
  e) -L-$D_1$-$C_{3-8}$ cycloalkyl;
  f) -L-$D_1$-thienyl; and
  g) -L-$D_1$-$C_{1-4}$-alkylene-thienyl; and
$R_5$ is selected from the group consisting of:
  a) —$C_{3-8}$ cycloalkyl;
  b) -thienyl; and
  c) —$C_{1-4}$-alkylene-thienyl.

In another embodiment of the compound of Formula (I), A is selected from the group consisting of:

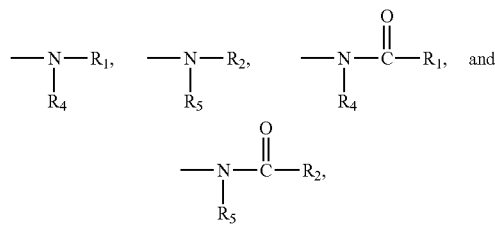

wherein
$R_1$ is selected from the group consisting of:
  a) —$(CH_2)_n$-$G_1$; and
  b) —$C_{5-7}$ cycloalkylene-$G_1$;
$R_2$ is selected from the group consisting of:
  a) -phenyl-$G_1$; and
  b) —$(CH_2)_n$-phenyl-$G_1$;
n is 1, 2, 3, or 4; and
$G_1$ is selected from the group consisting of: —$SO_3H$, —$CO_2H$, —$C(O)NHS(O)_2$-alkyl, —$C(O)NHS(O)_2$-phenyl, —$C(O)NHS(O)_2$-phenylene-alkyl, —$C(O)NHS(O)_2$-pyridyl, —$NHC(O)NH$—$SO_2$-alkyl, and an acid isostere.

In another embodiment of the compound of Formula (I), A is selected from the group consisting of:

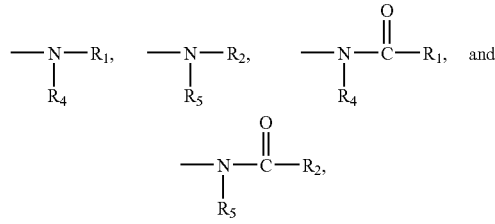

wherein
$R_1$ is selected from the group consisting of:
  a) -L-$D_1$-$C_{1-5}$-alkylene-$G_1$; and
  b) -L-$D_1$-$C_{3-8}$ cycloalkylene-$G_1$;
$R_2$ is selected from the group consisting of:
  a) -L-$D_1$-$C_{1-5}$-alkylene-$G_1$;
  b) -L-$D_1$-$C_{3-8}$ cycloalkylene-$G_1$;
  c) -L-$D_1$-$C_{1-3}$-alkylene-phenylene-$G_1$;
  d) -L-$D_1$-$C_{1-3}$-alkylene-phenylene-$C_{1-3}$-alkylene-$G_1$; and
  e) -L-$D_1$-phenylene-$G_1$;
$R_4$ is selected from the group consisting of: hydrogen, isopropyl, 3-methyl-butyl, cyclopentyl, phenyl, tert-butyl-phenyl, cyano-phenyl, trifluoromethoxy-phenyl, methyl-phenyl, 4-biphenyl, 3-biphenyl, methoxyphenyl, hydroxyphenyl, chlorophenyl, dichlorophenyl, dimethoxy-phenyl, benzyl, methoxybenzyl, trifluoromethoxy-benzyl, thienyl, thien-2yl-methyl, 3-thien-2-yl-propyl, 2-thien-2-yl-ethyl, furan-2yl-methyl, cyclobutylmethyl, and cyclohexylmethyl; and
$R_5$ is selected from cyclopentyl, cyclohexyl, thienyl, thien-2yl-methyl, 3-thien-2-yl-propyl, and 2-thien-2-yl-ethyl.

In another embodiment of the compound of Formula (I), A is selected from the group consisting of:

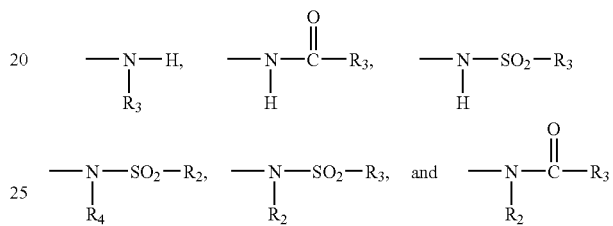

wherein
$R_2$ is selected from the group consisting of:
  a) -L-$D_1$-$C_{1-5}$-alkylene-$G_1$;
  b) -L-$D_1$-$C_{3-8}$ cycloalkylene-$G_1$;
  c) -L-$D_1$-$C_{1-3}$-alkylene-phenylene-$G_1$;
  d) -L-$D_1$-$C_{1-3}$-alkylene-phenylene-$C_{1-3}$-alkylene-$G_1$; and
  e) -L-$D_1$-phenylene-$G_1$;
$R_3$ is selected from the group consisting of:
  a) -L-$D_1$-phenyl;
  b) -L-$D_1$-$C_{1-4}$-alkylene-phenyl;
  c) -L-$D_1$-$C_{1-4}$-alkylene-$C_{3-8}$ cycloalkyl;
  d) -L-$D_1$-$C_{3-8}$ cycloalkyl;
  e) -L-$D_1$-thienyl; and
  f) -L-$D_1$-$C_{1-4}$-alkylene-thienyl; and
$R_4$ is selected from the group consisting of:
  a) hydrogen;
  b) -L-$D_1$-phenyl;
  c) -L-$D_1$-$C_{1-4}$-alkylene-phenyl;
  d) -L-$D_1$-$C_{1-4}$-alkylene-$C_{3-8}$ cycloalkyl;
  e) -L-$D_1$-$C_{3-8}$ cycloalkyl;
  f) -L-$D_1$-thienyl; and
  g) -L-$D_1$-$C_{1-4}$-alkylene-thienyl.

In another embodiment of the compound of Formula (I), A is selected from the group consisting of:

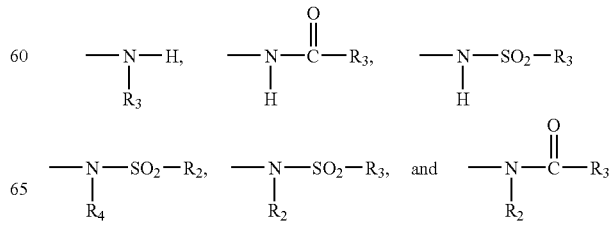

wherein
$R_2$ is selected from the group consisting of:
a) —$(CH_2)_n$-$G_1$;
b) —$C_{5-7}$ cycloalkylene-$G_1$;
c) -phenylene-$G_1$; and
d) —$(CH_2)_n$-phenylene-$G_1$;
wherein n is 1, 2, 3, or 4;
$R_3$ is selected from the group consisting of:
a) -L-$D_1$-phenyl;
b) -L-$D_1$-$C_{1-4}$-alkylene-phenyl;
c) -L-$D_1$-$C_{1-4}$-alkylene-$C_{3-8}$ cycloalkyl;
d) -L-$D_1$-$C_{3-8}$ cycloalkyl;
e) -L-$D_1$-thienyl; and
f) -L-$D_1$-$C_{1-4}$-alkylene-thienyl;
$R_4$ is selected from the group consisting of:
a) hydrogen;
b) -L-$D_1$-phenyl;
c) -L-$D_1$-$C_{1-4}$-alkylene-phenyl;
d) -L-$D_1$-$C_{1-4}$-alkylene-$C_{3-8}$ cycloalkyl;
e) -L-$D_1$-$C_{3-8}$ cycloalkyl;
f) -L-$D_1$-thienyl; and
g) -L-$D_1$-$C_{1-4}$-alkylene-thienyl; and
$G_1$ is selected from the group consisting of: —$SO_3H$, —$CO_2H$, —$C(O)NHS(O)_2$-alkyl, —$C(O)NHS(O)_2$-phenyl, —$C(O)NHS(O)_2$-phenylene-alkyl, —$C(O)NHS(O)_2$-pyridyl, —$NHC(O)NH$—$SO_2$-alkyl, and an acid isostere.

In another embodiment of the compound of Formula (I), A is selected from the group consisting of:

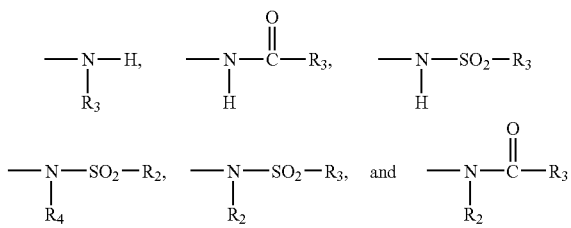

wherein
$R_2$ is selected from the group consisting of:
a) -L-$D_1$-$C_{1-5}$-alkylene-$G_1$;
b) -L-$D_1$-$C_{3-8}$ cycloalkylene-$G_1$;
c) -L-$D_1$-$C_{1-3}$-alkylene-phenyl-$G_1$;
d) -L-$D_1$-$C_{1-3}$-alkylene-phenylene-$C_{1-3}$-alkylene-$G_1$; and
e) -L-$D_1$-phenylene-$G_1$;
$R_3$ is selected from the group consisting of: isopropyl, 3-methyl-butyl, cyclopentyl, phenyl, tert-butyl-phenyl, cyano-phenyl, trifluoromethoxy-phenyl, methyl-phenyl, 4-biphenyl, 3-biphenyl, methoxyphenyl, hydroxyphenyl, chlorophenyl, dichlorophenyl, dimethoxy-phenyl, benzyl, methoxybenzyl, trifluoromethoxy-benzyl, thienyl, thien-2yl-methyl, 3-thien-2-yl-propyl, 2-thien-2-yl-ethyl, furan-2yl-methyl, cyclobutylmethyl, and cyclohexylmethyl; and
$R_4$ is selected from the group consisting of: hydrogen, isopropyl, 3-methyl-butyl, cyclopentyl, phenyl, tert-butyl-phenyl, cyano-phenyl, trifluoromethoxy-phenyl, methyl-phenyl, 4-biphenyl, 3-biphenyl, methoxyphenyl, hydroxyphenyl, chlorophenyl, dichlorophenyl, dimethoxy-phenyl, benzyl, methoxybenzyl, trifluoromethoxy-benzyl, thienyl, thien-2yl-methyl, 3-thien-2-yl-propyl, 2-thien-2-yl-ethyl, furan-2yl-methyl, cyclobutylmethyl, and cyclohexylmethyl.

In another embodiment of the compound of Formula (I), A is selected from the group consisting of:

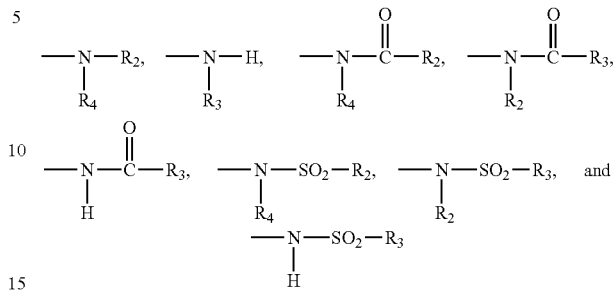

wherein
$R_2$ is selected from the group consisting of:
a) -L-$D_1$-$C_{1-5}$-alkylene-$G_1$;
b) -L-$D_1$-$C_{3-8}$ cycloalkylene-$G_1$;
c) -L-$D_1$-$C_{1-3}$-alkylene-phenyl-$G_1$;
d) -L-$D_1$-$C_{1-3}$-alkylene-phenylene-$C_{1-3}$-alkylene-$G_1$; and
e) -L-$D_1$-phenylene-$G_1$;
$R_3$ is selected from the group consisting of:
a) -L-$D_1$-phenyl;
b) -L-$D_1$-$C_{1-4}$-alkylene-phenyl;
c) -L-$D_1$-$C_{1-4}$-alkylene-$C_{3-8}$ cycloalkyl;
d) -L-$D_1$-$C_{3-8}$ cycloalkyl;
e) -L-$D_1$-thienyl; and
f) -L-$D_1$-$C_{1-4}$-alkylene-thienyl; and
$R_4$ is selected from the group consisting of:
a) hydrogen;
b) -L-$D_1$-phenyl;
c) -L-$D_1$-$C_{1-4}$-alkylene-phenyl;
d) -L-$D_1$-$C_{1-4}$-alkylene-$C_{3-8}$ cycloalkyl;
e) -L-$D_1$-$C_{3-8}$ cycloalkyl;
f) -L-$D_1$-thienyl; and
g) -L-$D_1$-$C_{1-4}$-alkylene-thienyl.

In another embodiment of the compound of Formula (I), A is selected from the group consisting of:

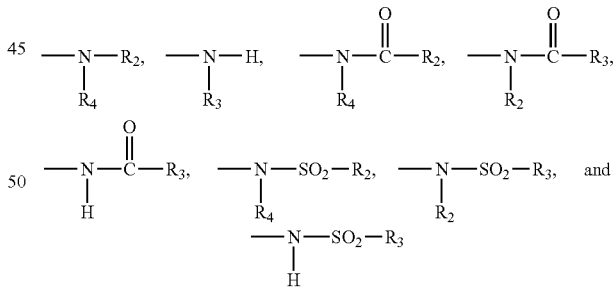

wherein
$R_2$ is selected from the group consisting of:
a) —$(CH_2)_n$-$G_1$;
b) —$C_{5-7}$ cycloalkylene-$G_1$;
c) -phenylene-$G_1$;
d) —$(CH_2)_r$-phenylene-$G_1$; and
wherein n is 1, 2, 3, or 4;
$R_3$ is selected from the group consisting of:
a) -L-$D_1$-phenyl;
b) -L-$D_1$-$C_{1-4}$-alkylene-phenyl;
c) -L-$D_1$-$C_{1-4}$-alkylene-$C_{3-8}$ cycloalkyl;

d) -L-$D_1$-$C_{3-8}$ cycloalkyl;
e) -L-$D_1$-thienyl; and
f) -L-$D_1$-$C_{1-4}$-alkylene-thienyl;

$R_4$ is selected from the group consisting of:
a) hydrogen;
b) -L-$D_1$-phenyl;
c) -L-$D_1$-$C_{1-4}$-alkylene-phenyl;
d) -L-$D_1$-$C_{1-4}$-alkylene-$C_{3-8}$ cycloalkyl;
e) -L-$D_1$-$C_{3-8}$ cycloalkyl;
f) -L-$D_1$-thienyl; and
g) -L-$D_1$-$C_{1-4}$-alkylene-thienyl; and $G_1$ is selected from the group consisting of: —$SO_3H$, —$CO_2H$, —$C(O)NHS(O)_2$-alkyl, —$C(O)NHS(O)_2$-phenyl, —$C(O)NHS(O)_2$-phenylene-alkyl, —$C(O)NHS(O)_2$-pyridyl, —$NHC(O)NH$—$SO_2$-alkyl, and an acid isostere.

In another embodiment of the compound of Formula (I), A is selected from the group consisting of:

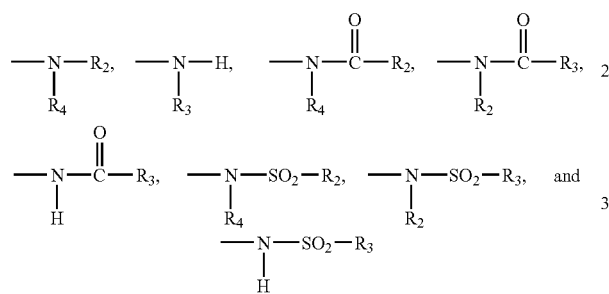

wherein
$R_2$ is selected from the group consisting of:
a) —$(CH_2)_n$-$G_1$;
b) —$C_{5-7}$ cycloalkylene-$G_1$;
c) -phenylene-$G_1$; and
d) —$(CH_2)_n$-phenylene-$G_1$;
wherein n is 1, 2, 3, or 4;

$R_3$ is selected from the group consisting of: isopropyl, 3-methyl-butyl, cyclohexylmethyl, cyclopentyl, phenyl, tert-butyl-phenyl, cyano-phenyl, trifluoromethoxy-phenyl, methyl-phenyl, 4-biphenyl, 3-biphenyl, methoxyphenyl, hydroxyphenyl, chlorophenyl, dichlorophenyl, dimethoxy-phenyl, benzyl, methoxybenzyl, trifluoromethoxy-benzyl, thienyl, thien-2yl-methyl, 3-thien-2-yl-propyl, 2-thien-2-yl-ethyl, furan-2yl-methyl, cyclobutylmethyl, and cyclohexylmethyl;

$R_4$ is selected from the group consisting of: hydrogen, isopropyl, 3-methyl-butyl, cyclohexylmethyl, cyclopentyl, phenyl, tert-butyl-phenyl, cyano-phenyl, trifluoromethoxy-phenyl, methyl-phenyl, 4-biphenyl, 3-biphenyl, methoxyphenyl, hydroxyphenyl, chlorophenyl, dichlorophenyl, dimethoxy-phenyl, benzyl, methoxybenzyl, trifluoromethoxy-benzyl, thienyl, thien-2yl-methyl, 3-thien-2-yl-propyl, 2-thien-2-yl-ethyl, furan-2yl-methyl, cyclobutylmethyl, and cyclohexylmethyl; and $G_1$ is selected from the group consisting of: —$SO_3H$, —$CO_2H$, —$C(O)NHS(O)_2$-alkyl, —$C(O)NHS(O)_2$-phenyl, —$C(O)NHS(O)_2$-phenylene-alkyl, —$C(O)NHS(O)_2$-pyridyl, —$NHC(O)NH$—$SO_2$-alkyl, and an acid isostere.

In another embodiment of the compound of Formula (I), A is selected from the group consisting of

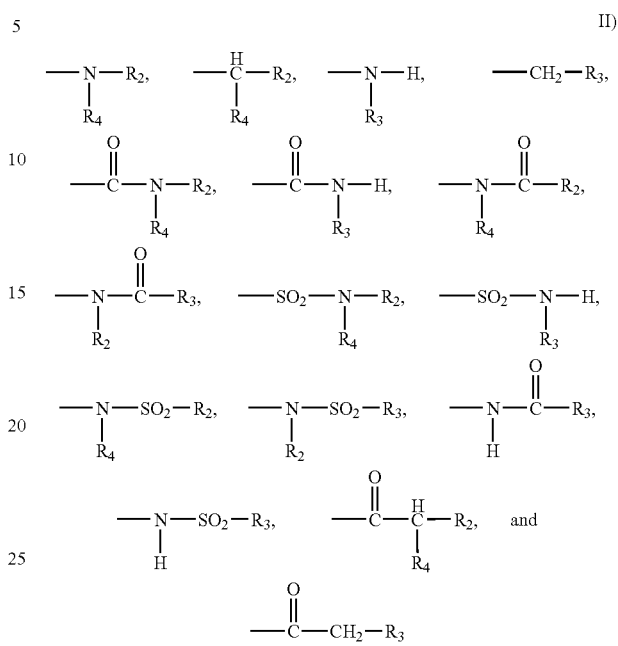

$R_6$ is selected from the group consisting of: hydrogen, halo, alkyl, or phenyl; and $R_7$ is selected from the group consisting of: phenyl, benzyloxy-phenyl, 4-biphenyl-3-yl, 4-biphenyl-4-yl, bromo-phenyl, chloro-methyl-phenyl, chloro-phenyl, cyano-phenyl, cyclohexylmethoxy-phenyl, cyclohexyloxy-phenyl, di-p-tolylmethyl, methoxy-phenyl, ethoxy-phenyl, isobutoxy-phenyl, trifluoromethoxy-phenyl, phenethyloxy-phenyl, phenoxy-phenyl, methylphenyl, isobutyl-phenyl, isopropyl-phenyl, tert-butyl-phenyl, trifluoromethyl-phenyl, dichloro-phenyl, difluoro-phenyl, dimethyl-phenyl, difluoro-phenyl, dihydroxy-phenyl, bis-trifluoromethyl-phenyl, di-tert-butyl-hydroxy-phenyl, benzoyl-phenyl, chloro-methyl-phenyl, (3-phenyl-propoxy)-phenyl, (methyl-cyclohexyloxy)-phenyl, (tert-butyl-cyclohexyloxy)-phenyl, (tetrahydropyran-4-yloxy)-phenyl, (tert-butyl-phenyl)-phenyl-methyl, bis-(chloro-fluoro-phenyl)-methyl, bis-(fluoro-phenyl)-methyl, bis-(trifluoromethyl-phenyl)-methyl, naphthalen-1-yl, naphthalen-2-yl, 5,5,8,8-tetramethyl-5,6,7,8-tetrahydro-naphthalen-2-yl, and 4-benzhydryl. In an further embodiment, $R_7$ is selected from the group consisting of: phenyl, bromo-phenyl, chloro-methyl-phenyl, chloro-phenyl, cyano-phenyl, di-p-tolylmethyl, methoxy-phenyl, ethoxy-phenyl, isobutoxy-phenyl, trifluoromethoxy-phenyl, methylphenyl, isobutyl-phenyl, isopropyl-phenyl, tert-butyl-phenyl, trifluoromethyl-phenyl, dichloro-phenyl, difluoro-phenyl, dimethyl-phenyl, difluoro-phenyl, dihydroxy-phenyl, bis-trifluoromethyl-phenyl, di-tert-butyl-hydroxy-phenyl, chloro-methyl-phenyl, (tert-butyl-phenyl)-phenyl-methyl, bis-(chloro-fluoro-phenyl)-methyl, bis-(fluoro-phenyl)-methyl, bis-(trifluoromethyl-phenyl)-methyl, naphthalen-1-yl, naphthalen-2-yl, and 5,5,8,8-tetramethyl-5,6,7,8-tetrahydro-naphthalen-2-yl.

In the compounds of Formula (I), the various functional groups represented should be understood to have a point of attachment at the functional group having the hyphen. In other words, in the case of —$C_{1-6}$ alkylaryl, it should be understood that the point of attachment is the alkyl group; an example would be benzyl. In the case of a group such as —C(O)—NH—C$_{1-6}$ alkylaryl, the point of attachment is the carbonyl carbon.

When any variable occurs more than one time in any one constituent (e.g., R$_{10}$), or multiple constituents (e.g. L, D$_1$, etc.) its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

Also included within the scope of the invention are the individual enantiomers of the compounds represented by Formula (I) above as well as any wholly or partially racemic mixtures thereof. The present invention also covers the individual enantiomers of the compounds represented by the Formula above as mixtures with diastereoisomers thereof in which one or more stereocenters are inverted.

In another aspect, the present invention provides a pharmaceutically acceptable salt, prodrug, or solvate of compounds of Formula (I). In an embodiment, the prodrug comprises a biohydrolyzable ester or biohydrolyzable amide of a compound of Formula (I).

Examples of compounds of Formula (I) or salts thereof having potentially useful biological activity are listed by name below in Table 1. The ability of compounds Formula (I) to inhibit AgRP interaction with MC-4R was established with representative compounds of Formula (I) listed in Table I using the assay described below. The compounds of Formula (I) in Table I showed an increase in cAMP production and a reduction in fluorescence polarization in the assay and possess an effective concentration for half maximal effect (EC50) in the assay of less than 15 μM.

Compounds that inhibit AgRP functional interaction with a melanocortion receptor are potentially useful in treating diseases or conditions that may be responsive to the modulation of melanocortin receptors. The compounds of Formula (I) of the present invention may therefore be potentially useful in the treatment of obesity and obesity-related disorders. The compounds of this invention may also potentially be useful in prevention of weight gain.

TABLE 1

| Example | Structure | Name |
| --- | --- | --- |
| 1 | 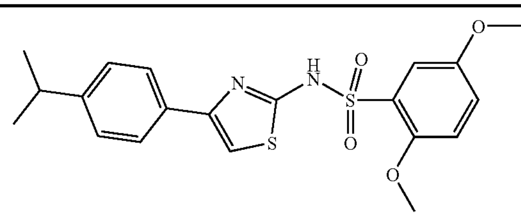 | N-[4-(4-Isopropyl-phenyl)-thiazol-2-yl]-2,5-dimethoxy-benzenesulfonamide |
| 2 | 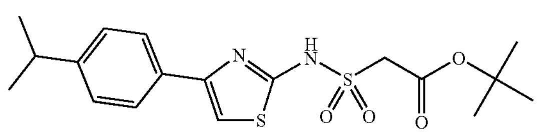 | [4-(4-Isopropyl-phenyl)-thiazol-2-ylsulfamol]-acetic acid tert-butyl ester |
| 3 | 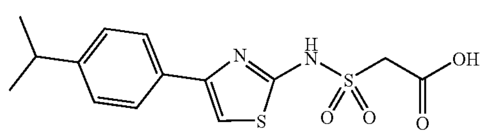 | [4-(4-Isopropyl-phenyl)-thiazol-2-ylsulfamoyl]-acetic acid |
| 4 | 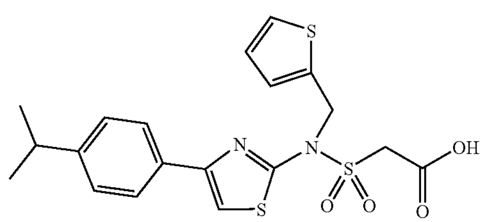 | {[4-(4-Isopropyl-phenyl)-thiazol-2-yl]-thiophen-2-ylmethyl-sulfamoyl}-acetic acid |
| 5 | 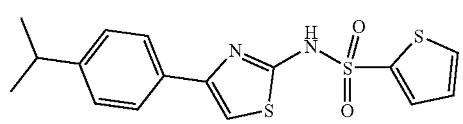 | Thiophene-2-sulfonic acid [4-(4-isopropyl-phenyl)-thiazol-2-yl]-amide |
| 6 | 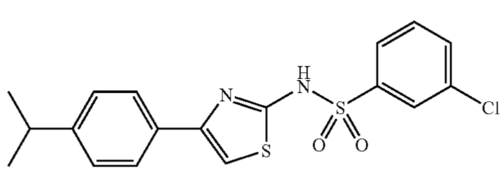 | 3-Chloro-N-[4-(4-isopropyl-phenyl)-thiazol-2-yl]-benzenesulfonamide |

TABLE 1-continued

| Example | Structure | Name |
|---|---|---|
| 7 | 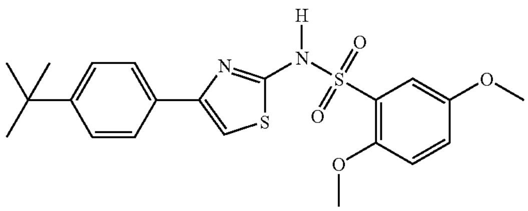 | N-[4-(4-tert-Butyl-phenyl)-thiazol-2-yl]-2,5-dimethoxy-benzenesulfonamide |
| 8 | 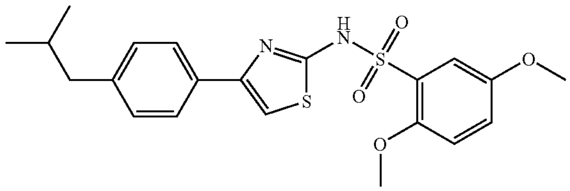 | N-[4-(4-Isobutyl-phenyl)-thiazol-2-yl]-2,5-dimethoxy-benzenesulfonamide |
| 9 | 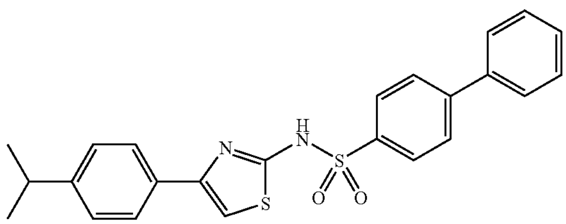 | Biphenyl-4-sulfonic acid [4-(4-isopropyl-phenyl)-thiazol-2-yl]-amide |
| 10 | 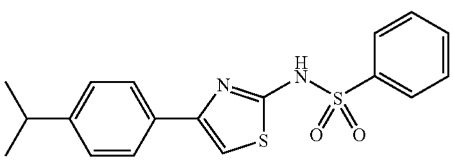 | N-[4-(4-Isopropyl-phenyl)-thiazol-2-yl]-benzenesulfonamide |
| 11 | 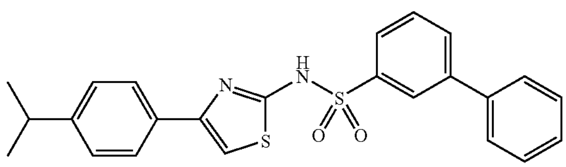 | Biphenyl-3-sulfonic acid [4-(4-isopropyl-phenyl)-thiazol-2-yl]-amide |
| 12 | 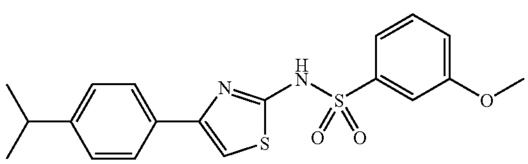 | N-[4-(4-Isopropyl-phenyl)-thiazol-2-yl]-3-methoxy-benzenesulfonamide |
| 13 | 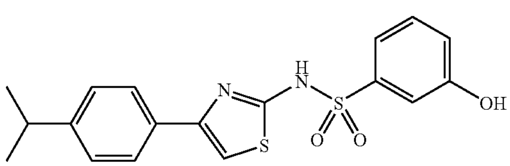 | 3-Hydroxy-N-[4-(4-isopropyl-phenyl)-thiazol-2-yl]-benzenesulfonamide |
| 14 | 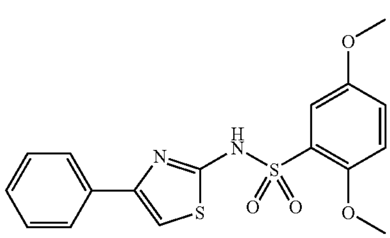 | 2,5-Dimethoxy-N-(4-phenyl-thiazol-2-yl)-benzenesulfonamide |

TABLE 1-continued

| Example | Structure | Name |
|---|---|---|
| 15 | 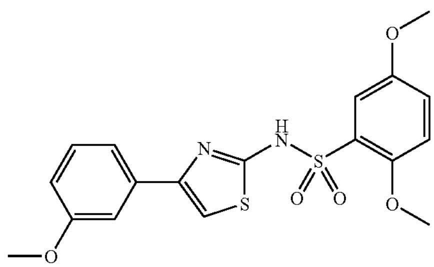 | 2,5-Dimethoxy-N-[4-(3-methoxy-phenyl)-thiazol-2-yl]-benzenesulfonamide |
| 16 | 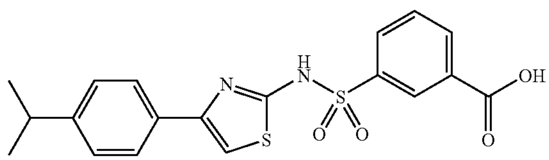 | 3-[4-(4-Isopropyl-phenyl)-thiazol-2-ylsulfamoyl]-benzoic acid |
| 17 | 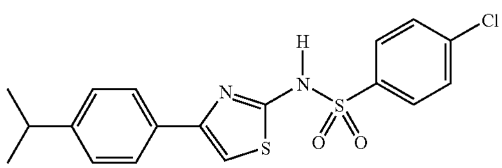 | 4-Chloro-N-[4-(4-isopropyl-phenyl)-thiazol-2-yl]-benzenesulfonamide |
| 18 | | 4-{(2,5-Dimethoxy-benzenesulfonyl)-[4-(4-isopropyl-phenyl)-thiazol-2-ylmethyl]-amino}-butyric acid |
| 18 | | 4-Fluoro-N-[4-(4-isopropyl-phenyl)-thiazol-2-yl]-benzenesulfonamide |
| 19 | 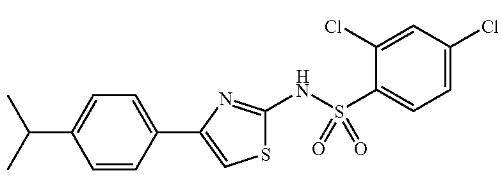 | 2,4-Dichloro-N-[4-(4-isopropyl-phenyl)-thiazol-2-yl]-benzenesulfonamide |
| 20 | 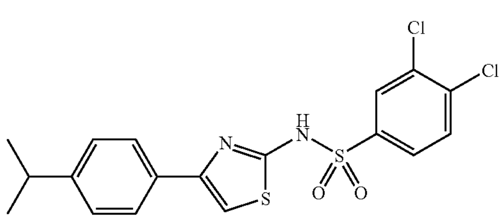 | 3,4-Dichloro-N-[4-(4-isopropyl-phenyl)-thiazol-2-yl]-benzenesulfonamide |

TABLE 1-continued

| Example | Structure | Name |
|---|---|---|
| 21 | 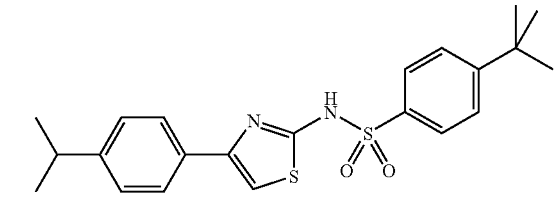 | 4-tert-Butyl-N-[4-(4-isopropyl-phenyl)-thiazol-2-yl]-benzenesulfonamide |
| 22 | 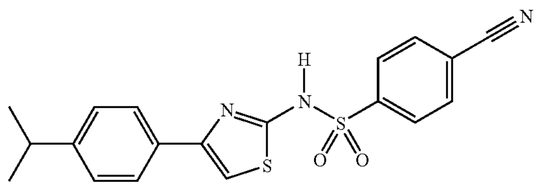 | 4-Cyano-N-[4-(4-isopropyl-phenyl)-thiazol-2-yl]-benzenesulfonamide |
| 23 | 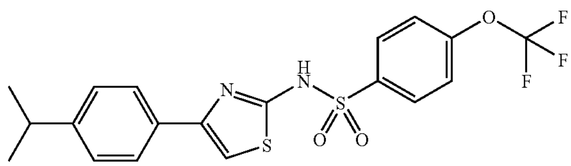 | N-[4-(4-Isopropyl-phenyl)-thiazol-2-yl]-4-trifluoromethoxy-benzenesulfonamide |
| 24 | 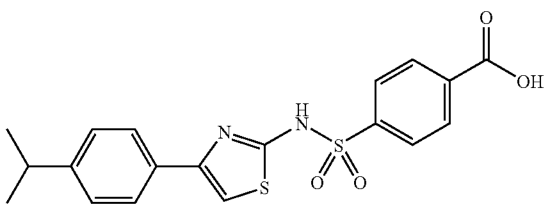 | 4-[4-(4-Isopropyl-phenyl)-thiazol-2-ylsulfamoyl]-benzoic acid |
| 25 | 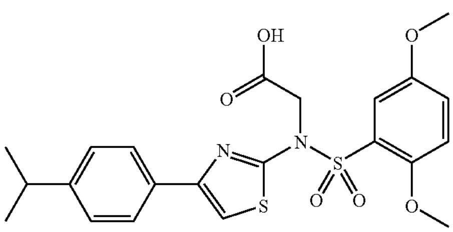 | {(2,5-Dimethoxy-benzenesulfonyl)-[4-(4-isopropyl-phenyl)-thiazol-2-yl]-amino}-acetic acid |
| 26 | 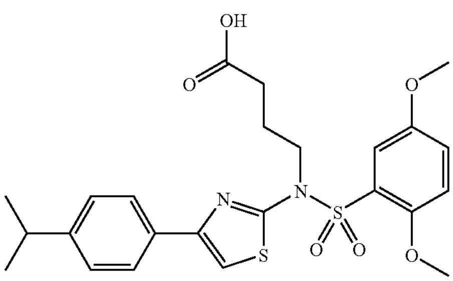 | 4-{(2,5-Dimethoxy-benzenesulfonyl)-[4-(4-isopropyl-phenyl)-thiazol-2-yl]-amino}-butyric acid |
| 27 | 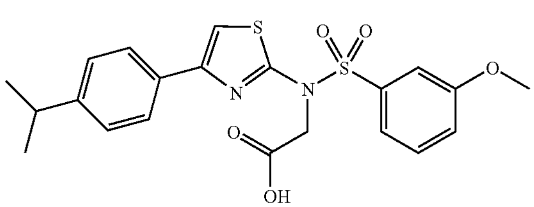 | [[4-(4-Isopropyl-phenyl)-thiazol-2-yl]-(3-methoxy-benzenesulfonyl)-amino]-acetic acid |

TABLE 1-continued

| Example | Structure | Name |
|---|---|---|
| 28 | 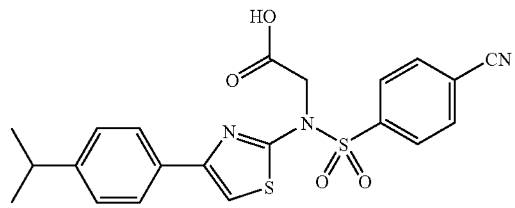 | {(4-Cyano-benzenesulfonyl)-[4-(4-isopropyl-phenyl)-thiazol-2-yl]-amino}-acetic acid |
| 29 | 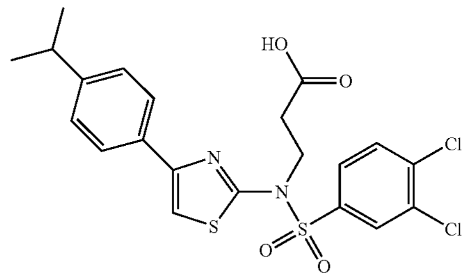 | 3-{(3,4-Dichloro-benzenesulfonyl)-[4-(4-isopropyl-phenyl)-thiazol-2-yl]-amino}-propionic acid |
| 30 | 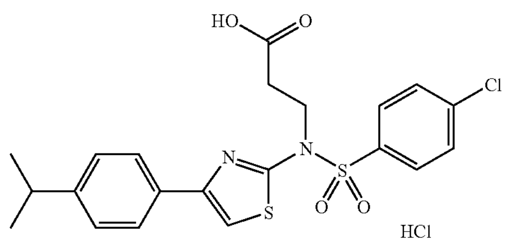 | 3-{(4-Chloro-benzenesulfonyl)-[4-(4-isopropyl-phenyl)-thiazol-2-yl]-amino}-propionic acid |
| 31 | 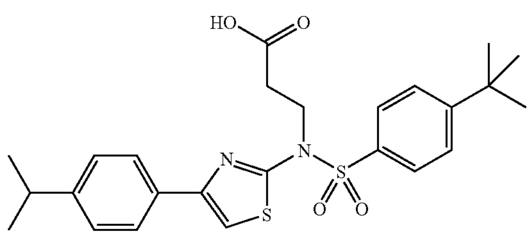 | 3-{(4-tert-Butyl-benzenesulfonyl)-[4-(4-isopropyl-phenyl)-thiazol-2-yl]-amino}-propionic acid |
| 32 | 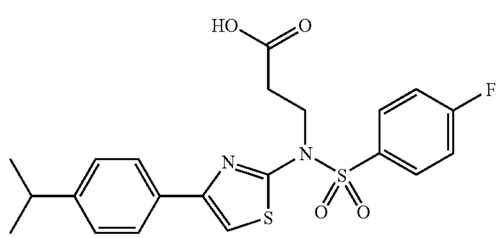 | 3-{(4-Fluoro-benzenesulfonyl)-[4-(4-isopropyl-phenyl)-thiazol-2-yl]-amino}-propionic acid |
| 33 | 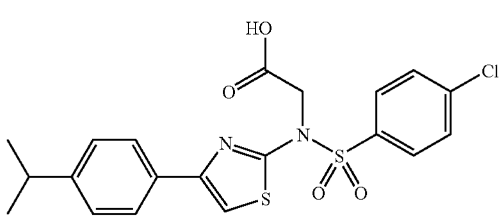 | {(4-Chloro-benzenesulfonyl)-[4-(4-isopropyl-phenyl)-thiazol-2-yl]-amino}-acetic acid |

TABLE 1-continued

| Example | Structure | Name |
|---|---|---|
| 34 | 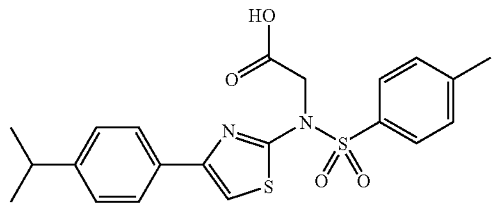 | [[4-(4-Isopropyl-phenyl)-thiazol-2-yl]-(toluene-4-sulfonyl)-amino]-acetic acid |
| 35 | 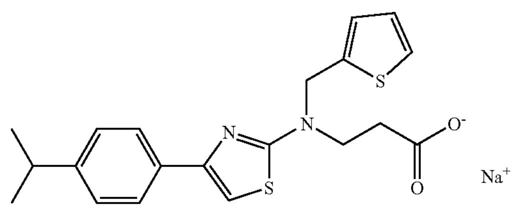 | Sodium 3-{[4-(4-isopropyl-phenyl)-thiazol-2-yl]-thiophen-2-ylmethyl-amino}-propionate |
| 36 | 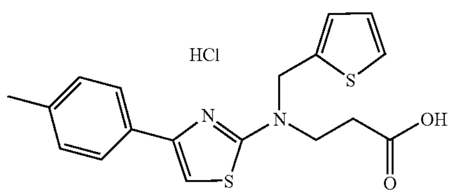 | 3-[Thiophen-2-ylmethyl-(4-p-tolyl-thiazol-2-yl)-amino]-propionic acid Hydrochloride |
| 37 | 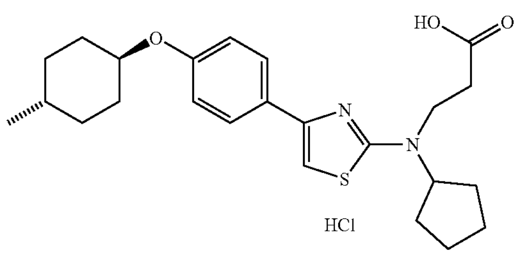 | 3-(Cyclopentyl-{4-[4-(trans-4-methyl-cyclohexyloxy)-phenyl]-thiazol-2-yl}-amino)-propionic acid Hydrochloride |
| 38 | 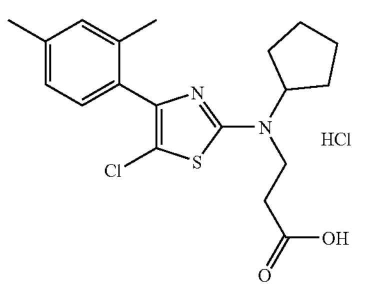 | 3-{[5-Chloro-4-(2,4-dimethyl-phenyl)-thiazol-2-yl]-cyclopentyl-amino}-propionic acid Hydrochloride |
| 39 | 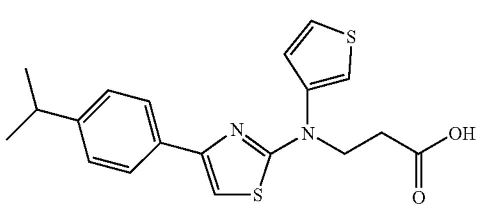 | 3-{[4-(4-Isopropyl-phenyl)-thiazol-2-yl]-thiophen-3-yl-amino}-propionic acid |
| 40 | 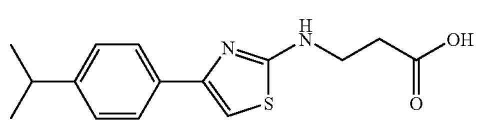 | 3-[4-(4-Isopropyl-phenyl)-thiazol-2-ylamino]-propionic acid |

TABLE 1-continued

| Example | Structure | Name |
|---|---|---|
| 41 | 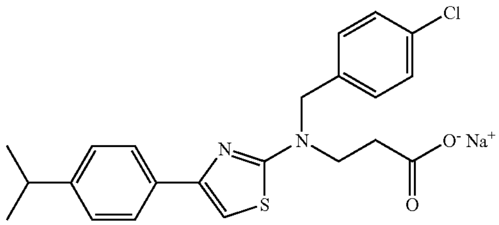 | Sodium 3-{(4-chloro-benzyl)-[4-(4-isopropyl-phenyl)-thiazol-2-yl]amino}-propionate |
| 42 | HCl | 3-{Benzyl-[4-(4-isopropyl-phenyl)-thiazol-2-yl]-amino}-propionic acid Hydrochloride |
| 43 | HCl | 3-{Furan-2-ylmethyl-[4-(4-isopropyl-phenyl)-thiazol-2-yl]-amino}-propionic acid Hydrochloride |
| 44 | HCl | 3-{[4-(4-Fluoro-phenyl)-thiazol-2-yl]-thiophen-2-ylmethyl-amino}-propionic acid Hydrochloride |
| 45 | HCl | 3-{[4-(4-Chloro-phenyl)-thiazol-2-yl]-thiophen-2-ylmethyl-amino}-propionic acid Hydrochloride |
| 46 | HCl | 3-{[4-(3,5-Bis-trifluoromethyl-phenyl)-thiazol-2-yl]-thiophen-2-ylmethyl-amino}-propionic acid Hydrochloride |
| 47 | HCl | 3-{[4-(4-Cyano-phenyl)-thiazol-2-yl]-thiophen-2-ylmethyl-amino}-propionic acid Hydrochloride |

TABLE 1-continued

| Example | Structure | Name |
|---|---|---|
| 48 | 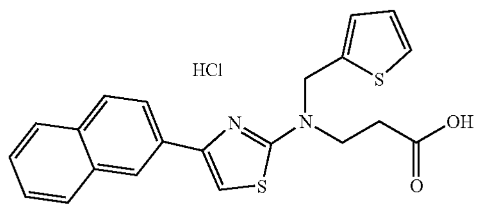 | 3-[(4-Naphthalen-2-yl-thiazol-2-yl)-thiophen-2-ylmethyl-amino]-propionic acid Hydrochloride |
| 49 | 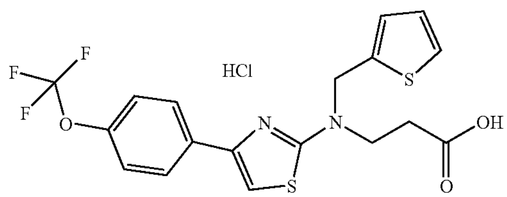 | 3-{Thiophen-2-ylmethyl-[4-(4-trifluoromethoxy-phenyl)-thiazol-2-yl]-amino}-propionic acid Hydrochloride |
| 50 | 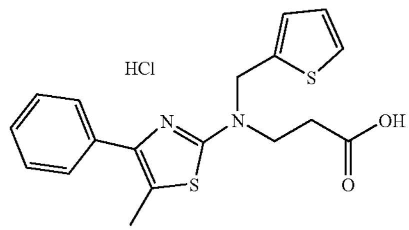 | 3-[(5-Methyl-4-phenyl-thiazol-2-yl)-thiophen-2-ylmethyl-amino]-propionic acid Hydrochloride |
| 51 | 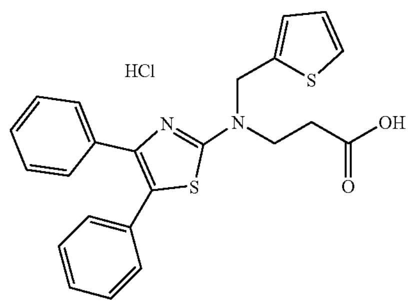 | 3-[(4,5-Diphenyl-thiazol-2-yl)-thiophen-2-ylmethyl-amino]-propionic acid Hydrochloride |
| 52 | 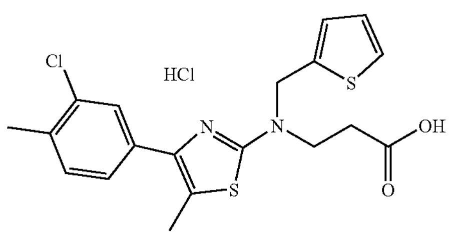 | 3-{[4-(3-Chloro-4-methyl-phenyl)-5-methyl-thiazol-2-yl]-thiophen-2-ylmethyl-amino}-propionic acid Hydrochloride |
| 53 | 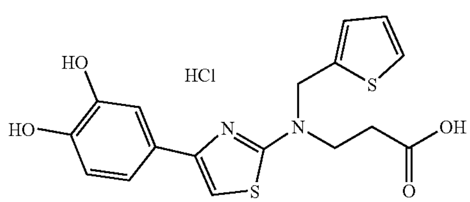 | 3-{[4-(3,4-Dihydroxy-phenyl)-thiazol-2-yl]-thiophen-2-ylmethyl-amino}-propionic acid Hydrochloride |
| 54 | 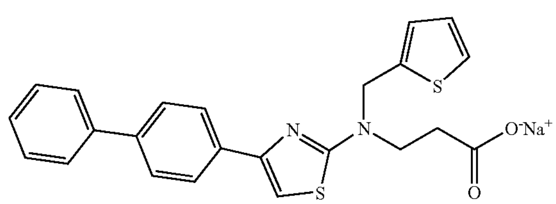 | Sodium 3-[(4-biphenyl-4-yl-thiazol-2-yl)-thiophen-2-ylmethylamino]-propionate |

TABLE 1-continued

| Example | Structure | Name |
|---|---|---|
| 55 | 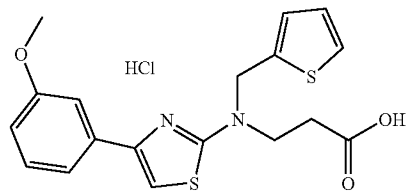 | 3-{[4-(3-Methoxy-phenyl)-thiazol-2-yl]-thiophen-2-ylmethyl-amino}-propionic acid Hydrochloride |
| 56 | 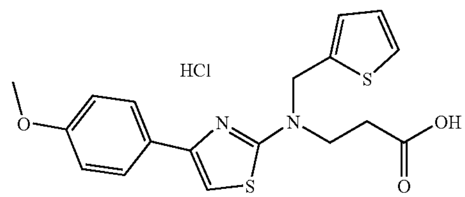 | 3-{[4-(4-Methoxy-phenyl)-thiazol-2-yl]-thiophen-2-ylmethyl-amino}-propionic acid Hydrochloride |
| 57 | 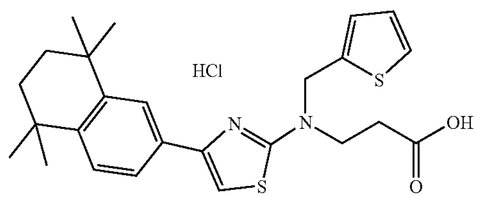 | 3-{[4-(5,5,8,8-Tetramethyl-5,6,7,8-tetrahydro-naphthalen-2-yl)-thiazol-2-yl]-thiophen-2-ylmethyl-amino}-propionic acid Hydrochloride |
| 58 | 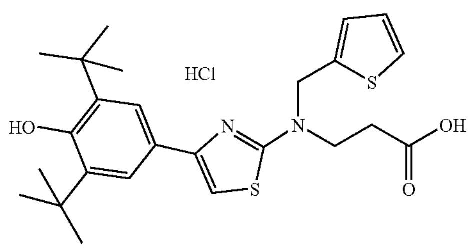 | 3-{[4-(3,5-Di-tert-butyl-4-hydroxy-phenyl)-thiazol-2-yl]-thiophen-2-ylmethyl-amino}-propionic acid Hydrochloride |
| 59 | 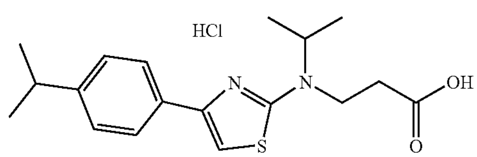 | 3-{Isopropyl-[4-(4-isopropyl-phenyl)-thiazol-2-yl]-amino}-propionic acid Hydrochloride |
| 60 | 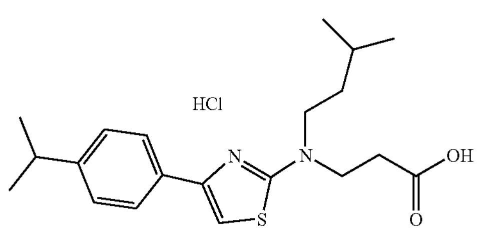 | 3-[[4-(4-Isopropyl-phenyl)-thiazol-2-yl]-(3-methyl-butyl)-amino]-propionic acid Hydrochloride |
| 61 | 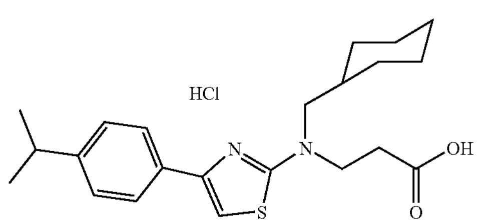 | 3-{Cyclohexylmethyl-[4-(4-isopropyl-phenyl)-thiazol-2-yl]-amino}-propionic acid Hydrochloride |

TABLE 1-continued

| Example | Structure | Name |
|---|---|---|
| 62 | 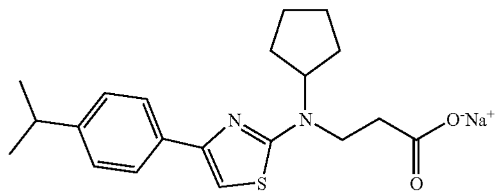 | Sodium 3-{cyclopentyl-[4-(4-isopropyl-phenyl)-thiazol-2-yl]-amino}-propionate |
| 63 | 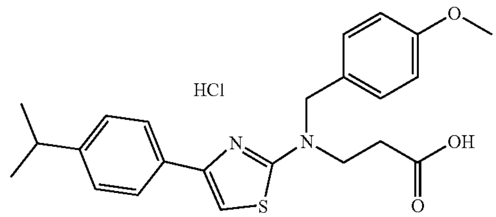 | 3-[[4-(4-Isopropyl-phenyl)-thiazol-2-yl]-(4-methoxy-benzyl)-amino]-propionic acid Hydrochloride |
| 64 | 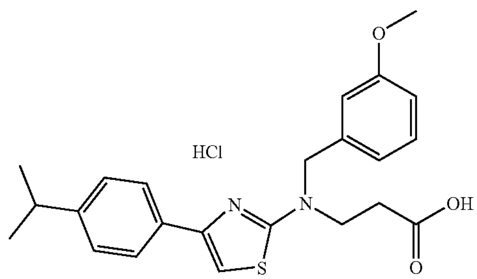 | 3-[[4-(4-Isopropyl-phenyl)-thiazol-2-yl]-(3-methoxy-benzyl)-amino]-propionic acid Hydrochloride |
| 65 | 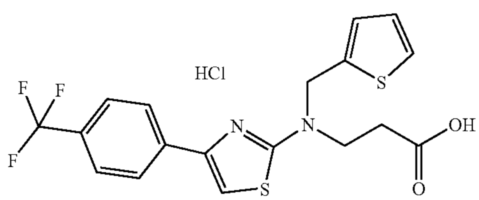 | 3-{Thiophen-2-ylmethyl-[4-(4-trifluoromethyl-phenyl)-thiazol-2-yl]-amino}-propionic acid Hydrochloride |
| 66 | 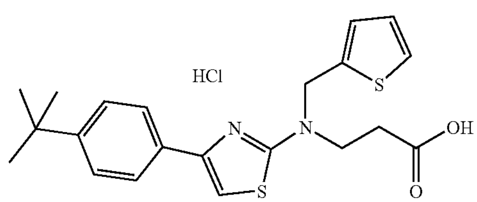 | 3-{[4-(4-tert-Butyl-phenyl)-thiazol-2-yl]-thiophen-2-ylmethyl-amino}-propionic acid Hydrochloride |
| 67 | 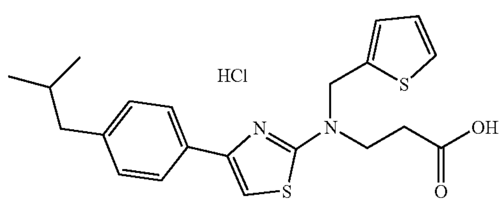 | 3-{[4-(4-Isobutyl-phenyl)-thiazol-2-yl]-thiophen-2-ylmethyl-amino}-propionic acid Hydrochloride |
| 68 | 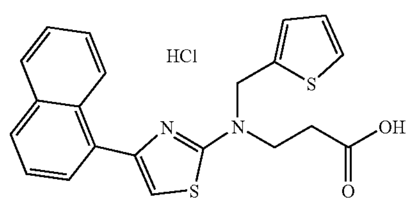 | 3-[(4-Naphthalen-1-yl-thiazol-2-yl)-thiophen-2-ylmethyl-amino]-propionic acid Hydrochloride |

TABLE 1-continued

| Example | Structure | Name |
|---|---|---|
| 69 | 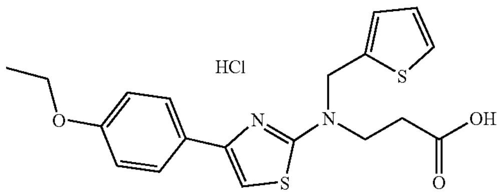 | 3-{[4-(4-Ethoxy-phenyl)-thiazol-2-yl]-thiophen-2-ylmethyl-amino}-propionic acid Hydrochloride |
| 70 | 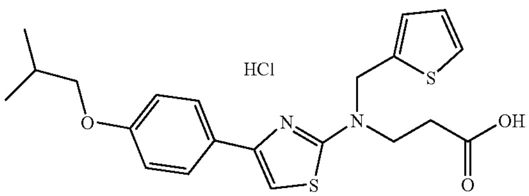 | 3-{[4-(4-Isobutoxy-phenyl)-thiazol-2-yl]-thiophen-2-ylmethyl-amino}-propionic acid Hydrochloride |
| 71 | 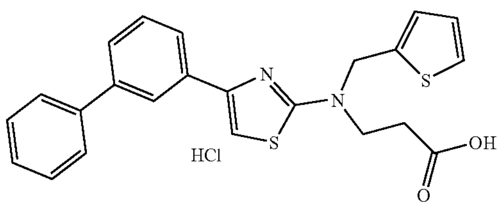 | 3-[(4-Biphenyl-3-yl-thiazol-2-yl)-thiophen-2-ylmethyl-amino]-propionic acid Hydrochloride |
| 72 | 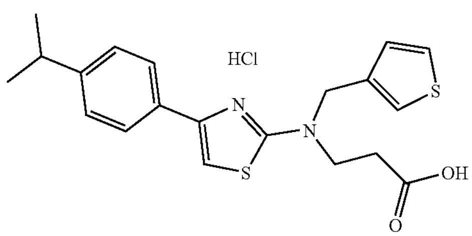 | 3-{[4-(4-Isopropyl-phenyl)-thiazol-2-yl]-thiophen-3-ylmethyl-amino}-propionic acid Hydrochloride |
| 73 | 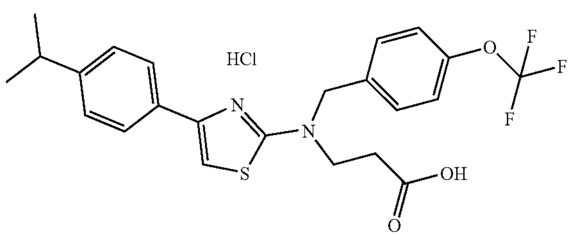 | 3-[[4-(4-Isopropyl-phenyl)-thiazol-2-yl]-(4-trifluoromethoxy-benzyl)-amino]-propionic acid Hydrochloride |
| 74 | 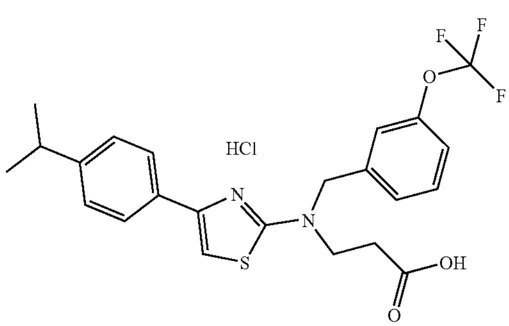 | 3-[[4-(4-Isopropyl-phenyl)-thiazol-2-yl]-(3-trifluoromethoxy-benzyl)-amino]-propionic acid Hydrochloride |

TABLE 1-continued

| Example | Structure | Name |
|---|---|---|
| 75 | 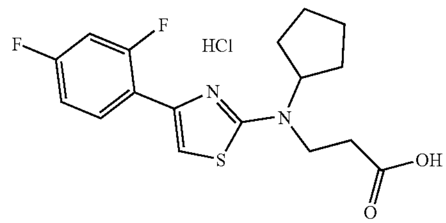 | 3-{Cyclopentyl-[4-(2,4-difluoro-phenyl)-thiazol-2-yl]-amino}-propionic acid Hydrochloride |
| 76 | 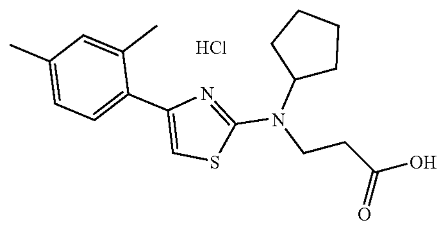 | 3-{Cyclopentyl-[4-(2,4-dimethyl-phenyl)-thiazol-2-yl]-amino}-propionic acid Hydrochloride |
| 77 | 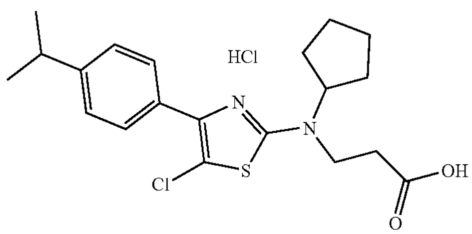 | 3-{[5-Chloro-4-(4-isopropyl-phenyl)-thiazol-2-yl]-cyclopentyl-amino}-propionic acid Hydrochloride |
| 78 | 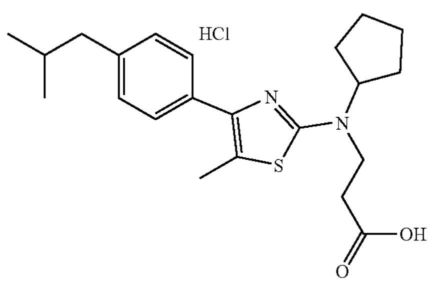 | 3-{Cyclopentyl-[4-(4-isobutyl-phenyl)-5-methyl-thiazol-2-yl]-amino}-propionic acid Hydrochloride |
| 79 | 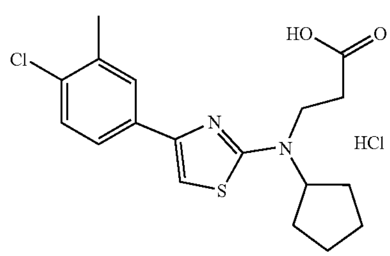 | 3-{[4-(4-Chloro-3-methyl-phenyl)-thiazol-2-yl]-cyclopentyl-amino}-propionic acid Hydrochloride |
| 80 | 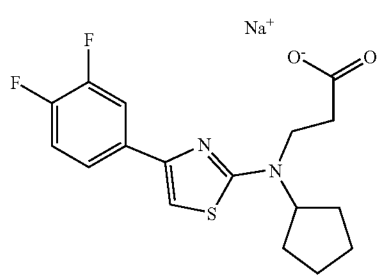 | Sodium 3-{cyclopentyl-[4-(3,4-difluoro-phenyl)-thiazol-2-yl]-amino}-propionate |

TABLE 1-continued

| Example | Structure | Name |
|---|---|---|
| 81 | 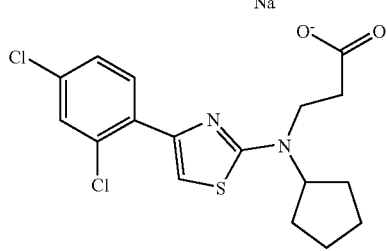 | Sodium 3-{cyclopentyl-[4-(2,4-dichloro-phenyl)-thiazol-2-yl]-amino}-propionate |
| 82 | 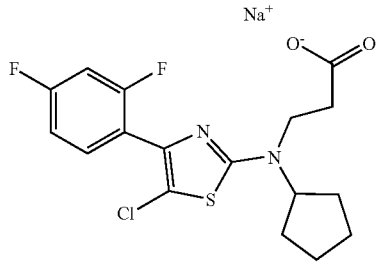 | Sodium 3-{[5-chloro-4-(2,4-difluoro-phenyl)-thiazol-2-yl]-cyclopentyl-amino}-propionate |
| 83 | 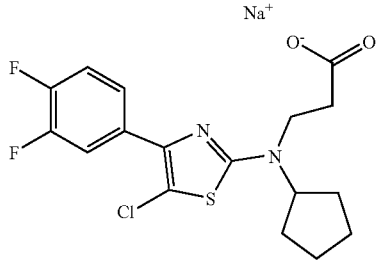 | Sodium 3-{[5-chloro-4-(3,4-difluoro-phenyl)-thiazol-2-yl]-cyclopentyl-amino}-propionate |
| 84 | 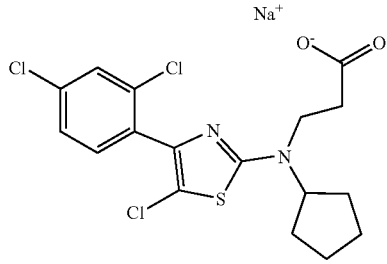 | Sodium 3-{[5-chloro-4-(2,4-dichloro-phenyl)-thiazol-2-yl]-cyclopentyl-amino}-propionate |
| 85 | 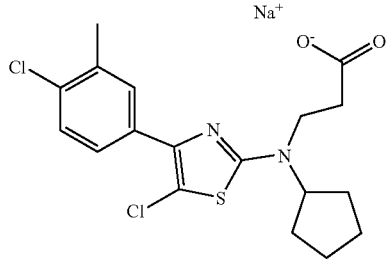 | Sodium 3-{[5-chloro-4-(4-chloro-3-methyl-phenyl)-thiazol-2-yl]-cyclopentyl-amino}-propionate |

TABLE 1-continued

| Example | Structure | Name |
|---|---|---|
| 86 | 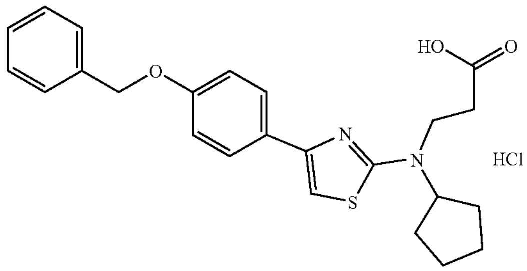 | 3-{[4-(4-Benzyloxy-phenyl)-thiazol-2-yl]-cyclopentyl-amino}-propionic acid Hydrochloride |
| 87 | 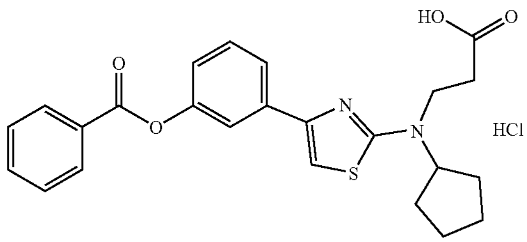 | Benzoic acid 3-{2-[(2-carboxy-ethyl)-cyclopentyl-amino]-thiazol-4-yl}-phenyl ester Hydrochloride |
| 88 | 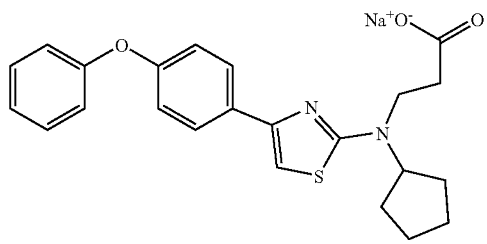 | Sodium; 3-{cyclopentyl-[4-(4-phenoxy-phenyl)-thiazol-2-yl]-amino}-propionate |
| 89 | 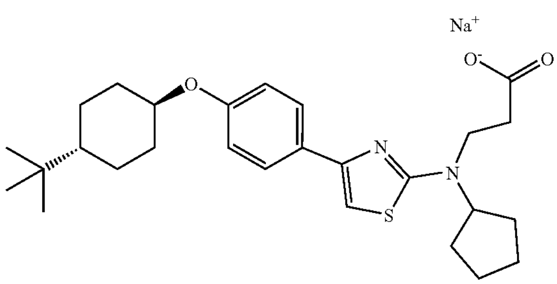 | Sodium 3-({4-[4-(trans-4-tert-butyl-cyclohexyloxy)-phenyl]-thiazol-2-yl}-cyclopentyl-amino)-propionate |
| 90 | 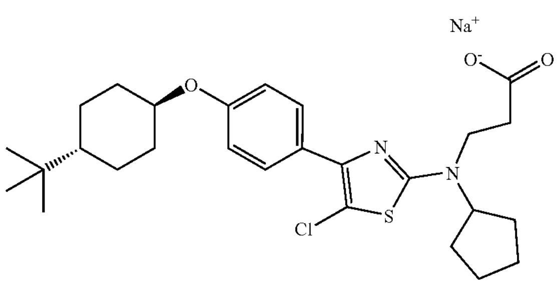 | Sodium 3-({4-[4-(trans-4-tert-butyl-cyclohexyloxy)-phenyl]-5-chloro-thiazol-2-yl}-cyclopentyl-amino)-propionate |
| 91 | 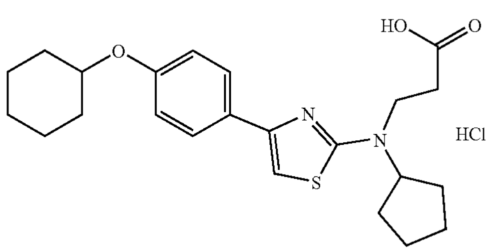 | 3-{[4-(4-Cyclohexyloxy-phenyl)-thiazol-2-yl]-cyclopentyl-amino}-propionic acid Hydrochloride |

TABLE 1-continued

| Example | Structure | Name |
|---|---|---|
| 92 | 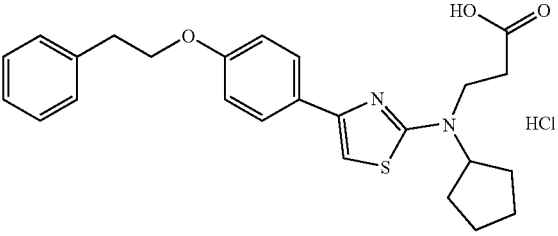 | 3-{Cyclopentyl-[4-(4-phenethyloxy-phenyl)-thiazol-2-yl]-amino}-propionic acid Hydrochloride |
| 93 | 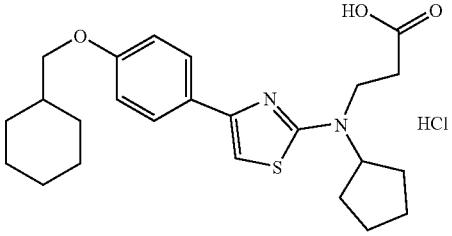 | 3-{[4-(4-Cyclohexylmethoxy-phenyl)-thiazol-2-yl]-cyclopentyl-amino}-propionic acid Hydrochloride |
| 94 | 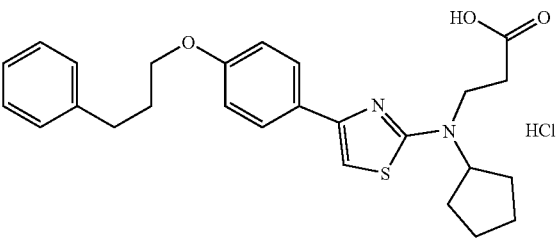 | 3-(Cyclopentyl-{4-[4-(3-phenyl-propoxy)-phenyl]-thiazol-2-yl}-amino)-propionic acid Hydrochloride |
| 95 | 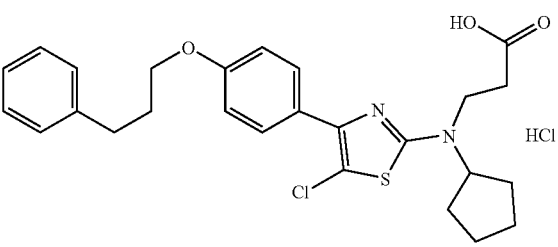 | 3-({5-Chloro-4-[4-(3-phenyl-propoxy)-phenyl]-thiazol-2-yl}-cyclopentyl-amino)-propionic acid Hydrochloride |
| 96 | 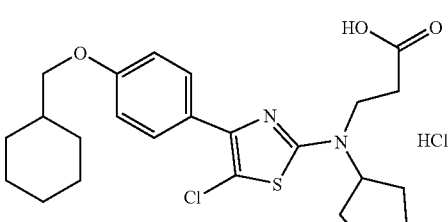 | 3-{[5-Chloro-4-(4-cyclohexylmethoxy-phenyl)-thiazol-2-yl]-cyclopentyl-amino}-propionic acid Hydrochloride |
| 97 | 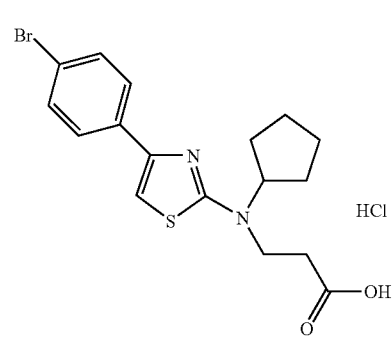 | 3-{[4-(4-Bromo-phenyl)-thiazol-2-yl]-cyclopentyl-amino}-propionic acid Hydrochloride |

TABLE 1-continued

| Example | Structure | Name |
|---|---|---|
| 98 | 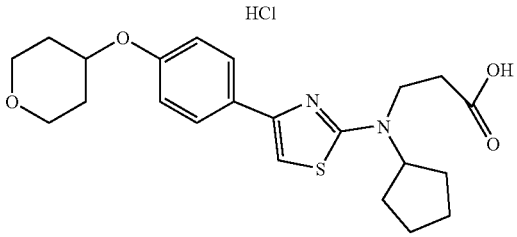 | 3-(Cyclopentyl-{4-[4-(tetrahydro-pyran-4-yloxy)-phenyl]-thiazol-2-yl}-amino)-propionic acid Hydrochloride |
| 99 | 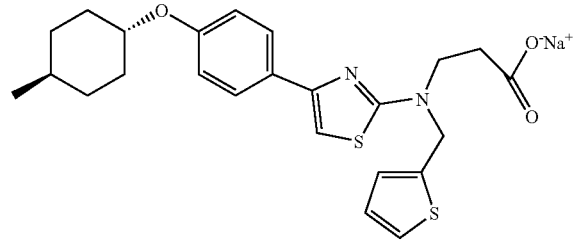 | Sodium 3-({4-[4-(trans-4-methyl-cyclohexyloxy)-phenyl]-thiazol-2-yl}-thiophen-2-ylmethyl-amino)-propionate |
| 100 | 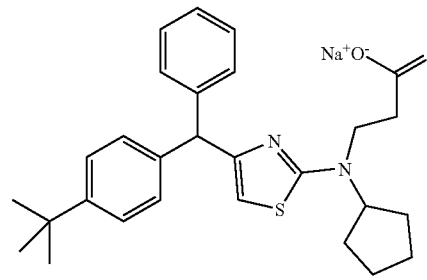 | Sodium 3-({4-[(4-tert-butyl-phenyl)-phenyl-methyl]-thiazol-2-yl}-cyclopentyl-amino)-propionate |
| 101 | 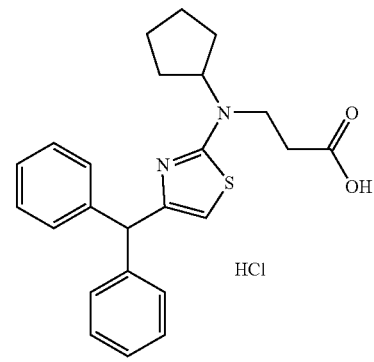 | 3-[(4-Benzhydryl-thiazol-2-yl)-cyclopentyl-amino]-propionic acid Hydrochloride |
| 102 | 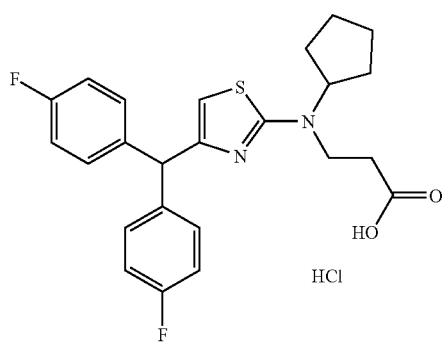 | 3-({4-[Bis-(4-fluoro-phenyl)-methyl]-thiazol-2-yl}-cyclopentyl-amino)-propionic acid Hydrochloride |

TABLE 1-continued

| Example | Structure | Name |
|---|---|---|
| 103 | 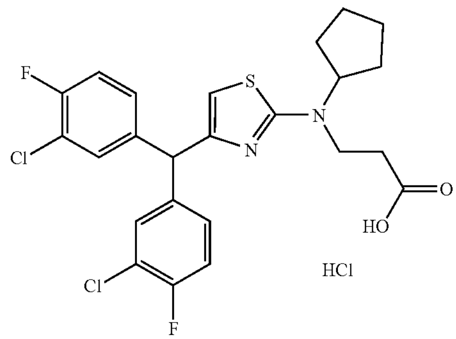 | 3-({4-[Bis-(3-chloro-4-fluoro-phenyl)-methyl]-thiazol-2-yl}-cyclopentyl-amino)-propionic acid Hydrochloride |
| 104 | 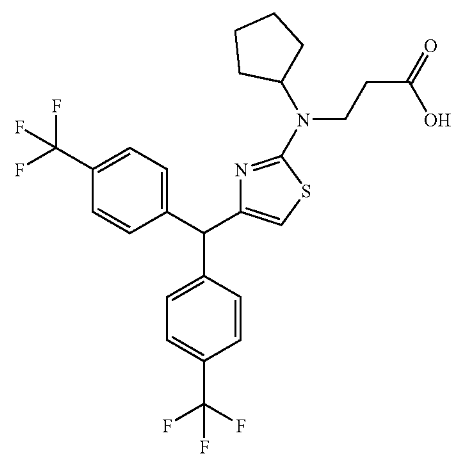 | 3-({4-[Bis-(4-trifluoromethyl-phenyl)-methyl]-thiazol-2-yl}-cyclopentyl-amino)-propionic acid |
| 105 | 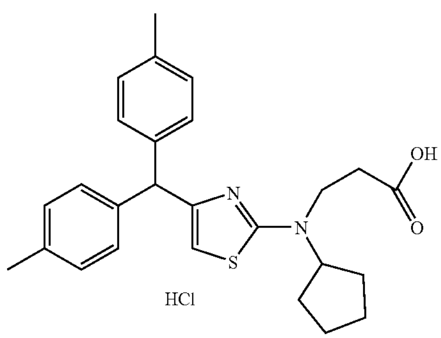 | 3-[Cyclopentyl-(4-di-p-tolyl methyl-thiazol-2-yl)-amino]-propionic acid Hydrochloride |
| 106 | 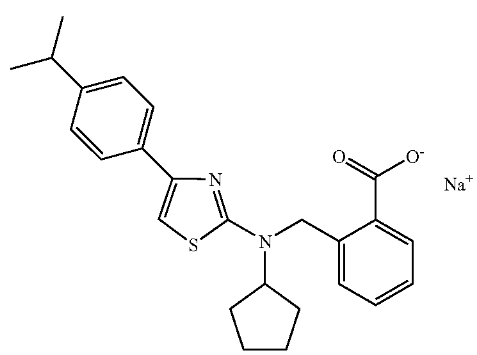 | Sodium 2-({cyclopentyl-[4-(4-isopropyl-phenyl)-thiazol-2-yl]-amino}-methyl)-benzoate |

TABLE 1-continued

| Example | Structure | Name |
|---|---|---|
| 107 | 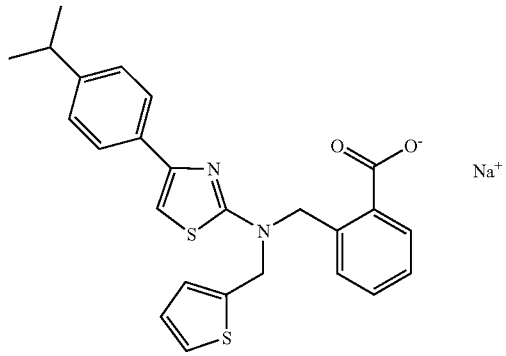 | Sodium 2-({[4-(4-isopropyl-phenyl)-thiazol-2-yl]-thiophen-2-ylmethyl-amino}-methyl)-benzoate |
| 108 | 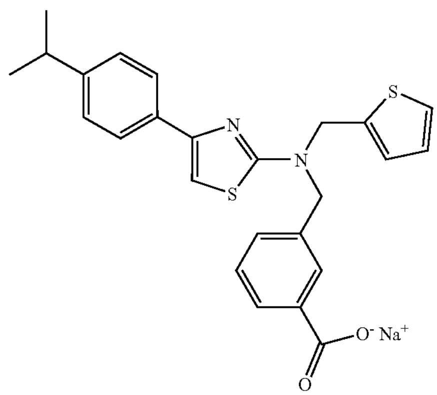 | Sodium 3-({[4-(4-isopropyl-phenyl)-thiazol-2-yl]-thiophen-2-ylmethyl-amino}-methyl)-benzoate |
| 109 | 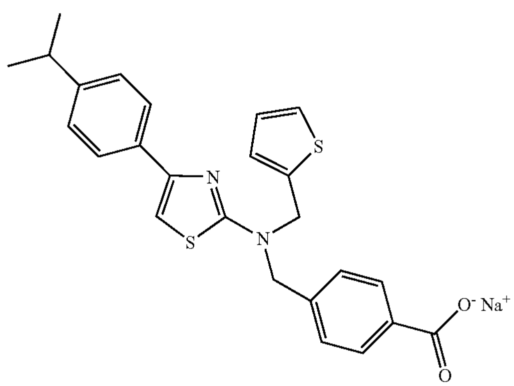 | Sodium 4-({[4-(4-isopropyl-phenyl)-thiazol-2-yl]-thiophen-2-ylmethyl-amino}-methyl)-benzoate |
| 110 | 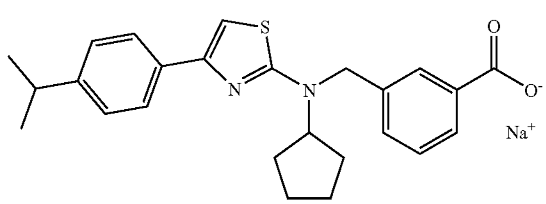 | Sodium 3-({cyclopentyl-[4-(4-isopropyl-phenyl)-thiazol-2-yl]-amino}-methyl)-benzoate |

TABLE 1-continued

| Example | Structure | Name |
|---|---|---|
| 111 | 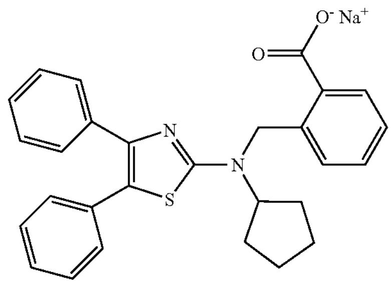 | Sodium 2-{[cyclopentyl-(4,5-diphenyl-thiazol-2-yl)-amino]-methyl}-benzoate |
| 112 | 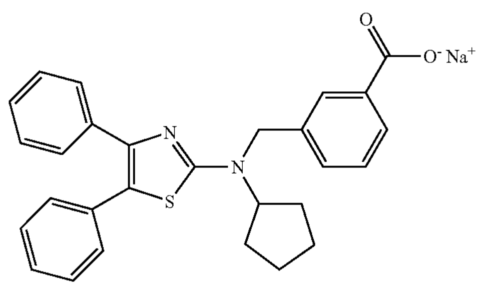 | Sodium 3-{[cyclopentyl-(4,5-diphenyl-thiazol-2-yl)-amino]-methyl}-benzoate |
| 113 | 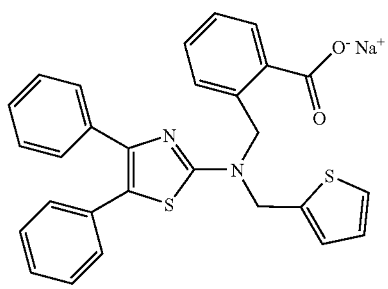 | Sodium 2-{[(4,5-diphenyl-thiazol-2-yl)-thiophen-2-ylmethyl-aminol-methyl}-benzoate |
| 114 | 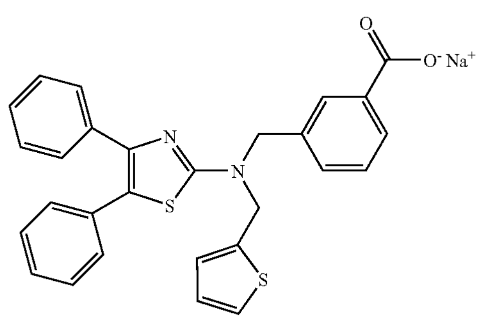 | Sodium 3-{[(4,5-diphenyl-thiazol-2-yl)-thiophen-2-ylmethyl-amino]-methyl}-benzoate |
| 115 | 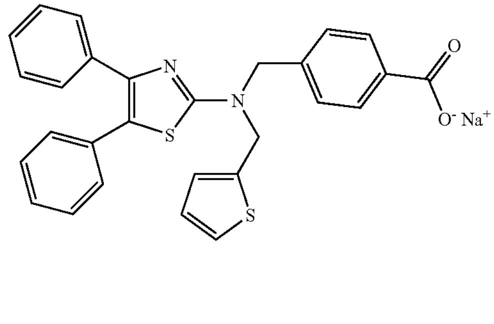 | Sodium 4-{[(4,5-diphenyl-thiazol-2-yl)-thiophen-2-ylmethyl-amino]-methyl}-benzoate |

TABLE 1-continued

| Example | Structure | Name |
|---|---|---|
| 116 | 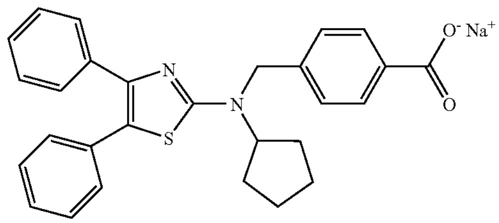 | Sodium 4-{[cyclopentyl-(4,5-diphenyl-thiazol-2-yl)-amino]-methyl}-benzoate |
| 117 | 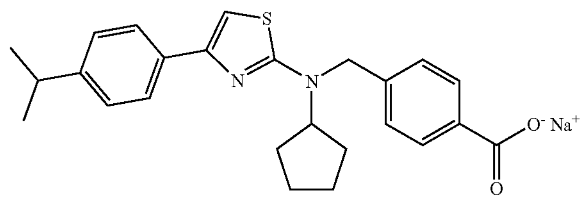 | Sodium 4-[(cyclopentyl-{4-[4-isopropylphenyl]-thiazol-2-yl}-amino)-methyl]-benzoate |
| 118 | 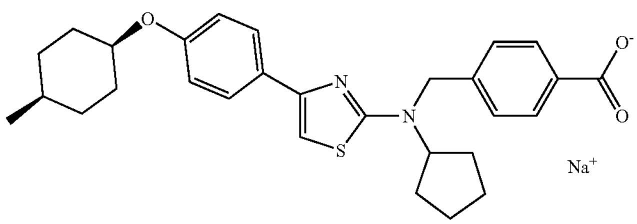 | Sodium 4-[(cyclopentyl-{4-[4-(cis-4-methyl-cyclohexyloxy)-phenyl]-thiazol-2-yl}-amino)-methyl]-benzoate |
| 119 | 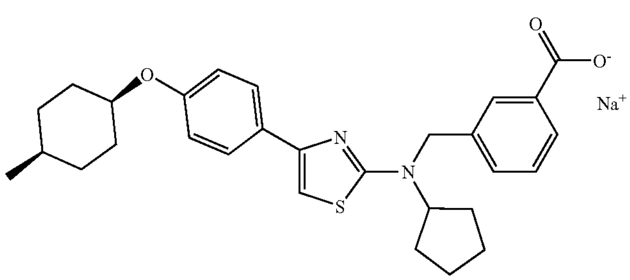 | Sodium 3-[(cyclopentyl-{4-[4-(cis-4-methyl-cyclohexyloxy)-phenyl]-thiazol-2-yl}-amino)-methyl]-benzoate |
| 120 | 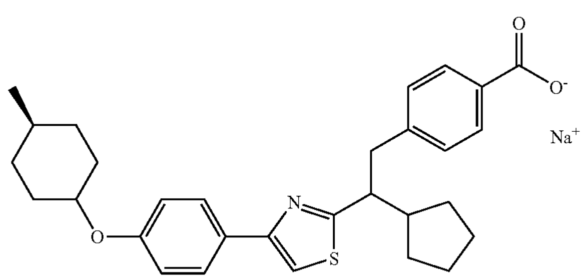 | Sodium 4-[(cyclopentyl-{4-[4-(trans-4-methyl-cyclohexyloxy)-phenyl]-thiazol-2-yl}-amino)-methyl]-benzoate |
| 121 | 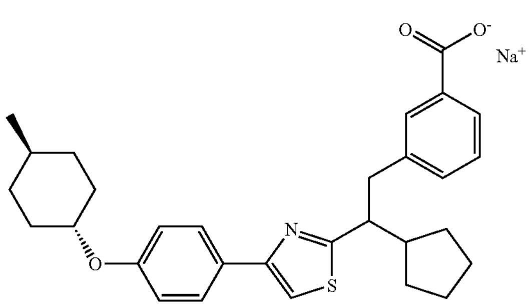 | Sodium 3-[(cyclopentyl-{4-[4-(trans-4-methyl-cyclohexyloxy)-phenyl]-thiazol-2-yl}-amino)-methyl]-benzoate |

TABLE 1-continued

| Example | Structure | Name |
|---|---|---|
| 122 | 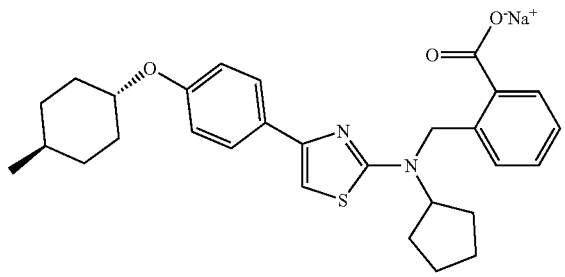 | Sodium 2-[(cyclopentyl-{4-[4-(trans-4-methyl-cyclohexyloxy)-phenyl]-thiazol-2-yl}-amino)-methyl]-benzoate |
| 123 | 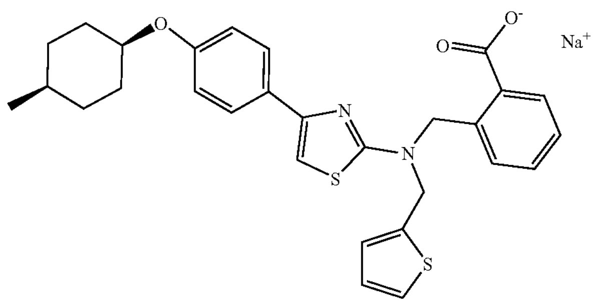 | Sodium 2-[({4-[4-(trans-4-methyl-cyclohexyloxy)-phenyl]-thiazol-2-yl}-thiophen-2-ylmethyl-amino)-methyl]-benzoate |
| 124 | 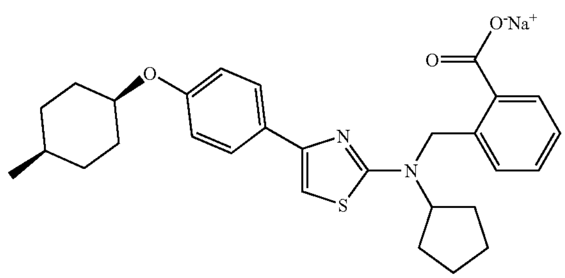 | Sodium 2-[(cyclopentyl-{4-[4-(cis-4-methyl-cyclohexyloxy)-phenyl]-thiazol-2-yl}-amino)-methyl)-benzoate |
| 125 | 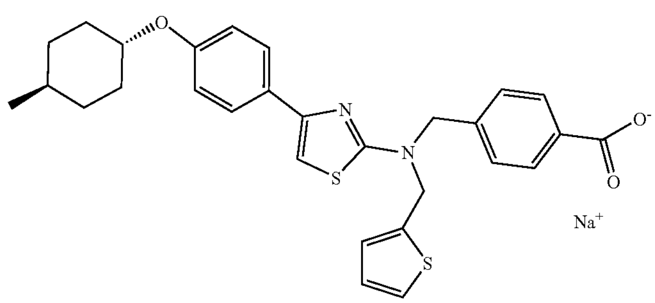 | Sodium 4-[({4-[4-(trans-4-methyl-cyclohexyloxy)-phenyl]-thiazol-2-yl}-thiophen-2-ylmethyl-amino)-methyl]-benzoate |
| 126 | 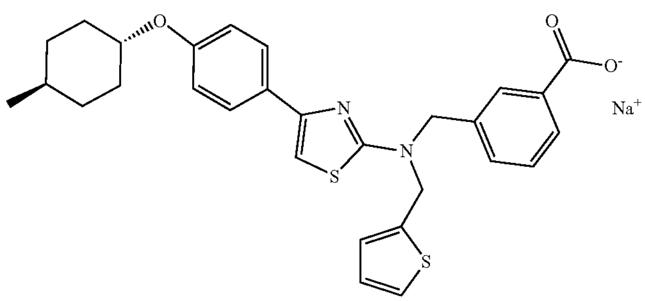 | Sodium 3-[({4-[4-(trans-4-methyl-cyclohexyloxy)-phenyl]-thiazol-2-yl}-thiophen-2-ylmethyl-amino)-methyl]-benzoate |

TABLE 1-continued

| Example | Structure | Name |
|---|---|---|
| 127 | 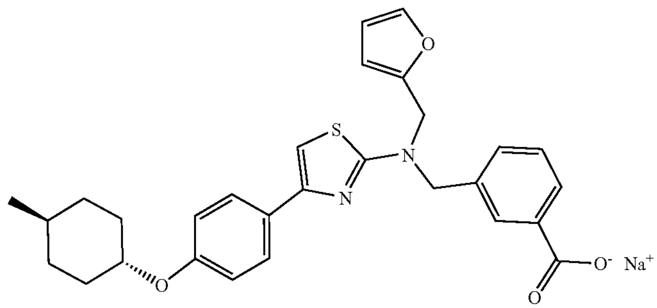 | Sodium 3-[(furan-2-ylmethyl-{4-[trans-4-(4-methyl-cyclohexyloxy)-phenyl]-thiazol-2-yl}-amino)-methyl]-benzoate |
| 128 | 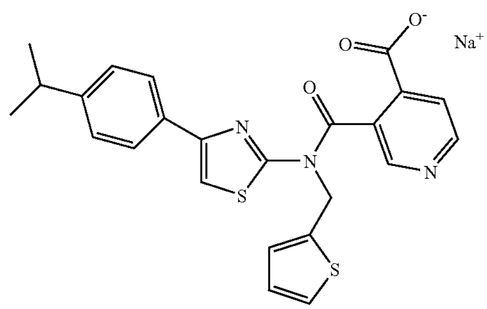 | Sodium 3-{[4-(4-isopropyl-phenyl)-thiazol-2-yl]-thiophen-2-ylmethyl-carbamoyl}-isonicotinate |
| 129 | 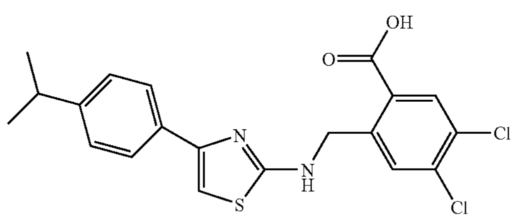 | 4,5-Dichloro-N-[4-(4-isopropyl-phenyl)-thiazol-2-yl]-phthalamic acid |
| 130 | 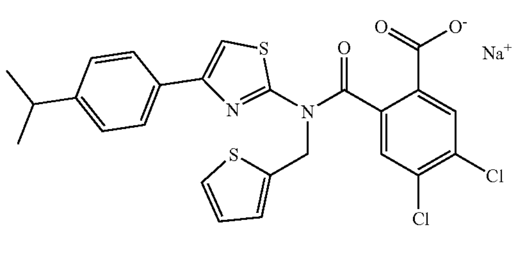 | Sodium 4,5-dichloro-2-{[4-(4-isopropyl-phenyl)-thiazol-2-yl]-thiophen-2-ylmethyl-carbamoyl}-benzoate |
| 131 | 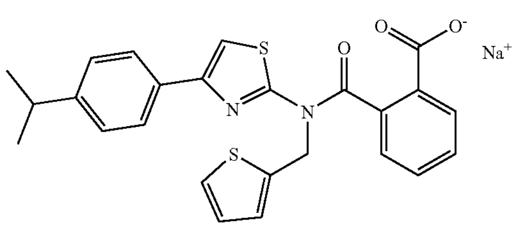 | Sodium 2-{[4-(4-isopropyl-phenyl)-thiazol-2-yl]-thiophen-2-ylmethyl-carbamoyl}-benzoate |

TABLE 1-continued

| Example | Structure | Name |
|---|---|---|
| 132 | 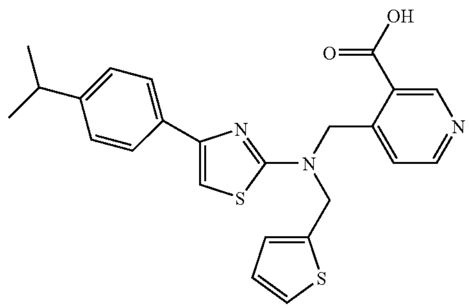 | 4-{[4-(4-Isopropyl-phenyl)-thiazol-2-yl]-thiophen-2-ylmethyl-carbamoyl}-nicotinic acid |
| 133 | 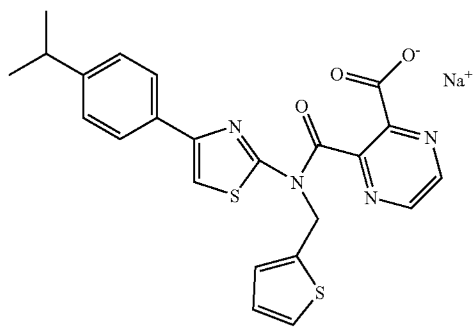 | Sodium 3-{[4-(4-isopropyl-phenyl)-thiazol-2-yl]-thiophen-2-ylmethyl-carbamoyl}-pyrazine-2-carboxylate |
| 134 | 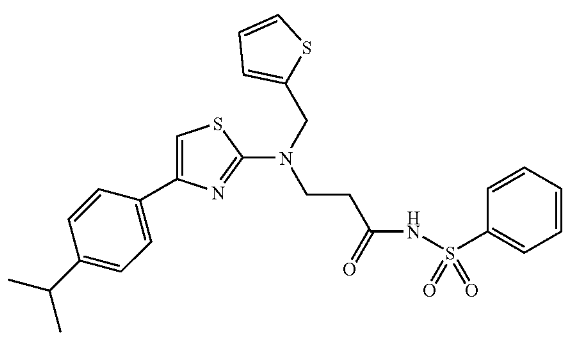 | N-(3-{[4-(4-Isopropyl-phenyl)-thiazol-2-yl]-thiophen-2-ylmethyl-amino}-propionyl)-benzenesulfonamide |
| 135 | 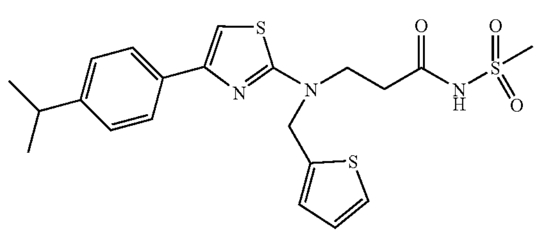 | N-(3-{[4-(4-Isopropyl-phenyl)-thiazol-2-yl]-thiophen-2-ylmethyl-amino}-propionyl)-methanesulfonamide |
| 136 | 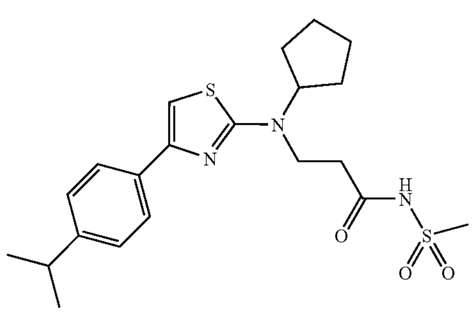 | N-(3-{Cyclopentyl-[4-(4-isopropyl-phenyl)-thiazol-2-yl]-amino}-propionyl)-methanesulfonamide |

TABLE 1-continued

| Example | Structure | Name |
|---|---|---|
| 137 | 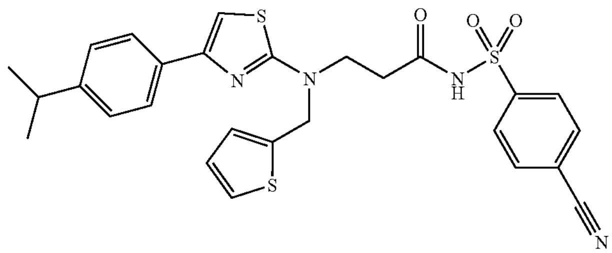 | 4-Cyano-N-(3-{[4-(4-isopropyl-phenyl)-thiazol-2-yl]-thiophen-2-ylmethyl-amino}-propionyl) benzenesulfonamide |
| 138 | 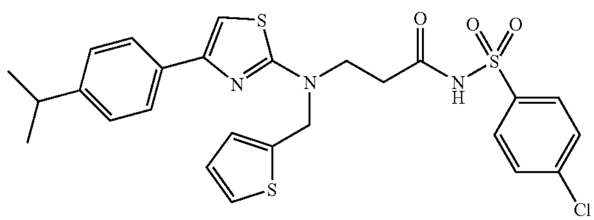 | 4-Chloro-N-(3-{[4-(4-isopropyl-phenyl)-thiazol-2-yl]-thiophen-2-ylmethyl-amino}-propionyl)-benzenesulfonamide |
| 139 | 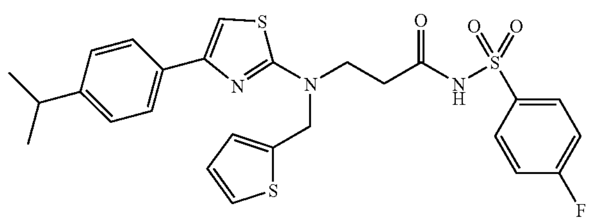 | 4-Fluoro-N-(3-{[4-(4-isopropyl-phenyl)-thiazol-2-yl]-thiophen-2-ylmethyl-amino}-propionyl)-benzenesulfonamide |
| 140 | 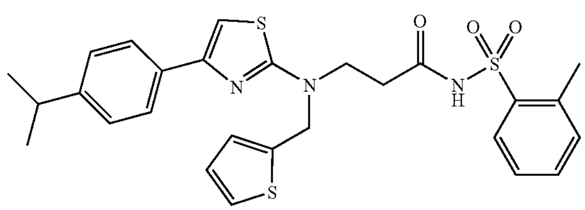 | N-(3-{[4-(4-Isopropyl-phenyl)-thiazol-2-yl]-thiophen-2-ylmethyl-amino}-propionyl)-2-methyl-benzenesulfonamide |
| 141 | 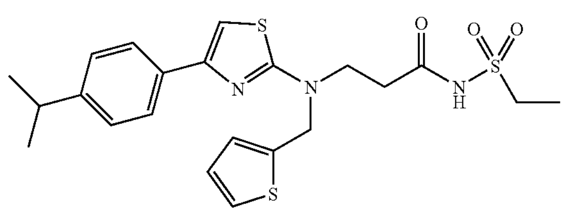 | Ethanesulfonic acid (3-{[4-(4-isopropyl-phenyl)-thiazol-2-yl]-thiophen-2-ylmethyl-amino}-propionyl)-amide |
| 142 | 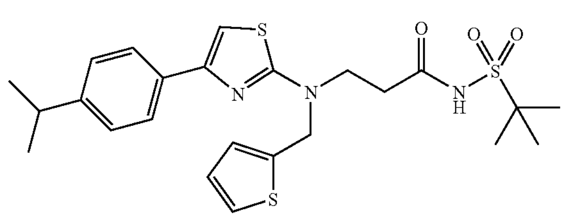 | 2-Methyl-propane-2-sulfonic acid (3-{[4-(4-isopropyl-phenyl)-thiazol-2-yl]-thiophen-2-ylmethyl-amino}-propionyl)-amide |

TABLE 1-continued

| Example | Structure | Name |
|---|---|---|
| 143 | 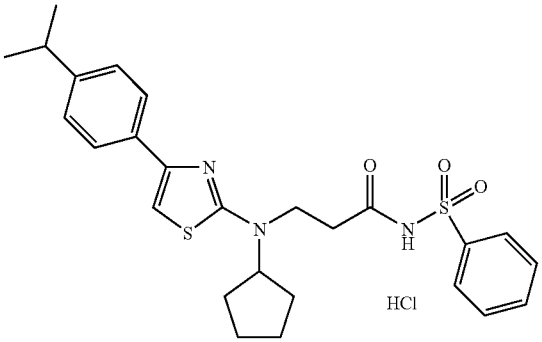 | N-(3-{Cyclopentyl-[4-(4-isopropyl-phenyl)-thiazol-2-yl]-amino}-propionyl)-benzenesulfonamide Hydrochloride |
| 144 | 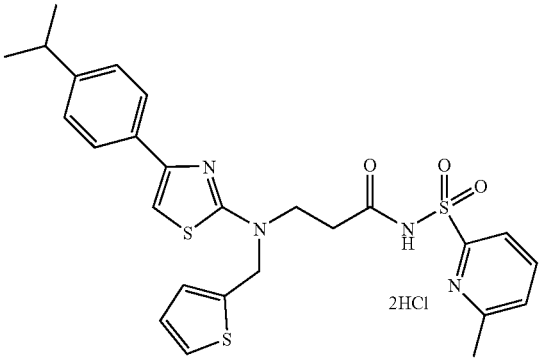 | 6-Methyl-pyridine-2-sulfonic acid (3-{[4-(4-isopropyl-phenyl)-thiazol-2-yl]-thiophen-2-ylmethyl-amino}-propionyl)-amide Dihydrochloride |
| 145 | 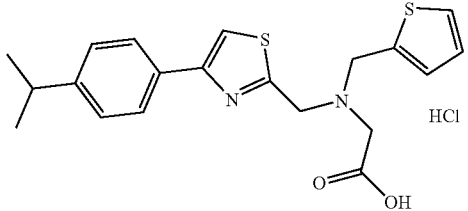 | {[4-(4-Isopropyl-phenyl)-thiazol-2-ylmethyl]-thiophen-2-ylmethyl-amino}-acetic acid Hydrochloride |
| 146 | 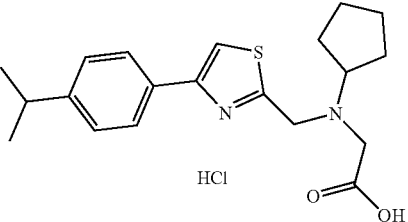 | {Cyclopentyl-[4-(4-isopropyl-phenyl)-thiazol-2-ylmethyl]-amino}-acetic acid Hydrochloride |
| 147 | 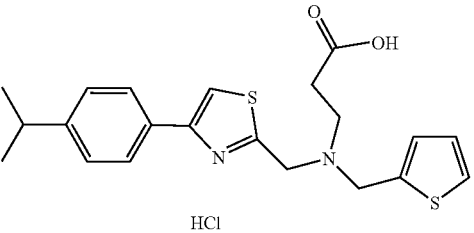 | 3-{[4-(4-Isopropyl-phenyl)-thiazol-2-ylmethyl]-thiophen-2-ylmethyl-amino}-propionic acid Hydrochloride |

TABLE 1-continued

| Example | Structure | Name |
|---|---|---|
| 148 | 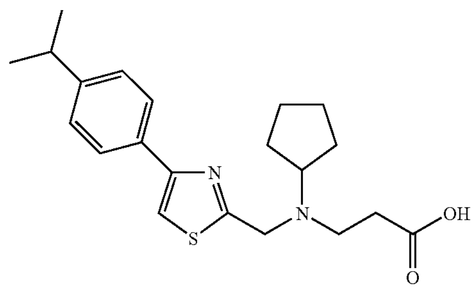 | 3-{Cyclopentyl-[4-(4-isopropyl-phenyl)-thiazol-2-ylmethyl]-amino}-propionic acid Hydrochloride |
| 149 | 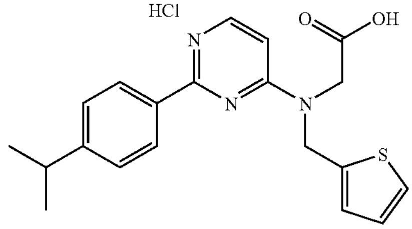 | {[2-(4-Isopropyl-phenyl)-pyrimidin-4-yl]-thiophen-2-ylmethyl-amino}-acetic acid Hydrochloride |
| 150 | 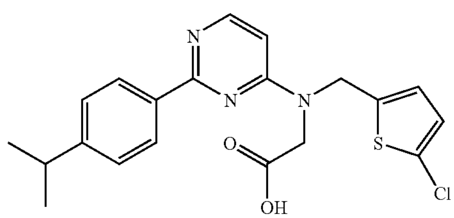 | {(5-Chloro-thiophen-2-ylmethyl)-[2-(4-isopropyl-phenyl)-pyrimidin-4-yl]-amino}-acetic acid Hydrochloride |
| 151 | 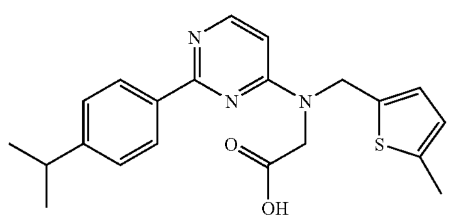 | [[2-(4-Isopropyl-phenyl)-pyrimidin-4-yl]-(5-methyl-thiophen-2-ylmethyl)-amino]-acetic acid |
| 152 | 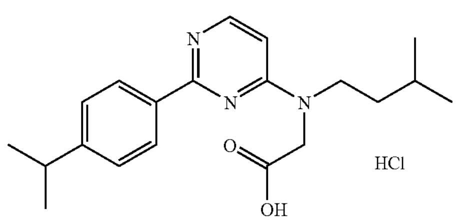 | [[2-(4-Isopropyl-phenyl)-pyrimidin-4-yl]-(3-methyl-butyl)-amino]-acetic acid Hydrochloride |
| 153 | 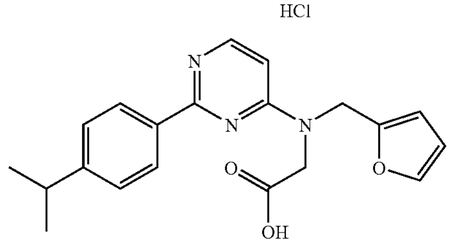 | {Furan-2-ylmethyl-[2-(4-isopropyl-phenyl)-pyrimidin-4-yl]-amino}-acetic acid Hydrochloride |

TABLE 1-continued

| Example | Structure | Name |
|---|---|---|
| 154 | 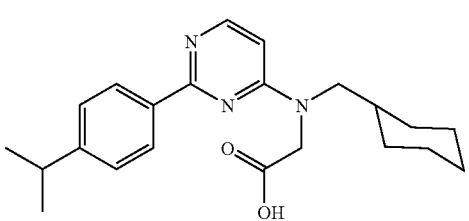 HCl | {Cyclohexylmethyl-[2-(4-isopropyl-phenyl)-pyrimidin-4-yl]-amino}-acetic acid Hydrochloride |
| 155 | 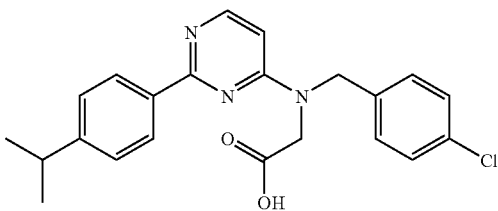 HCl | {(4-Chloro-benzyl)-[2-(4-isopropyl-phenyl)-pyrimidin-4-yl]-amino}-acetic acid Hydrochloride |
| 156 | 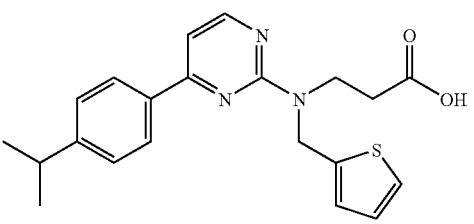 HCl | 3-{[4-(4-Isopropyl-phenyl)-pyrimidin-2-yl]-thiophen-2-ylmethyl-amino}-propionic acid Hydrochloride |
| 157 | 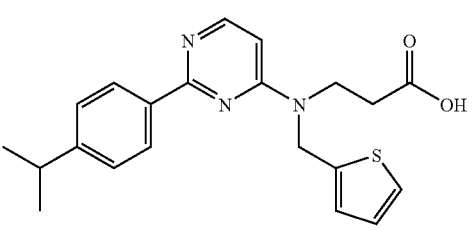 HCl | 3-{[2-(4-Isopropyl-phenyl)-pyrimidin-4-yl]-thiophen-2-ylmethyl-amino}-propionic acid Hydrochloride |
| 158 | 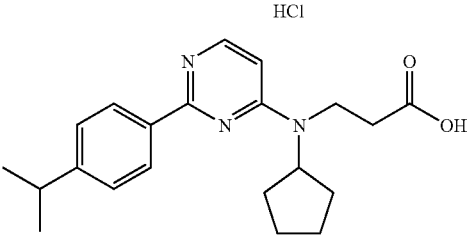 HCl | 3-{Cyclopentyl-[2-(4-isopropyl-phenyl)-pyrimidin-4-yl]-amino}-propionic acid Hydrochloride |
| 159 | 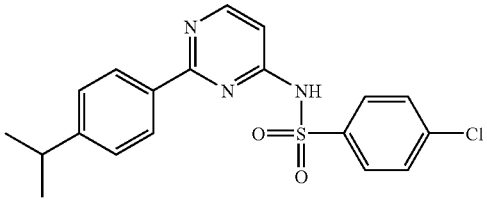 | 4-Chloro-N-[2-(4-isopropyl-phenyl)-pyrimidin-4-yl]-benzenesulfonamide |

TABLE 1-continued

| Example | Structure | Name |
|---|---|---|
| 160 | 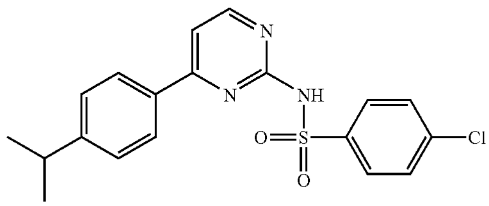 | 4-Chloro-N-[2-(4-isopropyl-phenyl)-pyrimidin-4-yl]-benzenesulfonamide |
| 161 | 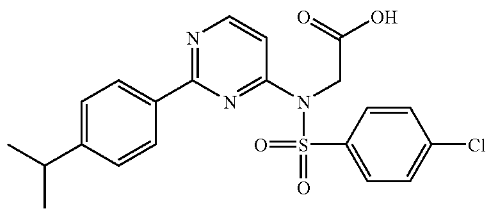 | {(4-Chloro-benzenesulfonyl)-[2-(4-isopropyl-phenyl)-pyrimidin-4-yl]-amino}-acetic acid |
| 162 | 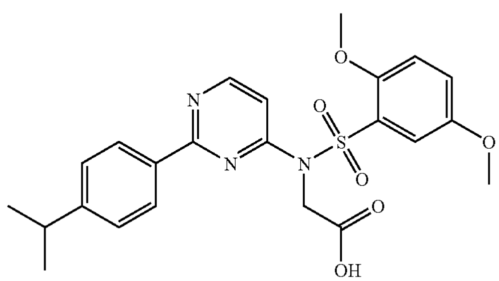 | {(2,5-Dimethoxy-benzenesulfonyl)-[2-(4-isopropyl-phenyl)-pyrimidin-4-yl]-amino}-acetic acid |
| 163 | 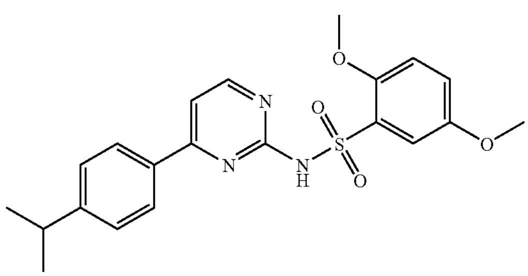 | N-[4-(4-Isopropyl-phenyl)-pyrimidin-2-yl]-2,5-dimethoxy-benzenesulfonamide |
| 164 | 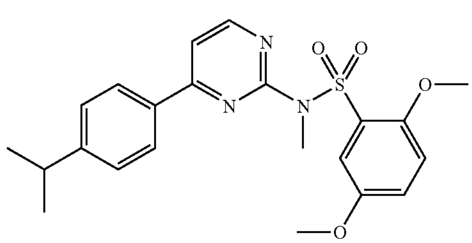 | N-[4-(4-Isopropyl-phenyl)-pyrimidin-2-yl]-2,5-dimethoxy-N-methyl-benzenesulfonamide |
| 165 | 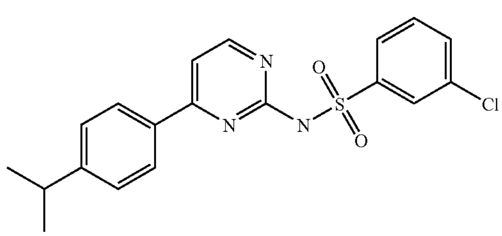 | 3-Chloro-N-[4-(4-isopropyl-phenyl)-pyrimidin-2-yl]-benzenesulfonamide |

TABLE 1-continued

| Example | Structure | Name |
|---|---|---|
| 166 | 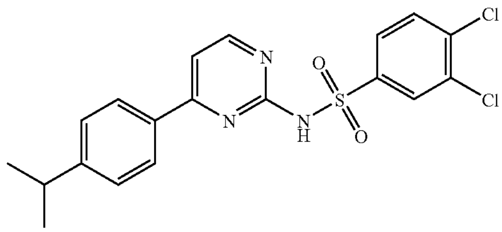 | 3,4-Dichloro-N-[4-(4-isopropyl-phenyl)-pyrimidin-2-yl]-benzenesulfonamide |
| 167 | 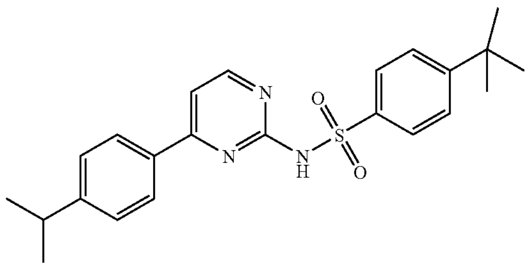 | 4-tert-Butyl-N-[4-(4-isopropyl-phenyl)-pyrimidin-2-yl]-benzenesulfonamide |
| 168 | 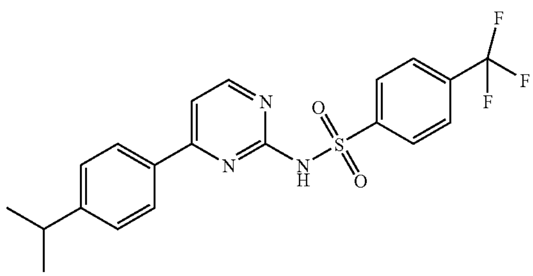 | N-[4-(4-Isopropyl-phenyl)-pyrimidin-2-yl]-4-trifluoromethyl-benzenesulfonamide |
| 169 | 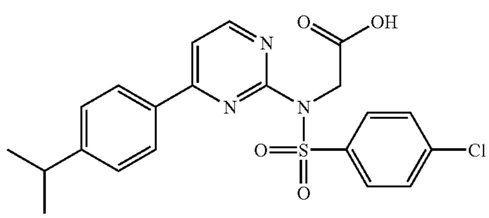 | {(4-Chloro-benzenesulfonyl)-[4-(4-isopropyl-phenyl)-pyrimidin-2-yl]-amino}-acetic acid |
| 170 | 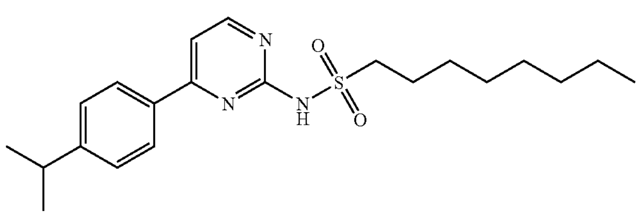 | Octane-1-sulfonic acid [4-(4-isopropyl-phenyl)-pyrimidin-2-yl]-amide |
| 171 | 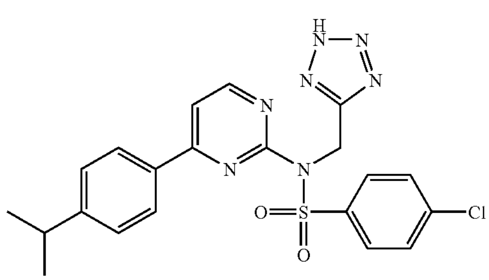 | 4-Chloro-N-[4-(4-isopropyl-phenyl)-pyrimidin-2-yl]-N-(1H-tetrazol-5-yl methyl)-benzenesulfonamide |

TABLE 1-continued

| Example | Structure | Name |
|---|---|---|
| 172 | 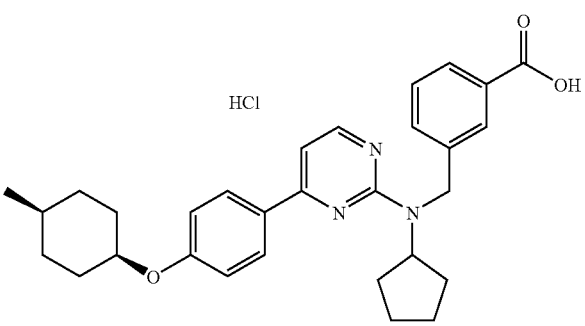 | 3-[(Cyclopentyl-{4-[4-(cis-4-methyl-cyclohexyloxy)-phenyl]-pyrimidin-2-yl}-amino)-methyl]-benzoic acid Hydrochloride |
| 173 | 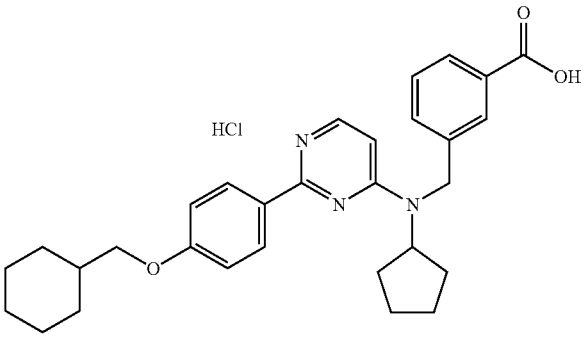 | 3-({[2-(4-Cyclohexylmethoxy-phenyl)-pyrimidin-4-yl]-cyclopentyl-amino}-methyl)-benzoic acid Hydrochloride |
| 174 | 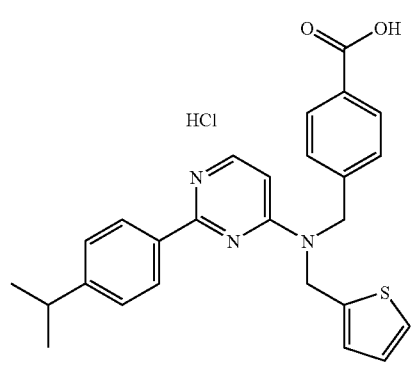 | 4-({[2-(4-Isopropyl-phenyl)-pyrimidin-4-yl]-thiophen-2-ylmethyl-amino}-methyl)-benzoic acid Hydrochloride |
| 175 | 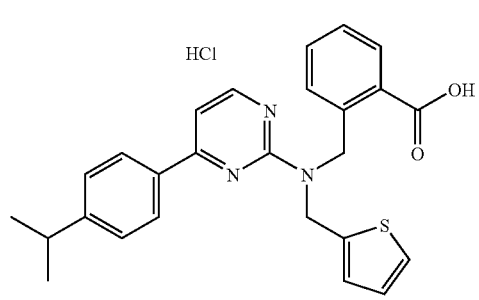 | 2-({[4-(4-Isopropyl-phenyl)-pyrimidin-2-yl]-thiophen-2-ylmethyl-amino}-methyl)-benzoic acid Hydrochloride |

TABLE 1-continued

| Example | Structure | Name |
|---|---|---|
| 176 | 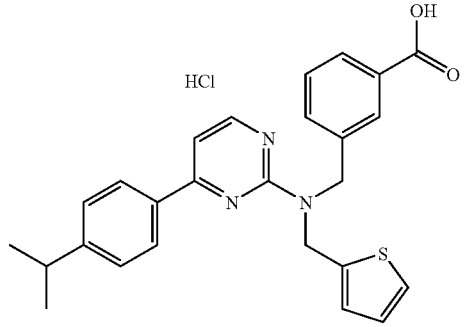 | 3-({[4-(4-Isopropyl-phenyl)-pyrimidin-2-yl]-thiophen-2-ylmethyl-amino}-methyl)-benzoic acid Hydrochloride |
| 177 | 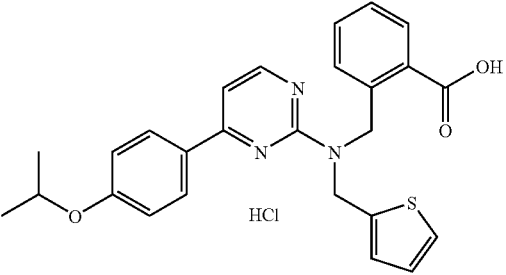 | 2-({[4-(4-Isopropoxy-phenyl)-pyrimidin-2-yl]-thiophen-2-ylmethyl-amino}-methyl)-benzoic acid Hydrochloride |
| 178 | 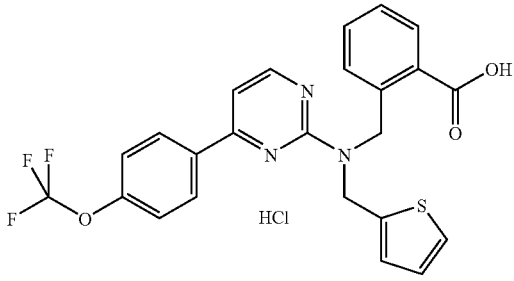 | 2-({Thiophen-2-ylmethyl-[4-(4-trifluoromethoxy-phenyl)-pyrimidin-2-yl]-amino}-methyl)-benzoic acid Hydrochloride |
| 179 | 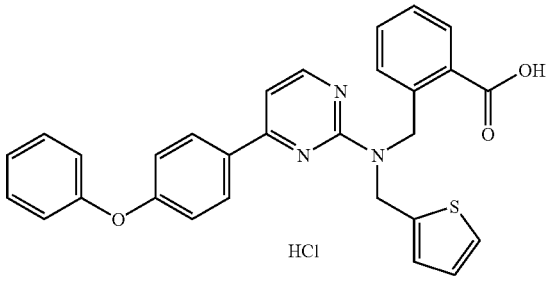 | 2-({[4-(4-Phenoxy-phenyl)-pyrimidin-2-yl]-thiophen-2-ylmethyl-amino}-methyl)-benzoic acid Hydrochloride |
| 180 | 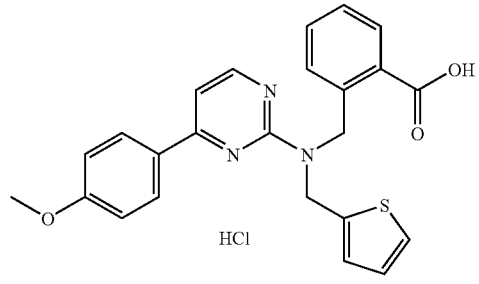 | 2-({[4-(4-Methoxy-phenyl)-pyrimidin-2-yl]-thiophen-2-ylmethyl-amino}-methyl)-benzoic acid Hydrochloride |

TABLE 1-continued

| Example | Structure | Name |
|---|---|---|
| 181 | 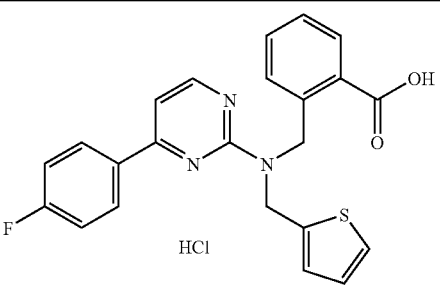 | 2-({[4-(4-Fluoro-phenyl)-pyrimidin-2-yl]-thiophen-2-ylmethyl-amino}-methyl)-benzoic acid Hydrochloride |
| 182 | 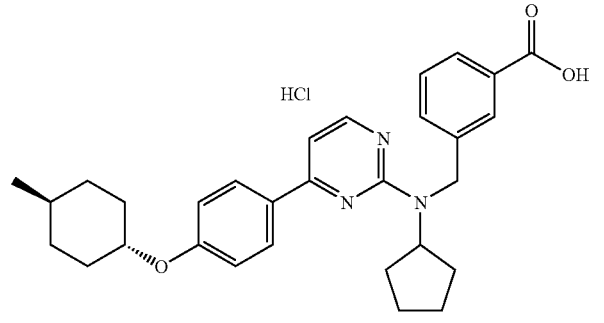 | 3-[(Cyclopentyl-{4-[4-(trans-4-methyl-cyclohexyloxy)-phenyl]-pyrimidin-2-yl}-amino)-methyl]-benzoic acid Hydrochloride |
| 183 | 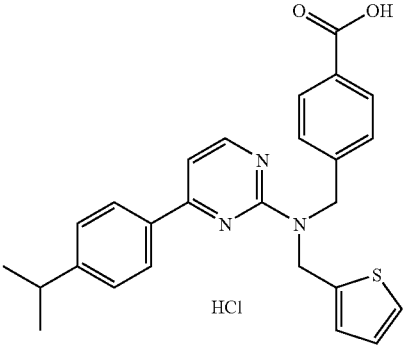 | 4-({[4-(4-Isopropyl-phenyl)-pyrimidin-2-yl]-thiophen-2-ylmethyl-amino}-methyl)-benzoic acid Hydrochloride |
| 184 | 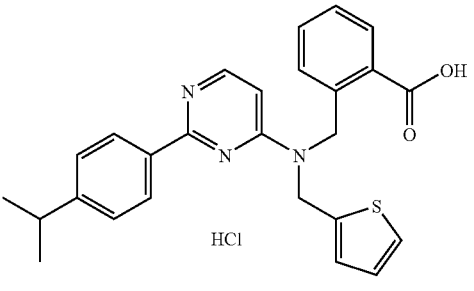 | 2-({[2-(4-Isopropyl-phenyl)-pyrimidin-4-yl]-thiophen-2-ylmethyl-amino}-methyl)-benzoic acid Hydrochloride |
| 185 | 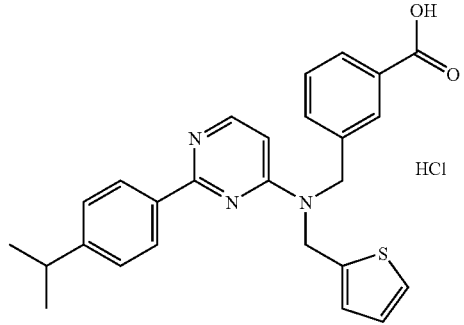 | 3-({[2-(4-Isopropyl-phenyl)-pyrimidin-4-yl]-thiophen-2-ylmethyl-amino}-methyl)-benzoic acid Hydrochloride |

TABLE 1-continued

| Example | Structure | Name |
|---|---|---|
| 186 | 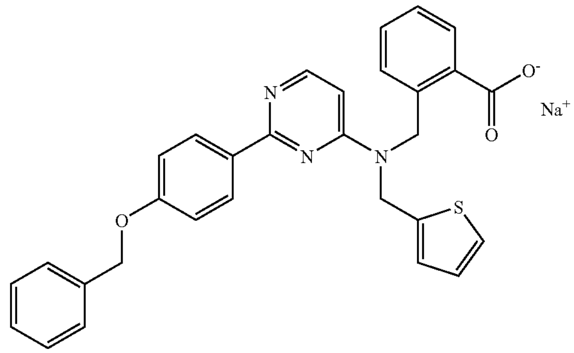 | Sodium 2-({[2-(4-benzyloxy-phenyl)-pyrimidin-4-yl]-thiophen-2-ylmethyl-amino}-methyl)-benzoate |
| 187 | 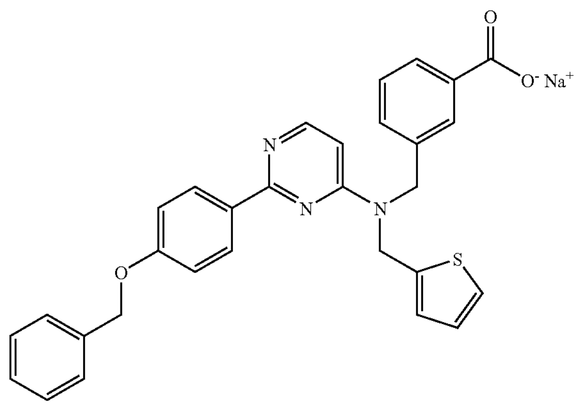 | Sodium 3-({[2-(4-benzyloxy-phenyl)-pyrimidin-4-yl]-thiophen-2-ylmethyl-amino}-methyl)-benzoate |
| 188 | 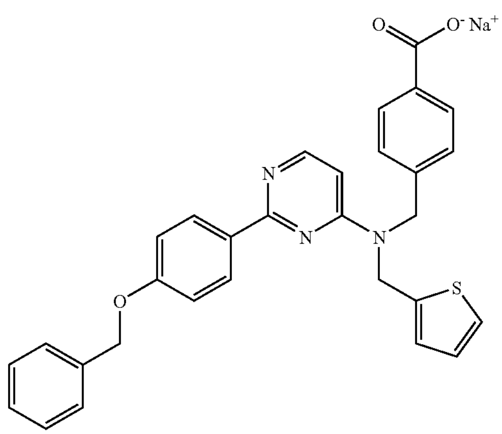 | Sodium 4-({[2-(4-benzyloxy-phenyl)-pyrimidin-4-yl]-thiophen-2-ylmethyl-amino}-methyl)-benzoate |
| 189 | 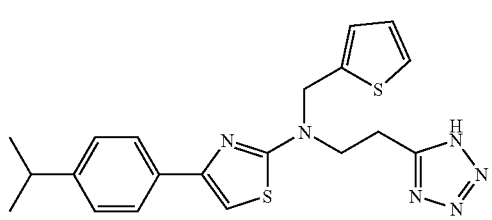 | [4-(4-Isopropyl-phenyl)-thiazol-2-yl]-[2-(1H-tetrazol-5-yl)-ethyl]-thiophen-2-ylmethyl-amine |

TABLE 1-continued

| Example | Structure | Name |
|---|---|---|
| 190 | 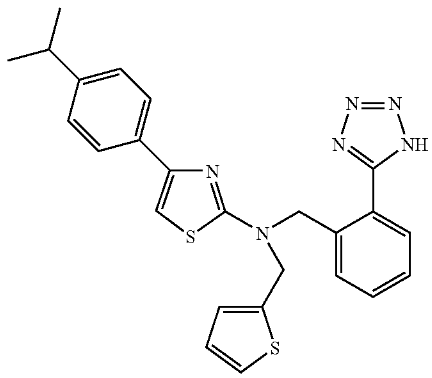 | [4-(4-Isopropyl-phenyl)-thiazol-2-yl]-[2-(1H-tetrazol-5-yl)-benzyl]-thiophen-2-ylmethyl-amine |
| 191 | 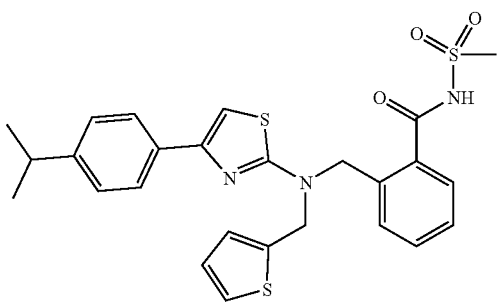 | N-[2-({[4-(4-Isopropyl-phenyl)-thiazol-2-yl]-thiophen-2-ylmethyl-amino}-methyl)-benzoyl]-methanesulfonamide |
| 192 | 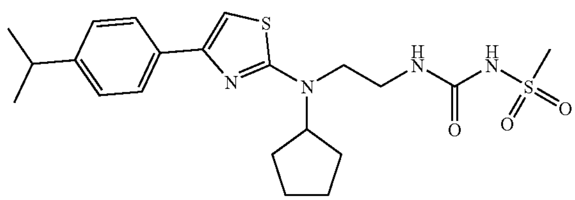 | N-[({2-[[4-(4-isopropylphenyl)-1,3-thiazol-2-yl](cyclopentyl)amino]ethyl}amino)carbonyl]methanesulfonamide |
| 193 | 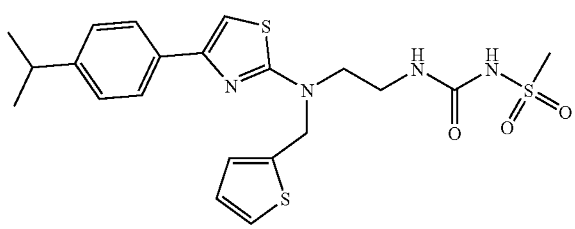 | N-[({2-[[4-(4-isopropylphenyl)-1,3-thiazol-2-yl](2-thiophenemethyl)amino]ethyl}amino)carbonyl]methanesulfonamide |
| 194 | 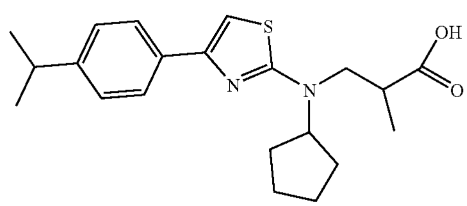 | 3-{Cyclopentyl-[4-(4-isopropyl-phenyl)-thiazol-2-yl]-amino}-2-methyl-propionic acid |
| 195 | 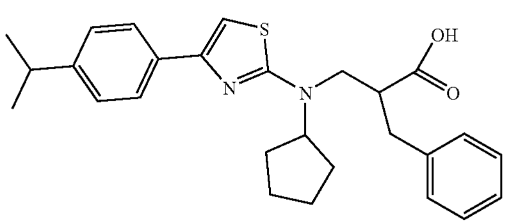 | 2-Benzyl-3-{cyclopentyl-[4-(4-isopropyl-phenyl)-thiazol-2-yl]-amino}-propionic acid |

TABLE 1-continued

| Example | Structure | Name |
|---|---|---|
| 196 | 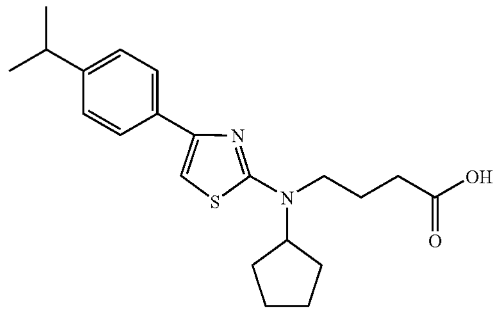 | 4-{Cyclopentyl-[4-(4-isopropyl-phenyl)-thiazol-2-yl]-amino}-butyric acid |
| 197 | 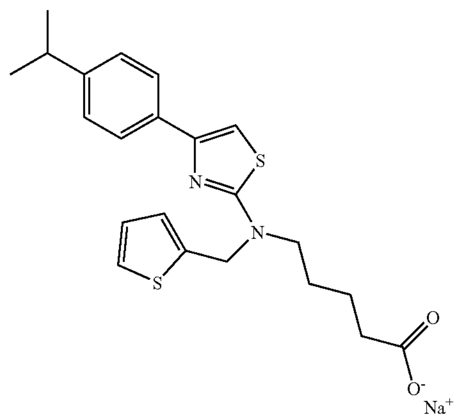 | Sodium 5-{[4-(4-isopropyl-phenyl)-thiazol-2-yl]-thiophen-2-ylmethyl-amino}-pentanoate |
| 198 | 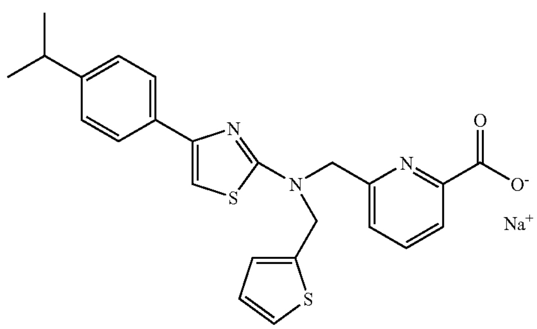 | Sodium 6-({[4-(4-isopropyl-phenyl)-thiazol-2-yl]-thiophen-2-ylmethyl-amino}-methyl) pyridine-2-carboxylate |
| 199 | 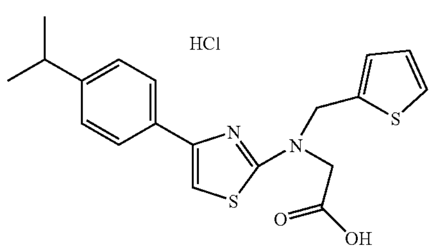 | {[4-(4-Isopropyl-phenyl)-thiazol-2-yl]-thiophen-2-ylmethyl-amino}-acetic acid Hydrochloride |
| 200 | 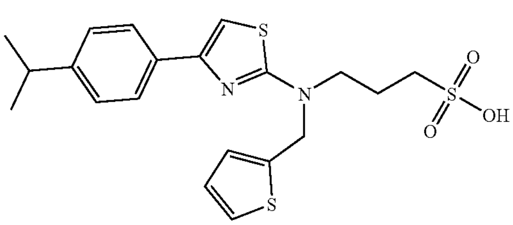 | 3-{[4-(4-Isopropyl-phenyl)-thiazol-2-yl]-thiophen-2-ylmethyl-amino}-propane-1-sulfonic acid |

TABLE 1-continued

| Example | Structure | Name |
|---|---|---|
| 201 | 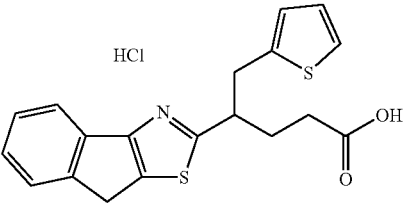 | 3-[(8H-Indeno[1,2-d]thiazol-2-yl)-thiophen-2-ylmethyl-amino]-propionic acid Hydrochloride |
| 202 | 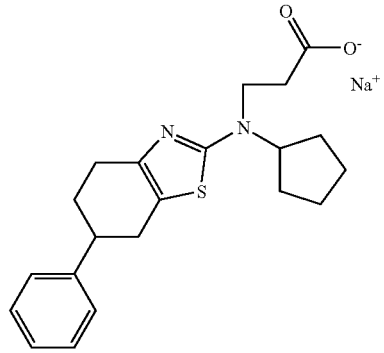 | Sodium 3-[Cyclopentyl-(6-phenyl-4,5,6,7-tetrahydro-benzothiazol-2-yl)-amino]-propionate |
| 203 | 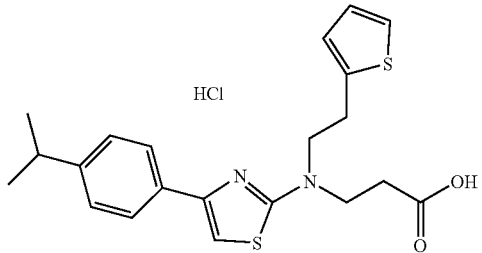 | 3-[[4-(4-Isopropyl-phenyl)-thiazol-2-yl]-(2-thiophen-2-yl-ethyl)-amino]-propionic acid Hydrochloride |
| 204 | 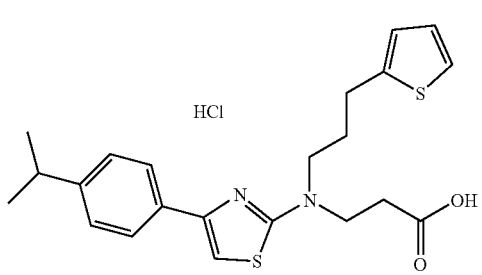 | 3-[[4-(4-isopropyl-phenyl)-thiazol-2-yl]-(3-thiophen-2-yl-propyl)-amino]-propionic acid Hydrochloride |
| 205 | 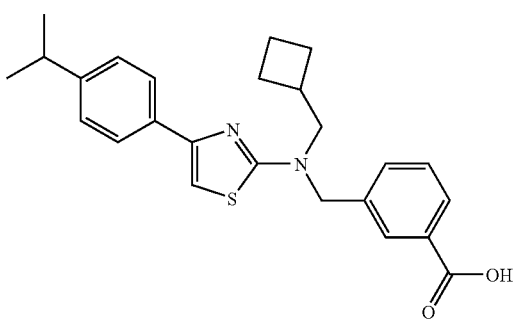 | 3-({Cyclobutylmethyl-[4-(4-isopropyl-phenyl)-thiazol-2-yl]-amino}-methyl)-benzoic acid |

TABLE 1-continued

| Example | Structure | Name |
|---|---|---|
| 206 | 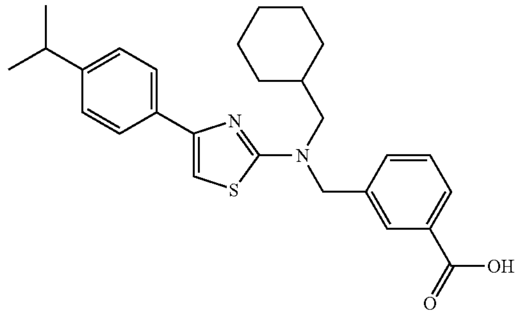 | 3-({Cyclohexylmethyl-[4-(4-isopropyl-phenyl)-thiazol-2-yl]-amino}-methyl)-benzoic acid |
| 207 | 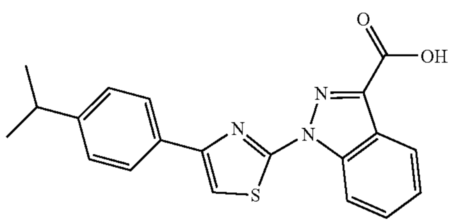 | 1-[4-(4-Isopropyl-phenyl)-thiazol-2-yl]-1H-indazole-3-carboxylic acid |
| 208 | 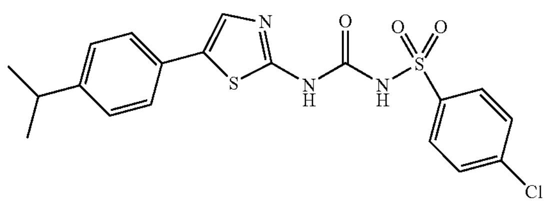 | 1-(4-Chloro-benzenesulfonyl)-3-[5-(4-isopropyl-phenyl)-thiazol-2-yl]-urea |
| 209 | 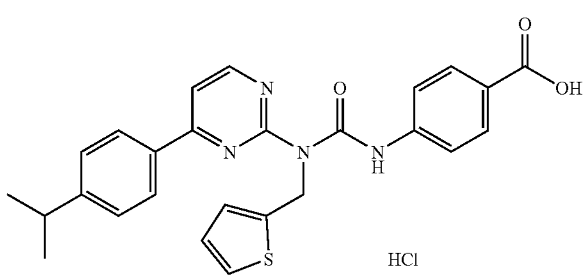 | 4-{3-[4-(4-isopropyl-phenyl)-pyrimidin-2-yl]-3-thiophen-2-ylmethyl-ureido}-benzoic acid Hydrochloride |
| 210 | 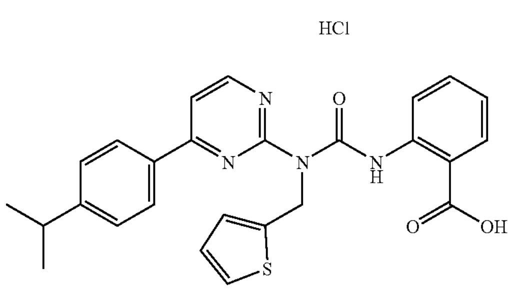 | 2-{3-[4-(4-Isopropyl-phenyl)-pyrimidin-2-yl]-3-thiophen-2-ylmethyl-ureido}-benzoic acid Hydrochloride |

TABLE 1-continued

| Example | Structure | Name |
|---|---|---|
| 211 | 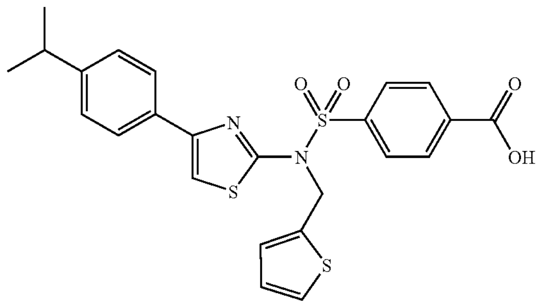 | 4-{[4-(4-Isopropyl-phenyl)thiazol-2-yl]-thiophen-2-ylmethyl-sulfamoyl}-benzoic acid |
| 212 | 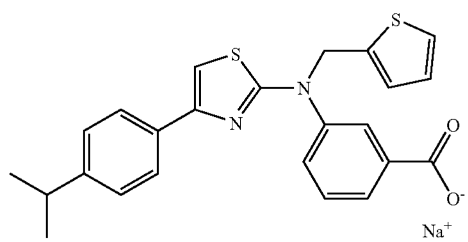 | Sodium 3-{[4-(4-Isopropyl-phenyl)-thiazol-2-yl]-thiophen-2-ylmethyl-amino}-benzoate |
| 213 | 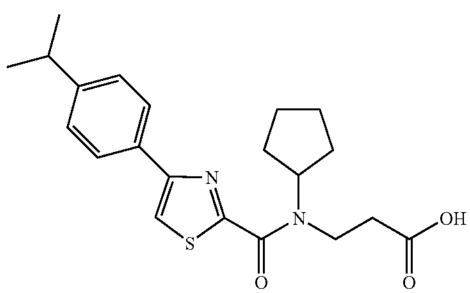 | 3-{Cyclopentyl-[4-(4-isopropyl-phenyl)-thiazole-2-carbonyl]-amino}-propionic acid |
| 214 | 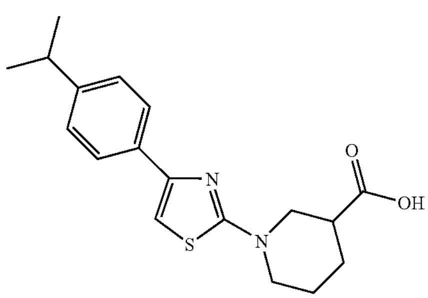 | 1-[4-(4-isopropyl-phenyl)-thiazol-2-yl]-piperidine-3-carboxylic acid |
| 215 | 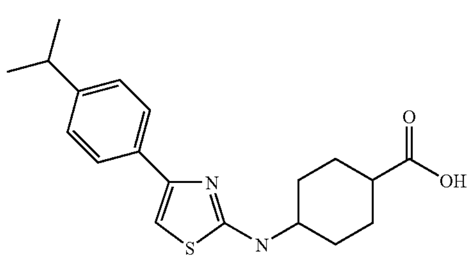 | 4-[4-(4-isopropyl-phenyl)-thiazol-2-ylamino]-cyclohexanecarboxylic acid |

TABLE 1-continued

| Example | Structure | Name |
|---|---|---|
| 216 | 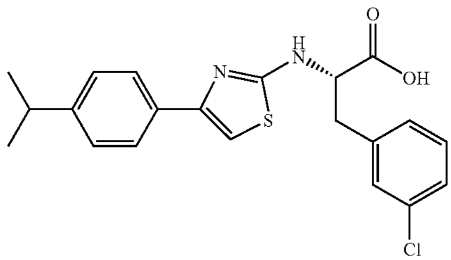 | 3-(3-Chloro-phenyl)-2-[4-(4-isopropyl phenyl)-thiazol-2-ylamino]-propionic acid |
| 217 | 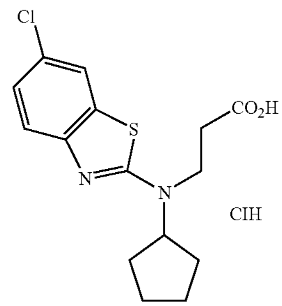 | 3-[(6-Chloro-benzothiazol-2-yl)-cyclopentyl-amino]-propionic acid Hydrochloride |
| 218 | 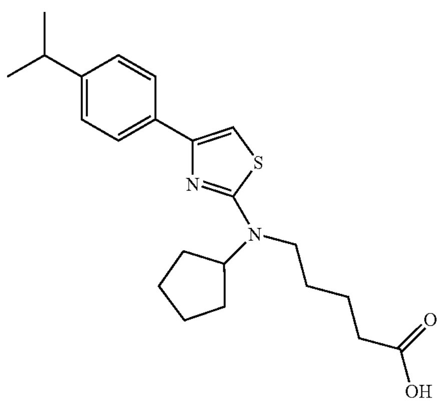 | 5-{Cyclopentyl-[4-(4-isopropyl-phenyl)-thiazol-2-yl]-amino}-pentanoic acid |

Incomplete valences for heteroatoms such as oxygen and nitrogen in the chemical structures listed in Table 1 are assumed to be completed by hydrogen.

In another aspect, the present invention comprises a pharmaceutical composition comprising the compound of Formula (I) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms. The term "alkylene" refers to a straight or branched chain divalent hydrocarbon radical having from one to ten carbon atoms. The term "alkyline" refers to a straight or branched chain trivalent hydrocarbon radical having from one to ten carbon atoms. Alkyl, alkylene, and alkyline groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl", "alkylene", or "alkyline" group may containing one or more O, S, S(O), or $S(O)_2$ atoms. Examples of "alkyl" as used herein include, but are not limited to, methyl, n-butyl, t-butyl, n-pentyl, isobutyl, and isopropyl, and the like. Examples of "alkylene" as used herein include, but are not limited to, methylene, ethylene, and the like. Examples of "alkyline" as used herein include, but are not limited to, methine, 1,1,2-ethyline, and the like. Examples of "alkyline" as used herein include, but are not limited to, methine, 1,1,2-ethyline, and the like.

As used herein, the term "alkenyl" refers to a hydrocarbon radical having from two to ten carbons and at least one carbon-carbon double bond. The term "alkenylene" refers to a straight or branched chain divalent hydrocarbon radical having from two to ten carbon atoms and one or more carbon-carbon double bonds. The term "alkenyline" refers to a hydrocarbon triradical having from two to ten carbons and at least one carbon-carbon double bond. The alkenyl, alkenylene, and alkenyline groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl", "alkenylene", and "alkenyline" group may containing one or more O, S, S(O), or $S(O)_2$ atoms. Examples of "alkenylene" as used herein include, but are not limited to, ethene-1,2-diyl, propene-1,3-diyl, and the like. Examples of "alkenyline" as used herein include, but are not limited to, 1,1,3-propene-1,1,2-triyl, ethene 1,1,2-triyl, and the like.

As used herein, the term "alkynyl" refers to a hydrocarbon radical having from two to ten carbons and at least one carbon-carbon triple bond. The term "alkynylene" refers to a straight or branched chain divalent hydrocarbon radical having from two to ten carbon atoms and one or more carbon-carbon triple bonds. The alkynyl and alkynylene groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ atoms. Examples of "alkynylene" as used herein include, but are not limited to, ethyne-1,2-diyl, propyne-1,3-diyl, and the like.

As used herein, "cycloalkyl" refers to an alicyclic hydrocarbon group optionally possessing one or more degrees of unsaturation, having from three to twelve carbon atoms. The term "cycloalkylene" refers to an non-aromatic alicyclic divalent hydrocarbon radical having from three to twelve carbon atoms and optionally possessing one or more degrees of unsaturation. The cycloalkyl and cycloalkylene groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring. The term "heterocyclylene" refers to a three to twelve-membered heterocyclic ring diradical. The heterocyclic or heterocyclyl groups may optionally possess one or more degrees of unsaturation, and must contain one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such heterocyclic or hetercyclylene may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to an optionally substituted benzene ring system fused to one or more optionally substituted benzene rings. The term "arylene" refers to a benzene ring diradical or to a benzene ring system diradical fused to one or more optionally substituted benzene rings. The aryl or arylene groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions. The term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions. The heteroaryl and heteroarylene groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to one or more cycloalkyl groups fused to an aryl group, the aryl and cycloalkyl groups having two atoms in common, and wherein the aryl group is the point of substitution. Examples of "fused cycloalkylaryl" used herein include 5-indanyl, 5,6,7,8-tetrahydro-2-naphthyl,

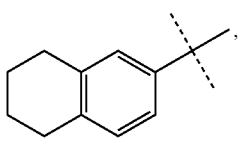

and the like.

As used herein, the term "fused cycloalkylarylene" refers to a fused cycloalkylaryl, wherein the aryl group is divalent. Examples include

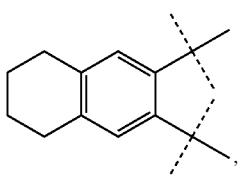

and the like.

As used herein, the term "fused arylcycloalkyl" refers to one or more aryl groups fused to a cycloalkyl group, the cycloalkyl and aryl groups having two atoms in common, and wherein the cycloalkyl group is the point of substitution. Examples of "fused arylcycloalkyl" used herein include 1-indanyl, 2-indanyl, 9-fluorenyl, 1-(1,2,3,4-tetrahydronaphthyl),

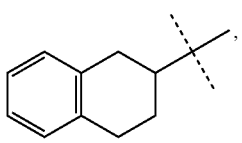

and the like.

As used herein, the term "fused arylcycloalkylene" refers to a fused arylcycloalkyl, wherein the cycloalkyl group is divalent. Examples include 9,1-fluorenylene,

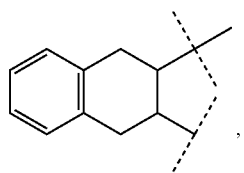 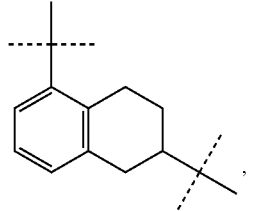

and the like.

As used herein, the term "fused heterocyclylaryl" refers to one or more heterocyclyl groups fused to an aryl group, the aryl and heterocyclyl groups having two atoms in common, and wherein the aryl group is the point of substitution.

Examples of "fused heterocyclylaryl" used herein include 3,4-methylenedioxy-1-phenyl,

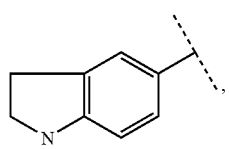

and the like.

As used herein, the term "fused heterocyclylarylene" refers to a fused heterocyclylaryl, wherein the aryl group is divalent. Examples include

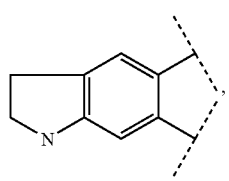

and the like.

As used herein, the term "fused arylheterocyclyl" refers to one or more aryl groups fused to a heterocyclyl group, the heterocyclyl and aryl groups having two atoms in common, and wherein the heterocyclyl group is the point of substitution. Examples of "fused arylheterocyclyl" used herein include 2-(1,3-benzodioxolyl),

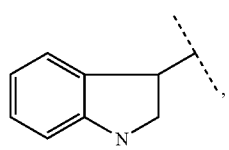

and the like.

As used herein, the term "fused arylheterocyclylene" refers to a fused arylheterocyclyl, wherein the heterocyclyl group is divalent. Examples include

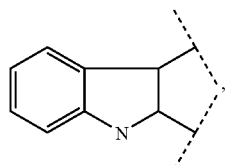

and the like.

As used herein, the term "fused cycloalkylheteroaryl" refers to one or more cycloalkyl groups fused to a heteroaryl group, the heteroaryl and cycloalkyl groups having two atoms in common, and wherein the heteroaryl group is the point of substitution. Examples of "fused cycloalkylheteroaryl" used herein include 5-aza-6-indanyl,

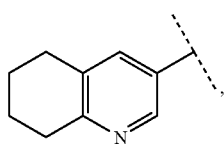

and the like.

As used herein, the term "fused cycloalkylheteroarylene" refers to a fused cycloalkylheteroaryl, wherein the heteroaryl group is divalent. Examples include

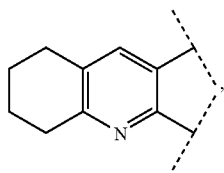

and the like.

As used herein, the term "fused heteroarylcycloalkyl" refers to one or more heteroaryl groups fused to a cycloalkyl group, the cycloalkyl and heteroaryl groups having two atoms in common, and wherein the cycloalkyl group is the point of substitution. Examples of "fused heteroarylcycloalkyl" used herein include 5-aza-1-indanyl,

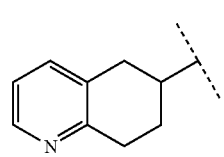

and the like.

As used herein, the term "fused heteroarylcycloalkylene" refers to a fused heteroarylcycloalkyl, wherein the cycloalkyl group is divalent. Examples include

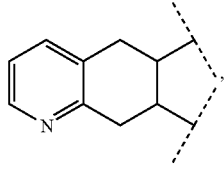

and the like.

As used herein, the term "fused heterocyclylheteroaryl" refers to one or more heterocyclyl groups fused to a heteroaryl group, the heteroaryl and heterocyclyl groups having two atoms in common, and wherein the heteroaryl group is the point of substitution. Examples of "fused heterocyclylheteroaryl" used herein include 1,2,3,4-tetrahydro-beta-carbolin-8-yl,

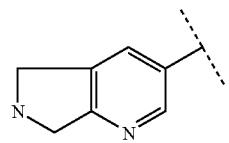

and the like.

As used herein, the term "fused heterocyclylheteroarylene" refers to a fused heterocyclylheteroaryl, wherein the heteroaryl group is divalent. Examples include

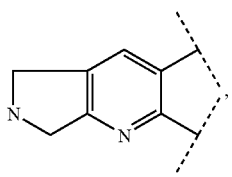

and the like.

As used herein, the term "fused heteroarylheterocyclyl" refers to one or more heteroaryl groups fused to a heterocyclyl group, the heterocyclyl and heteroaryl groups having two atoms in common, and wherein the heterocyclyl group is the point of substitution. Examples of "fused heteroarylheterocyclyl" used herein include -5-aza-2,3-dihydrobenzofuran-2-yl,

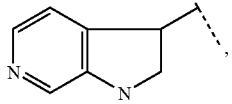

and the like.

As used herein, the term "fused heteroarylheterocyclylene" refers to a fused heteroarylheterocyclyl, wherein the heterocyclyl group is divalent. Examples include

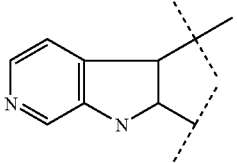

and the like.

As used herein, the term "acid isostere" refers to a substituent group which will ionize at physiological pH to bear a net negative charge. Examples of such "acid isosteres" include, but are not limited to, 1) heteroaryl groups such as, but not limited to, isoxazol-3-ol-5-yl, 1H-tetrazole-5-yl, or 2H-tetrazole-5-yl; 2) heterocyclyl groups such as, but not limited to, imidazolidine-2,4-dione-5-yl, imidazolidine-2,4-dione-1-yl, 1,3-thiazolidine-2,4-dione-5-yl, 5-hydroxy-4H-pyran-4-on-2-yl, 1,2,5-thiadiazolidin-3-one-1,1-dioxide-4-yl, 1,2-5-thiadiazolidin-3-one-1,1-dioxide-5-yl, 1,2,5-thiadiazolidin-3- one-1,1-dioxide-5-yl having substituents at the 2 and/or 4 position; and —N-acyl-alkylsulfonamides.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfenyl" refers to the group $R_aS(O)$—, where $R_a$ is alkyl.

As used herein, the term "alkenylsulfenyl" refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$-$CH_2$—, —$CH_2$—NH—$CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

As used herein, the term "sulfamoyl" shall refer to the substituent

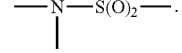

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester may be orally absorbed from the gut and transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide may be orally absorbed from the gut and transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of Formula (I): for example, the lactam formed by a carboxylic group in $R_1$ and $R_2$, and b) compounds which may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like.

The term "female sexual dysfunction" refers to a failure or dysfunction in female arousal, desire, reception, or orgasm which is related to disturbances or abnormality in the function of any or all of the female sexual organs. Such disturbances or abnormalities may occur spontaneously or be a by-product of disease or treatment of disease, such as cancer or surgery to treat cancers, in particular cancer of the breast or cervix.

The term "male sexual dysfunction" refers to a failure or dysfunction in male sexual function, which may involve impotence, erectile dysfunction, or loss of sexual desire.

The term "erectile dysfunction" refers to the failure of the male to achieve either erection and/or sexual function thereafter. "Erectile dysfunction" may be a by-product of factors such as but not limited to vascular disease, aging, surgery (particularly surgery involving organs of the male urogenital tract such as prostate), or diseases involving an imbalance of neurotransmitters or other biogenic amines or diseases involving the CNS such as depression.

The present invention also provides a method for the synthesis of compounds useful as intermediates in the preparation of compounds of Formula (I) along with methods for the preparation of compounds of Formula (I). Unless otherwise indicated, variables refer to those for Formula (I).

Scheme 1 illustrates a synthesis of compounds of formulae (3a) and (3b). Thiazole ring formation can be accomplished by combination of the alpha-bromoketone (1) and the thiourea derivative (2a) in a solvent, such as but not limited to MeOH, at a temperature of from 25° C. to 70° C., to afford (3a). The intermediate (2a) may be synthesized by treatment of an amine $R_1R_4NH$ with an isocyanate such as FMOC—N=C=S in a solvent such as DCM. The FMOC group may be removed by treatment of the FMOC thiourea intermediate with piperidine to afford (2a). Alternately, an intermediate K—H posessing a basic N—H group may be also reacted with a reagent FMOC—N=C=S to afford the isothiocyanate derivative, which may be analogously deprotected to afford the reagent (2b). Additionally, an intermediate K—C(O)—NH$_2$ may be treated with a thionating reagent such as Lawessons reagent in a solvent such as toluene at a temperature of from 80° C. to 110° C., to afford the intermediate (2b). Treatment of (2b) with (1) analogously to the above affords (3b).

$R_6$ and $R_7$ may be taken together to constitute a heterocyclic or cycloalkyl ring system, in which case the related alpha-bromoketone serves as a suitable intermediate en route to the thiazoles (3a) and (3b).

Scheme 1

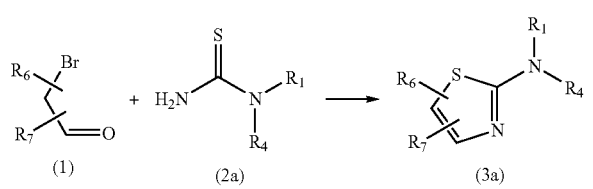

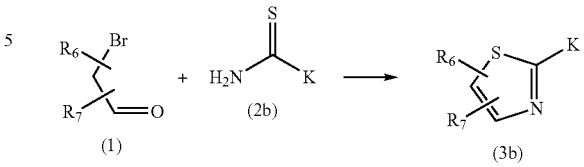

In one embodiment (Scheme 2), where $R_4$ of compound (3a) is H, the nitrogen of the heteroarylamine (3c) can be sulfenylated with sulfonyl chlorides (4a) in the presence of NaH, in a suitable solvent such as THF or DMF, at a temperature of from −30° C. to 50° C., to afford the required compound (5a). Alternately, (3c) may be treated with (4a) in a suitable solvent such as DCM, at a temperature of from −20° C. to 40° C., and a base such as pyridine or TEA with a catalytic amount of DMAP to afford the required sulfonamide (5a). Likewise, (3c) may be coupled with the compound (4b) where $LG_1$ is OH, in the presence of a coupling agent such as EDC, in a solvent such as DMF, THF, or DCM, to afford the amide (5b). Where $LG_1$ is Cl, (3c) may be treated with (4b) in the presence of NaH, in a suitable solvent such as THF or DMF, at a temperature of from −30° C. to 50° C., to afford the required compound (5b). Alternately, (3c) may be treated with (4b) in a suitable solvent such as DCM, at a temperature of from −20° C. to 40° C., and a base such as pyridine or TEA with a catalytic amount of DMAP to afford the required compound (5b). In Scheme 2 $R_{50}$ is a group such as but not limited to aryl, alkyl, or -alkylene-aryl, as defined for Formula I. $R_{50}$ may also be another group wherein the combination —S(O)$_2$—R$_{50}$ or —C(O)—R$_{50}$ meets the specification set forth for $R_4$ in Formula (I).

Scheme 2

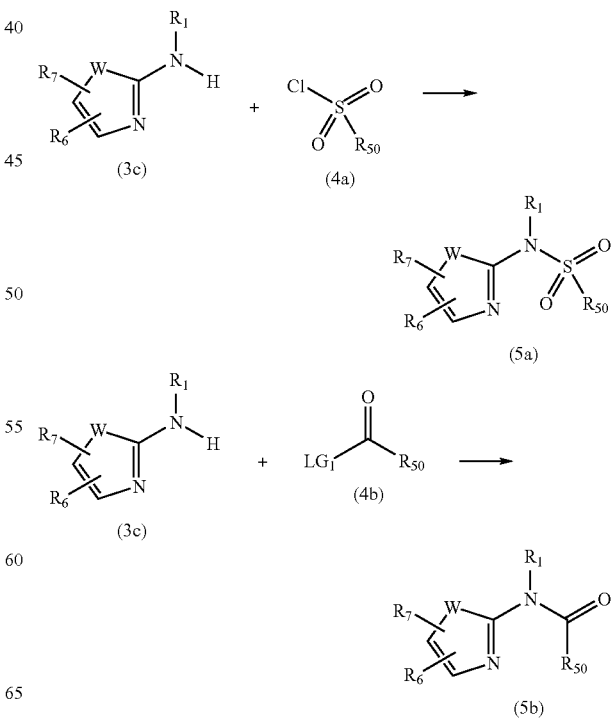

In another embodiment (Scheme 3), the amino group of the heteroarylamine (6) can be alkylated with a haloester (7), where (6) and (7) are treated with a base such as potassium carbonate, in a solvent such as DMF, at a temperature of from 25° C. to 130° C., to afford the ester intermediate (7). The carboxylate protecting group can be removed under appropriate conditions; for example, if $PG_2$ is a tert-butyl group, then treatment of (8) with an acid such as TFA or anhydrous HCl in dioxane at a temperature of from 0° C. to 30° C. furnishes the acid (9). $Z_1$ in this instance is a group such as but not limited to an alkylene group or an alkylene-arylene group.

AcOH, in a solvent such as THF or DCM or acetic acid The resulting secondary amine (14) can be condensed with FMOC-NCS as described previously to provide the thiourea derivative (15) after the FMOC group is removed by treatment with $Et_2NH$ or piperidine. The synthesis of the aminothiazole (16) can be accomplished as in Scheme 1, via thiourea condensation with the bromoketone and deprotection of the carboxyl protecting group $PG_2$ to afford (16). In this scheme, $R_{51}$ is a group such as substituted or unsubstituted alkyl, aryl, cycloalkyl, heteroaryl, alkylene-aryl, or alkylene-heteroaryl.

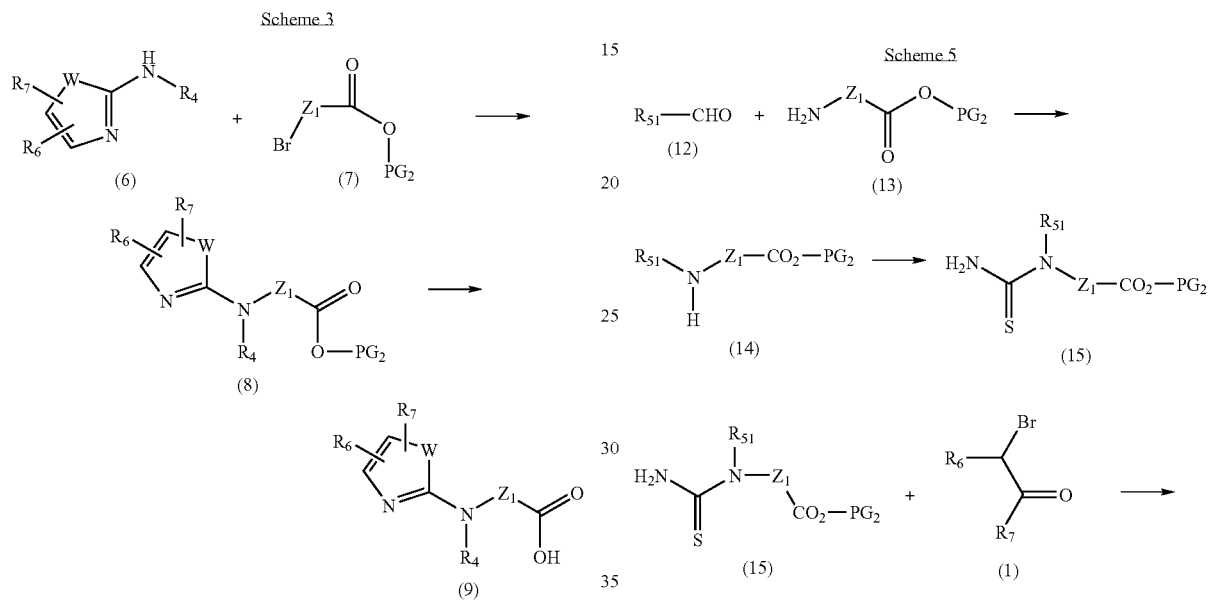

In Scheme 4, the heteroarylamine (3c) can be converted to the corresponding urea (11) by reaction with the sulfonyl isocyanate (10) in a solvent such as THF or DCM, at a temperature of from 0° C. to 100° C. The reagent (9) may be prepared by treatment of sodium or potassium cyanate with a reagent $R_{50}$—$SO_2Cl$ in a solvent such as THF. In this scheme $R_{50}$ may be defined as in schemes 2 and 3.

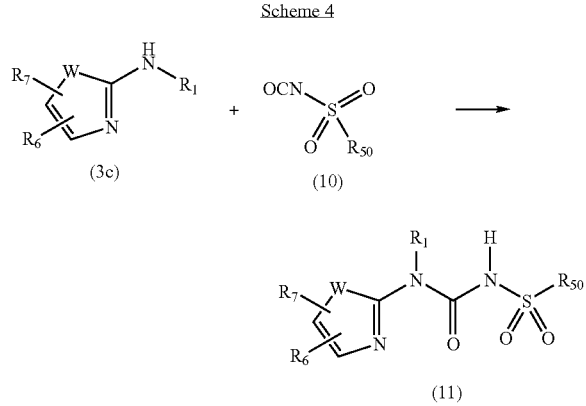

In another embodiment (Scheme 5) the secondary amine (14) can be prepared by treating (13) with the aldehyde (12) in the presence of a reducing agent such as $NaCNBH_3$ or $NaBH(OAc)_3$, in the presence or absence of an acid such as HCl or In Scheme 6, a modified route can be used to synthesize N-alkyl derivatives (22). In the event, the heteroaryl amine (17) can be acylated with the carboxylic acid (18) in the presence of a coupling agent such as EDC or TFFH, in the presence or absence of a base such as NMM or DIEA, in a solvent such as DMF, THF, or DCM, to provide the amide (19). Reduction of the amide can be effected with $BH_3$-THF to furnish the secondary amine (20). Lastly, N-alkylation of the heteroaryl amine (20) with (21) can be accomplished by treatment with NaH followed by reaction with a protected carboxyalkyl halide. Deprotection of the $PG_2$ protecting group may be accomplished as previously described where $PG_2$ is tert-butyl. Where $PG_2$ is lower alkyl such as but not limited to methyl or ethyl, aqueous LiOH or NaOH treatment in the presence or absence of an organic solvent such as methanol and/or THF, followed by mild neutralization, affords the carboxylic acid (22). In this scheme $R_5$, may have the meaning set forth previously.

Scheme 6

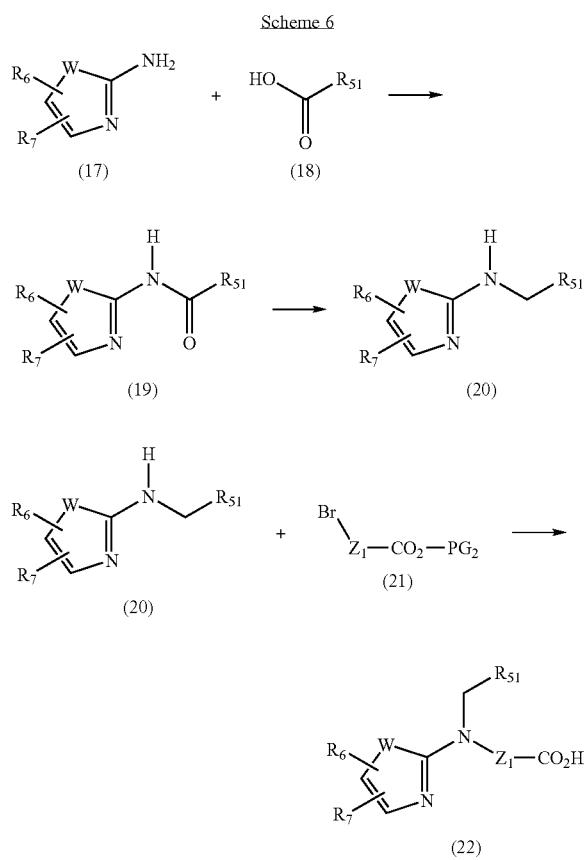

Scheme 7

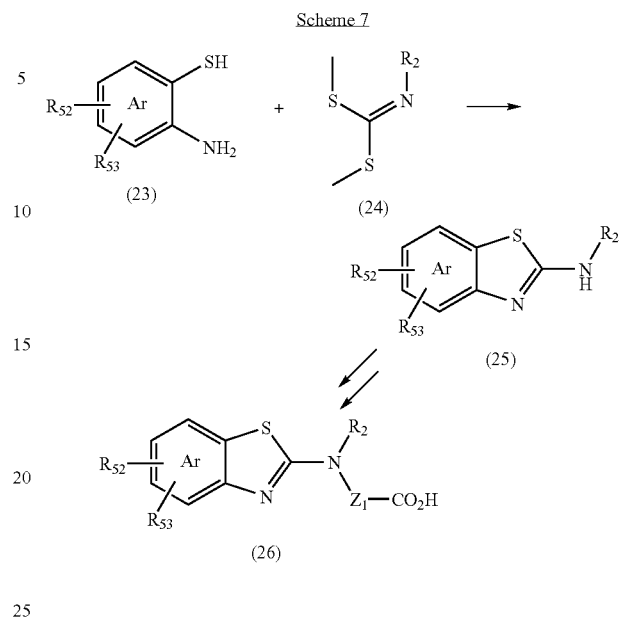

In Scheme 7, a heteroaromatic or aromatic ortho-mercaptoamine (23) may be treated with the reagent (24) in a solvent such as DMF or THF, at a temperature of from 0° C. to 100° C., to afford the fused aminothiazole moiety (25). Reagent (24) may be synthesized by condensation of the amine $R_2$—$NH_2$ with $CS_2$, in a solvent such as THF or dioxane, in the presence or absence of a base such as sodium hydride or triethylamine, at a temperature of from 0° C. to 60° C., followed by quenching with methyl iodide. The aminothiazole (25) may be employed in chemistry illustrated in the Schemes above to obtain compounds of Formula (I); for example, the chemistry illustrated in Scheme 6 may be utilized to arrive at the compound (26). In Scheme 7, $R_{52}$ and $R_{53}$ represent optional substituents as described for aromatic rings of the present compounds of Formula (I). Ar represents an optionally substituted aryl or heteroaryl ring system such as phenyl, pyridyl, pyrimidinyl, and the like.

Aminobenzothiazoles, such as compound (26) can also be prepared from the corresponding halobenzothiazoles and an appropriate amine. The reaction utilizes a metal catalyst such as, but not limited to, $Pd_2(dba)_3$ with an appropriate ligand such as, but not limited to, xantphos, BINAP or dppf. The present reaction also uses a base such as, but not limited to, $Cs_2CO_3$ at a temperature ranging from 25° C. to 120° C., in a solvent such as THF, dioxane or toluene. The resulting ester group can be hydrolyzed by using either acid using HCl in dioxane or basic conditions using NaOH to afford compound (26).

In Scheme 8, the intermediate (27) where $LG_2$ and $LG_3$ are bromide, chloride, or iodide may be treated with the amine (28) in a solvent such as THF or DMF at a temperature of from −20° C. to 110° C., to obtain the possible products (29) and (30). (29) and (30) may be obtained as a mixture of products, or one product may dominate over the other, depending in the nature of the variables in (29), as well as the nature of $R_{54}$ and $R_1$. $R_{54}$ may be defined as one of the variables $R_4$, or $R_{54}$ may be a protecting group $PG_3$, preferably a protecting group that allows the nitrogen in (30) to be both nucleophilic and basic; for example, a benzyl or substituted benzyl group, such as 4-methoxybenzyl or 2,4-dimethoxybenzyl. The products (29) and (30) may be transformed to (31) and (32) via steps analogous to those performed in the above schemes. For example, the halogen groups $LG_2$ and $LG_3$ in (31) or (32) may be replaced with an aryl group by treatment of (29) or (30) with a boronic acid $R_{55}$—$B(OH)_2$ in a solvent such as THF, DME, or toluene containing aqueous base such as sodium carbonate, in the presence of a metal catalyst such as $Pd(PPh_3)_4$, thermally at a temperature of from 25° C. to 110° C. or under microwave irradiation at a temperature of from 120° C.-170° C. Alternately, the products (29) or (30) may be deprotected; where $R_{54}$ is $PG_3$ and $PG_3$ is a substituted benzyl group such as 4-methoxybenzyl, treatment with a strong acid such as TFA affords the deprotected heteroaryl amine (31) where $R_1$ is H. Compound (31) where $R_1$ is H may be substituted according to previous Schemes to provide compounds where $R_1$ is as in the specification for Formula (I).

Scheme 8

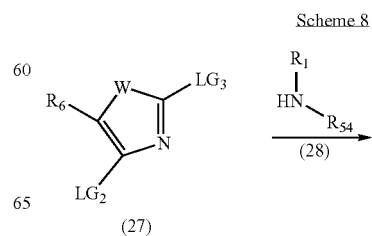

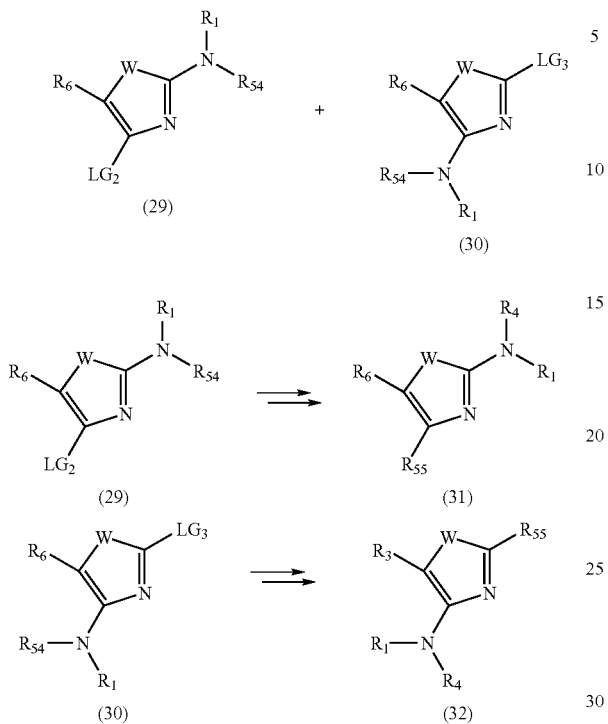

The synthesis of a compound of formula (36) is outlined in Scheme 9. Aldehyde (33), where W is S, may be synthesized by a multistep procedure starting with condensation of ethyl thiooxalate and a x-bromoketone in a solvent such as but not limited to MeOH. The ester group could be reduced to the aldehyde by a two-step protocol; however, compounds of this nature can also be arrived at by a one-step reduction procedure. The two-step method entails reduction with a reagent such as but not limited to LAH or LiBH$_4$ to the alcohol, followed by oxidation employing a reagent such as but not limited to pyridinium dichromate or pyridinium chlorochromate in DCM, to the aldehyde (33). The ester group may also be converted to the aldehyde by treatment with a limiting molar amount of diisobutylaluminum hydride in a solvent such as ether, at a temperature of from −78° C. to 0° C. Reductive amination of an amine by (33) can be accomplished as for similar operations in Scheme 5 by combining the aldehyde (33) with an amine such as but not limited to (34), in a solvent such as but not limited to DCM, to afford (35). Removal of the protecting group PG$_2$, which in this case is a group such as tertiary butyl, may be accomplished by treatment of (35) with TFA or anhydrous HCl to afford (36).

Acyl sulfonamides (Scheme 10) can be prepared from a carboxylic acid such as (37) via activation of the acid with a reagent such as but not limited to CDI or EDC in a solvent such as but not limited to THF or DMF. Treatment of the activated carboxylic acid intermediate with a sulfonamide (R$_{56}$SO$_2$NH$_2$) in the presence of a base such as but not limited to DBU or DIEA affords the desired acyl sulfonamide (38). R$_{56}$ may be a group such as but not limited to alkyl, aryl, or alkylene-aryl.

Scheme 10

N-sulfenyl ureas can be prepared (Scheme 11) from a carboxylic acid derivative such as (39) utilizing an acyl azide rearrangement performed by treatment of the acid (39) with a reagent such as but not limited to diphenylphosphoryl azide, in the presence of a weak base such as triethylamine, at a temperature of from −20° C. to 25° C., followed by heating at a temperature of from 25° C. to 100° C., followed by trapping with a sulfonamide (R$_{56}$SO$_2$NH$_2$) to afford the N-sulfenylurea (40). R$_{56}$ may be a group such as but not limited to alkyl, aryl, or alkylene-aryl.

Scheme 9

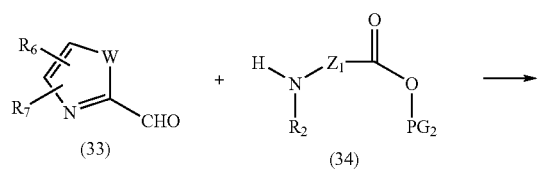

Scheme 11

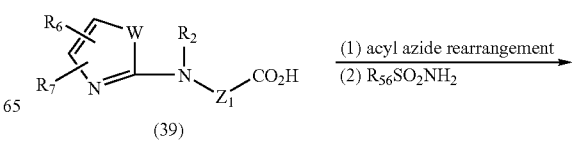

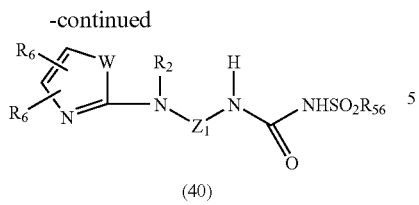

(40)

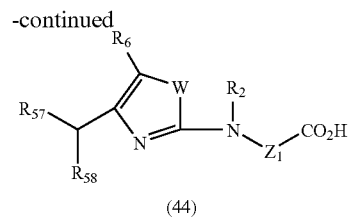

(44)

Benzhydryl derivatives (Scheme 12) may be prepared by methods such as but not limited to thiazole ring synthesis (W=S) using either ethyl bromopyruvate or 3-bromo-1-phenyl-propane-1,2-dione and a thiourea or thioamide (as outlined in Scheme 1) in a solvent such as but not limited to MeOH. Where ethyl bromopyruvate is employed, $R_{58}$ is —$OC_2H_5$, and treatment with at least 2 molar equivalents of an organometallic reagent such as an organomagnesium halide reagent $R_{57}MgX$ (X is Br, Cl, or I) in a solvent such as ether or THF, affords the benzhydrol intermediate. Reduction with a reagent such as triethylsilane in a solvent such as TFA or TFA/DCM mixture at a temperature of −20° C. to 25° C. affords (42). Alternately, (41) where $R_{58}$ is aryl or heteroaryl may be treated with one molar equivalent of a reagent such as an organomagnesium halide reagent $R_{57}MgX$ (X is Br, Cl, or I) in a solvent such as ether or THF to afford the benzhydrol adduct (43). This intermediate may be reduced as described above to afford (44). In this scheme $R_{57}$ may be a group such as but not limited to aryl or heteroaryl.

Scheme 12

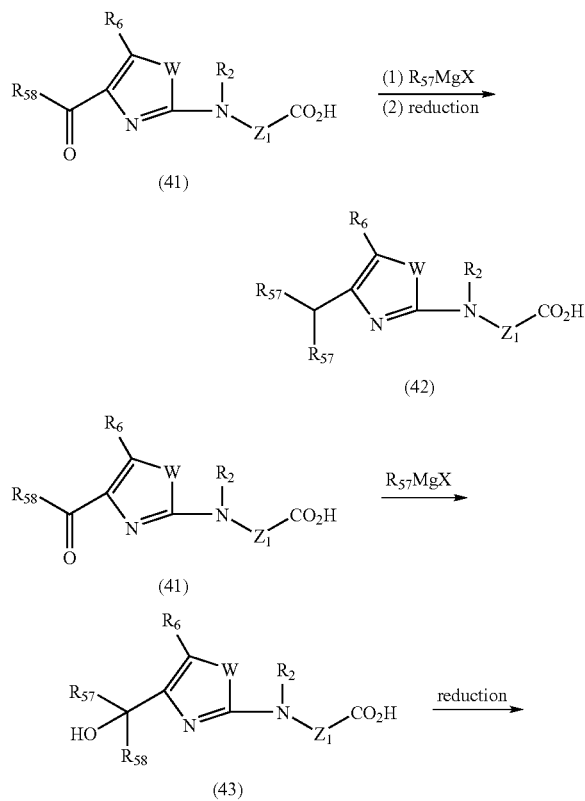

In the above schemes, "$PG_1$" represents an amino protecting group. The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups ($PG_1$ as used herein) such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropyl methoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In the above schemes, "$PG_2$" represents carboxyl protecting group. The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the methyl group, the ethyl group, the allyl group, the trimethylsilylethoxymethyl group, the 2,2,2-trichloroethyl group, the benzyl group, and the trialkylsilyl group, examples of such being trimethylsilyl, tert-butyidimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

The compounds of the present invention may be useful for the treatment of bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type II diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The compounds of the present invention may also be useful for treating physiological disorders related to, for example, regulation of insulin sensitivity, inflammatory response, plasma triglycerides, HDL, LDL, and cholesterol levels and the like. The compounds of the present invention may also be useful for treating female sexual disfunction, male sexual disfunction, and erectile disfunction. These conditions may be treated by modulating the functional interation of AgRP on a melanocortin receptor.

Thus in another aspect, the present invention provides pharmaceutical compositions and methods of treatment.

In an embodiment, the pharmaceutical compositions containing a compound of Formula (I) of the present invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

In another embodiment, formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

In another embodiment, the composition may comprise an aqueous suspension. Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Also, oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

In another embodiment, the compositions of the present invention may comprise a syrup or elixir. Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

In an embodiment, for topical use, creams, ointments, jellies, solutions of suspensions, etc., containing the compounds of the invention may be employed. For the purpose of this application, topical applications shall include mouth washes and gargles.

In an embodiment, the compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19. In an embodiment, the present invention provides a pharmaceutical formulation comprising a hydrochloric acidic salt of a compound of Formula (I). In another embodiment, the present invention provides a pharmaceutical formulation comprising a sodium salt of a compound of Formula (I).

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug thereof, and one or more pharmaceutically acceptable carriers, excipients, or diluents.

In another embodiment, the present invention provides a pharmaceutical composition comprising a therapeutically effective amount of a compound of Formula (I), or a pharmaceutically acceptable salt, in combination with a pharmaceutically acceptable carrier and one or more hypoglycemic agents. Hypoglycemic agents may include, but are not limited to, insulin or insulin mimetics; biguanidines such as metformin or buformin; PTP-1B inhibitors; PPAR-gamma agonists; sulfonylureas such as acetohexamide, chloropropamide, tolazamide, tolbutamide, glyburide, glipizide, glyciazide; or any other insulin secretagogue such as, for example, repaglinide and nateglinide; or α-glycosidase inhibitors such as acarbose, voglibose, or miglitol; or $\beta_3$-adrenoceptor agonists.

In another embodiment, the present invention provides a pharmaceutical composition comprising a therapeutically effective amount of a compound of Formula (I), or a pharmaceutically acceptable salt or ester thereof, in combination with a pharmaceutically acceptable carrier and HMG Co-A reductase inhibitors (statins), bile acid sequestrants, fibrates such as fenofibrate, cholesterol lowering agents, inhibitors of cholesterol absorption such as ACAT inhibitors, bile acid transport inhibitors, CETP inhibitors, or other antihyperlipidemic agents to improve the lipid profile of a subject.

In another embodiment, the present invention provides a pharmaceutical composition comprising a therapeutically effective amount of a compound of Formula (I), or a pharmaceutically acceptable salt or ester thereof, in combination with a pharmaceutically acceptable carrier and one or more agents selected from the group consisting of agents that modulate thermogenesis, lipolysis, gut motility, fat absorption, and satiety.

In another embodiment, the present invention provides a pharmaceutical composition comprising a therapeutically effective amount of a compound of Formula (I), or a pharmaceutically acceptable salt or ester thereof, in combination with a pharmaceutically acceptable carrier and one or more agents selected from the group consisting of agents that regulate hypertension (e.g., inhibitors of angiotension converting enzyme (ACE), 1-blockers, calcium channel blockers).

In another embodiment, the present invention provides a pharmaceutical composition comprising a therapeutically effective amount of a compound of Formula (I), or a pharmaceutically acceptable salt or ester thereof, in combination with a pharmaceutically acceptable carrier and one or more agents such as, but not limited to, antiobesity agents such as fenfluramine, dexfenfluramine, sibutramine, orlistat, or $\beta_3$ adrenoceptor agonists; feeding behavior modifying agents such as neuropeptide Y receptor antagonists, including those that antagonize the neuropeptide Y5 receptor; $\alpha$-MSH, $\alpha$-MSH mimetics, or $\alpha$-MSH derived peptides; MC4R agonists or partial agonists such as, but not limited to, those disclosed in U.S. Pat. No. 6,350,760; MC-3R agonists; glucokinase activators; PPAR-$\delta$ agonists; PPAR-$\alpha$/PPAR-$\gamma$ agonists; PPAR-$\alpha$/PPAR-$\gamma$/PPAR-$\delta$ agonists; PPAR-$\gamma$/PPAR-$\delta$ agonists; and agents useful in treatment of male and/or female sexual disfunction, such as type V phosphodiesterase inhibitors such as sildenafil or tendamifil, dopamine agonists, or $\alpha_2$-adrenoceptor antagonists.

In another embodiment, the present invention provides a pharmaceutical composition comprising a compound of Formula (I), wherein the amount of the compound of Formula (I) is an amount sufficient to inhibit the function of AgRP at a melanocortin receptor. In an embodiment, the melanocortin receptor is MC4R. In another embodiment, the melanocortin receptor is MC-3R.

The term "treatment" or "treating" as used herein, refers to the full spectrum of treatments for a given disorder from which the patient is suffering, including alleviation of one, most of all symptoms resulting from that disorder, to an outright cure for the particular disorder or prevention of the onset of the disorder. For example, within the context of obesity, successful treatment may include an alleviation of symptoms or halting progression of the disease, as measured by reduction in body weight, or a reduction in amount of food or energy intake. Treatment of type I or type II diabetes may include an alleviation of symptoms or halting progression of the disease, as measured by a decrease in serum glucose or insulin levels in, for example, hyperinsulinic or hyperglycemic subjects.

The term "pharmacologically effective amount" shall mean that amount of a drug or pharmaceutical agent that will elicit the biological or medical response of a tissue, animal or human that is being sought by a researcher or clinician. A pharmaceutically effective amount includes those amounts of the compounds of Formula (I) that detectably inhibits the function of AgRP at a melanocortin receptor, for example, by the assay described below, or any other assay known or prepared by one skilled in the art. A pharmaceutically effective amount can be a therapeutically effective amount.

The term "therapeutically effective amount" shall mean that amount of a drug or pharmaceutical agent that will elicit the therapeutic response of a subject that is being sought. For example, a therapeutically effective amount includes those amounts that may alleviate symptoms of a melanocortin receptor disorder, those amounts that may prevent weight gain in a subject, and those amounts that may induce weight lose in a subject.

A melanocortin receptor disorder, or a melanocortin receptor mediated disease, which may be treated by the methods provided herein, include, but are not limited to, any biological disorder or disease in which a melanocortin receptor is implicated, or which inhibition of a melanocortin receptor potentiates a biochemical pathway that is defective in the disorder or disease state. Factors which may influence what constitutes a therapeutically effective amount may depend upon the size and weight of the subject, the biodegradability of the therapeutic agent, the activity of the therapeutic agent, as well as its bioavailability.

As used herein, "a subject" includes mammalian subjects such as, but not limited to, humans In an embodiment, a subject is one who either suffers from one or more of the aforesaid diseases, disease states, or conditions, or are at risk for such. Accordingly, in the context of the therapeutic method of the invention, this method also is comprised of a method for treating a mammalian subject prophylactically, or prior to the onset of diagnosis such disease(s), disease state(s), or conditions.

In another aspect, the present invention provides a method of treatment comprising administering to a subject a compound of Formula (I)

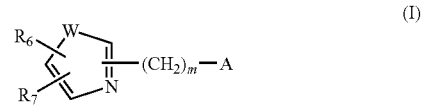

wherein
m is equal to 0, 1, or 2;
A is selected from the group consisting of:

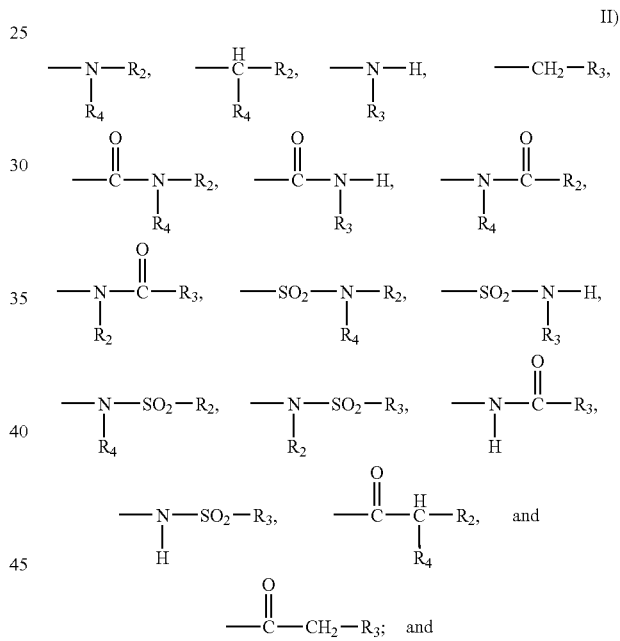

III) -K;
$R_2$ is selected from the group consisting of:
a) -L-$D_1$-$G_1$;
b) -L-$D_1$-alkyl;
c) -L-$D_1$-aryl;
d) -L-$D_1$-heteroaryl;
e) -L-$D_1$-cycloalkyl;
f) -L-$D_1$-heterocyclyl;
g) -L-$D_1$-arylene-alkyl;
h) -L-$D_1$-alkylene-arylene-alkyl;
i) -L-$D_1$-alkylene-aryl;
j) -L-$D_1$-alkylene-$G_1$;
k) -L-$D_1$-heteroarylene-$G_1$;
l) -L-$D_1$-cycloalkylene-$G_1$;
m) -L-$D_1$-heterocyclylene-$G_1$;

n)

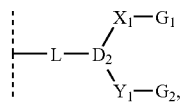

o) -L-D$_1$-arylene-G$_1$;
p) -L-D$_1$-arylene-alkylene-G$_1$;
q) -L-D$_1$-alkylene-arylene-alkylene-G$_1$; and
r) -L-D$_1$-alkylene-arylene-G$_1$;

R$_3$ is selected from the group consisting of:
a) -alkyl;
b) -L-D$_1$-H;
c) -L-D$_1$-alkyl;
d) -L-D$_1$-aryl;
e) -L-D$_1$-heteroaryl;
f) -L-D$_1$-alkylene-heteroaryl;
g) -L-D$_1$-cycloalkyl;
h) -L-D$_1$-heterocyclyl;
i) -L-D$_1$-arylene-alkyl;
j) -L-D$_1$-alkylene-arylene-alkyl;
k) -L-D$_1$-alkylene-aryl; and
l) -L-D$_1$-arylene-aryl;

R$_4$ is selected from the group consisting of:
a) -hydrogen;
b) -alkyl;
c) -L-D$_1$-H;
d) -L-D$_1$-alkyl;
e) -L-D$_1$-aryl;
f) -L-D$_1$-heteroaryl;
g) -L-D$_1$-alkylene-heteroaryl;
h) -L-D$_1$-cycloalkyl;
i) -L-D$_1$-heterocyclyl;
j) -L-D$_1$-arylene-alkyl;
k) -L-D$_1$-alkylene-arylene-alkyl;
l) -L-D$_1$-alkylene-aryl; and
m) -L-D$_1$-arylene-aryl;

R$_6$ and R$_7$ are independently selected from the group consisting of:
a) -hydrogen;
b) -halo;
c) -alkyl;
d) -L-D$_1$-H;
e) -L-D$_1$-alkyl;
f) -L-D$_1$-aryl;
g) -L-D$_1$-heteroaryl;
h) -L-D$_1$-cycloalkyl;
i) -L-D$_1$-heterocyclyl;
j) -L-D$_1$-arylene-alkyl;
k) -L-D$_1$-alkylene-arylene-alkyl;
l) -L-D$_1$-alkylene-aryl;
m) -L-D$_1$-arylene-aryl;
n) -L-D$_2$-(aryl)$_2$; and
o) -L-D$_2$-(arylene-alkyl)$_2$;
wherein at least one of R$_6$ and R$_7$ is not hydrogen; or R$_6$ and R$_7$ may be taken together to form part of a fused carbocyclic, fused aromatic, fused heteroaromatic, fused cycloalkylaryl, fused arylcycloalkyl, fused heterocyclylaryl, fused arylheterocyclyl, fused cycloalkylheterocyclyl, fused heteroarylcycloalkyl, fused heterocyclylheteroaryl, or fused heteroarylheterocyclyl rings, wherein the ring is optionally substituted 1-8 times with the group
a) -halo;
b) -nitro;
c) -L-D$_1$-G$_1$
d) -L-D$_1$-alkyl:
e) -L-D$_1$-aryl;
f) -L-D$_1$-heteroaryl;
g) -L-D$_1$-cycloalkyl;
h) -L-D$_1$-heterocyclyl;
i) -L-D$_1$-arylene-alkyl;
j) -L-D$_1$-alkylene-arylene-alkyl;
k) -L-D$_1$-alkylene-aryl;
l) -L-D$_1$-alkylene-G$_1$;
m) -L-D$_1$-heteroarylene-G$_1$;
n) -L-D$_1$-cycloalkylene-G$_1$;
o) -L-D$_1$-heterocyclylene-G$_1$; and
p)

W is S,

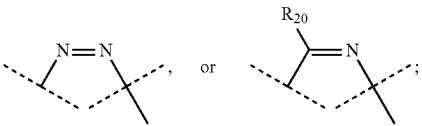

wherein
R$_{20}$ is
a) -hydrogen;
b) -halo;
c) -alkyl;
d) -L-D$_1$-H;
e) -L-D$_1$-alkyl;
f) -L-D$_1$-aryl;
g) -L-D$_1$-heteroaryl;
h) -L-D$_1$-cycloalkyl;
i) -L-D$_1$-heterocyclyl;
j) -L-D$_1$-arylene-alkyl;
k) -L-D$_1$-alkylene-arylene-alkyl;
l) -L-D$_1$-alkylene-aryl;
m) -L-D$_1$-arylene-aryl;
n) -L-D$_2$-(aryl)$_2$; or
o) -L-D$_2$-(arylene-alkyl)$_2$;

K is cycloalkyl, heterocyclyl, aryl, heteroaryl, fused cycloalkylaryl, arylcycloalkyl, fused heterocyclylaryl, fused arylheterocyclyl, fused cycloalkylheteroaryl, fused heteroarylcycloalkyl, fused heterocyclylheteroaryl, or fused heteroarylheterocyclyl, wherein K may be optionally substituted 1-3 times with a group selected from the group consisting of: halo, nitro, and R$_2$;

G$_1$ is selected from the group consisting of: —CN, —SO$_3$H, —P(O)(OH)$_2$, —P(O)(O-alkyl)(OH), —CO$_2$H, —CO$_2$-alkyl, —C(O)NHS(O)$_2$-alkyl, —C(O)NHS(O)$_2$-aryl, —C(O)NHS(O)$_2$-heteroaryl, —C(O)NHS(O)$_2$-alkylene-aryl, —C(O)NHS(O)$_2$-alkylene-heteteroaryl, —S(O)$_2$ NHC(O)-alkyl, —S(O)$_2$NHC(O)-aryl, —S(O)$_2$NHC(O)-heteroaryl, —S(O)$_2$N HC(O)-alkylene-aryl, —S(O)$_2$N HC(O)-alkylene-heteteroaryl, —NHC(O)NH—SO$_2$-alkyl, an acid isostere,

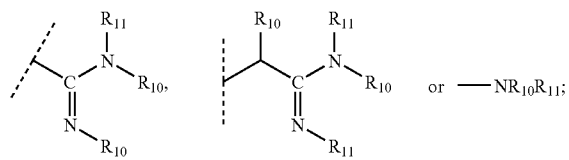

G$_2$ is selected from the group consisting of:
a) -hydrogen;
b) -alkylene;
c) -L-D$_1$-H;
d) -L-D$_1$-alkyl;
e) -L-D$_1$-aryl;
f) -L-D$_1$-heteroaryl;
g) -L-D$_1$-cycloalkyl;
h) -L-D$_1$-heterocyclyl;
i) -L-D$_1$-arylene-alkyl;
j) -L-D$_1$-alkylene-arylene-alkyl;
k) -L-D$_1$-alkylene-aryl; and
l) -L-D$_1$-arylene-aryl;

L is a direct bond, alkylene, alkenylene, alkynylene, or arylene;

D$_1$ is selected from the group consisting of: a direct bond, —CH$_2$—, —O—, —N(R$_8$)—, —C(O)—, —CON(R$_8$)—, —CON(R$_9$)SO$_2$—, —N(R$_9$)C(O)—, —N(R$_9$)CON(R$_8$)—, —N(R$_8$)C(O)O—, —OC(O)N(R$_8$)—, —N(R$_8$)SO$_2$—, —SO$_2$N(R$_8$)—, —C(O)—O—, —O—C(O)—, —S—, —S(O)—, —S(O$_2$)—, or —N(R$_8$)SO$_2$N(R$_9$)—, —N=N—, and —N(R$_8$)—N(R$_9$)—;

D$_2$ is N, alkylyne, or alkenylyne;

X$_1$ and Y$_1$ are independently selected from the group consisting of: a direct bond, alkylene, arylene, heteroarylene, cycloalkylene, heterocyclylene, arylene-alkylene, alkylene-arylene-alkylene, and alkylene-aryl;

R$_8$ and R$_9$ are independently selected from the group consisting of: -hydrogen, -alkyl, -aryl, -arylene-alkyl, -alkylene-aryl, and -alkylene-arylene-alkyl;

R$_{10}$ and R$_{11}$ are independently selected from the group consisting of: hydrogen, -alkyl, -L-D$_1$-alkyl, -L-D$_1$-aryl, —C(O)-alkyl, —C(O)-aryl, —SO$_2$-alkyl, and —SO$_2$-aryl, or R$_{10}$ and R$_{11}$ may be taken together to form a ring having the formula —(CH$_2$)$_m$-J-(CH$_2$)$_n$-bonded to the nitrogen atom to which R$_{10}$ and R$_{11}$, are attached, wherein m and n are 0, 1, 2, or 3, and J is selected from the group consisting of —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

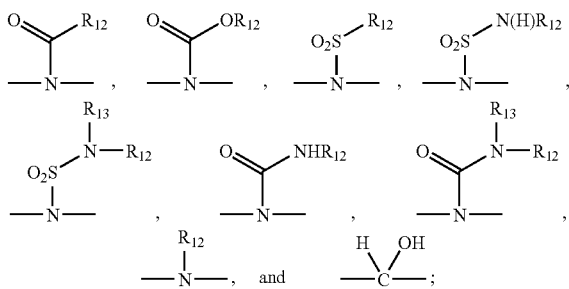

R$_{12}$ and R$_{13}$ are independently selected from the group consisting of hydrogen, aryl, alkyl, and alkylene-aryl;

and wherein the aryl, heteroaryl, heterocyclyl, cycloalkyl, and/or alkyl group(s) in R$_2$-R$_{13}$, and R$_{20}$, G$_1$, G$_2$, L, X$_1$, Y$_1$, may be optionally substituted 1-4 times with a substituent group selected from the group consisting of
a) -hydrogen;
b) halogen;
c) hydroxyl;
d) cyano;
e) carbamoyl;
f) —B-alkyl;
g) —B-perhaloalkyl;
h) —B-cycloalkyl;
i) —B-heterocyclyl;
j) —B-aryl;
k) —B-heteroaryl;
l) —B-alkylene-heteroaryl;
m) —B-alkylene-aryl;
n) —B-arylene-alkyl;
o) —B-perhaloalkyl;
p) —B-cycloalkylene-T-R$_{14}$;
q) —B-alkylene-N—R$_{14}$R$_{15}$;
r) —B-cycloalkylene-alkyl; and
s) —B-alkylene-cycloalkyl;

wherein
B and T are independently selected from the group consisting of: direct bond, alkylene, —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH, —O—S(O)$_2$—, and —O—C(O)—;

wherein
R$_{14}$ and R$_{15}$ are independently selected from the group consisting of: hydrogen, heteroaryl, cycloalkyl, heterocyclyl, aryl, alkyl, -alkylene-aryl, -alkylene-heteroaryl, and -alkylene-O-aryl; or R$_{14}$ and R$_{15}$ may be taken together to form a ring having the formula —(CH$_2$)$_q$-J-(CH$_2$)$_r$— bonded to the nitrogen atom to which R$_{14}$ and R$_{15}$ are attached wherein q and r are independently equal to 1, 2, 3, or 4; J comprises a direct bond, —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

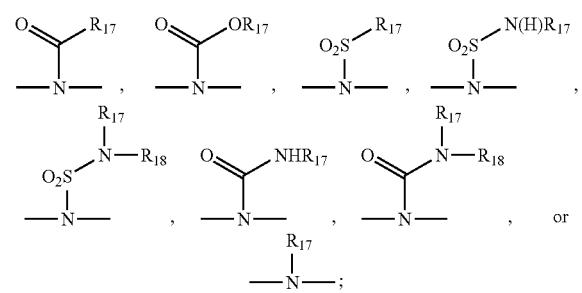

R$_{17}$ and R$_{18}$ are independently selected from the group consisting of: hydrogen, cycloalkyl, heterocyclyl, aryl, heteroaryl, alkyl, -alkyene-heteroaryl, or -alkylene-aryl;

and wherein the compound of Formula (I) is as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

In another embodiment, the present invention provides a method of treatment of an obesity-related disorder comprising: administering to a subject a therapeutically effective amount of a compound of Formula (I). In another embodiment, the obesity-related disorder is selected from the group consisting of: dyslipidemia, hypertriglyceridemia, hypertension, diabetes, Syndrome X, atherosclerotic disease, cardiovascular disease, cerebrovascular disease, peripheral vessel disease, cholesterol gallstones, cancer, menstrual abnormalities, infertility, polycystic ovaries, osteoarthritis, and sleep apnea.

In another embodiment, the present invention provides a method of treatment of a disorder comprising: administering to a subject a therapeutically effective amount of a compound of Formula (I), wherein the disorder is selected from the group consisting of female sexual disfunction, male sexual disfunction, and erectile disfunction The compounds of Formula (I) may be used in combination with one or more therapeutic agents which are used in the treatment, prevention, amelioration, and/or suppression of diseases for which the compounds of Formula (I) are useful; such other therapeutic agents may be administered by a like route or different route that the compound of Formula I. Where a compound of Formula (I) is utilized in combination with another therapeutic agent, the composition may contain the compound of Formula (I) in combination with the other therapeutic agent(s). Where separate dosage formulations are used, the compound of Formulae (I) and one or more additional therapeutic agents may be administered at essentially the same time (e.g., concurrently) or at separately staggered times (e.g., sequentially).

In another embodiment, the present invention provides a method of treatment of an obesity-related disorder comprising: administering to a subject a therapeutically effective amount of a compound of Formula (I) in combination with one or more hypoglycemic agents.

In another embodiment, the present invention provides a method of treatment of an obesity-related disorder comprising: administering to a subject a therapeutically effective amount of a compound of Formula (I) in combination with one or more agents that modulate digestion and/or metabolism. The agents that modulate digestion and/or metabolism may include, but are not limited to, agents that modulate thermogenesis, lipolysis, gut motility, fat absorption, and satiety.

In another embodiment, the present invention provides a method of treating obesity and obesity-related disorders comprising: administering to a subject a therapeutically effective amount of a compound of Formula (I) in combination with one or more agents selected from the group consisting of HMG CoA reductase inhibitor, bile acid binding agent, fibric acid derivative, and agent that regulates hypertension.

In another embodiment, the present invention provides a method of treatment comprising: administering to a subject a therapeutically effective amount of a compound of Formula (I) in combination with one or more agents such as, but not limited to, antiobesity agents such as fenfluramine, dexfenfluramine, sibutramine, orlistat, or 3 adrenoceptor agonists; feeding behavior modifying agents such as neuropeptide Y receptor antagonists, including those that antagonize the neuropeptide Y5 receptor; α-MSH, α-MSH mimetics, or α-MSH derived peptides; MC-4R agonists or partial agonists such as, but not limited to, those disclosed in U.S. Pat. No. 6,350,760; MC-3R agonists; glucokinase activators; PPAR-δ agonists; PPAR-α/PPAR-γ agonists; PPAR-α/PPAR-γ/PPAR-δ agonists; PPAR-γ/PPAR-δ agonists; and agents useful in treatment of male and/or female sexual disfunction, such as type V phosphodiesterase inhibitors such as sildenafil or tendamifil, dopamine agonists, or $α_2$-adrenoceptor antagonists.

In another embodiment, the present invention provides a method of treatment comprising: administering to a subject a therapeutically effective amount of at least one compound of Formula (I), wherein said therapeutically effective amount is sufficient to induce weight loss in the subject. In another embodiment, the present invention provides a method of prevention of weight gain comprising: administering to a subject a therapeutically effective amount of a compound of Formula (I) which is sufficient to prevent weight gain.

In another embodiment, the present invention provides a method of melanocortin receptor modulation comprising: administering to a subject a therapeutically effective amount of a compound of Formula (I). In another embodiment, the present invention provides a method of melanocortin receptor modulation comprising: administering to a subject a therapeutically effective amount of a compound of Formula (I), wherein said therapeutically effective amount is an amount that enhances the downstream effects of agonist binding to the melanocortin receptor in the subject.

In another embodiment, the present invention provides a method of melanocortin receptor modulation comprising: administering to a subject a therapeutically effective amount of a compound of Formula (I), wherein the compound of Formula (I) inhibits the function of AgRP on MC-4R. In another embodiment, the present invention provides a method of melanocortin receptor modulation comprising: administering to a subject a therapeutically effective amount of a compound of Formula (I), wherein the compound of Formula (I) inhibits the function of AgRP on MC-3R.

Generally speaking, a compound of Formula (I) may be administered at a dosage level of from about 0.003 to 500 mg/kg of the body weight of the subject being treated. In an embodiment, a compound of Formula (I) may be administered at a dosage range between about 0.003 and 200 mg/kg of body weight per day. In an embodiment, a compound of Formula (I) may be administered at a dosage range between about 0.1 to 100 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms may generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The general procedures used in the methods to prepare the compounds of the present invention are described below.

General Experimental

LC-MS data was obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Sepax GP-C18 4.6×50 mm column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. All MS data was obtained in the positive mode unless otherwise noted. $^1$H NMR data was obtained on a Varian 400 MHz spectrometer.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
CDI=1-(3-dimethylaminopropyl)-3-ethylcarbodiimide
d=day
DIAD=diisopropyl azodicarboxylate
DBU=1,8-diazabicyclo[5.4.0]undecene-7
DCC=dicyclohexylcarbodiimide
DCE=dichloroethane
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
Et=ethyl
iPr=isopropyl
Ph=phenyl
Bn=benzyl
Me=methyl
tBu=tert-butyl
Pr=propyl
Bu=butyl
iBu=isobutyl
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NBS=N-bromosuccinimide
NCS=N-chlorosuccinimide
NMM=N-methylmorpholine, 4-methylmorpholine
NMP=N-methylpyrrolidone
NMR=nuclear magnetic resonance spectroscopy
p.o.=per oral
PS-carbodiimide=N-cyclohexylcarbodiimide-N'-propyloxymethyl polystyrene
PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
TFFH=fluoro-N,N,N'',N''-tetramethylformamidinium hexafluorophosphate
THF=tetrahydrofuran
THP=tetrahydropyranyl
TLC=thin layer chromatography
TMSBr=bromotrimethylsilane, trimethylsilylbromide
$T_r$=retention time General Procedure A To a methanol solution of ketone (such as 1-phenyl-ethanone, 1-phenyl-propanone, 1,2-diphenyl ethanone, or 1-(4-isopropylphenyl) ethanone) (1.0 eq) was added pyrrolidone hydrotribromide (PyHBr$_3$) (1.1 eq) at 0° C. The reaction was slowly warmed to room temperature and stirred at the same temperature for 2 h by monitoring with TLC. The reaction mass was concentrated and partitioned between cold aqueous sodium bicarbonate and ethyl acetate (1:1). The organic phase was dried with Na$_2$SO$_4$, concentrated and filtered through a bed of silica gel to afford the alpha-bromo ketone.

General Procedure B

To an alpha-bromo ketone (Commercial or made from above procedure A, 1.0 eq) in methanol was added thiourea or 1,1-dialkylthiourea (1.1 eq) and the reaction was heated at 60° C. for 30 min. The reaction mass was concentrated and partitioned between aqueous sodium bicarbonate and ethyl acetate (1:1). Aqueous layer was washed with ethyl acetate (3×15 mL); combined organic layers were washed with brine, dried over Na$_2$SO$_4$ and concentrated. The crude residue was purified by silica gel chromatography to afford the 2-aminothiazole derivative. Other variations of the above reaction conditions consist of performing the reaction in THF (at 60° C., 1 h) or in NMP (at room temperature, 2-15 h).

General Procedure C

Method C1: A thiazol-2-ylamine (1.0 eq) and sulfonyl chloride (1.1 eq) were dissolved in THF, and NaH (1.5 eq, 60% suspension in mineral oil) was added at 0° C. After the NaH addition, the reaction was warmed to room temperature and stirred at the same temperature for 4 h. The reaction was quenched with the addition of brine. The reaction mixture was extracted into ethyl acetate (3×15 mL), combined organic layers were dried over $Na_2SO_4$ and concentrated. The crude residue was purified by silica gel chromatography to obtain the desired sulfonamide.

Method C2: A thiazol-2-yl amine (1.0 eq), sulfonyl chloride (1.3 eq), and pyridine (3.0 eq) were combined in DCM. After stirring at room temperature for 16 h, the reaction mixture was loaded directly on silica gel column. Purification by flash chromatography (ethyl acetate/hexanes) gave the sulfonamide compound.

Method C3: A thiazol-2-yl amine (1.0 eq), sulfonyl chloride (1.2 eq), triethylamine (2.0 eq), and DMAP (0.1 eq) were combined in DCM. After stirring at 0° C. for 4 h, saturated $NaHCO_3$ (aq) solution was added. The mixture was extracted with ethyl acetate (1×10 mL). The ethyl acetate layer was dried over $Na_2SO_4$. Purification by flash chromatography (silica gel, ethyl acetate/hexanes) gave the sulfonamide.

Method C4: A thiazol-2-yl amine (1.0 eq), sulfonyl chloride (1.2 eq), triethylamine (2.0 eq), and DMAP (0.1 eq) were combined in DCM. Resulting reaction mixture was heated in a CEM Exploer PLS™ microwave at 100° C. for 30 min. After cooling to room temperature, saturated $NaHCO_3$ (aq) solution was added. The mixture was extracted with DCM (2×4 mL). The combined organic layer was dried over $Na_2SO_4$ and concentrated. Purification was carried out by silica gel chromatography (silica gel, ethyl acetate/hexanes) to yield the desired sulfonamide.

General Procedure D

A mixture of aldehyde/ketone (1.0 eq) and amine (1.0 eq) in DCM was stirred for 5 min. Sodium triacetoxyborohydride (1.2 eq) was added in portions and stirred until completion of the reaction. The reaction mixture was partitioned between DCM and saturated aqueous $NaHCO_3$ solution. The aqueous layer was extracted again with DCM (1×15 mL). The combined organic extracts were dried over $K_2CO_3$. After evaporating the solvents, the crude product was dissolved in THF (20 mL) and Fmoc-isothiocyanate (0.9 eq) was added. The reaction Was stirred at room temperature for 0.5-15 h. After TLC indicated the completion of the reaction, diethyl amine was added and stirred for 1-2 h at room temperature. The solvents were evaporated, and the crude residue was filtered on a bed of silica gel to afford the desired 1,1-alkylated thiourea.

General Procedure E

A 1 M $BBr_3$ solution (3.0 eq) was added to a solution of the methoxybenzene or benzyloxycarbonyl compound (1.0 eq) in DCM at −40° C. The reaction mixture was stirred at temperature for 5 min. and was allowed to slowly warm up to room temperature. The reaction was quenched with small amount of MeOH. The product was purified by chromatography (silica gel).

General Procedure F

A mixture of sulfonamide or aminoheterocycle (1.0 eq), bromide (2.0 eq), potassium carbonate (3.0 eq) and DMF (or in some cases THF) was heated in an oil bath at 60° C. until the reaction was complete as indicated by TLC or LCMS. The reaction mixture was partitioned between ethyl acetate and saturated $NaHCO_3$ (aq) solution. The organic layer was dried over $Na_2SO_4$. The product was purified by chromatography (silica gel).

General Procedure G

Method G1: A 4 N HCl solution in dioxane was added to a solution of Boc-protected amine and/or tert-butyl ester. It was shaken or stirred until TLC or LCMS indicated that the reaction was complete. The volatiles were evaporated. The remaining solid was purified by trituration in hexanes or ether.

Method G2: To a solution of compound in dichloromethane was added 4 N HCl in dioxane (ca. 5 equiv). The reaction mixture was stirred 1 h at ambient temperature. The mixture was evaporated to dryness. A small amount of dichloromethane was added and the mixture was concentrated in vacuo; this process was repeated twice. The remaining solid was purified by trituration with hexanes or ether. The solid was collected and dried in vacuo to afford the HCl salt.

General Procedure H

A mixture of nitrile (1.0 eq), sodium azide (13.2 eq), ammonium chloride (13.2 eq) and DMF was heated in an oil bath at 120° C. for 1 h. The reaction mixture was partitioned between ethyl acetate and water. The organic layer was dried over $Na_2SO_4$. The product was purified by chromatography (silica gel).

General Procedure I

A mixture of nitrile (1.0 eq), 1 N NaOH (aq) solution and ethanol was refluxed until the reaction was complete as indicated by TLC or LCMS. The reaction mixture was concentrated and partitioned between ether and water. The aqueous layer was acidified with 10% HCl (aq) solution and extracted with ether (1×30 mL). The organic layer was dried over $Na_2SO_4$. The solvents were evaporated. The remaining solid was purified by trituration in hexanes.

General Procedure J

A 1 N NaOH (aq) solution (1.0 eq) was added to a solution of carboxylic acid (1.0 eq) in THF (1 mL) and MeOH (1 mL). The volatiles were evaporated and the residue dried under high vacuum. The remaining solid was purified by trituration in hexanes or ether.

General Procedure K

A thiazole carboxylic acid (1.0 eq) was stirred at RT with CDI (3.0 eq) in anhydrous THF. After 20 hours, a prepared solution of the corresponding sulfonamide (2.0 eq), and DBU (1.5 eq) in THF was added, and the mixture was stirred at RT. The formation of the product was monitored via LCMS. After the reaction completed, the volatiles were removed, and residue was partitioned between EtOAc and 10% citric acid. The organic layer was washed with citric acid, brine. The solution was dried over $MgSO_4$, filtered and concentrated. The crude product was purified by silica gel column chromatography.

General Procedure L

The alcohol (1.5 eq) was dissolved in DMF (0.5 M) and NaH (1.1 eq, 60% suspension in mineral oil) was added in portions. The resulting slurry was sonicated for 20-40 min. until all the NaH was consumed. The resulting purple solution was charged with 4'-fluoroacetophenone (1.0 eq) and the reaction was stirred at 60° C. for 2-3 h. The reaction was quenched by the addition of water and saturated citric acid. The aqueous layer was extracted with methyl tert-butyl ether (MTBE, 3×20 mL) and the combined organic layer was washed with water (4×15 mL) and brine. The organic layer was dried over MgSO$_4$, filtered, and concentrated. The crude residue was purified on a silica gel column (gradient, hexane →4% EtOAc-hexane) to obtain the desired ether derivative. In some cases NMP was used. In addition, sonication may not be necessary when primary alcohols are utilized. In these cases the deprotonation can be done at room temperature for 10-20 min.

General Procedure M

The aminothiazole (1.0 eq.) was dissolved in MeCN (4 mL, 0.1 M) and N-chlorosuccinimide (NCS) (1.05 eq.) was added. The reaction was heated to 70° C. for 2 h until complete by TLC analysis. The reaction mixture was then cooled to room temperature. Saturated NaHCO$_3$ and brine were added. The aqueous layer was extracted with EtOAc (3×15 mL) and dried over MgSO$_4$. The residue was then filtered through silica gel (5% EtOAc-hexane).

General Procedure N

The ester (1.0 eq) was dissolved in THF (3 mL) and cooled to −78° C. The aryl Grignard reagent (3.0 eq) was added dropwise and slowly warmed to 0° C. over 2-3 h. The reaction was quenched by the addition of saturated ammonium chloride and extracted with EtOAc (3×15 mL). The combined organic layer was dried over MgSO$_4$, filtered and concentrated. The residue was purified by silica gel chromatography (gradient, hexane→3% EtOAc-hexane).

General Procedure O

TFA (2 mL) was added to the alcohol (1.0 eq.). Upon cooling to 0° C., Et$_3$SiH (2.0 eq) was added and the mixture was warmed to room temperature and stirred for 2 h. The volatiles were removed and aqueous NaOH (1.0 eq) was added. The mixture was extracted with CH$_2$Cl$_2$ (3×15 mL) and the combined organic layer was dried over MgSO$_4$, filtered and concentrated. Purification of the residue was accomplished by silica gel chromatography (gradient, hexane→1/1 EtOAc-hexane).

General Procedure P

Method P1: To a THF solution of 2,4-dichloropyrimidine was (1.0 eq) added benzylamine (1.1 eq) at 0° C. The cooling bath was removed and the reaction was stirred for 3 h at room temperature before adding aq. sodium carbonate solution. The aqueous layer was then extracted into ethyl acetate (3×20 mL), and the combined ethyl acetate extracts were dried over sodium sulfate and concentrated. The crude solid was purified by silica gel chromatography to obtain two different regioisomers in ~3:1 ratio.

Method P2: To a DMF or THF solution of 2,4-dichloropyrimidine (1 eq) was added the amine (1.5 eq) and DIEA (3.0 eq). The reaction was stirred at room temperature until complete (by TLC or LCMS). A saturated NaHCO$_3$ (aq) solution was added to the reaction. The aqueous layer was extracted with ethyl acetate (3×5 mL), and combined ethyl acetate extracts were dried over sodium sulfate and concentrated. The crude solid was purified by silica gel chromatography.

General Procedure Q

Method Q1: The boronic acid (1.5 eq), the chloropyrimidine (1.0 eq) and tetrakis(triphenylphosphino)palladium (5 mol % relative to the boronic acid) were added sequentially to degassed dimethoxyethylene (2 mL) and to this mixture degassed sodium carbonate solution was added (2.0 eq). Resulting reaction mixture was stirred under nitrogen for 12 h at 80° C. After cooling to room temperature, ethyl acetate (15 mL) was added. It washed with brine, dried over sodium sulfate and concentrated. The crude product was purified on a silica gel column to provide the cross-coupling compound.

Method Q2: The boronic acid (1.5 eq), the chloropyrimidine (1.0 eq) and tetrakis(triphenylphosphino)palladium (5 mol % relative to the boronic acid) were added sequentially to degassed dimethoxyethylene (2 mL) and to this mixture degassed sodium carbonate solution was added (2.0 eq). Resulting reaction mixture was heated in a CEM Exployer PLS™ microwave at 150° C. for 30 min. After cooling to room temperature, ethyl acetate (5 mL) was added. The reaction mixture washed with brine, dried over sodium sulfate and concentrated. The crude product was purified by silica gel chromatography to yield the coupling compound.

General Procedure R

To the 2,4-dimethoxybenzyl derivative (1.0 eq) was added 20% TFA in DCM (10 mL) and stirred at room temperature for 1 h. The reaction mass was concentrated, and the residue was partitioned between DCM and sodium bicarbonate solution. The turbid DCM layer was concentrated and loaded onto silica gel column and eluted with 20% ethyl acetate in DCM to provide the amino compound.

General Procedure S

Method S1: To the N-alkyl or N-sulfonyl aminopyrimidine (1.1 eq) and alkyl bromide (1.0 eq) added NaH (60% suspension, 1.5 eq) at 0° C. The cooling bath was removed, and the reaction stirred at room temperature until complete. After quenching the reaction by adding small amount of methanol, brine (10 mL) and ethyl acetate (10 mL) were added. The brine layer was extracted with ethyl acetate (2×10 mL), and the combined ethyl acetate extracts were dried over sodium sulfate and concentrated. The obtained residue was purified on silica gel column to provide the alkylated compound.

Method S2: To the N-alkylamino compound (1.0 eq) and alkyl bromide (1.5 eq) was added NaH (60% suspension, 2.0 eq) at room temperature. The reaction was stirred at room temperature until complete. After quenching the reaction by adding small amount of methanol, brine (10 mL) and ethyl acetate (10 mL) were added. The brine layer was extracted with ethyl acetate (2×10 mL), and the combined ethyl acetate extracts were dried over sodium sulfate and concentrated. The obtained residue was purified on silica gel column to provide the alkylated compound.

General Procedure T

To a THF solution of the ester (1.0 eq) was added either LiOH or NaOH (5.0 eq) dissolved in H$_2$O-MeOH (1:1). The reaction was stirred at room temperature until complete. The solvent was evaporated, and the residue was partitioned between DCM and water. The pH of the aqueous layer was adjusted to ~pH 7 with 10% HCl (aq) solution and then extracted with DCM (3×2 mL). The combined organic layers were dried over Na$_2$SO$_4$ and concentrated.

Example 1

2-Bromo-1-(4-isopropyl-phenyl)-ethanone was prepared (0.95 g) following general procedure A using 1-(4-isopropyl-phenyl)-ethanone (0.66 mL, 3.92 mmol) and pyrrolidone hydrotribromide (2.1 g, 4.31 mmol).

4-(4-Isopropyl-phenyl)-thiazol-2-ylamine was prepared (0.41 g) following general procedure B using 2-bromo-1-(4-isopropyl-phenyl)-ethanone (0.5 g, 2.07 mmol), thiourea (173 mg, 2.28 mmol) and MeOH (10 mL). LCMS m/z: 219 (M+1)$^+$.

N-[4-(4-Isopropyl-phenyl)-thiazol-2-yl]-2,5-dimethoxy-benzenesulfonamide was prepared (62 mg) following general procedure C (method 1) using 4-(4-isopropyl-phenyl)-thiazol-2-yl amine (50 mg, 0.23 mmol), 2,5-dimethoxybenzenesulfonyl chloride (59 mg, 0.25 mmol), NaH (14 mg, 60%, 0.34 mmol) and THF (1 mL). LCMS m/z: 419 (M+1)$^+$; $^1$H NMR (CDCl$_3$, 400 MHz): δ 1.27 (d, 6H); 2.95 (m, 1H), 3.75 (s, 3H), 3.81 (3, 3H), 6.52 (s, 1H), 6.9 (d, 1H), 7.0 (dd, 1H), 7.31 (m, 2H), 7.44 (m, 2H), 7.6 (d, 1H), 10.2 (brs, 1H).

Example 2

To a solution of t-butanol (0.3 mL) in THF (3 mL) was added 2-chlorosulfonylacetyl chloride (0.1 mL, 1.0 mmol) at room temperature for 1 h. The volatiles were removed to provide the chlorosulfonyl-acetic acid tert-butyl ester (230 mg). The crude product was used without further purification.

4-(4-Isopropyl-phenyl)-thiazol-2-ylamine, chlorosulfonyl-acetic acid tert-butyl ester, DMAP (10 mol %) were combined using general procedure C (method 2) to afford [4-(4-Isopropyl-phenyl)-thiazol-2-ylsulfamoyl]-acetic acid tert-butyl ester. LCMS m/z: 398 (M+1)$^+$; $^1$H NMR (CDCl$_3$, 400 MHz): δ 1.27 (d, 6H); 1.44 (s, 9H); 2.95 (m, 1H); 4.06 (s, 2H); 6.48 (s, 1H); 7.32 (d, 2H); 7.39 (d, 2H); 10.5 (brs, 1H).

Example 3

[4-(4-Isopropyl-phenyl)-thiazol-2-ylsulfamoyl]-acetic acid tert-butyl ester was combined with 4M HCl in dioxane as in general procedure G1 to furnish [4-(4-Isopropyl-phenyl)-thiazol-2-ylsulfamoyl]-acetic acid. LCMS m/z: 342 (M+1)$^+$; $^1$HNMR (DMSO-d$_6$, 400 MHz): δ 1.22 (d, 6H); 2.92 (m, 1H); 4.04 (s, 2H); 7.17 (s, 1H); 7.33 (d, 2H); 7.66 (d, 2H); 12.98 (s); 13.2 (s).

Example 4

Thiophen-2-yl-methyl-thiourea was prepared (146 mg) following general procedure D, using 2-aminomethyl-thiophene (0.1 mL, 0.97 mmol)), Fmoc-isothiocyante (300 mg, 1.1 mmol) add diethylamine (0.5 mL). LC-MS m/z: 173 (M+1)$^+$.

[4-(4-Isopropyl-phenyl)-thiazol-2-yl]-thiophen-2-ylmethyl-amine was prepared (85 mg) following general procedure B using 2-bromo-1-(4-isopropyl-phenyl)-ethanone (72 mg, 0.3 mmol), thiophen-2-yl-methyl-thiourea (57 mg, 0.33 mmol). LC-MS (m/z): 315 (M+1)$^+$.

[4-(4-Isopropyl-phenyl)-thiazol-2-yl]-thiophen-2-ylmethyl-amine, chlorosulfonyl-acetic acid tert-butyl ester were combined according to general procedure C (method 2) to provide {[4-(4-isopropyl-phenyl)-thiazol-2-yl]-thiophen-2-ylmethyl-sulfamoyl}-acetic acid tert-butyl ester. LCMS m/z: 494 (M+1)$^+$.

The above ester was treated with 4M HCl as outlined in general procedure G1 to provide {[4-(4-Isopropyl-phenyl)-thiazol-2-yl]-thiophen-2-ylmethyl-sulfamoyl}-acetic acid. LCMS m/z: 438 (M+1)$^+$.

By analogous methods to those used to prepare Examples 1-3 and those in the relevant above Schemes, the following compounds were synthesized. In addition to methods used to prepare Examples 1-3, the compound of Example 13 was prepared from Example 12 following general procedure E to demethylate the methyl ether.

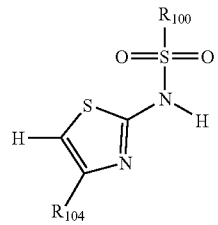

| EX. | R$_{100}$ | R$_{104}$ | LCMS m/z (M + 1)$^+$ |
|---|---|---|---|
| 5 | ![thiophene] | ![isopropylphenyl] | 365 |
| 6 | ![chlorophenyl] | ![isopropylphenyl] | 393 |

-continued

[Structure: thiazole with R100-SO2-NH- at 2-position and R104 at 4-position]

| EX. | R100 | R104 | LCMS m/z (M + 1)+ |
|---|---|---|---|
| 7 | 2,5-dimethoxyphenyl | 4-tert-butylphenyl | 433 |
| 8 | 2,5-dimethoxyphenyl | 4-isobutylphenyl | 433 |
| 9 | 4-biphenyl | 4-isopropylphenyl | 435 |
| 10 | phenyl | 4-isopropylphenyl | 359 |
| 11 | 3-biphenyl | 4-isopropylphenyl | 435 |
| 12 | 3-methoxyphenyl | 4-isopropylphenyl | 389 |
| 13 | 3-hydroxyphenyl | 4-isopropylphenyl | 375 |

-continued

| EX. | R$_{100}$ | R$_{104}$ | LCMS m/z (M + 1)$^+$ |
|---|---|---|---|
| 14 | 2,5-dimethoxyphenyl | phenyl | 377 |
| 15 | 2,5-dimethoxyphenyl | 3-methoxyphenyl | 407 |
| 16 | 3-carboxyphenyl | 4-isopropylphenyl | 403 |
| 17 | 4-chlorophenyl | 4-isopropylphenyl | 394 |
| 18 | 4-fluorophenyl | 4-isopropylphenyl | 378 |
| 19 | 2,4-dichlorophenyl | 4-isopropylphenyl | 428 |
| 20 | 3,4-dichlorophenyl | 4-isopropylphenyl | 428 |

-continued

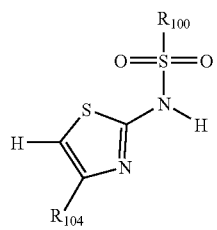

| EX. | R₁₀₀ | R₁₀₄ | LCMS m/z (M + 1)⁺ |
|---|---|---|---|
| 21 | 4-tert-butylphenyl | 4-isopropylphenyl | 416 |
| 22 | 4-cyanophenyl | 4-isopropylphenyl | 385 |
| 23 | 4-trifluoromethoxyphenyl | 4-isopropylphenyl | 444 |
| 24 | 4-carboxyphenyl | 4-isopropylphenyl | 404 |

Example 25

{(2,5-Dimethoxy-benzenesulfonyl)-[4-(4-isopropyl-phenyl)-thiazol-2-yl]-amino}-acetic acid tert-butyl ester was prepared following general procedure F using N-[4-(4-isopropyl-phenyl)-thiazol-2-yl]-2,5-dimethoxy-benzenesulfonamide (126 mg, 0.3 mmol), tert-butyl bromoacetate (90.4 μL, 98%, 0.6 mmol), potassium carbonate (124 mg, 0.9 mmol) and DMF (1 mL). Purification (silica gel, ethyl acetate/hexanes 1:4) gave the product compound (111 mg, 0.208 mmol). LCMS m/z: 533 (M+1)⁺.

{(2,5-Dimethoxy-benzenesulfonyl)-[4-(4-isopropyl-phenyl)-thiazol-2-yl]-amino}-acetic acid was prepared following general procedure G1 using a solution of {(2,5-dimethoxy-benzenesulfonyl)-[4-(4-isopropyl-phenyl)-thiazol-2-yl]-amino}-acetic acid tert-butyl ester (96.8 mg, 0.182 mmol) in DCM (3 mL) and 4 N HCl solution in dioxane (2.5 mL) followed by trituration in hexanes to give {(2,5-Dimethoxy-benzenesulfonyl)-[4-(4-isopropyl-phenyl)-thiazol-2-yl]-amino}-acetic acid. ¹H-NMR (400 MHz, CDCl₃): 7.64 (d, 2H), 7.55 (d, 1H), 7.09-7.26 (m, 3H), 6.87 (d, 1H), 4.85 (s, 2H), 3.82 (s, 3H), 3.66 (s, 3H), 2.92 (sept, 1H), 1.25 (d, 6H); LCMS m/z: 477 (M+1)⁺.

By analogous methods to those used to prepare Example 25 and those in the relevant above Schemes, the following compounds were synthesized.

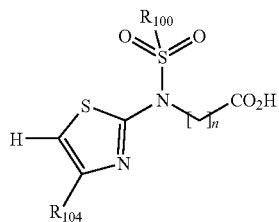
| EX | R$_{100}$ | R$_{104}$ | n | LCMS m/z (M + 1)$^+$ |
|---|---|---|---|---|
| 26 | 2,5-dimethoxyphenyl | 4-isopropylphenyl | 3 | 505 |
| 27 | 3-methoxyphenyl | 4-isopropylphenyl | 1 | 448 |
| 28 | 4-cyanophenyl | 4-isopropylphenyl | 1 | 443 |
| 29 | 3,4-dichlorophenyl | 4-isopropylphenyl | 2 | 500 |
| 30 | 4-chlorophenyl | 4-isopropylphenyl | 2 | 466 |
| 31 | 4-tert-butylphenyl | 4-isopropylphenyl | 2 | 488 |
| 32 | 4-fluorophenyl | 4-isopropylphenyl | 2 | 450 |

-continued

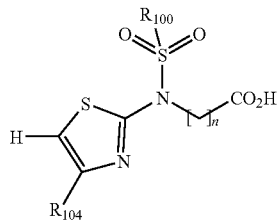

| EX | $R_{100}$ | $R_{104}$ | n | LCMS m/z $(M+1)^+$ |
|----|-----------|-----------|---|--------------------|
| 33 | 4-Cl-phenyl | 4-isopropyl-phenyl | 1 | 452 |
| 34 | 4-Me-phenyl | 4-isopropyl-phenyl | 1 | 502 |

Example 35

3-[(Thiophen-2-ylmethyl)-amino]-propionitrile was prepared following general procedure D using thiophene-2-carboxaldehyde (477 µL, 98%, 5 mmol), 3-amino-propionitrile (373 µL, 99%, 5 mmol), 1 M acetic acid solution in DCE (6 mL), DCE (9 mL) and sodium triacetoxyborohydride (1.31 g, 97%, 6 mmol). The crude product was used without further purification. LCMS m/z: 167 $(M+1)^+$.

3-[(thiophen-2-ylmethyl)-amino]-propionitrile (from previous step) and Fmoc isothiocyanate (1.48 g, 5 mmol) were dissolved in THF (8 mL). The mixture was stirred for 35 min. and diethyl amine (2 mL) was added. The reaction was stirred for a further 2 h. The resulting thiourea, after treating with hexanes, was used without further purification. LCMS m/z: 226 $(M+1)^+$.

3-{4-(4-isopropyl-phenyl)-thiazol-2-yl]-thiophen-2-ylmethyl-amino}-propionitrile was prepared following general procedure B using 2-bromo-1-(4-isopropyl-phenyl)-ethanone (5 mmol), 1-(2-cyano-ethyl)-1-thiophen-2-ylmethylthiourea (from previous step) and MeOH (15 mL). Purification by flash chromatography (ethyl acetate/hexanes 1:7, 1:4) gave the propionitrile (1.013 g, 2.76 mmol). LCMS m/z: 368 $(M+1)^+$.

3-{[4-(4-Isopropyl-phenyl)-thiazol-2-yl]-thiophen-2-ylmethyl-amino}-propionic acid was prepared following general procedure I using 3-{[4-(4-isopropyl-phenyl)-thiazol-2-yl]-thiophen-2-ylmethyl-amino}-propionitrile (368 mg, 1 mmol), 1 N NaOH (aq) solution (4 mL) and ethanol (2 mL). The mixture was refluxed for 15 h. Trituration in hexanes gave 3-{[4-(4-isopropyl-phenyl)-thiazol-2-yl]-thiophen-2-ylmethyl-amino}-propionic acid. LCMS m/z: 387 $(M+1)^+$. The sodium salt was prepared following general procedure J using 3-{[4-(4-isopropyl-phenyl)-thiazol-2-yl]-thiophen-2-ylmethyl-amino}-propionic acid (93.8 mg, 0.243 mmol), 1 N NaOH (aq) solution (0.243 mL), THF (1 mL) and MeOH (1 mL). Trituration in hexanes gave sodium 3-{[4-(4-isopropyl-phenyl)-thiazol-2-yl]-thiophen-2-ylmethyl-amino}-propionate.

$^1$H-NMR (400 MHz, $CD_3OD$): 7.78-7.81 (m, 2H), 7.22-7.28 (m, 3H), 7.13-7.14 (m, 1H), 6.94-6.96 (m, 1H), 6.83 (s, 1H), 4.99 (s, 2H), 3.70 (dd, 2H), 2.91 (sept, 1H), 2.56-2.59 (m, 2H), 1.26 (d, 6H); LCMS m/z: 387 $(M+1)^+$.

Example 36

3-(1-Thiophen-2-ylmethyl-thioureido)-propionic acid tert-butyl ester was prepared (750 mg) following general procedure D using thiophene-2-carbaldehyde (0.466 mL, 5 mmol), beta-alanine tert-butyl ester hydrochloride (905 mg, 5 mmol), sodium triacetoxyborohydride (1.27 g, 6 mmol), Fmoc isothiocyanate (1.4 g, 95.3%, 5 mmol), and diethyl amine (2 mL). LCMS m/z: 301 $(M+1)^+$.

3-{Thiophen-2-ylmethyl-[4-(4-p-tolyl)-thiazol-2-yl]-amino}-propionic acid tert-butyl ester was prepared (37 mg, 89%) following general procedure B using 2-bromo-1-(4-tolyl)-ethanone (21 mg, 0.1 mmol), 3-(1-thiophen-2-ylmethyl-thioureido)-propionic acid tert-butyl ester (30 mg, 0.1 mmol). LCMS m/z: 416 $(M+1)^+$.

3-{Thiophen-2-ylmethyl-[4-(4-p-tolyl)-thiazol-2-yl]-amino}propionic acid hydrochloride was prepared (35 mg) following general procedure G1 using 3-{thiophen-2-ylmethyl-[4-(4-tolyl)-thiazol-2-yl]-amino}propionic acid tert-butyl ester (37 mg, 0.089 mmol) and 4 N HCl solution in dioxane (1.0 mL). LCMS m/z: 360 $(M+1)^+$. $^1$H NMR ($CDCl_3$, 400 MHz): δ 2.4 (s, 3H), 3.1 (t, 2H), 4.3 (t, 2H), 5.2 (s, 2H), 6-5-7.8 (Ar—H, 8H).

Example 37

Trans-4-methyl-cyclohexanol (4.0 g, 35.03 mmol), 4'-fluoroacetophenone (166.1 mg, 1.202 mmol), DMF (60 mL) and NaH (1.33 g, 33.3 mmol, 60% suspension in mineral oil) were combined as outlined in general procedure L using sonication. After aqueous workup the residue was purified by silica gel chromatography (gradient, hexane→4% EtOAc-hexane) to obtain the desired ether (2.86 g).

The above acetophenone derivative (2.30 g, 9.91 mmol), pyrrolidone hydrotribromide (5.2 g, 10.48 mmol) and MeOH (70 mL) were combined according to general procedure A. After aqueous workup, the resulting 2-bromoketone was used without further purification.

The 2-bromo-1-[4-(trans-4-methyl-cyclohexyloxy)-phenyl]-ethanone (764 mg, 3.44 mmol), 3-(1-cyclopentyl-thioureido)-propionic acid tert-butyl ester (935 mg, 2.46 mmol), NMP (6 mL) were combined as indicated in general procedure B. The reaction was stirred at room temperature overnight. After an aqueous work up, the crude product was purified by silica gel chromatography (gradient, hexane→3% EtOAc-hexane) to afford 3-(cyclopentyl-{4-[4-(trans-4-methyl-cyclohexyloxy)-phenyl]-thiazol-2-yl}-amino)-propionic acid tert-butyl ester (1.05 g).

The above ester (94.6 mg, 0.195 mmol) and 4M HCl in dioxane (3 mL) were combined utilizing general procedure G1 to afford the HCl salt of 3-(cyclopentyl-{4-[4-(trans 4-methyl-cyclohexyloxy)-phenyl]-thiazol-2-yl}-amino)-propionic acid (77.5 mg), LCMS m/z: 430 (M+1)$^+$.

Example 38

3-(1-Cyclopentyl-thioureido)-propionic acid tert-butyl ester was prepared using general procedure D with cyclopentanone, beta-alanine tert-butyl ester hydrochloride, sodium triacetoxyborohydride, Fmoc isothiocyanate, and diethyl amine.

3-{[5-Chloro-4-(2,4-dimethyl-phenyl)-thiazol-2-yl]-cyclopentyl-amino}-propionic acid tert-butyl ester was prepared from 2-bromo-1-(2,4-dimethyl-phenyl)-ethanone (216 mg, 0.952 mmol), 3-(1-cyclopentyl-thioureido)-propionic acid tert-butyl ester (520 mg, 1.911 mmol), and MeOH (6 mL) following general procedure B. After aqueous workup, the residue was purified by silica gel chromatography (gradient, hexane→5% EtOAc-hexane) to afford the thiazole ester (330 mg).

The above ester (135.4 mg, 0.339 mmol), NCS (46.7 mg, 0.349 mmol) and MeCN (4 mL) were combined according to general procedure M. After aqueous workup, the chlorothiazole was purified by silica gel chromatography (gradient, hexane→5% EtOAc-hexane) to furnish 3-{[5-chloro-4-(2,4-dimethyl-phenyl)-thiazol-2-yl]-cyclopentyl-amino}-propionic acid tert-butyl ester (134.4 mg).

The above ester (134 mg, 0.308 mmol) and 4M HCl in dioxane (2 mL) were combined utilizing general procedure G1 to afford the HCl salt of 3-{[5-chloro-4-(2,4-dimethyl-phenyl)-thiazol-2-yl]-cyclopentyl-amino}-propionic acid (113.5 mg, 89%), LCMS m/z: 380 (M+1)$^+$.

Example 39

3-[4-(4-Isopropyl-phenyl)-thiazol-2-ylamino]-propionic acid tert-butyl ester was prepared from 3-amino-propionic acid tert-butyl ester (570 mg, 3.13 mmol), Fmoc-NCS (968 mg), via general procedure D to yield the Fmoc protected 3-thioureido-propionic acid tert-butyl ester (1.3 g). The Fmoc group was removed with Et$_2$NH (2 mL).

Combination of the above thiourea, 2-Bromo-1-(4-isopropyl-phenyl)-ethanone by means of general procedure B furnished 3-[4-(4-Isopropyl-phenyl)-thiazol-2-ylamino]-propionic acid tert-butyl ester (850 mg). LCMS m/z: 348 (M+1)$^+$.

3-{[4-(4-Isopropyl-phenyl)-thiazol-2-yl]-thiophen-3-yl-amino}-propionic acid tert-butyl ester was synthesized by combining the above prepared 2-aminothiazole ester (200 mg, 0.577 mmol), Cu(OAc)$_2$ (208 mg, 1.154 mmol), thiophene-3-boronic acid (110 mg, 0.866 mmol), and powdered 4 Å molecular sieves (200 mg). The reaction mixture was diluted with dichloromethane (5 mL) and triethylamine (0.42 mL, 2.886 mmol). After stirring the heterogenous reaction mixture for 24 h at room temperature under ambient atmosphere, the resulting slurry was filtered and the product was isolated from the organic filtrate by flash chromatography (eluant: 20% ethyl acetate in hexanes). Yield 16 mg. LCMS m/z: 430 (M+1)$^+$.

3-{[4-(4-Isopropyl-phenyl)-thiazol-2-yl]-thiophen-3-yl-amino}-propionic acid was prepared from the above ester using general procedure G1. $^1$H NMR (DMSO-d$_6$, 400 MHz): δ 1.22 (d, 6H); 2.70 (m, 2H), 2.90 (m, 1H); 3.81 (brs, 1H); 4.16 (m, 2H), 7.15 (s, 1H), 7.29 (m, 3H); 7.67 (m, 2H); 7.77 (m, 2H).

By analogous methods to those used to prepare Examples 35-39 and those in the relevant above Schemes, the following compounds were synthesized. HCl salts were prepared using general procedure G1. Sodium salts were prepared using general procedure J. All other compounds in the table below were prepared as the neutral free carboxylic acid.

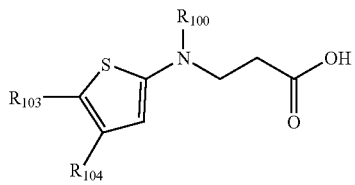

| Ex | R$_{100}$ | R$_{103}$ | R$_{104}$ | Salt form | LCMS m/z (M + 1)$^+$ |
|---|---|---|---|---|---|
| 40 | H | H | 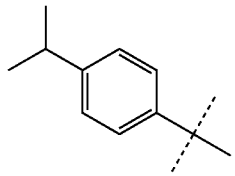 | | 291 |

-continued
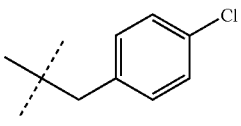
| Ex | R$_{100}$ | R$_{103}$ | R$_{104}$ | Salt form | LCMS m/z (M + 1)$^+$ |
|---|---|---|---|---|---|
| 41 | 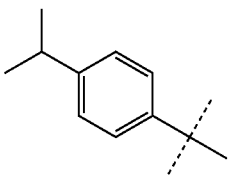 | H | 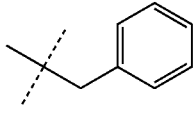 | Na | 415 |
| 42 | 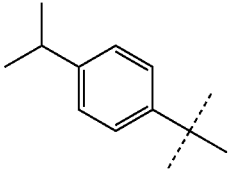 | H | 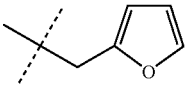 | HCl | 381 |
| 43 | 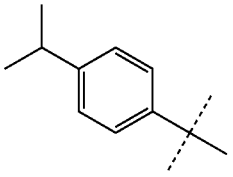 | H | 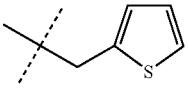 | HCl | 371 |
| 44 | 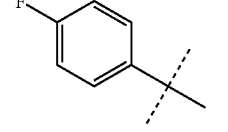 | H | 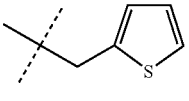 | HCl | 364 |
| 45 | 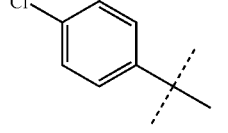 | H | 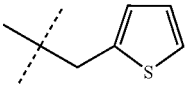 | HCl | 380 |
| 46 | 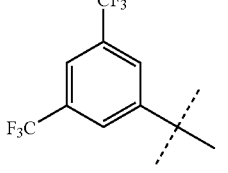 | H | 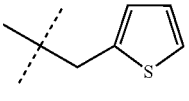 | HCl | 482 |
| 47 | 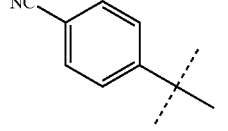 | H |  | HCl | 371 |

-continued

[Structure: thiophene with R103 at 5-position, R104 at 4-position, N(R100) at 2-position bearing CH2CH2COOH]

| Ex | R<sub>100</sub> | R<sub>103</sub> | R<sub>104</sub> | Salt form | LCMS m/z (M + 1)<sup>+</sup> |
|---|---|---|---|---|---|
| 48 | CH2-(2-thienyl) | H | 2-naphthyl | HCl | 396 |
| 49 | CH2-(2-thienyl) | H | 4-(CF3O)-phenyl | HCl | 430 |
| 50 | CH2-(2-thienyl) | Me | phenyl | HCl | 360 |
| 51 | CH2-(2-thienyl) | phenyl | phenyl | HCl | 422 |
| 52 | CH2-(2-thienyl) | Me | 3-chloro-4-methylphenyl | HCl | 408 |
| 53 | CH2-(2-thienyl) | H | 3,4-dihydroxyphenyl | HCl | 378 |
| 54 | CH2-(2-thienyl) | H | 4-Ph-phenyl | Na | 422 |
| 55 | CH2-(2-thienyl) | H | 3-OMe-phenyl | HCl | 376 |

-continued

| Ex | R$_{100}$ | R$_{103}$ | R$_{104}$ | Salt form | LCMS m/z (M + 1)$^+$ |
|---|---|---|---|---|---|
| 56 | 2-thienylmethyl (CH$_2$-thiophene) | H | 4-methoxyphenyl | HCl | 376 |
| 57 | 2-thienylmethyl | H | 5,5,8,8-tetramethyl-5,6,7,8-tetrahydronaphthalen-2-yl | HCl | 456 |
| 58 | 2-thienylmethyl | H | 3,5-di-tert-butyl-4-hydroxyphenyl | HCl | 474 |
| 59 | 3,3-dimethylbut-2-yl | H | 4-isopropylphenyl |  | 334 |
| 60 | 2,5-dimethylhexyl | H | 4-isopropylphenyl | HCl | 362 |
| 61 | 2-cyclohexyl-1,1-dimethylethyl | H | 4-isopropylphenyl | HCl | 388 |
| 62 | 2-cyclopentyl-2-methylpropyl | H | 4-isopropylphenyl | Na | 360 |

-continued

[Structure: thiophene with R103 at 5-position, R104 at 4-position, and N(R100)-CH2CH2-COOH at 2-position]

| Ex | R₁₀₀ | R₁₀₃ | R₁₀₄ | Salt form | LCMS m/z (M+1)⁺ |
|---|---|---|---|---|---|
| 63 | 4-MeO-benzyl | H | 4-isopropylphenyl | | 412 |
| 64 | 3-MeO-benzyl | H | 4-isopropylphenyl | | 412 |
| 65 | 2-thienylmethyl | H | 4-CF₃-phenyl | HCl | 414 |
| 66 | 2-thienylmethyl | H | 4-tert-butylphenyl | HCl | 402 |
| 67 | 2-thienylmethyl | H | 4-isobutylphenyl | HCl | 402 |
| 68 | 2-thienylmethyl | H | 1-naphthyl | HCl | 396 |
| 69 | 2-thienylmethyl | H | 4-ethoxyphenyl | HCl | 390 |

-continued

| Ex | R₁₀₀ | R₁₀₃ | R₁₀₄ | Salt form | LCMS m/z (M + 1)⁺ |
|---|---|---|---|---|---|
| 70 | -CH₂-C(CH₃)₂-(2-thienyl) | H | 4-(isobutoxy)-phenyl with t-Bu (4-tert-butyl-2-isobutoxyphenyl) | HCl | 418 |
| 71 | -CH₂-C(CH₃)₂-(2-thienyl) | H | 3-phenyl-phenyl-tBu | HCl | 422 |
| 72 | -CH₂-C(CH₃)₂-(3-thienyl) | H | 4-isopropylphenyl-tBu | HCl | 388 |
| 73 | -CH₂-C(CH₃)₂-(4-OCF₃-phenyl) | H | 4-isopropylphenyl-tBu | HCl | 466 |
| 74 | -CH₂-C(CH₃)₂-(3-OCF₃-phenyl) | H | 4-isopropylphenyl-tBu | HCl | 466 |
| 75 | -C(CH₃)₂-cyclopentyl | H | 2,4-difluorophenyl-tBu | HCl | 354 |
| 76 | -C(CH₃)₂-cyclopentyl | H | 2,4-dimethylphenyl-tBu | HCl | 346 |

-continued

| Ex | R₁₀₀ | R₁₀₃ | R₁₀₄ | Salt form | LCMS m/z (M + 1)⁺ |
|---|---|---|---|---|---|
| 77 | cyclopentylmethyl | Cl | 4-isopropylphenyl | HCl | 394 |
| 78 | cyclopentylmethyl | Me | 4-isobutylphenyl | HCl | 388 |
| 79 | cyclopentylmethyl | H | 4-chloro-3-methylphenyl | HCl | 366 |
| 80 | cyclopentylmethyl | H | 3,4-difluorophenyl | Na | 354 |
| 81 | cyclopentylmethyl | H | 2,4-dichlorophenyl | Na | 386 |
| 82 | cyclopentylmethyl | Cl | 2,4-difluorophenyl | Na | 388 |
| 83 | cyclopentylmethyl | Cl | 3,4-difluorophenyl | Na | 388 |

-continued
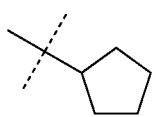
| Ex | R<sub>100</sub> | R<sub>103</sub> | R<sub>104</sub> | Salt form | LCMS m/z $(M+1)^+$ |
|---|---|---|---|---|---|
| 84 | 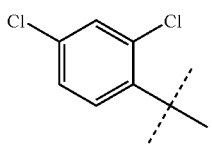 | Cl | 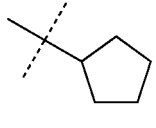 | Na | 420 |
| 85 | 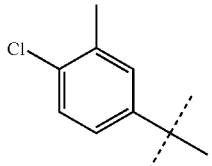 | Cl | 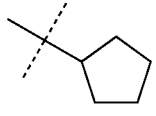 | Na | 400 |
| 86 | 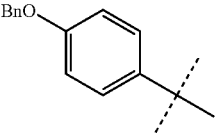 | H | 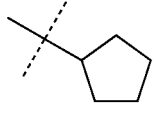 | HCl | 424 |
| 87 | 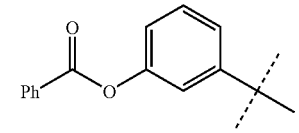 | H | 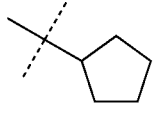 | HCl | 438 |
| 88 | 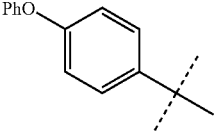 | H | 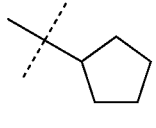 | Na | 410 |
| 89 | 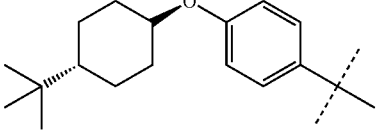 | H | 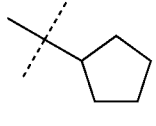 | Na | 471 |
| 90 | 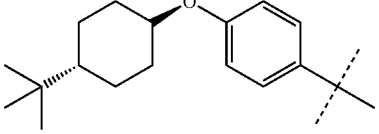 | Cl | 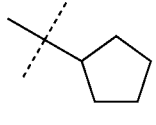 | Na | 506 |
| 91 | 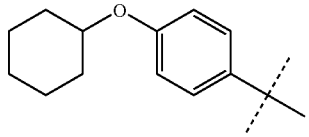 | H | | HCl | 416 |

-continued

[Structure: R103-thiophene(R104)-N(R100)-CH2CH2-C(=O)-OH]

| Ex | R100 | R103 | R104 | Salt form | LCMS m/z (M + 1)+ |
|---|---|---|---|---|---|
| 92 | cyclopentyl-CH(CH3)- | H | Ph-CH2CH2-O-C6H4-C(CH3)2- | HCl | 438 |
| 93 | cyclopentyl-CH(CH3)- | H | cyclohexyl-CH2-O-C6H4-C(CH3)2- | HCl | 430 |
| 94 | cyclopentyl-CH(CH3)- | H | Ph-CH2CH2CH2-O-C6H4-C(CH3)2- | HCl | 452 |
| 95 | cyclopentyl-CH(CH3)- | Cl | Ph-CH2CH2CH2-O-C6H4-C(CH3)2- | HCl | 486 |
| 96 | cyclopentyl-CH(CH3)- | Cl | cyclohexyl-CH2-O-C6H4-C(CH3)2- | HCl | 464 |
| 97 | cyclopentyl-CH(CH3)- | H | Br-C6H4-C(CH3)2- | HCl | 397 |
| 98 | cyclopentyl-CH(CH3)- | H | tetrahydropyran-4-yl-O-C6H4-C(CH3)2- | HCl | 418 |
| 99 | 2-thienyl-CH2-C(CH3)- | H | 4-methylcyclohexyl-O-C6H4-C(CH3)2- | Na | 458 |

Example 100

To a solution of 1-phenyl-propane-1,2-dione (1.72 g, 0.0116 mol) in DCE (5 mL) was added $Br_2$ (1.87 g, 0.0169 mol). The reaction mixture was stirred for 75 min. and the volatiles were removed to yield 3.21 g of 3-bromo-1-phenyl-propane-1,2-dione. The crude bromoketone (0.1046 mol) was combined at room temperature with 3-(1-cyclopentyl-thioureido)-propionic acid tert-butyl ester (7.00 g, 0.031 mol) in NMP (50 mL) following general procedure B. The reaction was purified by silica gel chromatography (gradient, hexane→8% EtOAc-hexane) to yield 3-[(4-Benzoyl-thiazol-2-yl)-cyclopentyl-amino]-propionic acid tert-butyl ester (4.0 g).

The above tert-butyl ester (78.8 mg, 0.197 mmol) was combined with 4M HCl in dioxane (2 mL) following general procedure G1 to afford 3-[(4-benzoyl-thiazol-2-yl)-cyclopentyl-amino]-propionic acid (60.7 mg).

The above ketoacid (40 mg, 0.105 mmol), 4-tert-butylphenylmagnesium bromide (0.384 mmol) and THF (3 mL) were combined as outlined in general procedure N. After aqueous workup the residue was purified by silica gel chromatography (gradient, $CH_2Cl_2$ →2% MeOH—$CH_2Cl_2$) to afford the desired 3-({4-[(4-tert-Butyl-phenyl)-hydroxy-phenyl-methyl]-thiazol-2-yl}-cyclopentyl-amino)-propionic acid (24 mg).

The alcohol (24 mg, 0.0502 mmol), TFA (1.0 mL) and $Et_3SiH$ (0.10 mL) were combined according to general procedure O. After aqueous workup the residue was purified by silica gel chromatography (gradient, $CH_2Cl_2$→2% MeOH—$CH_2Cl_2$). The sodium salt was prepared via general procedure J to afford sodium 3-({4-[(4-tert-butyl-phenyl)-phenyl-methyl]-thiazol-2-yl}-cyclopentyl-amino)-propionate (10.3 mg). LCMS m/z: 464 (M+1).

Example 101

Ethyl bromopyruvate (0.13 mL, 0.932 mmol), 3-(1-Cyclopentyl-thioureido)-propionic acid tert-butyl ester (243 mg, 0.893 mmol) were combined in THF (3 mL) following general procedure B. The reaction was purified by silica gel chromatography (gradient, hexane→10% EtOAc-hexane) to yield 2-[Cyclopentyl-(2-ethoxycarbonyl-ethyl)-amino]-thiazole-4-carboxylic acid tert-butyl ester (208 mg).

3-{Cyclopentyl-[4-(hydroxy-diphenyl-methyl)-thiazol-2-yl]-amino}-propionic acid tert-butyl ester was prepared using general procedure N. The diester (185 mg, 0.503 mmol) in THF (3 ml) was combined with phenylmagnesium bromide (1.53 mmol) at −78° C. After aqueous workup the residue was purified by silica gel chromatography (gradient, hexane→3% EtOAc-hexane) to afford the desired 3° alcohol (131 mg).

The above alcohol (131 mg, 0.274 mmol), TFA (2.0 mL) and $Et_3SiH$ (0.23 mL) were combined according to general procedure O. After aqueous workup the residue was purified by silica gel chromatography (gradient, hexane→1/1 EtOAc-hexane). After concentration and trituration from hexane, 3-[(4-Benzhydryl-thiazol-2-yl)-cyclopentyl-amino]-propionic acid (45 mg, 40%) was obtained. LCMS m/z: 408 (M+1). The HCl salt was also prepared, using general procedure G2, by the addition of 4 M HCl in dioxane.

By analogous methods to those used to prepare Example 100-101 and those in the relevant above Schemes, the following compounds were synthesized. HCl salts were prepared using general procedure G1. All other compounds in the table below were prepared as the neutral free carboxylic acid.

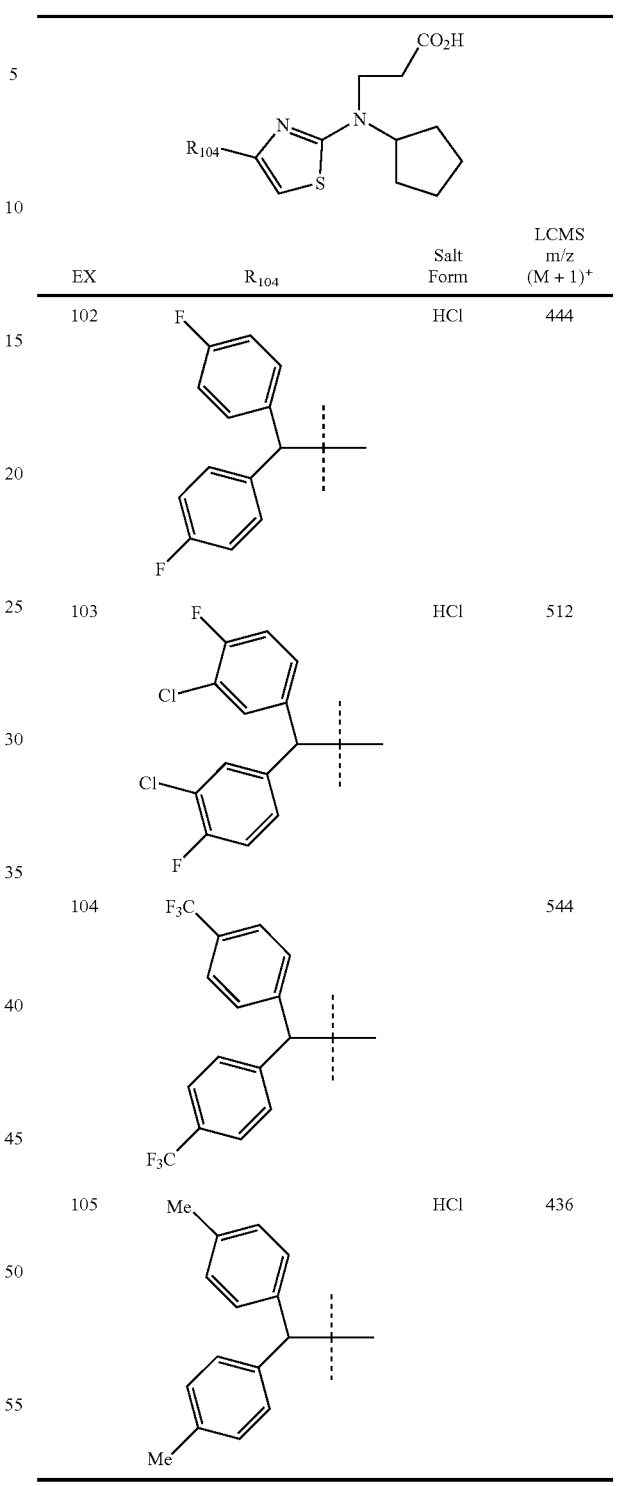

| EX | $R_{104}$ | Salt Form | LCMS m/z $(M + 1)^+$ |
|---|---|---|---|
| 102 | | HCl | 444 |
| 103 | | HCl | 512 |
| 104 | | | 544 |
| 105 | | HCl | 436 |

Example 106

2-bromomethyl-benzoic acid methyl ester (Dvornikovs, V.; Smithrud, D. B.; *J. Org. Chem.*; 2002, 67, 2160-2167) was prepared, via the cited literature preparation, from methyl 2-methylbenzoate by alpha-bromination (NBS, benzoyl peroxide, $CCl_4$, 80° C.).

Cyclopentyl-thiourea was prepared following procedure D using cyclopentyl amine (2.4 g, 28 mmol), and Fmoc-isothiocyanate (5.6 g, 20 mmol). Purification (Silica gel, ethyl acetate/hexane 1:1, 100%) provided the product (1.6 g) as white a solid. LCMS m/z: 145 (M+1)$^+$.

Cyclopentyl-[4-(4-isopropyl-phenyl)-thiazol-2-yl]-amine was prepared following procedure B using cyclopentyl-thiourea (1.6 g, 10.7 mmol) and 2-bromo-1-(4-isopropyl-phenyl)-ethanone (2.6 g, 10.7 mmol). Purification (Silica gel, ethyl acetate/hexane 5:95) provided the product (2.9 g). LCMS m/z: 287 (M+1)$^+$.

2-({Cyclopentyl-[4-(4-isopropyl-phenyl)-thiazol-2-yl]-amino}-methyl)-benzoic acid (19 mg) was prepared following general method S2 using cyclopentyl-[4-(4-isopropyl-phenyl)-thiazol-2-yl]-amine (80 mg, 0.28 mmol), 2-bromomethyl-benzoic acid methyl ester (68 mg, 0.33 mmol) and NaH (34 mg, 60%, 0.84 mmol). Purification (Silica gel, ethyl acetate/hexane 5:95) provided the ester, which was hydrolyzed following general procedure T. Sodium 2-({cyclopentyl-[4-(4-isopropyl-phenyl)-thiazol-2-yl]-amino}-methyl)-benzoate was prepared following procedure J. LCMS m/z: 422 (M+1)$^+$.

By analogous methods to those used to prepare Example 106 and those in the relevant above Schemes, the following compounds were synthesized. The starting 3- or 4-bromomethyl benzoic acid methyl esters used in Examples 108-110, 112, and 114-117 were obtained from commercial sources.

| EX | $R_{100}$ | $R_{103}$ | $R_{104}$ | Acid position | LCMS m/z (M+1)$^+$ |
|---|---|---|---|---|---|
| 107 | CH$_2$-thiophen-2-yl | H | 4-isopropylphenyl | 2 | 450 |
| 108 | CH$_2$-thiophen-2-yl | H | 4-isopropylphenyl | 3 | 450 |
| 109 | CH$_2$-thiophen-2-yl | H | 4-isopropylphenyl | 4 | 450 |
| 110 | cyclopentyl | H | 4-isopropylphenyl | 3 | 422 |
| 111 | cyclopentyl | Ph | Ph | 2 | 456 |

-continued

[Structure: thiazole with R103 at 5-position, R104 at 4-position, N-R100 and N-CH2-phenyl-COO⁻Na⁺ at 2-position]

| EX | $R_{100}$ | $R_{103}$ | $R_{104}$ | Acid position | LCMS m/z $(M + 1)^+$ |
|---|---|---|---|---|---|
| 112 | CH(CH3)-cyclopentyl | Ph | Ph | 3 | 456 |
| 113 | CH(CH3)-CH2-(2-thienyl) | Ph | Ph | 2 | 484 |
| 114 | CH(CH3)-CH2-(2-thienyl) | Ph | Ph | 3 | 484 |
| 115 | CH(CH3)-CH2-(2-thienyl) | Ph | Ph | 4 | 484 |
| 116 | CH(CH3)-cyclopentyl | Ph | Ph | 4 | 456 |
| 117 | CH(CH3)-cyclopentyl | H | 4-isopropylphenyl-C(CH3)- | 4 | 422 |

Example 118

4-[(1-Cyclopentyl-thioureido)-methyl]-benzoic acid methyl ester (550 mg) compound was prepared following general procedure D using cyclopentylamine (935 mg, 11.0 mmol), 4-formylmethylbenzoate (1.64 g, 10.0 mmol), and Fmoc-isothiocyanate (9 mmol). Purification: (Silica gel, ethyl acetate/hexane 1:1). LCMS m/z: 293.0 $(M+1)^+$.

cis-4-Methyl-cyclohexanol (3.28 g, 28.7 mmol), NaH (1.09 g, 27.3 mmol, 60% suspension in mineral oil) and DMF (50 mL) were combined and sonicated as in general procedure L. The mixture was charged with 4'-fluoroacetophenone (2.18 mL, 17.8 mmol) and heated. After aqueous workup, the crude residue was purified on a silica gel column (gradient, hexane→2% EtOAc-hexane) to obtain 1-[4-(cis-4-Methyl-cyclohexyloxy)-phenyl]-ethanone (976 mg).

2-Bromo-1-[4-(cis-4-methyl-cyclohexyloxy)-phenyl]-ethanone (650 mg) was prepared following procedure A using 1-[4-(4-Methyl-cyclohexyloxy)-phenyl]-ethanone (464 mg, 2.0 mmol) and pyrrolidone hydrotribromide (701 mg, 2.2 mmol).

4-[(Cyclopentyl-{4-[4-(cis-4-methyl-cyclohexyloxy)-phenyl]-thiazol-2-yl}-amino)-methyl]-benzoic acid (90 mg) was prepared following procedure B using 4-[(1-cyclopentyl-thioureido)-methyl]-benzoic acid methyl ester (150 mg, 0.5 mmol) and 2-bromo-1-[4-(4-methyl-cyclohexyloxy)-phenyl]-ethanone (0.5 mmol). Purification (Silica gel, ethyl acetate/hexane 5:95) provided the ester, which was hydrolyzed following procedure T. Sodium 4-[(cyclopentyl-{4-[4-(cis-4-methyl-cyclohexyloxy)-phenyl]-thiazol-2-yl}-amino)-methyl]-benzoate was made following procedure J. LCMS m/z: 492 $(M+1)^+$.

By analogous methods to those used to prepare Example 118 and those in the relevant above Schemes, the following compounds were synthesized. The starting 2-bromomethyl benzoic acid methyl ester (Dvornikovs, V.; Smithrud, D. B.; *J. Org. Chem.;* 2002, 67, 2160-2167) used in Examples 122-124 was prepared via the cited literature preparation, from methyl 2-methylbenzoate by alpha-bromination (NBS, benzoyl peroxide, $CCl_4$, 80° C.).

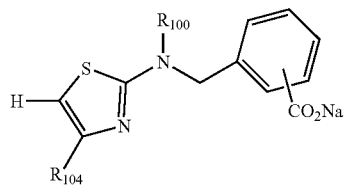

| EX | R₁₀₀ | R₁₀₄ | Acid position | LCMS m/z (M + 1)⁺ |
|---|---|---|---|---|
| 119 | cyclopentylmethyl | trans-4-(4-tert-butylphenoxy)cyclohexyl | 3 | 492 |
| 120 | cyclopentylmethyl | trans-4-(4-tert-butylphenoxy)cyclohexyl | 4 | 492 |
| 121 | cyclopentylmethyl | trans-4-(4-tert-butylphenoxy)cyclohexyl | 3 | 492 |
| 122 | cyclopentylmethyl | trans-4-(4-tert-butylphenoxy)cyclohexyl | 2 | 492 |
| 123 | 2-thienylmethyl | trans-4-(4-tert-butylphenoxy)cyclohexyl | 2 | 520 |
| 124 | cyclopentylmethyl | trans-4-(4-tert-butylphenoxy)cyclohexyl | 2 | 492 |
| 125 | 2-thienylmethyl | trans-4-(4-tert-butylphenoxy)cyclohexyl | 4 | 520 |
| 126 | 2-thienylmethyl | trans-4-(4-tert-butylphenoxy)cyclohexyl | 3 | 520 |

-continued

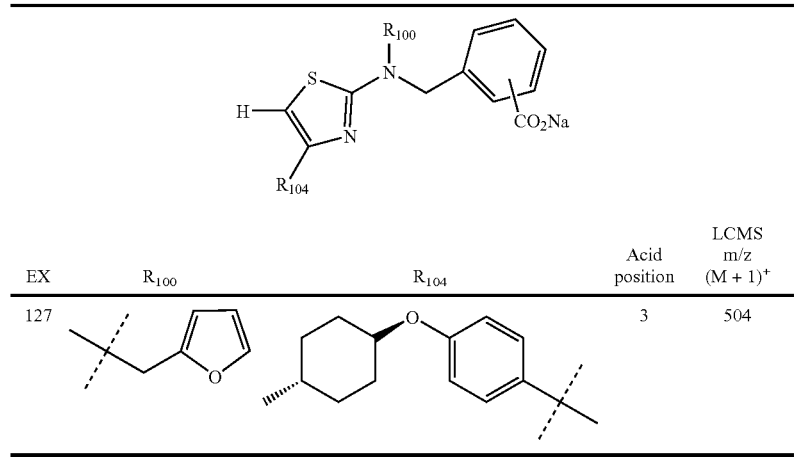

| EX | R₁₀₀ | R₁₀₄ | Acid position | LCMS m/z (M + 1)⁺ |
|---|---|---|---|---|
| 127 | furfuryl | cyclohexyl-O-phenyl-tBu | 3 | 504 |

Example 128

3-Chlorocarbonyl-isonicotinic acid methyl ester was prepared by refluxing a mixture of pyridine-3,4-dicarboxylic acid 4-methyl ester (100 mg) and thionyl chloride (75 µl) in chloroform (5 ml) for 3 h. After cooling to room temperature, volatiles were evaporated, and the residue was dried under high vacuum to give the product (100 mg).

3-{[4-(4-Isopropyl-phenyl)-thiazol-2-yl]-thiophen-2-yl-methyl-carbamoyl}-isonicotinic acid (20 mg) was prepared by adding 3-chlorocarbonyl-isonicotic acid methyl ester added to (4-(-isopropyl-phenyl)-thiazol-2-yl)-thiophen-2-yl-methyl-amine (80 mg. 0.43 mmol), TEA (300 µL), and DMAP (10 mg) in THF (3 mL). After 7 h reaction was partitioned between EtOAc (30 mL) and water (10 mL), the organic layer washed with brine (10 ml), dried (MgSO₄), filtered, and concentrated. The residual oil was purified by column chromatography eluting with (10-40-%) EtOAc in hexane to give the ester (30 mg), which was hydrolyzed according to general procedure T.: Sodium 3-{[4-(4-isopropyl-phenyl)-thiazol-2-yl]-thiophen-2-ylmethyl-carbamoyl}-isonicotinate was made following procedure J. LCMS m/z: 465 (M+1)⁺.

Example 129

4,5-Dichloro-N-[4-(4-isopropyl-phenyl)-thiazol-2-yl]-phthalamic acid (20 mg) was prepared by heating (40° C.) a mixture of (4-(-isopropyl-phenyl)-thiazol-2-yl)-thiophen-2-ylmethyl-amine (44 mg, 0.22 mmol), 4,5-dichloro-2,3-benzenedicarboxylic anhydride (44.0 mg, 0.2 mmol) in acetonitrile (3.0 ml) for 2.0 h. The volatiles removed under high vacuum, and the residue was purified by column chromatography eluting with 5% methanol in DCM. LCMS m/z: 436 (M+1)⁺.

By analogous methods to those used to prepare Examples 128 and 129 and those in the relevant above Schemes, the following compounds were synthesized.

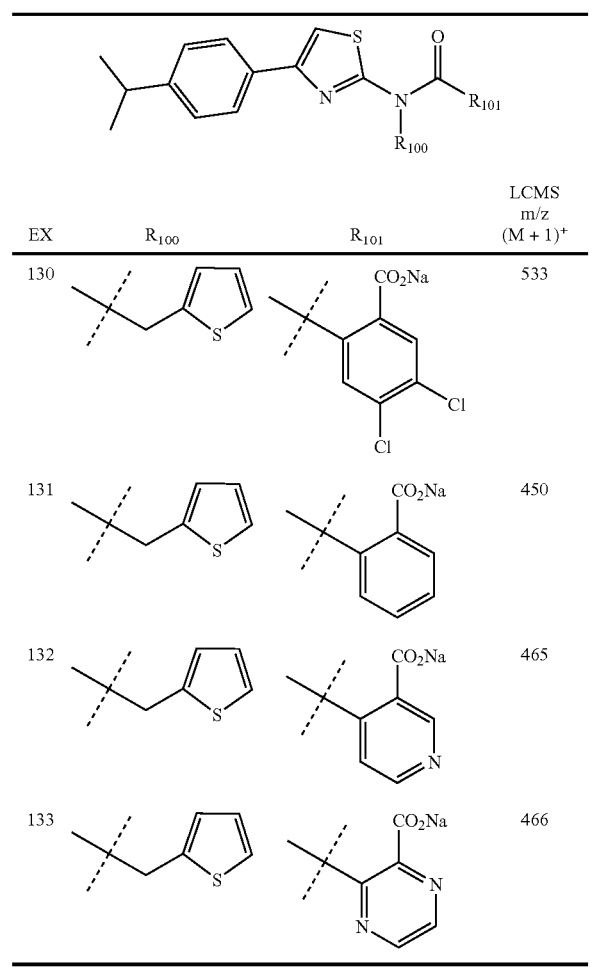

| EX | R₁₀₀ | R₁₀₁ | LCMS m/z (M + 1)⁺ |
|---|---|---|---|
| 130 | thiophen-2-ylmethyl | 4,5-dichloro-2-CO₂Na-phenyl | 533 |
| 131 | thiophen-2-ylmethyl | 2-CO₂Na-phenyl | 450 |
| 132 | thiophen-2-ylmethyl | 4-CO₂Na-pyridin-3-yl | 465 |
| 133 | thiophen-2-ylmethyl | 3-CO₂Na-pyrazin-2-yl | 466 |

Example 134

N-(3-{[4-(4-isopropyl-phenyl)-thiazol-2-yl]-thiophen-2-ylmethyl-amino}-propionyl)-benzenesulfonamide was prepared following procedure K using 3-{[4-(4-isopropyl-phenyl)-thiazol-2-yl]-thiophen-2-ylmethyl-amino}-propionic acid (Prepared in Example 35) (50 mg, 0.125 mmol), CDI (62 mg, 0.39 mmol), DBU (30 μl, 0.2. mmol), and benzene sulfonamide (41 mg, 0.26 mmol). Purification (Silica gel, ethyl acetate/hexane 1:4) provided the product (10 mg). LCMS m/z: 527 (M+1)$^+$.

By analogous methods to those used to prepare Example 134 and those in the relevant above Schemes, the following compounds were synthesized. Examples 143-144 in the table below were prepared as the HCl salt using general procedure G2. Example 144 was prepared as the dihydrochloride salt. Examples 135-142 were prepared as the neutral compound.

| EX | $R_{100}$ | $R_{101}$ | LCMS m/z (M+1)$^+$ |
|---|---|---|---|
| 135 | 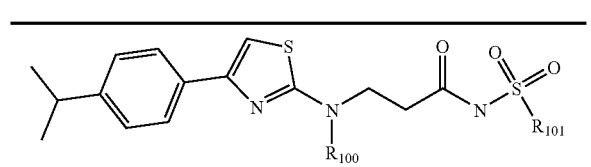 | Me | 465 |
| 136 | | Me | 437 |
| 137 | 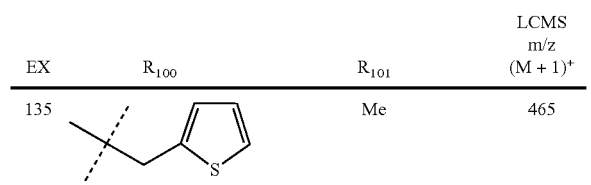 | | 552 |
| | | CN | |
| 138 |  | Cl | 561 |
| 139 | 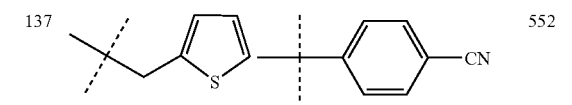 | F | 545 |
| 140 | 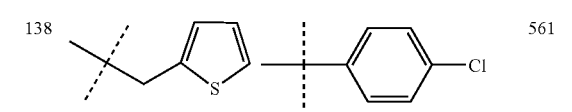 | Me | 541 |
| 141 | 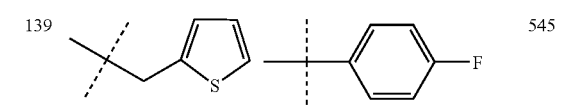 | Et | 479 |
| 142 | 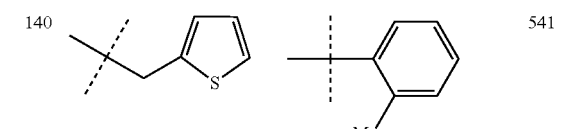 | t-Bu | 507 |
| 143 |  | Ph | 499 |

-continued

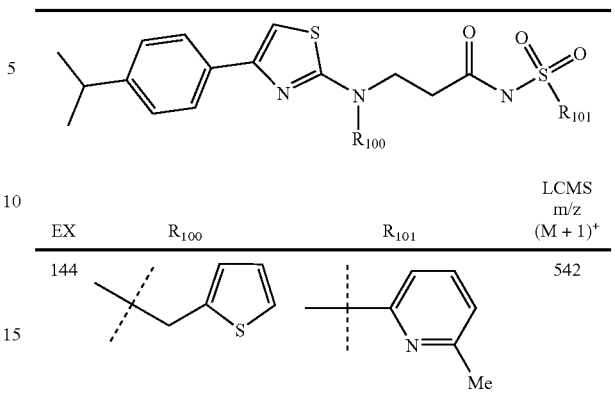

| EX | $R_{100}$ | $R_{101}$ | LCMS m/z (M+1)$^+$ |
|---|---|---|---|
| 144 |  |  | 542 |

Example 145 t-Butylbromoacetate (1.45 mL, 10 mmol) was added to 2-aminomethyl thiophene (1.13 g. 10.0 mmol) and DIEA (2.0 ml) in THF (20 mL). The mixture was warmed to room temperature (4 h), diluted with ether (100 mL) and washed with water (20 mL), brine (20 mL), dried (MgSO$_4$), filtered and evaporated in vacuum. The product was purified by column chromatography eluting with 10-25% EtOAc in hexane to give [(thiophen-2-ylmethyl)-amino]-acetic acid tert-butyl ester (1.2 g). LCMS m/z: 229 (M+1)$^+$.

A mixture of ethylthiooxamate (2.1 g, 15.8 mmol) and 2-bromo-4'-isopropylacetophenone (3.8 g, 15.8 mmol) in ethanol (10 mL) was heated at 60° C. for 15 h. After cooling to room temperature, ethanol was evaporated, and the residue was partioned between saturated sodium bicarbonate solution and EtOAc, organic layer was washed with brine, dried (MgSO$_4$), filtered, and concentrated in vacuum. The residue was purified by flash chromatography eluting with 5% EtOAc in hexane to give the ester (3.0 g).

Lithium aluminum hydride (205 mg, 5.5 mmol) was added to a cooled (0° C.) THF (15 mL) solution of the ester, after 3 h NaOH (1.0 M, 1.0 ml) was added, and stirring continued for another 1.0 h to give a white precipitate, which was removed by filtration, the filtrate was diluted with Et$_2$O (50 mL), dried (MgSO$_4$) filtered, and concentrated in vacuum to give the corresponding alcohol. LCMS m/z: 235 (M+1)$^+$.

The crude alcohol was then taken in DCM (5 ml) and added to a suspension of PCC (1.8 g), and celite (3.6 g) in DCM (20 mL), stirring continued for 3 h. The reaction mixture was diluted with Et$_2$O (100 mL) and filtered through a plug of silica gel, the filtrate was concentrated in vacuum to give 4-(4-Isopropyl-phenyl)-thiazole-2-carbaldehyde (650 mg), which was used without further purification. LCMS m/z: 232 (M+1)$^+$.

4-(4-Isopropyl-phenyl)-thiazole-2-carbaldehyde (100 mg, 0.43 mmol) and ((thiophen-2-ylmethyl)-amino) acetic acid t-butyl ester (196 mg, 0.86 mmol) were combined according to general procedure D. Purification (Silica gel, ethyl acetate/hexane 5:95) provided the ester (100 mg), which was hydrolyzed to provide the HCl salt of {[4-(4-Isopropyl-phenyl)-thiazol-2-ylmethyl]-thiophen-2-ylmethyl-amino}-acetic acid following procedure G1. LCMS m/z: 389 (M+1)$^+$.

By analogous methods to those used to prepare Example 145 and those in the relevant above schemes, the following compounds were synthesized.

| Ex | R$_{100}$ | n | LCMS m/z (M + 1)$^+$ |
|---|---|---|---|
| 146 | (cyclopentylmethyl) | 1 | 361 |
| 147 | (thiophen-2-ylmethyl) | 2 | 401 |
| 148 | (cyclopentylmethyl) | 2 | 375 |

Example 149

The regioisomeric aminopyrimidines were obtained from 2,4-dichloropyrimidine (150 mg, 1 mmol) and thiophen-2-yl-methylamine (1.1 mmol) by following general procedure P (method 1). (2-chloro-pyrimidin-4-yl)-thiophen-2-ylmethyl-amine was obtained in 60% yield (135 mg) LCMS (m/z): 227 (M+1)$^+$. (4-Chloro-pyrimidin-2-yl)-thiophen-2-ylmethyl-amine was obtained in 15% yield (34 mg). LCMS (m/z): 227 (M+1)$^+$.

[2-(4-Isopropyl-phenyl)-pyrimidin-4-yl]-thiophen-2-ylm-ethyl-amine (142 mg) was obtained by following general procedure Q1 from (2-chloro-pyrimidin-4-yl)-thiophen-2-yl-methyl-amine (130 mg, 0.58 mmol) and 4-isopropylphenyl-boronic acid (140 mg, 0.86 mmol). LCMS m/z: 311 (M+1)$^+$. [4-(4-Isopropyl-phenyl)-pyrimidin-4-yl]-thiophen-2-ylm-ethyl-amine was obtained by following general procedure Q1 from (4-Chloro-pyrimidin-2-yl)-thiophen-2-ylmethyl-amine and 4-isopropylphenylboronic acid.

{[2-(4-Isopropyl-phenyl)-pyrimidin-4-yl]-thiophen-2-yl-methyl-amino}-acetic acid tert-butyl ester was prepared (149 mg) from [2-(4-isopropyl-phenyl)-pyrimidin-4-yl]-thiophen-2-ylmethyl-amine (135 mg, 0.44 mmol) and bromoacetic acid tert-butyl ester in THF by following the general procedure F. LCMS m/z: 425 (M+1)$^+$.

{[2-(4-isopropyl-phenyl)-pyrimidin-4-yl]-thiophen-2-yl-methyl-amino}-acetic acid was prepared (120 mg) from {[2-(4-isopropyl-phenyl)-pyrimidin-4-yl]-thiophen-2-ylmethyl-amino}-acetic acid tert-butyl ester (130 mg, 0.35 mmol) by following the general procedure G1. LCMS m/z: 369 (M+1)$^+$.

By analogous methods to those used to prepare Example 149 and those in the relevant above Schemes, the following compounds were synthesized. Examples 150 and 152-158 were isolated as the HCl salt. Example 151 was prepared as a neutral compound.

| Ex | R$_{100}$ | X | Y | n | LCMS m/z (M + 1)$^+$ |
|---|---|---|---|---|---|
| 150 | (5-chlorothiophen-2-ylmethyl) | N | CH | 1 | 403 |
| 151 | (5-methylthiophen-2-ylmethyl) | N | CH | 1 | 383 |
| 152 | (isobutyl/isopentyl) | N | CH | 1 | 343 |
| 153 | (furan-2-ylmethyl) | N | CH | 1 | 353 |
| 154 | (cyclohexylmethyl) | N | CH | 1 | 369 |
| 155 | (4-chlorobenzyl) | N | CH | 1 | 397 |
| 156 | (thiophen-2-ylmethyl) | CH | N | 2 | 383 |
| 157 | (thiophen-2-ylmethyl) | N | CH | 2 | 383 |
| 158 | (cyclopentylmethyl) | N | CH | 2 | 354 |

Preparation of Pyrimidine-4-yl Amines and Pyrimidine-2-yl Amines

The regioisomeric (2-chloro-pyrimidin-4-yl)-(2,4-dimethoxy-benzyl)-amine and (4-chloro-pyrimidin-2-yl)-(2, 4-dimethoxy-benzyl)-amine were obtained from 2,4-dichloropyrimidine (300 mg, 2 mmol) and 2,4-dimethoxybenzylamine (0.33 mL, 2.2 mmol) by following general procedure P (method 1). (2-Chloro-pyrimidin-4-yl)-(2,4-dimethoxybenzyl)-amine was obtained (347 mg). LCMS m/z: 281 (M+1)$^+$. (4-Chloro-pyrimidin-2-yl)-(2,4-dimethoxy-benzyl)-amine was obtained (100 mg). LCMS m/z: 281 (M+1)$^+$.

(2,4-Dimethoxy-benzyl)-[2-(4-isopropyl-phenyl)-pyrimidin-4-yl]-amine (323 mg) was obtained, via Suzuki cross-coupling, following general procedure Q1 from (2-chloro-pyrimidin-4-yl)-(2,4-dimethoxy-benzyl)-amine (340 mg, 1.22 mmol) and 4-isopropylphenylboronic acid (300 mg, 1.83 mmol). LCMS m/z: 365 (M+1)$^+$.

2-(4-Isopropyl-phenyl)-pyrimidin-4-ylamine was obtained (155 mg) by following the general procedure R from (2,4-dimethoxy-benzyl)-[2-(4-isopropyl-phenyl)-pyrimidin-4-yl]-amine (310 mg, 0.85 mmol). LCMS m/z: 214 (M+1)$^+$.

Example 159

4-Chloro-N-[2-(4-isopropyl-phenyl)-pyrimidin-4-yl]-benzenesulfonamide was obtained (240 mg) by following general procedure C2 from 2-(4-isopropyl-phenyl)-pyrimidin-4-ylamine (150 mg, 0.7 mmol) and 4-chlorobenzenesulfonyl chloride (163 mg, 0.78 mmol). LCMS m/z: 389 (M+1)$^+$.

Example 160

4-Chloro-N-[4-(4-isopropyl-phenyl)-pyrimidin-2-yl]-benzenesulfonamide was prepared (69 mg) by following general methods P, Q1, R and C-2 as explained above by using (4-chloro-pyrimidin-2-yl)-(2,4-dimethoxy-benzyl)-amine (100 mg, 0.36 mmol), 4-isoprpylboronic acid, and 4-chlorobenzenesulfonyl chloride. LCMS m/z: 389 (M+1)$^+$. $^1$H NMR (CDCl$_3$): δ 1.31 (d, 6H), 3.0 (m, 1H), 7.35 (m, 3H), 7.45 (d, 2H), 7.90 (d, 2H), 8.13 (d, 2H), 8.62 (d, 1H) 10.2 (s, 1H).

Example 161

{(4-Chloro-benzenesulfonyl)-[2-(4-isopropyl-phenyl)-pyrimidin-4-yl]-amino}-acetic acid tert-butyl ester was prepared (97 mg) from 4-chloro-N-[2-(4-isopropyl-phenyl)-pyrimidin-4-yl]-benzenesulfonamide (100 mg, 0.26 mmol) (Prepared in Example 158) and bromoacetic acid tert-butyl ester by following the general procedure S (method 1). LCMS m/z: 503 (M+1)$^+$.

{(4-Chloro-benzenesulfonyl)-[2-(4-isopropyl-phenyl)-pyrimidin-4-yl]-amino}-acetic acid was prepared (80 mg) from {(4-chloro-benzenesulfonyl)-[2-(4-isopropyl-phenyl)-pyrimidin-4-yl]-amino}-acetic acid tert-butyl ester (90 mg, 0.18 mmol) by following the general procedure G1. LCMS m/z: 447 (M+1)$^+$. $^1$H NMR (CDCl$_3$): δ 1.2 (d, 6H), 2.98 (m, 1H), 4.98 (s, 2H), 7.2-8.6 (Ar—H, 10H).

By analogous methods to those used to prepare Examples 159-161 and those in the relevant above Schemes, the following compounds were synthesized.

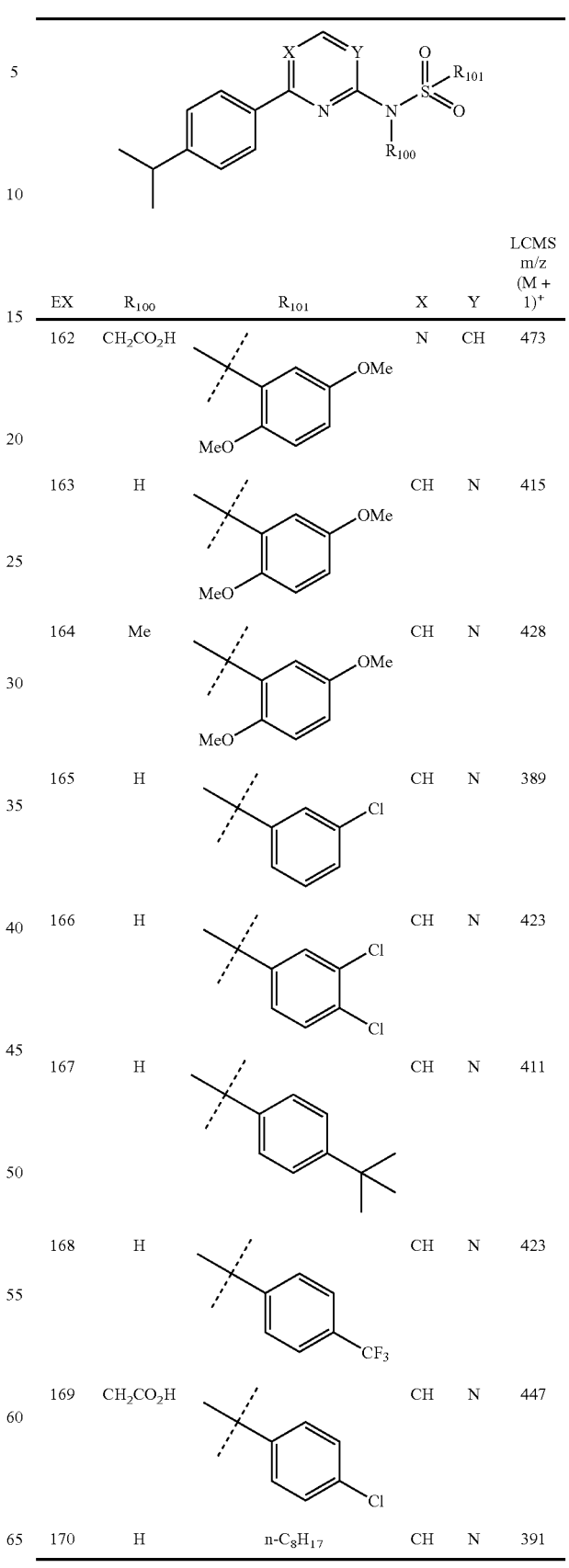

| EX | R$_{100}$ | R$_{101}$ | X | Y | LCMS m/z (M+1)$^+$ |
|---|---|---|---|---|---|
| 162 | CH$_2$CO$_2$H | 2,5-dimethoxyphenyl (2-OMe, 5-OMe) | N | CH | 473 |
| 163 | H | 2,5-dimethoxyphenyl | CH | N | 415 |
| 164 | Me | 2,5-dimethoxyphenyl | CH | N | 428 |
| 165 | H | 3-chlorophenyl | CH | N | 389 |
| 166 | H | 3,4-dichlorophenyl | CH | N | 423 |
| 167 | H | 4-tert-butylphenyl | CH | N | 411 |
| 168 | H | 4-trifluoromethylphenyl | CH | N | 423 |
| 169 | CH$_2$CO$_2$H | 4-chlorophenyl | CH | N | 447 |
| 170 | H | n-C$_8$H$_{17}$ | CH | N | 391 |

Example 171

4-Chloro-N-[4-(4-isopropyl-phenyl)-pyrimidin-2-yl]-N-(1H-tetrazol-5-yl methyl)-benzenesulfonamide was prepared from 4-chloro-N-[4-(4-isopropyl-phenyl)-pyrimidin-2yl]-benzenesulfonamide via N-alkylation with bromoacetonitrile using general procedure S (method 1) followed by tetrazole formation using general procedure H. LCMS m/z: 471 (M+1)$^+$.

Example 172

(2-Chloro-pyrimidin-4yl)-cyclopentyl-amine and (4-chloro-pyrimidin-2yl)-cyclopentyl-amine were synthesized from 2,4 dichloropyrimidine (1.0 g, 6.7 mmol), cyclopentylamine (860 mg, 10.1 mmol) and DIEA (3.5 mL, 20.2 mmol) following procedure P, method P2, using THF as solvent. The crude products were purified by silica gel chromatography eluting with DCM/ethyl acetate (9:1) to afford 2-Chloro-pyrimidin-4-yl)-cyclopentyl-amine (598 mg). LCMS m/z: 199 (M+1)$^+$, and (4-chloro-pyrimidin-2-yl)-cyclopentyl-amine (285 mg). LCMS m/z: 199 (M+1)$^+$.

(4-chloro-pyrimidin-2-yl)-cyclopentyl-amine (100 mg, 0.51 mmol) was reacted with (4-benzyloxyphenyl)boronic acid (173 mg, 0.76 mmol), tetrakis(triphenylphosphino)palladium (44 mg, 0.04 mmol), and aq. 2 N sodium carbonate (1.01 mmol, 0.51 mL) as described in general procedure Q, method Q1, to give 108 mg (62%) of [4-(4-benzyloxy-phenyl)-pyrimidin-2-yl]cyclopentyl-amine. Purification was carried out by silica gel chromatography eluting with hexanes/ethyl acetate, 4:1 then 1:1. LCMS m/z: 346 (M+1)$^+$.

[4-(4-benzyloxy-phenyl)-pyrimidin-2-yl]cyclopentyl-amine (108 mg, 0.313 mmol) was reacted with methyl-3-(bromomethyl) benzoate (107 mg, 0.47 mmol) and NaH (60% suspension, 25 mg, 0.626 mmol) following general procedure S, method S2. Purification was carried out by silica gel chromatography eluting with hexanes/ethyl acetate 4:1 to give 133 mg of 3-({[4-(4-benzyloxy-phenyl)-pyrimidin-2-yl]cyclopentyl-amine}-methyl)-benzoic acid methyl ester. LCMS m/z: 495 (M+1)$^+$.

To a MeOH-DCM solution (4:1, 4 mL) of 3-({[4-(4-benzyloxy-phenyl)-pyrimidin-2-yl]cyclopentyl-amine}-methyl)-benzoic acid methyl ester (127 mg, 0.26 mmol) was added 10% Pd/C (28 mg), and the reaction mixture was stirred at room temperature for 2 h under a hydrogen atmosphere (balloon). The mixture was filtered through a pad of Celite and then concentrated. The 3-({cyclopentyl-[4-(4-hydroxy-phenyl)-pyrimidin-2-yl]-amino}-methyl)-benzoic acid methyl ester obtained was used without further purification. LCMS m/z: 405 (M+1)$^+$.

To a THF (2 mL) solution of 3-({cyclopentyl-[4-(4-hydroxy-phenyl)-pyrimidin-2-yl]-amino}-methyl)-benzoic acid methyl ester (44 mg, 0.11 mmol) was added trans-4-methyl-cyclohexanol (12.5 mg, 0.11 mmol) and triphenylphosphine (27 mg, 0.11 mmol). After the mixture was cooled 5 min. in an ice bath, diisopropyl azodicarboxylate (DIAD, 21.5 µL, 0.11 mmol) was added. The solution was stirred at room temperature until complete. Water was added, and the mixture was extracted with ethyl acetate (3×2 mL). The ethyl acetate layer was dried over Na$_2$SO$_4$ and concentrated. Purification was carried out by silica gel chromatography eluting with hexanes/ethyl acetate 9:1 then 4:1 to give 16 mg (30%) of 3-[(cyclopentyl-{4-[4-(cis-4-methyl-cyclohexyloxy)-phenyl]-pyrimidin-2-yl}-amino)-methyl]-benzoic acid methyl ester. LCMS m/z: 501 (M+1)$^+$.

This product was hydrolyzed according to general procedure T. The 3-[(cyclopentyl-{4-[4-(cis-4-methyl-cyclohexyloxy)-phenyl]-pyrimidin-2-yl)-amino}-methyl]-benzoic acid produced was then converted to its corresponding HCl salt following general procedure G2 to give 3-[(cyclopentyl-{4-[4-(cis-4-methyl-cyclohexyloxy)-phenyl]-pyrimidin-2-yl}-amino)-methyl]-benzoic acid hydrochloride (16 mg, 94%). LCMS (m/z): 487 (M+1)$^+$.

Example 173

(2-chloro-pyrimidin-4-yl)-cyclopentylamine (100 mg, 0.51 mmol) was reacted with (4-benzyloxyphenyl)boronic acid (173 mg, 0.76 mmol), tetrakis(triphenylphosphino)palladium (44 mg, 0.04 mmol), and aq. 2 N sodium carbonate (1.01 mmol, 0.51 mL) as described in general procedure Q, method Q2, to give 164 mg of [2-(4-benzyloxy-phenyl)-pyrimidin-4-yl]-cyclopentyl-amine. Purification was carried out by silica gel chromatography eluting with hexanes/ethyl acetate 4:1 then 1:1. LCMS m/z: 346 (M+1)$^+$.

[2-(4-benzyloxy-phenyl)-pyrimidin-4-yl]-cyclopentyl-amine (164 mg, 0.475 mmol) was reacted with methyl-3-(bromomethyl) benzoate (163 mg, 0.71 mmol) and NaH (60% suspension, 38 mg, 0.95 mmol) following general procedure S, method S2. Purification was carried out by silica gel chromatography eluting with hexanes/ethyl acetate 4:1 then 2:1, and 116 mg of 3-({[2-(4-benzyloxy-phenyl)-pyrimidin-4-yl]-cyclopentyl-amino}-methyl)-benzoic acid methyl ester was obtained. LCMS m/z: 495 (M+1)$^+$.

To a MeOH-DCM solution (4:1, 4 mL) of 3-({[2-(4-benzyloxy-phenyl)-pyrimidin-4-yl]-cyclopentyl-amino}-methyl)-benzoic acid methyl ester (116 mg, 0.235 mmol) was added 10% Pd/C (25 mg), and the reaction mixture was stirred at room temperature for 2 h under a hydrogen atmosphere (balloon). The mixture was filtered through a pad of Celite and then concentrated. The 3-({cyclopentyl-[2-(4-hydroxy-phenyl)-pyrimidin-4-yl]-amino}-methyl)-benzoic acid methyl ester obtained was used without further purification. LCMS m/z: 405 (M+1)$^+$.

To an acetone (3 mL) solution of 3-({cyclopentyl-[2-(4-hydroxy-phenyl)-pyrimidin-4-yl]-amino}-methyl)-benzoic acid methyl ester (23 mg, 0.057 mmol) was added (bromomethyl)cyclohexane (11 mg, 0.063 mmol), K$_2$CO$_3$ (36 mg, 0.26 mmol) and tetrabutyammonium bromide (0.4 mg, 0.003 mmol). The resulting reaction mixture was heated in a CEM Explorer PLS™ microwave at 100° C. for 30 min. After cooling to room temperature the reaction mixture was filtered, and the residue was washed with acetone (4 mL). The solution was concentrated, and the crude solid was purified by silica gel chromatography eluting with hexanes/ethyl acetate 4:1 then 2:1 to yield 22 mg of 3-({[2-(4-cyclohexylmethoxy-phenyl)-pyrimidin-4-yl]-cyclopentyl-amino}-methyl)-benzoic acid methyl ester. LCMS m/z: 501 (M+1)$^+$.

This product was hydrolyzed according to general procedure T. The 3-({[2-(4-cyclohexylmethoxy-phenyl)-pyrimidin-4-yl]-cyclopentyl-amino}-methyl)-benzoic acid produced was then converted to its corresponding HCl salt following general procedure G2 to give 3-({[2-(4-cyclohexylmethoxy-phenyl)-pyrimidin-4-yl]-cyclopentyl-amino}methyl)-benzoic acid hydrochloride (22 mg). LCMS m/z: 487 (M+1)$^+$.

Example 174

[4-(4-isopropyl-phenyl)-pyrimidin-2-yl]-thiophen-2-ylmethyl-amine (50 mg, 0.16 mmol) (prepared in Example 149) was reacted with methyl-4-(bromomethyl) benzoate (55 mg, 0.24 mmol) and NaH (60% suspension, 13 mg, 0.32 mmol) following general procedure S, method S2. Purification was carried out by silica gel chromatography eluting with hexanes/ethyl acetate 4:1 to give 42 mg of 4-({[4-(4-isopropyl-phenyl)-pyrimidin-2-yl]-thiophen-2-ylmethyl-amino}-methyl)-benzoic acid methyl ester. LCMS m/z: 459 (M+1)⁺.

This ester was hydrolyzed according to general procedure T. The hydrolysis product was then converted to its corresponding HCl salt following general procedure G2. LCMS m/z: 445 (M+1)⁺.

By analogous methods to those used to prepare Example 174 and those in the relevant above schemes, the following compounds were synthesized. Examples 175-181 in the table below were prepared in the HCl salt form using general procedure G2.

| EX | $R_{100}$ | $R_{105}$ | X | Y | Acid position | LCMS m/z (M + 1)⁺ |
|---|---|---|---|---|---|---|
| 175 |  |  | iPr | CH | N | 2 | 445 |
| 176 |  |  | iPr | CH | N | 3 | 445 |
| 177 |  |  | OiPr | CH | N | 2 | 461 |
| 178 |  |  | OCF₃ | CH | N | 2 | 487 |
| 179 |  |  | OPh | CH | N | 2 | 495 |
| 180 |  |  | OMe | CH | N | 2 | 433 |
| 181 |  |  | F | CH | N | 2 | 421 |

Example 182

To a THF (2 mL) solution of 3-({cyclopentyl-[4-(4-hydroxy-phenyl)-pyrimidin-2-yl]-amino}-methyl)-benzoic acid methyl ester (39 mg, 0.10 mmol) (prepared in Example 172) was added cis-4-methyl-cyclohexanol (11 mg, 0.10 mmol) and triphenylphosphine (25 mg, 0.10 mmol). After the mixture was cooled 5 min. in an ice bath, diisopropyl azodicarboxylate (DIAD, 19.1 µL, 0.10 mmol) was added. The solution was stirred at room temperature until complete. Water was added, and the mixture was extracted with ethyl acetate (3×2 mL). The ethyl acetate layer was dried over Na₂SO₄ and concentrated. Purification was carried out by silica gel chromatography eluting with hexanes/ethyl acetate 9:1 then 4:1 to give 16 mg of 3-[(cyclopentyl-{4-[4-(trans-4-methyl-cyclohexyloxy)-phenyl]-pyrimidin-2-yl}-amino)-methyl]-benzoic acid methyl ester. LCMS m/z: 501 (M+1)⁺.

This ester was hydrolyzed according to general procedure T. The hydrolysis product was then converted to its corresponding HCl salt following general procedure G2 (16 mg). LCMS m/z: 487 (M+1)⁺.

Example 183

[2-(4-isopropyl-phenyl)-pyrimidin-4-yl]-thiophen-2-ylmethyl-amine (50 mg, 0.16 mmol) (prepared in Example 149) was reacted with methyl-4-(bromomethyl) benzoate (55 mg, 0.24 mmol) and NaH (60% suspension, 13 mg, 0.32 mmol) following general procedure S, method S2. Purification was carried out by silica gel chromatography eluting with hexanes/ethyl acetate 4:1 to give 25 mg of 4-({[2-(4-isopropyl-phenyl)-pyrimidin-4-yl]-thiophen-2-ylmethyl-amino}-methyl)-benzoic acid methyl ester. LCMS m/z: 459 (M+1)⁺.

By analogous methods to those used to prepare Example 183 and those in the relevant above schemes, the following compounds were synthesized. Examples 184-188 in the table below were prepared in the HCl salt form using general procedure G2.

Examples 187 and 188 were prepared as the sodium salt via general procedure J.

| EX | $R_{100}$ | $R_{105}$ | X | Y | Acid position | LCMS m/z (M + 1)⁺ |
|---|---|---|---|---|---|---|
| 184 |  |  | iPr | N | CH | 2 | 445 |
| 185 |  |  | iPr | N | CH | 3 | 445 |
| 186 |  |  | OBn | N | CH | 2 | 509 |
| 187 |  |  | OBn | N | CH | 3 | 509 |
| 188 |  |  | OBn | N | CH | 4 | 509 |

Example 189

[4-(4-Isopropyl-phenyl)-thiazol-2-yl]-[2-(1H-tetrazol-5-yl)-ethyl]-thiophen-2-ylmethyl-amine was prepared following general procedure H using 3-{[4-(4-isopropyl-phenyl)-thiazol-2-yl]-thiophen-2-ylmethyl-amino}-propionitrile (278 mg, 0.756 mmol), sodium azide (657 mg, 99%, 10 mmol), ammonium chloride (535 mg, 10 mmol) and DMF (3 mL). Purification by flash chromatography (ethyl acetate/hexanes 1:1, with 0.5% v/v acetic acid) gave the product compound (110 g, 0.268 mmol).
$^1$H-NMR (400 MHz, CDCl$_3$): 7.75-7.77 (m, 2H), 7.26-7.33 (m, 3H), 6.98-7.06 (m, 2H), 6.75 (s, 1H), 4.74 (s, 2H), 4.23 (t, 2H), 3.40 (t, 2H), 2.95 (sept, 1H), 1.28 (d, 6H); LCMS m/z: 411 (M+1)$^+$.

Example 190

2-({[4-(4-Isopropyl-phenyl)-thiazol-2-yl]-thiophen-2-ylmethyl-amino}-methyl)-benzonitrile was prepared by stirring (4-(-isopropyl-phenyl)-thiazol-2-yl)-thiophen-2-ylmethyl-amine (100 mg, 0.31 mmol), NaH (26 mg, 60%, 0.62 mmol), and 2-bromomethylbenzonitrile (72 mg, 0.372 mmol) in THF (50 mL) at room temperature. After 3 h, the reaction mixture was concentrated under high vacuum. The crude product used without purification.

[4-(4-Isopropyl-phenyl)-thiazol-2-yl]-[2-(1H-tetrazol-5-yl)-benzyl]-thiophen-2-ylmethyl-amine (6.0 mg) was prepared following general procedure H from the corresponding nitrile (130 mg, 0.31 mmol), ammonium chloride (3.1 mmol) and sodium azide (3.1 mmol). Purification (Silica gel, methanol/DCM 3:97) provided the product. LCMS m/z: 474 (M+1)$^+$.

Example 191

N-[2-({[4-(4-Isopropyl-phenyl)-thiazol-2-yl]-thiophen-2-yl methyl-amino}-methyl)-benzoyl]methanesulfonamide was prepared following procedure K using 2-({[4-(4-Isopropyl-phenyl)-thiazol-2-yl]-thiophen-2-ylmethyl-amino}-methyl)-benzoic acid (200 mg, 0.44 mmol), CDI (215 mg, 0.133 mmol), DBU (102 µl, 0.66. mmol), and methane sulfonamide (90 mg, 0.888 mmol). Purification (Silica gel, methanol/DCM 3:97) provided the product (100 mg). LCMS m/z: 527 (M+1)$^+$.

Example 192

A mixture of 3-{cyclopentyl-[4-(4-isopropyl-phenyl)-thiazol-2-yl]-amino}-propionic acid (100 mg, 0.28 mmol), diphenyl phosphoryl azide (70 ul, 0.25 mmol) and DIEA (150 µl) was heated in CH$_3$CN at 60° C. for 1 hour. After cooling to room temperature methane sulfonamide (50 mg, 0.52 mmol) was added and reaction mixture was stirred. After 16 h, the reaction mixture was concentrated in high vacuum. The crude residue was purified on a silica gel column (ethyl acetate/hexane 1:1) to afford 1-(2-{cyclopentyl-[4-(4-isopropyl-phenyl)-thiazol-2-yl]-amino}-ethyl)-3-methanesulfonyl-urea (25 mg). LCMS m/z: 452 (M+1)$^+$.

Example 193

A mixture of 3-{[4-(4-Isopropyl-phenyl)-thiazol-2-yl]-thiophen-2-ylmethyl-amino}-propionic acid (50 mg, 0.14 mmol), diphenyl phosphoryl azide (50 uL, 0.18 mmol) and DIEA (100 µL) was heated in CH$_3$CN at 60° C. for 1 hour. After cooling to room temperature methane sulfonamide (30 mg, 0.32 mmol) was added and reaction mixture was stirred. After 16 h, the reaction mixture was concentrated in high vacuum. The crude residue was purified on silica gel column (ethyl acetate/hexane 1:1) to afford (2-{[4-(4-Isopropyl-phenyl)-thiazol-2-yl]-thiophen-2-ylmethyl-amino}-ethyl) 3-methanesulfonyl-urea (15 mg). LCMS m/z: 480 (M+1)$^+$.

Example 194

LDA (1.5 ml, 2.0 M solution in THF) added to THF solution of 3-(cyclopentyl-(4-(4-isopropyl-phenyl)-2-yl)-amino)-propionic acid methyl ester (373.0 mg, 1.0 mmol) at −78° C. After 30 min., methyl iodide (75 µl, 1.2 mmol) was added. After 90 min., the cooling bath was removed and reaction warmed to room temperature. The reaction was quenched with ammonium chloride solution and extracted with Et$_2$O (1×50 ml). The organic layer was dried (MgSO$_4$), filtered and concentrated. The residual oil purified on silica gel column to afford ester (150 mg). The ester was hydrolyzed to the title compound following general procedure T to give 3-{Cyclopentyl-[4-(4-isopropyl-phenyl)-thiazol-2-yl]-amino}-2-methyl-propionic acid (150 mg). LCMS m/z: 374 (M+1)$^+$.

Example 195

LDA (1.0 ml, 2.0 M solution in THF) added to THF solution of 3-(cyclopentyl-(4-(4-isopropyl-phenyl)-2-yl)-amino)-propionic acid methyl ester (250.0 mg, 0.67 mmol) at −78° C. After 30 min., benzyl bromide (120 µL, 1.0 mmol) was added. After 90 min., the cooling bath removed and the reaction was warmed to room temperature, quenched with ammonium chloride solution, extracted with Et$_2$O (1×50 ml), organic layer dried (MgSO$_4$), and filtered and concentrated under high vacuum. The residual oil was purified on silica gel column to afford ester (50 mg). The ester was hydrolyzed to the title compound following general procedure T to give 2-Benzyl-3-{cyclopentyl-[4-(4-isopropyl-phenyl)-thiazol-2-yl]-amino}-propionic acid (40 mg) LCMS m/z: 450 (M+1)$^+$.

Example 196

4-{Cyclopentyl-[4-(4-isopropyl-phenyl)-thiazol-2-yl]-amino}-butyric acid was prepared according to general procedure B using 4-(1-cyclopentyl-thioureido)-butyric acid methyl ester (70 mg, 0.3 mmol) and 2-bromo-4'-isopropylacetophenone (80.0 mg, 0.3 mmol). Purification (Silica gel, ethyl acetate/hexane 5:95) provided the ester, which was hydrolyzed following general procedure T. LCMS m/z: 374 (M+1)$^+$.

Example 197

To the THF solution of [4-(4-isopropyl-phenyl)-thiazol-2-yl]-thiophen-2-ylmethyl-amine (150.0 mg, 0.5 mmol) and methyl 5-bromopentaoate (215 µL, 0.1.5 mmol) was added NaH (60 mg, 60%, 0.1.5 mmol) and the resulting mixture was heated at 60° C. for 5 h, after cooling to room temperature methanol (2.0 ml). NaOH (2.0 ml, 1.0 M) added and mix was stirred at room temperature for 15 h. HCl added dropwise to pH 7.0. The acid was extracted with EtOAc (2×20 ml), combined organic extracts dried (Na$_2$SO$_4$), filtered, concentrated, and purified on silica gel column. The sodium salt was made following procedure J to afford the sodium 5-{[4-(4-isopropyl-phenyl)-thiazol-2-yl]-thiophen-2-ylmethyl-amino}-pentanoate (110 mg). LCMS m/z: 416 (M+1)$^+$.

Example 198

A mixture of 6-methyl-pyridine-2-carboxylic acid ethyl ester (1.65 g, 10 mmol), NBS (1.77 g, 10 mmol), and benzoyl peroxide (100 mg) in carbon tetrachloride (20 ml) was refluxed for 14 h. After cooling to room temperature, the reaction mixture was partitioned between diethyl ether and water (120 ml, 4:1), organic layer was washed with water (2×20 ml), brine, dried (MgSO$_4$), filtered and concentrated to give 6-bromomethyl-pyridine-2-carboxylic acid ethyl ester (2.4 g) which was used without further purification. LCMS m/z: 245 (M+1)$^+$.

6-({[4-(4-Isopropyl-phenyl)-thiazol-2-yl]-thiophen-2-ylmethyl-amino}-methyl) pyridine-2-carboxylic acid ethyl ester was prepared following general method S2 using (4-(-isopropyl-phenyl)-thiazol-2-yl)-thiophen-2-ylmethyl-amine (62 mg, 0.20 mmol), 6-bromomethyl-pyridine-2-carboxylic acid ethyl ester (60 mg, 0.24 mmol) and NaH (34 mg, 60%, 0.84 mmol). Purification (Silica gel, ethyl acetate/hexane 1:4) provided the ester, which was hydrolyzed following general procedure T. Sodium 6-({[4-(4-isopropyl-phenyl)-thiazol-2-yl]-thiophen-2-ylmethyl-amino}-methyl) pyridine-2-carboxylate was made following procedure J. LCMS m/z: 451 (M+1)$^+$.

Example 199

To a THF solution of [4-(4-isopropyl-phenyl)-thiazol-2-yl]-thiophen-2-ylmethyl-amine (80 mg, 0.25 mmol) and tert-butyl bromoacetate (41 µL, 0.28 mmol) was added NaH (15 mg, 60%, 0.38 mmol) and the resulting mixture was stirred at room temperature for 30 min. The reaction was quenched with brine and extracted with ethyl acetate (3×5 mL). Combined ethyl acetate extracts were dried over sodium sulfate, concentrated and purified on silica gel column to afford 2-{thiophen-2-ylmethyl-[4-(4-isopropyl-phenyl)-thiazol-2-yl]-amino}acetic acid tert-butyl ester (75 mg). LCMS m/z: 430 (M+1)$^+$.

2-{Thiophen-2-ylmethyl-[4-(4-isopropyl-phenyl)-thiazol-2-yl]-amino}acetic acid hydrochloride was prepared (63 mg) following general procedure G1 using 2-{thiophen-2-ylmethyl-[4-(4-isopropyl-phenyl)-thiazol-2-yl]-amino}acetic acid tert-butyl ester (66 mg, 0.155 mmol) and 4 N HCl solution in dioxane (1.0 mL). LCMS m/z: 474 (M+1)$^+$.

Example 200

3-{[4-(4-Isopropyl-phenyl)-thiazol-2-yl]-thiophen-2-ylmethyl-amino}-propane-1-sulfonic acid was prepared following general method S2 using (4-(-isopropyl-phenyl)-thiazol-2-yl)-thiophen-2-ylmethyl-amine (54 mg, 0.17 mmol), [1,2]-oxathiolane 2,2-dioxide (26.0 mg, 0.2 mmol) and NaH (20 mg, 60%, 0.5 mmol). After 2 h, the volatiles were evaporated, and the residue was washed with hexane (2×5 ml) and then partitioned between ethyl acetate and water. The aqueous layer was adjusted to pH 6, and extracted with ethyl acetate (2×10 mL). The combined organic extracts were dried over Na$_2$SO$_4$, filtered, and concentrated to give the product (40 mg). LCMS m/z: 437 (M+1)$^+$.

Example 201

3-[(8H-Indeno[1,2-d]thiazol-2-yl)-thiophen-2-ylmethyl-amino]-propionic acid tert-butyl ester was prepared (35 mg) following general procedure B using 2-bromo-indan-1-one (22 mg, 0.1 mmol), and 3-(1-thiophen-2-ylmethyl-thioureido)-propionic acid tert-butyl ester (30 mg, 0.1 mmol). LCMS m/z: 414 (M+1)$^+$.

3-[(8H-Indeno[1,2-d]thiazol-2-yl)-thiophen-2-ylmethyl-amino]-propionic acid hydrochloride was prepared (32 mg) following general procedure G1 using 3-[(8H-indeno[1,2-d]thiazol-2-yl)-thiophen-2-ylmethyl-amino]-propionic acid tert-butyl ester (35 mg, 0.085 mmol) and 4 N HCl solution in dioxane (1.0 mL). LCMS m/z: 358 (M+1)$^+$. $^1$H NMR (CD$_3$OD, 400 MHz): δ 2.8 (t, 3H), 3.80 (s, 2H) 3.9 (t, 2H), 5.0 (s, 2H), 7.08 (dd, 1H), 7.21 (dd, 1H), 7.28 (t, 1H), 7.38 (t, 1H), 7.42 (dd, 1H), 7.56 (dd, 1H), 7.7 (dd, 1H).

Example 202

4-Phenylcyclohexanone (401 mg, 2.30 mmol) was dissolved in EtOAc (10 mL) and CuBr$_2$ (509 mg, 2.29 mmol) was added. The reaction mixture was stirred at 40° C. for 3 h followed by room temperature overnight. Ethyl acetate (15 mL) and hexane (15 mL) were added and the organic layer was washed with water (4×20 mL) followed by brine (20 mL). The solution was dried over MgSO$_4$, filtered, and concentrated. The crude product (mixture of cis and trans isomers) was used without further purification.

The 2-bromo-4-phenylcyclohexanone (2.30 mmol) and 3-(1-Cyclopentyl-thioureido)-propionic acid tert-butyl ester (257 mg, 0.945 mmol) were combined as in general procedure B (13 mL THF, 40° C., 15 h). After aqueous workup, the crude product was purified by silica gel chromatography (gradient, hexane→10% EtOAc-hexane) to afford 3-[cyclopentyl-(6-phenyl-4,5,6,7-tetrahydro-benzothiazol-2-yl)-amino]-propionic acid tert-butyl ester (398 mg). The ester was dissolved in CH$_2$Cl$_2$ (2 mL) and TFA (2 mL) was added. The reaction mixture was stirred at room temperature, until the starting material, was consumed by TLC. The volatiles were removed and the residue was dissolved in MeOH. NaOH solution (0.90 mmol) was added followed by half-saturated NaCl (20 mL). The aqueous layer was extracted with CH$_2$Cl$_2$ (3×15 mL) and dried over MgSO$_4$ to provide 3-[Cyclopentylcyclopentyl-(6-phenyl-4,5,6,7-tetrahydro-benzothiazol-2-yl)-amino]-propionic acid. The sodium salt was prepared by general procedure J and triturated with hexane to yield 3-[cyclopentyl-(6-phenyl-4,5,6,7-tetrahydro-benzothiazol-2-yl)-amino]-propionic acid, sodium salt (336 mg) LCMS m/z: 372 (M+1)$^+$.

Example 203

To the mixture of fluoro-N,N,N",N"'-tetramethylformamidinium hexafluorophosphate (TFFH) (290 mg, 1.1 mmol) and thiophen-2-acetic acid (156 mg, 1 mmol) at 0° C. was added diisopropylethylamine (0.35 mL, 2 mmol) and stirred at same temperature for 20 min. before adding 2-aminothiazole (261 mg, 1.2 mmol). The reaction mixture was warmed to room temperature and stirred for 12 h. The mixture was concentrated and loaded onto silica gel column to provide N-[4-(4-isopropyl-phenyl)-thiazol-2-yl]-2-thiophen-2-yl-acetamide (273 mg). LCMS m/z: 344 (M+1)$^+$.

To N-[4-(4-isopropyl-phenyl)-thiazol-2-yl]-2-thiophen-2-yl-acetamide (270 mg, 0.79 mmol) was added diborane in THF (1.6 mL, 1M solution, 1.58 mmol). The mixture was stirred at room temperature for 2 h. Saturated NaHCO$_3$ solution was added, and the mixture was extracted into ethyl acetate (3×5 mL). Combined ethyl acetate extracts were dried over Na$_2$SO$_4$, concentrated and purified on silica gel column to afford [4-(4-isopropyl-phenyl)-thiazol-2-yl]-(2-thiophen-2-yl-ethyl)-amine (103 mg). LCMS m/z: 330 (M+1)$^+$.

To a THF solution of [4-(4-isopropyl-phenyl)-thiazol-2-yl]-(2-thiophen-2-yl-ethyl)-amine (100 mg, 0.3 mmol) and ethyl bromopropionate (42 µL, 0.33 mmol) was added NaH (18 mg, 60%, 0.45 mmol). The mixture was stirred at room temperature for 30 min, and the excess NaH was quenched with brine and extracted into ethyl acetate (3×5 mL). The combined ethyl acetate extracts were dried over sodium sulfate, concentrated and purified on silica gel column to afford 3-[[4-(4-isopropyl-phenyl)-thiazol-2-yl]-(2-thiophen-2-yl-ethyl)-amino]-propionic acid ethyl ester (98 mg). LCMS m/z: 430 (M+1)$^+$.

To the 3-[[4-(4-isopropyl-phenyl)-thiazol-2-yl]-(2-thiophen-2-yl-ethyl)-amino]-propionic acid ethyl ester (95 mg, 0.22 mmol) was added LiOH (3 mL; 2N LiOH-MeOH-THF=1:1:4) and the reaction was stirred at room temperature for 4 h before acidifying with 1 N HCl. Brine was added, and the mixture was extracted with DCM (3×10 ml). The combined extracts were dried over Na$_2$SO$_4$, concentrated and purified on silica gel column to provide 3-[[4-(4-isopropyl-phenyl)-thiazol-2-yl]-(2-thiophen-2-yl-ethyl)-amino]-propionic acid hydrochloride salt (58 mg). LCMS m/z: 402 (M+1)$^+$.

Example 204

3-[[4-(4-Isopropyl-phenyl)-thiazol-2-yl]-(3-thiophen-2-yl-propyl)-amino]-propionic acid hydrochloride salt was prepared (50 mg) following the procedure described in Example 202 using 4-(4-Isopropyl-phenyl)-thiazol-2-yl-amine (261 g, 1.2 mmol), thiophen-2-propionic acid (165 mg, 1 mmol), TFFH (290 mg, 1.1 mmol), diisopropylethylamine (0.35 mL, 2 mmol) diborane-THF (1.6 mL, 1M, 1.6 mmol), NaH (18 mg, 60%, 0.45 mmol), ethyl bromopropionate (42 µL, 0.33 mmol) and LiOH (3 mL, aq 2N LiOH-MeOH-THF 1:1:4). The HCl salt was formed as in the above experiment using 1 N HCl in the workup procedure. LCMS m/z: 416 (M+1)$^+$.

Example 205

4-(4-Isopropyl-phenyl)-thiazol-2-yl amine (90 mg, 0.41 mmol) was acylated in CH$_2$Cl$_2$ using cyclobutane carbonyl chloride (60 µL, 0.52 mmol, 1.25 eq.) in the presence of excess pyridine. The reaction was quenched with sat. NH$_4$Cl, extracted with EtOAc and dried over MgSO$_4$. Purification by silica gel chromatography (10% EtOAc in hexanes) afforded 95 mg (80%) of cyclobutanecarboxylic acid [4-(4-isopropyl-phenyl)-thiazol-2-yl]-amide.

The thiazole-amide (95 mg, 0.32 mmol) was dissolved in THF (3 mL), cooled to 0° C. and treated with 1.0 mL of borane (1M THF, 3 eq.). The reaction was stirred for 24 h at room temperature. After the excess borane was quenched with MeOH, the reaction mixture was concentrated, diluted with EtOAc, and washed with sat. NaHCO$_3$. The organic layer was dried over MgSO$_4$. Purification by silica gel chromatography (0-5% EtOAc in hexanes) yielded 28 mg cyclobutylmethyl-[4-(4-isopropyl-phenyl)-thiazol-2-yl]-amine.

Alkylation of the above N-alkyl aminothiazole was accomplished with NaH (5 mgs, 1.8 eq.) and methyl 4-(bromomethyl)benzoate (27 mg, 1.8 eq) according to general procedure S2. Purification provided 3-({cyclobutylmethyl-[4-(4-isopropyl-phenyl)-thiazol-2-yl]-amino}-methyl)-benzoic acid methyl ester 18.5 mg.

Hydrolysis of the above benzoic ester as described in general procedure T afforded 12 mg of 3-({cyclobutylmethyl-[4-(4-isopropyl-phenyl)-thiazol-2-yl]-amino}-methyl)-benzoic acid. LCMS m/z: 422 (M+1)$^+$.

Example 206

4-(4-Isopropyl-phenyl)-thiazol-2-yl amine (100 mg, 0.46 mmol) was acylated in CH$_2$Cl$_2$ using cyclohexane carbonyl chloride (85 µL, 0.57 mmol, 1.25 eq.) in the presence of excess pyridine. The reaction was quenched with sat. NH$_4$Cl, extracted with EtOAc and dried over MgSO$_4$. Purification by silica gel chromatography (10% EtOAc in hexanes) afforded 123 mgs cyclohexanecarboxylic acid [4-(4-isopropyl-phenyl)-thiazol-2-yl]-amide.

The thiazole-amide (95 mg, 0.37 mmol) was dissolved in THF (3 mL), cooled to 0° C. and treated with 1.3 mL of borane (1M THF, 3 eq.). The reaction was stirred for 24 h at room temperature. After the excess borane was quenched with MeOH, the reaction mixture was concentrated, diluted with EtOAc and washed with sat. NaHCO$_3$. The organic layer was dried over MgSO$_4$. Purification by silica gel chromatography (0-5% EtOAc in hexanes) yielded 40 mg cyclohexylmethyl-[4-(4-isopropyl-phenyl)-thiazol-2-yl]-amine.

Alkylation of the above N-alkyl aminothiazole was accomplished with NaH (7 mg, 1.8 eq.) and methyl 4-(bromomethyl)benzoate (34 mg, 1.8 eq.) according to general procedure S2. Purification provided 3-({cyclohexylmethyl-[4-(4-isopropyl-phenyl)-thiazol-2-yl]-amino}-methyl)-benzoic acid methyl ester 39 mg.

Hydrolysis of the above benzoic ester as described in general procedure T afforded 19 mg of 3-({cyclohexylmethyl-[4-(4-isopropyl-phenyl)-thiazol-2-yl]-amino}-methyl)-benzoic acid. LCMS m/z: 450 (M+1)$^+$.

Example 207

To the methanol solution of 1H-indazole-3-carboxylic acid (162 mg, 1 mmol) was added 4N HCl in dioxane (2 mL) and the mixture was stirred at the room temperature for 24 h. After evaporation of the volatiles, the mixture was partitioned between aqueous NaHCO$_3$ solution and ethyl acetate. The aqueous phase was extracted with ethyl acetate (2×15 mL), and the combined organic layer was dried over sodium sulfate. The volatiles were removed, and the residue was filtered over silica gel to provide 1H-Indazole-3-carboxylic acid methyl ester (123 mg). LCMS m/z: 177 (M+1)$^+$.

1-Thiocarbamoyl-1H-indazole-3-carboxylic acid methyl ester was prepared (113 mg) following general procedure D using 1H-Indazole-3-carboxylic acid methyl ester (120 mg, 0.69 mmol), Fmoc isothiocyanate (213 mg, 0.76 mmol), and diethyl amine (0.5 mL). LCMS m/z: 236 (M+1)$^+$.

1-[4-(4-Isopropyl-phenyl)-thiazol-2-yl]-1H-indazole-3-carboxylic acid methyl ester was prepared (150 mg) following general procedure B using 2-bromo-1-(4-isopropyl)-ethanone (110 mg, 0.46 mmol), and 1-thiocarbamoyl-1H-indazole-3-carboxylic acid methyl ester (110 mg, 0.46 mmol). LCMS m/z: 379 (M+1)$^+$.

To the 1-[4-(4-isopropyl-phenyl)-thiazol-2-yl]-1H-indazole-3-carboxylic acid methyl ester (150 mg, 0.22 mmol) was added LiOH (5 mL; 2N LiOH-MeOH-THF=1:1:4) and stirred at room temperature for 4 h before acidifying with 1N HCl. Brine was added and the aqueous was extracted with DCM (3×15 ml). Combined extracts were dried over Na$_2$SO$_4$, concentrated and purified on silica gel column to provide 1-[4-(4-Isopropyl-phenyl)-thiazol-2-yl]-1H-indazole-3-carboxylic acid hydrochloride salt (48 mg). LCMS m/z: 365 (M+1)$^+$.

Example 208

To 4-(4-Isopropyl-phenyl)-thiazol-2-ylamine (50 mg, 0.23 mmol) in THF (1 mL) was added 4-chlorobenzenesulfonyl isocyanate (36 µL, 0.25 mmol). Purification was accomplished by silica gel chromatography to yield N-(4-(4-isobutyl-phenyl)-thiazol-2-yl]-N'-(4-chloro-benzenesulfonyl) urea (85 mg). LCMS m/z: 437 (M+1)$^+$; $^1$H NMR (CDCl$_3$, 400 MHz): δ 1.27 (d, 6H); 2.95 (m, 1H), 6.75 (s, 1H), 7.3 (m, 2H), 7.5 (m, 2H), 7.6 (m, 2H), 8.0 (m, 2H).

Example 209

(2-Chloro-pyrimidin-4-yl)-thiophen-2-ylmethyl-amine and (4-chloro-pyrimidin-2-yl)-thiophen-2-ylmethyl-amine were obtained from 2,4-dichloropyrimidine (7.5 g, 50.34 mmol) and thiophen-2-yl-methylamine (6.25 g, 55.22 mmol) by following general procedure P, method P1. Purification was carried out by silica gel chromatography (DCM/ethyl acetate, 9:1 then 3:1) to afford (2-chloro-pyrimidin-4-yl)-thiophen-2-ylmethyl-amine (6.58 g). LCMS m/z: 227 (M+1)$^+$; and (4-Chloro-pyrimidin-2-yl)-thiophen-2-ylmethyl-amine (1.55 g). LCMS m/z: 227 (M+1)$^+$.

[4-(4-Isopropyl-phenyl)-pyrimidin-2-yl]-thiophen-2-ylmethyl-amine (1.02 g, 99% yield) was obtained by following general procedure Q, method Q1, using (4-chloro-pyrimidin-2-yl)-thiophen-2-ylmethyl-amine (750 mg, 3.32 mmol), 4-isopropylphenylboronic acid (817 mg, 4.98 mmol), tetrakis (triphenylphosphino)palladium (288 mg, 0.25 mmol), and aq. 2 N sodium carbonate (6.64 mmol, 3.32 mL). Purification was carried out by silica gel chromatography eluting with DCM/ethyl acetate (9:1 then 4:1). LCMS m/z: 311 (M+1)$^+$.

To a solution of [4-(4-isopropyl-phenyl)-pyrimidin-2-yl]-thiophen-2-ylmethyl-amine (50 mg, 0.16 mmol) in DCM (2 mL) was added triethylamine (33 µL, 0.24 mmol) and 4-(ethoxycarbonyl)phenyl isocyanate (34 mg, 0.18 mmol). The resulting reaction mixture was heated in a CEM Explorer PLS™ microwave at 100° C. for 30 min. After cooling to room temperature the solvent was evaporated. Purification was carried out by silica gel chromatography eluting with hexanes/ethyl acetate 9:1 to give 11 mg of 4-{3-[4-(4-Isopropyl-phenyl)-pyrimidin-2-yl]-3-thiophen-2-ylmethyl-ureido}-benzoic acid ethyl ester. LCMS m/z: 502 (M+1)$^+$.

This product was hydrolyzed according to general procedure T to provide 4-{3-[4-(4-isopropyl-phenyl)-pyrimidin-2-yl}-3-thiophen-2-ylmethyl-ureido}-benzoic acid. The acid was then converted to its corresponding HCl salt following general procedure G2 to give 4-{3-[4-(4-isopropyl-phenyl)-pyrimidin-2-yl}-3-thiophen-2-ylmethyl-ureido}-benzoic acid hydrochloride (10 mg). LCMS m/z: 474 (M+1)$^+$.

Example 210

To a solution of [4-(4-isopropyl-phenyl)-pyrimidin-2-yl]-thiophen-2-ylmethyl-amine (50 mg, 0.16 mmol) in DCM (2 mL) was added triethylamine (33 µL, 0.24 mmol) and methyl 2-isocyanatobenzoate (32 mg, 0.18 mmol). The resulting reaction mixture was heated in a CEM Explorer PLS™ microwave at 100° C. for 30 min. After cooling to room temperature the solvent was evaporated. Purification was carried out by silica gel chromatography eluting with hexanes/ethyl acetate 9:1 to give 2 mg of 2-{3-[4-(4-isopropyl-phenyl)-pyrimidin-2-yl]-3-thiophen-2-ylmethyl-ureido}-benzoic acid methyl ester. LCMS m/z: 488 (M+1)$^+$.

This product was hydrolyzed according to general procedure T to provide 2-{3-[4-(4-isopropyl-phenyl)-pyrimidin-2-yl}-3-thiophen-2-ylmethyl-ureido}-benzoic acid. The acid was then converted to its corresponding HCl salt following general procedure G2 to give 2-{3-[4-(4-isopropyl-phenyl)-pyrimidin-2-yl}-3-thiophen-2-ylmethyl-ureido}-benzoic acid hydrochloride (1.4 mg). LCMS m/z: 474 (M+1)$^+$.

Example 211

[4-(4-Isopropyl-phenyl)-thiazol-2-yl]-thiophen-2-ylmethyl-amine (50 mg, 0.16 mmol), 4-(chlorosulfonyl)benzoic acid (53 mg, 0.24 mmol), triethylamine (45 µL, 0.32 mmol), and DMAP (2 mg, 0.016 mmol) were combined in DCM (2 mL). The resulting reaction mixture was heated in a CEM Explorer PLS™ microwave at 100° C. for 30 min. After cooling to room temperature, saturated NaHCO$_3$ (aq) solution (5 mL) was added. The mixture was extracted with DCM (2×4 mL). The combined organic layer was dried over Na$_2$SO$_4$ and concentrated. Purification of the crude product was carried out using silica gel chromatography eluting with DCM/MeOH 9:1, yielding 4-{[4-(4-isopropyl-phenyl)thiazol-2-yl]-thiophen-2-ylmethyl-sulfamoyl}-benzoic acid. LCMS m/z: 500 (M+1)$^+$.

Example 212

3-Amino-benzoic acid methyl ester (455 mg, 3.0 mmol), thiophene carboxaldehyde (290 µL, 3.15 mmol) and sodium triacetoxyborohydride (765 mg, 3.6 mmol) were combined according to general procedure D. 189 mg of the crude 3-[(thiophen-2-ylmethyl)-amino]-benzoic acid methyl ester (0.75 mmol) was treated with 1 eq. Fmoc-NCS to afford 206 mg 3-(1-thiophen-2-ylmethyl-thioureido)-benzoic acid methyl ester after purification.

Condensation of the 1-alkyl-1-aryl thiourea (100 mg, 0.32 mmol) with 2-bromo-1-(4-isopropyl-phenyl)-ethanone (80 mg, 0.32 mmol) according to general procedure B afforded 51 mg 3-{[4-(4-isopropyl-phenyl)-thiazol-2-yl]-thiophen-2-ylmethyl-amino}-benzoic acid methyl ester after purification.

The ester was hydrolyzed following general procedure T to provide 3-{[4-(4-Isopropyl-phenyl)-thiazol-2-yl]-thiophen-2-ylmethyl-amino}-benzoic acid (18 mg) after column chromatography (25% EtOAc in hexanes).

Using general procedure J, 3.1 mg of 3-{[4-(4-isopropyl-phenyl)-thiazol-2-yl]-thiophen-2-ylmethyl-amino}-benzoic acid sodium salt was prepared from 3.0 mg of the corresponding acid. LCMS m/z: 436 (M+1)$^+$.

Example 213

4-(4-Isopropyl-phenyl)-thiazole-2-carboxylic acid (50 mg) was prepared following general procedure T using the corresponding ethyl ester (170 mg, prepared in example 145).

4-(4-Isopropyl-phenyl)-thiazole-2-carbonyl chloride was prepared by refluxing a mixture of 4-(4-Isopropyl-phenyl)-thiazole-2-carboxylic acid (50 mg) and oxalyl chloride (300 µl) in chloroform (5 mL). After 3 h, the volatiles were evaporated and the residue was dried under high vacuum to provide the acid chloride (50 mg).

4-(4-Isopropyl-phenyl)-thiazole-2-carbonyl chloride (50 mg), 3-Cyclopentylamino-propionic acid tert-butyl ester (60 mg), TEA (200 ul), and DMAP (20 mg) in THF were combined at room temperature. After 4 h, the reaction mixture was partitioned between EtOAc and water (50 ml, 4:1), the EtOAc layer was washed with brine, dried (MgSO$_4$), filtered, and concentrated. The residue was purified on silica gel column (EtOAc/hexane 5:95) to afford the ester (50 mg), which was hydrolyzed to the acid following procedure G 1 to provide 3-{cyclopentyl-[4-(4-isopropyl-phenyl)-thiazole-2-carbonyl]-amino}-propionic acid. LCMS m/z: 388 (M+1)$^+$.

Example 214

1-Thiocarbamoyl-piperdine-3-carboxylic acid ethyl ester (400 mg) was prepared following general procedure D using piperdine-3-carboxylic acid ethyl ester (315 mg, 2.0 mmol), and Fmoc-isothiocyanate (562 mg, 2.0 mmol). Purification: (Silica gel, ethyl acetate/hexane 1:1). LCMS m/z 217.0 (M+1)+

A mixture of the above 1-thiocarbamoyl-piperdine-3-carboxylic acid ethyl ester (200 mg, 0.925 mmol) and 2-bromo-4'-isopropylacetophenone (220 mg, 0.925 mmol) in ethanol (5 ml) was heated at 60° C. for 2 h. The reaction was concentrated and partitioned between $Et_2O$ and sodium bicarbonate (1:1). The organic phase was dried ($MgSO_4$), filtered and concentrated under high vacuum. The crude residue was purified (Silica gel, ethyl acetate/hexane 5:95) afford ester (100 mg), which was hydrolyzed according to the general procedure T to give 1-[4-(4-Isopropyl-phenyl)-thiazol-2-yl]-piperidine-3-carboxylic acid (90 mg). LCMS m/z: 332 (M+1)$^+$.

Example 215

4-Thioureido-cyclohexanecarboxylic acid methyl ester (150 mg) compound was prepared following general procedure D using 4-Amino-cyclohexanecarboxylic acid methyl ester (500 mg, 11.0 mmol), and Fmoc-isothiocyanate (730 mg). Purification: (Silica gel, ethyl acetate/hexane 1:1). LCMS m/z: 217.0 (M+1)$^+$.

A mixture of the above 4-thioureido-cyclohexanecarboxylic acid methyl ester (150 mg, 0.7 mmol) and 2-bromo-4'-isopropylacetophenone (100 mg, 0.4 mmol) in methanol (5 mL) was heated at 60° C. for 2 h. The reaction was concentrated and partitioned between $Et_2O$ and sodium bicarbonate (1:1). The organic phase was dried ($MgSO_4$), filtered and concentrated under high vacuum. The crude residue was purified (Silica gel, ethyl acetate/hexane 5:95) to afford the ester (120 mg), which was hydrolyzed according to the general procedure T to give 4-[4-(4-Isopropyl-phenyl)-thiazol-2-ylamino]-cyclohexanecarboxylic acid (110 mg). LCMS m/z: 345 (M+1)$^+$.

Example 216

(S)-3-(3-Chloro-phenyl)-2-thioureido-propionic acid was prepared following general procedure D using (S)-2-amino-3-(3-chloro-phenyl)-propionic acid (399 mg, 2 mmol), Fmoc isothiocyanate (590 mg, 2 mmol) and DMF (6 mL). The residue was combined with DCM (8 mL) and diethyl amine (2 mL). LCMS m/z: 259 (M+1)$^+$. (S)-3-(3-Chloro-phenyl)-2-[4-(4-isopropyl-phenyl)-thiazol-2-ylamino]-propionic acid was prepared following general procedure B using 2-bromo-1-(4-isopropyl-phenyl)-ethanone (2 mmol), (S)-3-(3-chloro-phenyl)-2-thioureido-propionic acid and MeOH (10 mL). Purification by flash chromatography (ethyl acetate/hexanes 1:2, 1:1, with 0.5% v/v acetic acid) gave the product (545 mg). LCMS m/z: 401 (M+1)$^+$; $^1$H-NMR (400 MHz, $CDCl_3$): 7.39-7.45 (m, 3H), 7.18-7.25 (m, 5H), 6.37 (s, 1H), 4.15 (t, 1H), 3.38 (dd, 1H), 3.26 (dd, 1H), 2.92 (sept, 1H), 1.27 (d, 6H).

Example 217

2,6-Dichloro-benzothiazole (160 mg, 0.784 mmol), 3-cyclopentylamino-propionic acid tert-butyl ester (349 mg, 1.638 mmol), $Pd_2(dba)_3$ (55.0 mg, 0.06 mmol), 9,9-dimethyl-4,5-bis(diphenylphosphino)xanthene (71.1 mg, 0.123 mmol) and $Cs_2CO_3$ (670 mg, 2.055 mmol) were combined in dioxane (6 mL). The reaction mixture was heated to 85° C. (oil bath temperature) for 15 h. The reaction was cooled to room temperature and $NH_4Cl$ (aq) was added. The product was extracted with EtOAc (4×15 mL), dried over $MgSO_4$, filtered and concentrated. The residue was purified by silica gel chromatography (2% EtOAc-hexane) to furnish 66 mg of the product. The ester (66 mg) was charged with 4M HCl in dioxane (3 mL) and the reaction was stirred overnight at room temperature as indicated in general procedure G1 to afford the HCl salt of 3-[(6-Chloro-benzothiazol-2-yl)-cyclopentyl-amino]-propionic acid (66 mg). LCMS m/z: 326.

Example 218

5-{Cyclopentyl-[4-(4-isopropyl-phenyl)-thiazol-2-yl]-amino}-pentanoic acid (6.0 mg) was prepared following general method S2 using cyclopentyl-[4-(4-isopropyl-phenyl)-thiazol-2-yl]-amine (75 mg, 0.27 mmol)(prepared in example 106), 5-bromopetanoic acid methyl ester (150 mg, 0.76 mmol) and NaH (40 mg, 60% in oil, 1.0 mmol). Purification (Silica gel, ethyl acetate/hexane 5:95) provided the ester, which was hydrolyzed following general procedure T. LCMS m/z: 387

Some of the compounds were prepared in multiple salt forms. For example, Examples 35, 41, 54, 62, 88, and 100 (all sodium salts) were also prepared as the corresponding HCl salt using general procedure G1 or G2. Example 37 appears as the HCl salt, however, the sodium salt was also prepared using general procedure J.

Biological Assay

The following methods are illustrative of the technique employed to measure the ability of the compounds of Formula (I) to functionally modulate the binding of AgRP to melanocortin receptors. The following example illustrates, in particular, the technique employed to measure the ability of compounds of Formula (I) to functionally modulate the binding of AgRP to MC4R in the presence of a MC-4R agonist, such as alpha-MSH.

Cell Culture and Maintenance

HEK293 cells stably expressing human MC-4R receptors (See U.S. Pat. No. 5,622,860 and related applications, herein incorporated by reference) were grown in high glucose Dulbecco's Modified Eagle Medium (DMEM) with 4500 mg glucose/L, L-glutamine, $NaHCO_3$, pyrdoxin HCl, 10 mM HEPES (pH 7.4), 0.1 mM NEAA (non-essential amino acid medium) (GIBCO Cat#11140-050), 10% fetal bovine serum and 700 μg/mL G418. Cells were grown in T-225 flasks at 37° C. with $CO_2$ and humidity control.

Test Compound Treatment and cAMP Measurement

On the day of assay, cells were washed twice with phosphate buffered saline without calcium and magnesium (PBS) and incubated with 10 mL PBS until the cells were detached from the flask. The detached cells were centrifuged at 240 g for 5 min. The cell pellet was re-suspended in assay buffer (Earle's balanced salt solution (Sigma E3024) supplemented with 10 mM HEPES, pH 7.4, 1 mM $MgCl_2$, 0.5 mM IBMX and protease inhibitor cocktail (Roche, 1 complete tablet/75 mL buffer)) containing anti-cAMP antibodies (Perkin Elmer FP cAMPfire kit FPA203002KT).

Activity Assay

The inhibitory or enhancement effect of compounds on AgRP activity was measured in a multi-component assay containing testing compounds, AgRP (human, Pheonix Pharma, cat no. 003-53), cells expressing MC-4R, and αMSH (Bachem, cat no. H-1075). Test compounds, AgRP and αMSH were diluted with assay buffer. Test compounds and AgRP were mixed to 4 times of the final concentration and incubated at room temperature for 30 min. Five μL of testing compound/AgRP solution followed with 10 μL of cells (20,000 cells/well) were added to each well of a 384-well reaction plate and pre-incubated for 15 min at 37° C. before 5 μL of αMSH was added. Cells were stimulated with αMSH for an additional 30 min at 37° C.

Stimulation of cells was stopped and cells were lysed by adding 20 μL of detection buffer containing Alexa Fluor 594-cAMP (Perkin Elmer FP cAMPfire kit FPA203002KT) and incubation at room temperature for an hour. The intracellular cAMP concentration was measured using fluorescence polarization. Fluorescence polarization was measured using Envision (Perkin Elmer). Each data point was measured in triplicate and compiled as the mean of the three measurements±the error of the mean of the three measurements. The data were fit with non-linear curve fitting algorithm using sigmoid curves in GraphPad Prism.

Compounds of Formula (I) in Table 1 of the present invention inhibit the functional interaction of AgRP on MC-4R. The inhibition was shown by an increase in cAMP production and a reduction in fluorescence polarization in the assay. Such compounds possess an effective concentration for half maximal effect (EC50) in the assay of less than 15 μM.

Control Assay 1

In a control experiment, the direct effect of the test compounds on cells (referred to as basal activity) was measured in the absence of AgRP and αMSH. Briefly, 10 μl of of testing compounds in assay buffer containing anti-cAMP antibodies and 10 μl of cells (20,000 cells/well) in the same buffer were added to each well of a 384-well reaction plate and incubated at 37° C. for 30 min. The reaction was stopped by adding 20 μl detection buffer containing Alexa Fluor 594-cAMP. The fluorescence polarization reading was measured using Envision. Each data point was measured in triplicate and presented as the mean of the three measurements±the error of the mean of the three measurements. The data were fit with non-linear curve fitting algorithm using sigmoid curves in GraphPad Prism. Compounds of the present invention showed minimal basal activity at MC-4R in this assay.

Control Assay 2

The potentiating effect of test compounds on αMSH activity was also measured. Five μL of test article solution in assay buffer was mixed with 10 μL cells (20,000 cells/well) and incubated at 37° C. for 15 min before 5 μL αMSH solution was added. Cells were stimulated with αMSH at 37° C. for additional 30 min. The reaction was stopped by adding 20 μL detection buffer. The fluorescence polarization reading was measured using Envision. Each data point was measured in triplicate and presented as the mean of the three measurements±the error of the mean of the three measurements. The data were fit with non-linear curve fitting algorithm using sigmoid curves in GraphPad Prism. Compounds of Formula (I) in Table 1 showed minimal effect on (MSH activity at the MC-4R in this assay.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the mammal being treated for melanocortin receptor—mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A compound of Formula I,

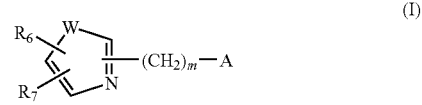

wherein
m is 0;
A is

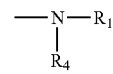

$R_1$ is —$C_{1-5}$ alkylene-$G_1$:
$R_4$ is selected from the group consisting of: -thienyl and —$C_{1-4}$ alkylene-thienyl;
$R_6$ and $R_7$ are independently selected from the group consisting of:
a) -hydrogen;
b) -halo;
c) -alkyl;
d) -L-$D_1$-H;
e) -L-$D_1$-alkyl;
f) -L-$D_1$-aryl;
g) -L-$D_1$-heteroaryl;
h) -L-$D_1$-cycloalkyl;
i) -L-$D_1$-heterocyclyl;
j) -L-$D_1$-arylene-alkyl;
k) -L-$D_1$-alkylene-arylene-alkyl;
l) -L-$D_1$-alkylene-aryl;
m) -L-$D_1$-arylene-aryl;
n) -L-$D_2$-(aryl)$_2$; and
o) -L-$D_2$-(arylene-alkyl)$_2$;
wherein at least one of $R_6$ and $R_7$ is not hydrogen;
W is S;
$G_1$ is —$CO_2H$;
L is a direct bond, alkylene, alkenylene, alkynylene, or arylene;
$D_1$ is selected from the group consisting of: a direct bond, —$CH_2$—, —O—, —N($R_8$)—, —C(O)—, —CON($R_8$)—, —CON($R_9$)$SO_2$—, —N($R_9$)C(O)—, —N($R_9$)CON($R_8$)—, —N($R_8$)C(O)O—, —OC(O)N($R_8$)—, —N($R_8$)$SO_2$—, —$SO_2$N($R_8$)—, —C(O)—O—, —O—C(O)—, —S—, —S(O)—, —S($O_2$)—, or —N($R_8$)$SO_2$N($R_9$)—, —N=N—, and —N($R_8$)—N($R_9$)—;
$D_2$ is N, alkylyne, or alkenylyne;
$R_8$ and $R_9$ are independently selected from the group consisting of: -hydrogen, -alkyl, -aryl, -arylene-alkyl, -alkylene-aryl, and -alkylene-arylene-alkyl;
and
wherein the aryl, heteroaryl, heterocyclyl, cycloalkyl, and/or alkyl group(s) in $R_1$, $R_4$, $R_6$, $R_7$, $R_8$, $R_9$, and L may be optionally substituted 1-4 times with a substituent group selected from the group consisting of
a) -hydrogen;
b) halogen;
c) hydroxyl;
d) cyano;
e) carbamoyl;
f) —B-alkyl;
g) —B-perhaloalkyl;
h) —B-cycloalkyl;
i) —B-heterocyclyl;
j) —B-aryl;
k) —B-heteroaryl;
l) —B-alkylene-heteroaryl;
m) —B-alkylene-aryl;
n) —B-arylene-alkyl;
o) —B-perhaloalkyl;
p) —B-cycloalkylene-T-$R_{14}$;
q) —B-alkylene-N—$R_{14}R_{15}$;
r) —B-cycloalkylene-alkyl; and
s) —B-alkylene-cycloalkyl;
wherein
B and T are independently selected from the group consisting of: direct bond, alkylene, —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$, —O—S(O)$_2$—, and —O—C(O)—;
wherein
$R_{14}$ and $R_{15}$ are independently selected from the group consisting of: hydrogen, heteroaryl, cycloalkyl, heterocyclyl, aryl, alkyl, -alkylene-aryl, -alkylene-heteroaryl, and alkylene-O-aryl; or
$R_{14}$ and $R_{15}$ may be taken together to form a ring having the formula —$(CH_2)_q$-J-$(CH_2)_r$— bonded to the nitrogen atom to which $R_{14}$ and $R_{15}$ are attached wherein q and r are independently equal to 1, 2, 3, or 4; J is a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

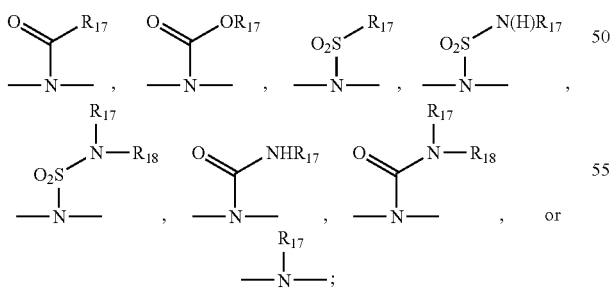

$R_{17}$ and $R_{18}$ are independently selected from the group consisting of: hydrogen, cycloalkyl, heterocyclyl, aryl, heteroaryl, alkyl, -alkyene-heteroaryl, and -alkylene-aryl;

or a pharmaceutically acceptable salt, prodrug, or solvate thereof.

2. The compound of Formula (I) in claim 1, having the formula (Ib)

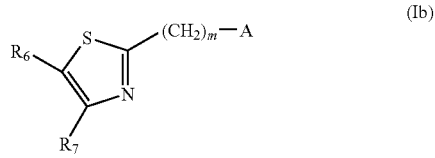

or pharmaceutically acceptable salt, or solvate thereof.

3. The compound of Formula (I) in claim 1 or a pharmaceutically acceptable salt, or solvate thereof, wherein $R_6$ is selected from the group consisting of: hydrogen, halo, alkyl, and phenyl.

4. The compound of Formula (I) in claim 1 or a pharmaceutically acceptable salt, or solvate thereof, wherein $R_6$ is selected from the group consisting of: halo, alkyl, and phenyl.

5. The compound of Formula (I) in claim 1 or a pharmaceutically acceptable salt, or solvate thereof, wherein
$R_7$ is selected from the group consisting of:
a) -L-$D_1$-alkyl;
b) -L-$D_1$-aryl;
c) -L-$D_1$-cycloalkyl;
d) -L-$D_1$-heterocyclyl;
e) -L-$D_1$-arylene-alkyl;
f) -L-$D_1$-alkylene-arylene-alkyl;
g) -L-$D_1$-alkylene-aryl;
h) -L-$D_1$-arylene-aryl;
i) -L-$D_2$-(aryl)$_2$; and
j) -L-$D_2$-(arylene-alkyl)$_2$;
wherein
L is a direct bond, $C_{1-6}$ alkylene, or phenylene; and
$D_1$ is selected from the group consisting of: a direct bond, —$CH_2$—, —O—, —C(O)—, —C(O)—O—, and —O—C(O)—.

6. The compound of Formula (I) in claim 1 or a pharmaceutically acceptable salt, or solvate thereof, wherein
$R_7$ is selected from the group consisting of:
a) -L-$D_1$-alkyl;
b) -L-$D_1$-aryl;
c) -L-$D_1$-cycloalkyl;
d) -L-$D_1$-heterocyclyl;
e) -L-$D_1$-arylene-alkyl;
f) -L-$D_1$-alkylene-arylene-alkyl;
g) -L-$D_1$-alkylene-aryl; and
h) -L-$D_1$-arylene-aryl;
i) -L-$D_2$-(aryl)$_2$; and
j) -L-$D_2$-(arylene-alkyl)$_2$;
wherein
L is a direct bond, $C_{1-6}$ alkylene, or phenylene; and
$D_1$ is selected from the group consisting of: a direct bond, —$CH_2$—, —O—, —C(O)—, —C(O)—O—, and —O—C(O)—,
wherein the aryl, heterocyclyl, cycloalkyl, and/or alkyl group(s) in $R_7$ and L may be optionally substituted 1-4 times with a substituent group selected from the group consisting of
a) —H;
b) halogen;
c) hydroxyl;
d) cyano;
e) —B-alkyl;
f) —B-perhaloalkyl;
g) —B-cycloalkyl;

h) —B-heterocyclyl;
i) —B-aryl;
j) —B-heteroaryl;
k) —B-alkylene-heteroaryl;
l) —B-alkylene-aryl;
m) —B-arylene-alkyl;
n) —B-perhaloalkyl;
o) —B-cycloalkylene-T-$R_{14}$;
p) —B-cycloalkylene-alkyl; and
q) —B-alkylene-cycloalkyl;
wherein
B and T are independently selected from the group consisting of: direct bond, alkylene, —$CH_2$—, and —O—;
wherein
$R_{14}$ is selected from the group consisting of: hydrogen, heteroaryl, cycloalkyl, heterocyclyl, aryl, alkyl, -alkylene-aryl, -alkylene-heteroaryl, and alkylene-O-aryl.

7. The compound of Formula (I) in claim 1 or a pharmaceutically acceptable salt, or solvate thereof, wherein
$R_7$ is selected from the group consisting of:
a) -L-$D_1$-alkyl;
b) -L-$D_1$-phenyl;
c) -L-$D_1$-$C_{5-8}$ cycloalkyl;
d) -L-$D_1$-tetrahydropyranyl;
e) -L-$D_1$-phenylene-alkyl;
f) -L-$D_1$-alkylene-phenylene-alkyl;
g) -L-$D_1$-alkylene-phenyl;
h) -L-$D_1$-phenylene-phenyl;
i) -L-$D_2$-(phenyl)$_2$; and
j) -L-$D_2$-(phenylene-alkyl)$_2$;
wherein
L is a direct bond, $C_{1-6}$ alkylene, or phenylene; and
$D_1$ is selected from the group consisting of: a direct bond, —$CH_2$—, —O—, —C(O)—, —C(O)—O—, and —O—C(O)—,
wherein the aryl, cycloalkyl, and/or alkyl group(s) in $R_7$ and L may be optionally substituted 1-4 times with a substituent group selected from the group consisting of
a) —H;
b) halogen;
c) hydroxyl;
d) cyano;
e) —B-alkyl;
f) —B-perhaloalkyl;
g) —B-cycloalkyl; and
h) —B-aryl;
wherein
B is selected from the group consisting of: direct bond, alkylene, —$CH_2$—, and —O—.

8. The compound of Formula (I) in claim 1 or a pharmaceutically acceptable salt, or solvate thereof, wherein
$R_6$ is selected from the group consisting of: hydrogen, halo, alkyl, and phenyl, and
$R_7$ is selected from the group consisting of:
phenyl,
benzyloxy-phenyl,
4-biphenyl-3-yl,
4-biphenyl-4-yl,
bromo-phenyl,
chloro-methyl-phenyl,
chloro-phenyl,
cyano-phenyl,
cyclohexylmethoxy-phenyl,
cyclohexyloxy-phenyl,
di-p-tolylmethyl,
methoxy-phenyl,
isobutoxy-phenyl,
trifluoromethoxy-phenyl,
phenethyloxy-phenyl,
phenoxy-phenyl,
methylphenyl,
isobutyl-phenyl,
isopropyl-phenyl,
tert-butyl-phenyl,
trifluoromethyl-phenyl,
dichloro-phenyl,
difluoro-phenyl,
dimethyl-phenyl,
dihydroxy-phenyl,
bis-trifluoromethyl-phenyl,
di-tert-butyl-hydroxy-phenyl,
benzoyl-phenyl,
(3-phenyl-propoxy)-phenyl,
(methyl-cyclohexyloxy)-phenyl,
(tert-butyl-cyclohexyloxy)-phenyl, and
(tetrahydropyran-4-yloxy)-phenyl.

9. The compound of Formula (I) in claim 1 or a pharmaceutically acceptable salt, or solvate thereof, wherein
$R_6$ is selected from the group consisting of: hydrogen, halo, alkyl, and phenyl, and
$R_7$ is selected from the group consisting of:
(tert-butyl-phenyl)-phenyl-methyl,
bis-(chloro-fluoro-phenyl)-methyl,
bis-(fluoro-phenyl)-methyl,
bis-(trifluoromethyl-phenyl)-methyl,
naphthalen-1-yl,
naphthalen-2-yl,
5,5,8,8-tetramethyl-5,6,7,8-tetrahydro-naphthalen-2-yl, and
4-benzhydryl.

10. The compound of Formula (I) in claim 1 or a pharmaceutically acceptable salt, or solvate thereof, wherein
$R_1$ is
$(CH_2)_n$-$G_1$; and
n is 1, 2, 3, or 4.

11. The compound of Formula (I) in claim 1 or a pharmaceutically acceptable salt, or solvate thereof, wherein
$R_4$ is selected from the group consisting of: thienyl, thien-2-yl-methyl, 3-thien-2-yl-propyl, and 2-thien-2-yl-ethyl.

12. A compound of Formula (Ib),

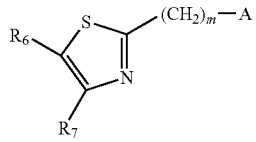
(Ib)

wherein
m is 0;
A is

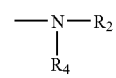

$R_2$ is —$C_{1-5}$ alkylene-$G_1$:
$R_4$ is selected from the group consisting of: -thien-2-yl and —$C_{1-4}$ thien-2-yl;

$R_6$ is selected from the group consisting of: hydrogen, halo, alkyl, and phenyl;

$R_7$ is selected from the group consisting of: phenyl, benzyloxy-phenyl, 4-biphenyl-3-yl, 4-biphenyl-4-yl, bromo-phenyl, chloro-methyl-phenyl, chloro-phenyl, cyano-phenyl, cyclohexylmethoxy-phenyl, cyclohexyloxy-phenyl, di-p-tolylmethyl, methoxy-phenyl, ethoxy-phenyl, isobutoxy-phenyl, trifluoromethoxy-phenyl, phenethyloxy-phenyl, phenoxy-phenyl, methylphenyl, isobutyl-phenyl, isopropyl-phenyl, tert-butyl-phenyl, trifluoromethyl-phenyl, dichloro-phenyl, difluoro-phenyl, dimethyl-phenyl, dihydroxy-phenyl, bis-trifluoromethyl-phenyl, di-tert-butyl-hydroxy-phenyl, benzoyl-phenyl, (3-phenyl-propoxy)-phenyl, (methyl-cyclohexyloxy)-phenyl, (tert-butyl-cyclohexyloxy)-phenyl, (tetrahydropyran-4-yloxy)-phenyl, (tert-butyl-phenyl)-phenyl-methyl, bis-(chloro-fluoro-phenyl)-methyl, bis-(fluoro-phenyl)-methyl, bis-(trifluoromethyl-phenyl)-methyl, naphthalen-1-yl, naphthalen-2-yl, 5,5,8,8-tetramethyl-5,6,7,8-tetrahydro-naphthalen-2-yl, and 4-benzhydryl;

W is —S—;

$G_1$ is —$CO_2H$, and wherein the aryl, heteroaryl, heterocyclyl, cycloalkyl, and/or alkyl group(s) in $R_2$, $R_4$, and $R_6$ may be optionally substituted 1-4 times with a substituent group selected from the group consisting of
a) -hydrogen;
b) halogen;
c) hydroxyl;
d) cyano;
e) carbamoyl;
f) —B-alkyl;
g) —B-perhaloalkyl;
h) —B-cycloalkyl;
i) —B-heterocyclyl;
j) —B-aryl;
k) —B-heteroaryl;
l) —B-alkylene-heteroaryl;
m) —B-alkylene-aryl;
n) —B-arylene-alkyl;
o) —B-perhaloalkyl;
p) —B-cycloalkylene-T-$R_{14}$;
q) —B-alkylene-N—$R_{14}R_{15}$;
r) —B-cycloalkylene-alkyl; and
s) —B-alkylene-cycloalkyl;
wherein
B and T are independently selected from the group consisting of: direct bond, alkylene, —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$, —O—$S(O)_2$—, and —O—C(O)—;
wherein
$R_{14}$ and $R_{15}$ are independently selected from the group consisting of: hydrogen, heteroaryl, cycloalkyl, heterocyclyl, aryl, alkyl, -alkylene-aryl, -alkylene-heteroaryl, and alkylene-O-aryl; or
$R_{14}$ and $R_{15}$ may be taken together to form a ring having the formula —$(CH_2)_q$-J-$(CH_2)_r$— bonded to the nitrogen atom to which $R_{14}$ and $R_{15}$ are attached wherein q and r are independently equal to 1, 2, 3, or 4; J is a direct bond, —$CH_2$—, —O—, —S—, —$S(O_2)$—, —C(O)—, —CON(H)—, —NHC(O)—,
—NHCON(H)—, —$NHSO_2$—, —$SO_2N(H)$—,
—C(O)—O—, —O—C(O)—,
—$NHSO_2NH$—,

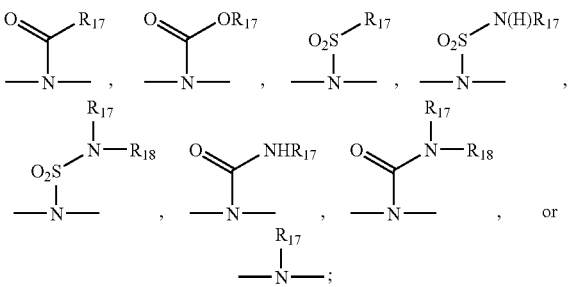

$R_{17}$ and $R_{18}$ are independently selected from the group consisting of: hydrogen, cycloalkyl, heterocyclyl, aryl, heteroaryl, alkyl, -alkylene-heteroaryl, and -alkylene-aryl;

or a pharmaceutically acceptable salt, prodrug, or solvate thereof.

13. The compound of Formula (Ib) in claim 12 or pharmaceutically acceptable salt, or solvate thereof, wherein
$R_7$ is selected from the group consisting of: phenyl, bromo-phenyl, chloro-methyl-phenyl, chloro-phenyl, cyano-phenyl, di-p-tolylmethyl, methoxy-phenyl, ethoxy-phenyl, isobutoxy-phenyl, trifluoromethoxy-phenyl, methylphenyl, isobutyl-phenyl, isopropyl-phenyl, tert-butyl-phenyl, trifluoromethyl-phenyl, dichloro-phenyl, difluoro-phenyl, dimethyl-phenyl, dihydroxy-phenyl, bis-trifluoromethyl-phenyl, di-tert-butyl-hydroxy-phenyl, (tert-butyl-phenyl)-phenyl-methyl, bis-(chloro-fluoro-phenyl)-methyl, bis-(fluoro-phenyl)-methyl, bis-(trifluoromethyl-phenyl)-methyl, naphthalen-1-yl, naphthalen-2-yl, and 5,5,8,8-tetramethyl-5,6,7,8-tetrahydro-naphthalen-2-yl.

14. A compound selected from the group consisting of:
3-{[4-(4-isopropyl-phenyl)-thiazol-2-yl]-thiophen-2-ylmethyl-amino}-propionic acid;
3-[(4-biphenyl-4-yl-thiazol-2-yl)-thiophen-2-ylmethylamino]-propionic acid;
3-({4-[4-(trans-4-methyl-cyclohexyloxy)-phenyl]-thiazol-2-yl}-thiophen-2-ylmethyl-amino)-propionic acid;
3-{[4-(4-Isopropyl-phenyl)-thiazol-2-yl]-thiophen-3-yl-amino}-propionic acid;
5-{[4-(4-isopropyl-phenyl)-thiazol-2-yl]-thiophen-2-ylmethyl-amino}-propionic acid;
3-[[4-(4-Isopropyl-phenyl)-thiazol-2-yl]-(2-thiophen-2-yl-ethyl)-amino]-propionic acid; and
3-[[4-(4-Isopropyl-phenyl)-thiazol-2-yl]-(3-thiophen-2-yl-propyl)-amino]-propionic acid;
or a pharmaceutically acceptable salt, prodrug, or solvate thereof.

15. A pharmaceutical composition comprising a compound of Formula (I) in claim 1, or a pharmaceutically salt, solvate, or prodrug thereof.

16. The pharmaceutical composition of claim 15, wherein the compound of Formula (I) is in the form of a hydrochloric acid salt or a sodium salt.

17. The pharmaceutical composition of claim 15 further comprising one or more pharmaceutically acceptable carriers, excipients, or diluents.

18. A pharmaceutical composition comprising the compound of Formula (I) in claim 2 or a pharmaceutically acceptable salt, or solvate thereof and one or more pharmaceutically acceptable carriers, excipients, or diluents.

19. A pharmaceutical composition comprising the compound of Formula (I) in claim 3 or a pharmaceutically acceptable salt, or solvate thereof and one or more pharmaceutically acceptable carriers, excipients, or diluents.

20. A pharmaceutical composition comprising the compound of Formula (I) in claim 4 or a pharmaceutically acceptable salt, or solvate thereof and one or more pharmaceutically acceptable carriers, excipients, or diluents.

21. A pharmaceutical composition comprising the compound of Formula (I) in claim 5 or a pharmaceutically acceptable salt, or solvate thereof and one or more pharmaceutically acceptable carriers, excipients, or diluents.

22. A pharmaceutical composition comprising the compound of Formula (I) in claim 6 or a pharmaceutically acceptable salt, or solvate thereof and one or more pharmaceutically acceptable carriers, excipients, or diluents.

23. A pharmaceutical composition comprising the compound of Formula (I) in claim 7 or a pharmaceutically acceptable salt, or solvate thereof and one or more pharmaceutically acceptable carriers, excipients, or diluents.

24. A pharmaceutical composition comprising the compound of Formula (I) in claim 8 or a pharmaceutically acceptable salt, or solvate thereof and one or more pharmaceutically acceptable carriers, excipients, or diluents.

25. A pharmaceutical composition comprising the compound of Formula (I) in claim 9 or a pharmaceutically acceptable salt, or solvate thereof and one or more pharmaceutically acceptable carriers, excipients, or diluents.

26. A pharmaceutical composition comprising the compound of Formula (I) in claim 10 or a pharmaceutically acceptable salt, or solvate thereof and one or more pharmaceutically acceptable carriers, excipients, or diluents.

27. A pharmaceutical composition comprising the compound of Formula (I) in claim 11 or a pharmaceutically acceptable salt, or solvate thereof and one or more pharmaceutically acceptable carriers, excipients, or diluents.

28. A pharmaceutical composition comprising the compound of Formula (I) in claim 12 or a pharmaceutically acceptable salt, or solvate thereof and one or more pharmaceutically acceptable carriers, excipients, or diluents.

29. A pharmaceutical composition comprising the compound of Formula (I) in claim 13 or a pharmaceutically acceptable salt, or solvate thereof and one or more pharmaceutically acceptable carriers, excipients, or diluents.

30. A pharmaceutical composition comprising the compound of Formula (I) in claim 14 or a pharmaceutically acceptable salt, or solvate thereof and one or more pharmaceutically acceptable carriers, excipients, or diluents.

31. 3-{[4-(4-isopropyl-phenyl)-thiazol-2-yl]-thiophen-2-ylmethyl-amino}-propionic acid or a pharmaceutically acceptable salt, or solvate thereof.

32. The compound of claim 31, wherein 3-{[4-(4-isopropyl-phenyl)-thiazol-2-yl]-thiophen-2-ylmethyl-amino}-propionic acid is in the form of a hydrochloric acid salt or a sodium salt.

33. A pharmaceutical composition comprising the compound of claim 31 and one or more pharmaceutically acceptable carriers, excipients, or diluents.

34. A pharmaceutical composition comprising the compound of claim 32 and one or more pharmaceutically acceptable carriers, excipients, or diluents.

35. 3-{[4-(4-isobutyl-phenyl)-thiazol-2-yl]-thiophen-2-ylmethyl-amino}-propionic acid or a pharmaceutically acceptable salt, or solvate thereof.

36. The compound of claim 35, wherein 3-{[4-(4-isobutyl-phenyl)-thiazol-2-yl]-thiophen-2-ylmethyl-amino}-propionic acid is in the form of a hydrochloric acid salt or a sodium salt.

37. A pharmaceutical composition comprising the compound of claim 35 and one or more pharmaceutically acceptable carriers, excipients, or diluents.

38. A pharmaceutical composition comprising the compound of claim 36 and one or more pharmaceutically acceptable carriers, excipients, or diluents.

39. 3-{[4-(4-isopropyl-phenyl)-thiazol-2-yl]-thiophen-2-ylmethyl-amino}-propionic acid or a pharmaceutically acceptable salt thereof.

40. 3-{[4-(4-isopropyl-phenyl)-thiazol-2-yl]-thiophen-2-ylmethyl-amino}-propionic acid.

41. A pharmaceutical composition comprising the compound of claim 39 or a pharmaceutically acceptable salt thereof and one or more pharmaceutically acceptable carriers, excipients, or diluents.

42. A pharmaceutical composition comprising the compound of claim 40 and one or more pharmaceutically acceptable carriers, excipients, or diluents.

* * * * *